US012648907B2

(12) United States Patent
Dooley et al.

(10) Patent No.: US 12,648,907 B2
(45) Date of Patent: Jun. 9, 2026

(54) MEMBRANE PROTEIN SCAFFOLDS FOR EXOSOME ENGINEERING

(71) Applicant: LONZA SALES AG, Basel (CH)

(72) Inventors: Kevin P. Dooley, Boston, MA (US); Douglas E. Williams, Boston, MA (US); James E. Thornton, Cambridge, MA (US)

(73) Assignee: LONZA SALES AG, Basel (CH)

( * ) Notice: Subject to any disclaimer, the term of this patent is extended or adjusted under 35 U.S.C. 154(b) by 1265 days.

(21) Appl. No.: 17/428,245

(22) PCT Filed: Feb. 4, 2020

(86) PCT No.: PCT/US2020/016629
§ 371 (c)(1),
(2) Date: Aug. 3, 2021

(87) PCT Pub. No.: WO2020/163370
PCT Pub. Date: Aug. 13, 2020

(65) Prior Publication Data
US 2022/0249373 A1      Aug. 11, 2022

Related U.S. Application Data

(60) Provisional application No. 62/851,581, filed on May 22, 2019, provisional application No. 62/801,636, filed on Feb. 5, 2019, provisional application No. 62/801,065, filed on Feb. 4, 2019.

(51) Int. Cl.

| | |
|---|---|
| *C12N 15/88* | (2006.01) |
| *A61K 9/127* | (2025.01) |
| *A61K 35/12* | (2015.01) |
| *A61K 35/15* | (2015.01) |
| *A61K 35/28* | (2015.01) |
| *A61K 38/00* | (2006.01) |
| *A61K 47/62* | (2017.01) |
| *C07K 14/705* | (2006.01) |
| *C12N 9/48* | (2006.01) |

(52) U.S. Cl.
CPC .............. *A61K 9/127* (2013.01); *A61K 35/15* (2013.01); *A61K 35/28* (2013.01); *A61K 47/62* (2017.08); *C07K 14/70596* (2013.01); *A61K 2035/124* (2013.01); *A61K 38/00* (2013.01); *C07K 2319/43* (2013.01)

(58) Field of Classification Search
CPC ........ A61K 9/127; A61K 35/15; A61K 35/28; A61K 47/62; A61K 38/00; A61K 2035/124; A61K 35/13; A61K 35/33; A61K 35/44; C07K 14/70596; C07K 2319/43; C12N 9/485
See application file for complete search history.

(56) References Cited

U.S. PATENT DOCUMENTS

| | | | |
|---|---|---|---|
| 10,195,290 B1 | 2/2019 | Dooley et al. | |
| 10,561,740 B2 * | 2/2020 | Dooley ........... | C07K 14/70596 |
| 11,679,164 B2 * | 6/2023 | Dooley ............... | C07K 14/755 |
| | | | 514/5.3 |
| 12,030,924 B2 * | 7/2024 | Lewis ................ | C07K 14/475 |
| 12,257,313 B2 * | 3/2025 | Dooley ............... | C07K 14/755 |
| 12,331,100 B2 * | 6/2025 | Lewis ............... | C07K 14/7151 |
| 2010/0029585 A1 | 2/2010 | Howbert et al. | |
| 2012/0219615 A1 | 8/2012 | Hershberg et al. | |
| 2013/0202707 A1 | 8/2013 | Ali et al. | |
| 2014/0356382 A1 * | 12/2014 | Wood ..................... | A61K 47/42 |
| | | | 424/178.1 |

FOREIGN PATENT DOCUMENTS

| | | | | |
|---|---|---|---|---|
| CA | 3030342 A1 * | 1/2018 | .............. | A61K 9/48 |
| WO | WO-2008115319 A2 | 9/2008 | | |
| WO | WO-2009030996 A1 | 3/2009 | | |
| WO | WO-2009088401 A2 | 7/2009 | | |
| WO | WO-2011044246 A1 | 4/2011 | | |
| WO | 2015002956 A1 | 1/2014 | | |
| WO | WO-2017203260 A1 | 11/2017 | | |
| WO | 2018011191 A1 | 1/2018 | | |
| WO | 2018015539 A1 | 1/2018 | | |
| WO | WO-2018015535 A1 | 1/2018 | | |
| WO | WO-2019040920 A1 | 2/2019 | | |
| WO | WO-2019099942 A1 | 5/2019 | | |
| WO | WO-2020163370 A1 | 8/2020 | | |

OTHER PUBLICATIONS

Doron, "Bacterial Infections: Overview," International encyclopedia of Public health, 2008:273-282 (Year: 2008).*
National Institute of Cancer—understanding and related topics, accessed Aug. 21, 2014 at URL: cancer.gov/cancertopics/understandingcancer, 63 pages (Year: 2014).*
Viruses overview, Merck Manual, accessed Feb. 19, 2019 at URL merckmanuals.com/professional/infectious-diseases/viruses/overview-of-viruses, 6 pages (Year: 2019).*
Margolis, "Diagnosis of Huntington disease," Clin. Chem. 49:1726-32 (2003) (Year: 2003).*
Alzheimer's disease, Merck Manual, accessed Nov. 2, 2023 at URL merckmanuals.com/professional/neurologic-disorders/delirium-and-dementia/alzheimer-disease, pp. 1-9 (Year: 2023).*
Metabolic disease, Encyclopedia Britannica, accessed Feb. 12, 2020 at URL: britannica.com/science/metabolic-disease; pp. 1-17 (2019 ) (Year: 2019).*

(Continued)

*Primary Examiner* — Julie Ha
*Assistant Examiner* — Kristina M Hellman
(74) *Attorney, Agent, or Firm* — MEDLER FERRO WOODHOUSE & MILLS PLLC

(57) ABSTRACT

The present disclosure relates to heterologous exosomal vesicle proteins (HEVPs), engineered exosomes comprising HEVPs, and methods of preparing and using these compositions, including therapeutic applications.

Figure 1:
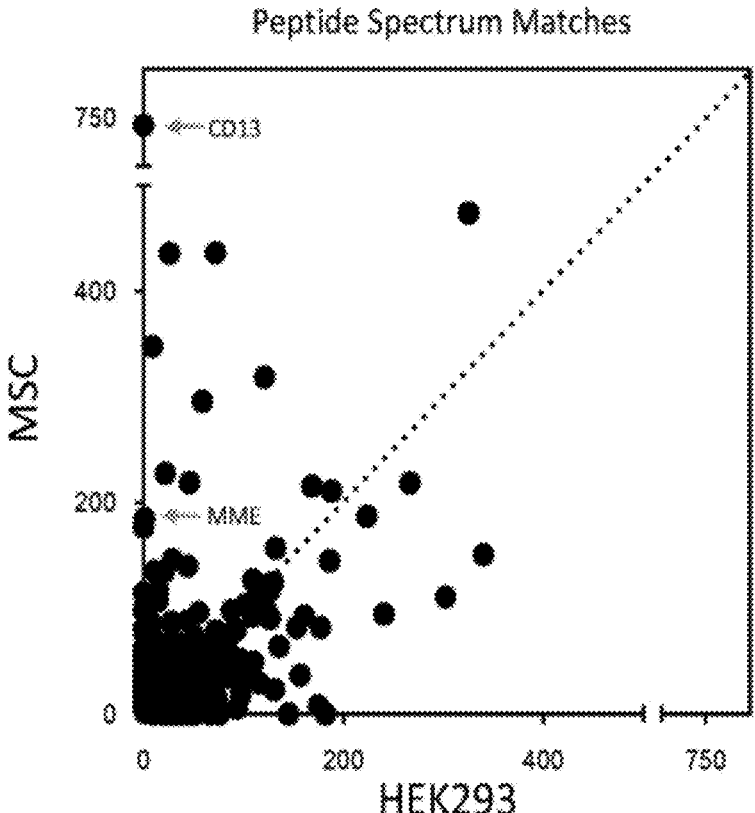

14 Claims, 4 Drawing Sheets
Specification includes a Sequence Listing.

(56) References Cited

OTHER PUBLICATIONS

Rountree et al., "Exosome Targeting of Tumor Antigens Expressed by Cancer Vaccines Can Improve Antigen Immunogenicity and Therapeutic Efficacy," Can Res 15:5235-5244 (2011) (Year: 2011).*

Drumm et al, Genetic Variation and Clinical Heterogeneity in Cystic Fibrosis, Annu. Rev. Pathol. Mech. Dis., 2012, 7, pp. 267-282 (Year: 2012).*

Yampolsky et al, The Exchangeability of Amino Acids in Proteins, Genetics, 2005, 170, pp. 1459-1472. (Year: 2005).*

Banaszynski, L.A., et al., "Characterization of the FKBP.rapamycin. FRB Ternary Complex," Journal of the American Chemical Society 127(13):4715-4721, American Chemical Society, United States (Apr. 2005).

Chen, X., et al., "Fusion Protein Linkers: Property, Design and Functionality," Advanced Drug Delivery Reviews 65(10):1357-1369, Elsevier Science Publishers, B.V., Netherlands (Oct. 2013).

Corpet, F., "Multiple Sequence Alignment With Hierarchical Clustering," Nucleic Acids Research 16(22):10881-10890, Oxford University Press, England (Nov. 1988).

Dobeli, H., et al., "Role of the Carboxy-terminal Sequence on the Biological Activity of Human Interferon (IFN-y)," Journal of Biotechnology 7:199-216, Elsevier, Netherlands (Mar. 1988).

Frank, A.M., "A Ranking-based Scoring Function for Peptide-spectrum Matches," Journal of Proteome Research 8(5):2241-2252, American Chemical Society, United States (May 2009).

Gayle, R.B., III., et al., "Identification of Regions in Interleukin-1 Alpha Important for Activity," The Journal of Biological Chemistry 268(29):22105-22111, Elsevier Inc. on behalf of American Society for Biochemistry and Molecular Biology, United States (Oct. 1993).

Gupta, S.C., et al., "Inhibiting NF-κB Activation by Small Molecules as a Therapeutic Strategy," Biochimica Et Biophysica Acta 1799(10-12):775-787, Elsevier Pub. Co., Netherlands (Oct.-Dec. 2010).

Higgins, D.G. and Sharp, P.M., "Clustal: A Package for Performing Multiple Sequence Alignment on a Microcomputer," Gene 73(1):237-244, Elsevier/North-Holland, Netherlands (Dec. 1988).

Higgins, D.G. and Sharp, P.M., "Fast and Sensitive Multiple Sequence Alignments on a Microcomputer," Computer Applications in the Biosciences 5(2):151-153, Oxford University Press, England (Apr. 1989).

Huang, X., et al., "Parallelization of a Local Similarity Algorithm," Computer Applications in the Biosciences 8(2):155-165, Oxford University Press, England (Apr. 1992).

International Search Report and Written Opinion mailed May 8, 2020 in International Application No. PCT/US2020/016629, EPO, Netherlands, 10 pages.

Kuypers, F.A., et al., "Survival of Rabbit and Horse Erythrocytes in Vivo after Changing the Fatty Acyl Composition of their Phosphatidylcholine," Biochimica et Biophysica Acta 819(2):170-178, Elsevier Pub. Co., Netherlands (Oct. 1985).

Mei, B., et al., "Rational Design of a Fully active, Long-acting PEGylated Factor VIII for Hemophilia A Treatment," Blood 116(2):270-279, The American Society of Hematology, United States (Jul. 2010).

Needleman, S.B. and Wunsch, C.D., "A General Method Applicable to the Search for Similarities in the Amino Acid Sequence of Two Proteins," Journal of Molecular Biology 48(3):443-453, Academic Press, United Kingdom (Mar. 1970).

Pearson, W.R., "Using the FASTA Program to Search Protein and DNA Sequence Databases," Methods in Molecular Biology 24:307-331, Humana Press, United States (Feb. 1994).

Pitt, J.M., et al., "Dendritic Cell-Derived Exosomes for Cancer Therapy," The Journal of Clinical Investigation 126(4):1224-1232, American Society for Clinical Investigation, United States (Apr. 2016).

Ron, D., et al., "Expression of Biologically Active Recombinant Keratinocyte Growth Factor. Structure/Function Analysis of Amino-terminal Truncation Mutants," The Journal of Biological Chemistry 268(4):2984-2988, Elsevier Inc. on behalf of American Society for Biochemistry and Molecular Biology, United States (Feb. 1993).

Smith, T.F. and Waterman, M.S., "Comparison of Biosequences," Advances in Applied Mathematics 2(4):482-489, Academic Press, Inc., United States (Dec. 1981).

* cited by examiner

| Gene | MW | HEK | MSC |
|------|------|-----|-----|
| CD13 | 110 kDa | 0 | 742 |
| MME | 86 kDa | 0 | 177 |

SEQUENCE LISTING

<160> NUMBER OF SEQ ID NOS: 50

<210> SEQ ID NO 1
<211> LENGTH: 879
<212> TYPE: PRT
<213> ORGANISM: Homo sapiens

<400> SEQUENCE: 1

```
Met Gly Arg Leu Ala Ser Arg Pro Leu Leu Leu Ala Leu Leu Ser Leu
1               5                   10                  15

Ala Leu Cys Arg Gly Arg Val Val Arg Val Pro Thr Ala Thr Leu Val
            20                  25                  30

Arg Val Val Gly Thr Glu Leu Val Ile Pro Cys Asn Val Ser Asp Tyr
        35                  40                  45

Asp Gly Pro Ser Glu Gln Asn Phe Asp Trp Ser Phe Ser Ser Leu Gly
    50                  55                  60

Ser Ser Phe Val Glu Leu Ala Ser Thr Trp Glu Val Gly Phe Pro Ala
65                  70                  75                  80

Gln Leu Tyr Gln Glu Arg Leu Gln Arg Gly Glu Ile Leu Leu Arg Arg
                85                  90                  95

Thr Ala Asn Asp Ala Val Glu Leu His Ile Lys Asn Val Gln Pro Ser
            100                 105                 110

Asp Gln Gly His Tyr Lys Cys Ser Thr Pro Ser Thr Asp Ala Thr Val
            115                 120                 125

Gln Gly Asn Tyr Glu Asp Thr Val Gln Val Lys Val Leu Ala Asp Ser
    130                 135                 140

Leu His Val Gly Pro Ser Ala Arg Pro Pro Pro Ser Leu Ser Leu Arg
145                 150                 155                 160

Glu Gly Glu Pro Phe Glu Leu Arg Cys Thr Ala Ala Ser Ala Ser Pro
                165                 170                 175

Leu His Thr His Leu Ala Leu Leu Trp Glu Val His Arg Gly Pro Ala
            180                 185                 190

Arg Arg Ser Val Leu Ala Leu Thr His Glu Gly Arg Phe His Pro Gly
            195                 200                 205

Leu Gly Tyr Glu Gln Arg Tyr His Ser Gly Asp Val Arg Leu Asp Thr
    210                 215                 220

Val Gly Ser Asp Ala Tyr Arg Leu Ser Val Ser Arg Ala Leu Ser Ala
225                 230                 235                 240

Asp Gln Gly Ser Tyr Arg Cys Ile Val Ser Glu Trp Ile Ala Glu Gln
                245                 250                 255

Gly Asn Trp Gln Glu Ile Gln Glu Lys Ala Val Glu Val Ala Thr Val
            260                 265                 270

Val Ile Gln Pro Ser Val Leu Arg Ala Ala Val Pro Lys Asn Val Ser
            275                 280                 285

Val Ala Glu Gly Lys Glu Leu Asp Leu Thr Cys Asn Ile Thr Thr Asp
    290                 295                 300

Arg Ala Asp Asp Val Arg Pro Glu Val Thr Trp Ser Phe Ser Arg Met
305                 310                 315                 320

Pro Asp Ser Thr Leu Pro Gly Ser Arg Val Leu Ala Arg Leu Asp Arg
                325                 330                 335

Asp Ser Leu Val His Ser Ser Pro His Val Ala Leu Ser His Val Asp
            340                 345                 350

Ala Arg Ser Tyr His Leu Leu Val Arg Asp Val Ser Lys Glu Asn Ser
            355                 360                 365
```

-continued

```
Gly Tyr Tyr Tyr Cys His Val Ser Leu Trp Ala Pro Gly His Asn Arg
    370             375             380

Ser Trp His Lys Val Ala Glu Ala Val Ser Ser Pro Ala Gly Val Gly
385             390             395             400

Val Thr Trp Leu Glu Pro Asp Tyr Gln Val Tyr Leu Asn Ala Ser Lys
            405             410             415

Val Pro Gly Phe Ala Asp Asp Pro Thr Glu Leu Ala Cys Arg Val Val
            420             425             430

Asp Thr Lys Ser Gly Glu Ala Asn Val Arg Phe Thr Val Ser Trp Tyr
            435             440             445

Tyr Arg Met Asn Arg Arg Ser Asp Asn Val Val Thr Ser Glu Leu Leu
    450             455             460

Ala Val Met Asp Gly Asp Trp Thr Leu Lys Tyr Gly Glu Arg Ser Lys
465             470             475             480

Gln Arg Ala Gln Asp Gly Asp Phe Ile Phe Ser Lys Glu His Thr Asp
            485             490             495

Thr Phe Asn Phe Arg Ile Gln Arg Thr Thr Glu Glu Asp Arg Gly Asn
            500             505             510

Tyr Tyr Cys Val Val Ser Ala Trp Thr Lys Gln Arg Asn Asn Ser Trp
    515             520             525

Val Lys Ser Lys Asp Val Phe Ser Lys Pro Val Asn Ile Phe Trp Ala
    530             535             540

Leu Glu Asp Ser Val Leu Val Val Lys Ala Arg Gln Pro Lys Pro Phe
545             550             555             560

Phe Ala Ala Gly Asn Thr Phe Glu Met Thr Cys Lys Val Ser Ser Lys
            565             570             575

Asn Ile Lys Ser Pro Arg Tyr Ser Val Leu Ile Met Ala Glu Lys Pro
            580             585             590

Val Gly Asp Leu Ser Ser Pro Asn Glu Thr Lys Tyr Ile Ile Ser Leu
            595             600             605

Asp Gln Asp Ser Val Val Lys Leu Glu Asn Trp Thr Asp Ala Ser Arg
    610             615             620

Val Asp Gly Val Val Leu Glu Lys Val Gln Glu Asp Glu Phe Arg Tyr
625             630             635             640

Arg Met Tyr Gln Thr Gln Val Ser Asp Ala Gly Leu Tyr Arg Cys Met
            645             650             655

Val Thr Ala Trp Ser Pro Val Arg Gly Ser Leu Trp Arg Glu Ala Ala
            660             665             670

Thr Ser Leu Ser Asn Pro Ile Glu Ile Asp Phe Gln Thr Ser Gly Pro
            675             680             685

Ile Phe Asn Ala Ser Val His Ser Asp Thr Pro Ser Val Ile Arg Gly
    690             695             700

Asp Leu Ile Lys Leu Phe Cys Ile Ile Thr Val Glu Gly Ala Ala Leu
705             710             715             720

Asp Pro Asp Asp Met Ala Phe Asp Val Ser Trp Phe Ala Val His Ser
            725             730             735

Phe Gly Leu Asp Lys Ala Pro Val Leu Leu Ser Ser Leu Asp Arg Lys
            740             745             750

Gly Ile Val Thr Thr Ser Arg Arg Asp Trp Lys Ser Asp Leu Ser Leu
            755             760             765

Glu Arg Val Ser Val Leu Glu Phe Leu Leu Gln Val His Gly Ser Glu
    770             775             780

Asp Gln Asp Phe Gly Asn Tyr Tyr Cys Ser Val Thr Pro Trp Val Lys
```

-continued

```
785              790              795              800

Ser Pro Thr Gly Ser Trp Gln Lys Glu Ala Glu Ile His Ser Lys Pro
             805              810              815

Val Phe Ile Thr Val Lys Met Asp Val Leu Asn Ala Phe Lys Tyr Pro
             820              825              830

Leu Leu Ile Gly Val Gly Leu Ser Thr Val Ile Gly Leu Leu Ser Cys
             835              840              845

Leu Ile Gly Tyr Cys Ser Ser His Trp Cys Cys Lys Lys Glu Val Gln
             850              855              860

Glu Thr Arg Arg Glu Arg Arg Arg Leu Met Ser Met Glu Met Asp
865              870              875

<210> SEQ ID NO 2
<211> LENGTH: 731
<212> TYPE: PRT
<213> ORGANISM: Homo sapiens

<400> SEQUENCE: 2

Pro Ser Ala Arg Pro Pro Pro Ser Leu Ser Leu Arg Glu Gly Glu Pro
1               5               10              15

Phe Glu Leu Arg Cys Thr Ala Ala Ser Ala Ser Pro Leu His Thr His
             20              25              30

Leu Ala Leu Leu Trp Glu Val His Arg Gly Pro Ala Arg Arg Ser Val
             35              40              45

Leu Ala Leu Thr His Glu Gly Arg Phe His Pro Gly Leu Gly Tyr Glu
             50              55              60

Gln Arg Tyr His Ser Gly Asp Val Arg Leu Asp Thr Val Gly Ser Asp
65              70              75              80

Ala Tyr Arg Leu Ser Val Ser Arg Ala Leu Ser Ala Asp Gln Gly Ser
             85              90              95

Tyr Arg Cys Ile Val Ser Glu Trp Ile Ala Glu Gln Gly Asn Trp Gln
             100             105             110

Glu Ile Gln Glu Lys Ala Val Glu Val Ala Thr Val Val Ile Gln Pro
             115             120             125

Ser Val Leu Arg Ala Ala Val Pro Lys Asn Val Ser Val Ala Glu Gly
             130             135             140

Lys Glu Leu Asp Leu Thr Cys Asn Ile Thr Thr Asp Arg Ala Asp Asp
145             150             155             160

Val Arg Pro Glu Val Thr Trp Ser Phe Ser Arg Met Pro Asp Ser Thr
             165             170             175

Leu Pro Gly Ser Arg Val Leu Ala Arg Leu Asp Arg Asp Ser Leu Val
             180             185             190

His Ser Ser Pro His Val Ala Leu Ser His Val Asp Ala Arg Ser Tyr
             195             200             205

His Leu Leu Val Arg Asp Val Ser Lys Glu Asn Ser Gly Tyr Tyr Tyr
             210             215             220

Cys His Val Ser Leu Trp Ala Pro Gly His Asn Arg Ser Trp His Lys
225             230             235             240

Val Ala Glu Ala Val Ser Ser Pro Ala Gly Val Gly Val Thr Trp Leu
             245             250             255

Glu Pro Asp Tyr Gln Val Tyr Leu Asn Ala Ser Lys Val Pro Gly Phe
             260             265             270

Ala Asp Asp Pro Thr Glu Leu Ala Cys Arg Val Val Asp Thr Lys Ser
             275             280             285
```

-continued

```
Gly Glu Ala Asn Val Arg Phe Thr Val Ser Trp Tyr Tyr Arg Met Asn
    290                 295                 300

Arg Arg Ser Asp Asn Val Val Thr Ser Glu Leu Leu Ala Val Met Asp
305                 310                 315                 320

Gly Asp Trp Thr Leu Lys Tyr Gly Glu Arg Ser Lys Gln Arg Ala Gln
                325                 330                 335

Asp Gly Asp Phe Ile Phe Ser Lys Glu His Thr Asp Thr Phe Asn Phe
                340                 345                 350

Arg Ile Gln Arg Thr Thr Glu Glu Asp Arg Gly Asn Tyr Tyr Cys Val
            355                 360                 365

Val Ser Ala Trp Thr Lys Gln Arg Asn Asn Ser Trp Val Lys Ser Lys
    370                 375                 380

Asp Val Phe Ser Lys Pro Val Asn Ile Phe Trp Ala Leu Glu Asp Ser
385                 390                 395                 400

Val Leu Val Val Lys Ala Arg Gln Pro Lys Pro Phe Phe Ala Ala Gly
                405                 410                 415

Asn Thr Phe Glu Met Thr Cys Lys Val Ser Ser Lys Asn Ile Lys Ser
                420                 425                 430

Pro Arg Tyr Ser Val Leu Ile Met Ala Glu Lys Pro Val Gly Asp Leu
            435                 440                 445

Ser Ser Pro Asn Glu Thr Lys Tyr Ile Ile Ser Leu Asp Gln Asp Ser
    450                 455                 460

Val Val Lys Leu Glu Asn Trp Thr Asp Ala Ser Arg Val Asp Gly Val
465                 470                 475                 480

Val Leu Glu Lys Val Gln Glu Asp Glu Phe Arg Tyr Arg Met Tyr Gln
                485                 490                 495

Thr Gln Val Ser Asp Ala Gly Leu Tyr Arg Cys Met Val Thr Ala Trp
                500                 505                 510

Ser Pro Val Arg Gly Ser Leu Trp Arg Glu Ala Ala Thr Ser Leu Ser
            515                 520                 525

Asn Pro Ile Glu Ile Asp Phe Gln Thr Ser Gly Pro Ile Phe Asn Ala
    530                 535                 540

Ser Val His Ser Asp Thr Pro Ser Val Ile Arg Gly Asp Leu Ile Lys
545                 550                 555                 560

Leu Phe Cys Ile Ile Thr Val Glu Gly Ala Ala Leu Asp Pro Asp Asp
                565                 570                 575

Met Ala Phe Asp Val Ser Trp Phe Ala Val His Ser Phe Gly Leu Asp
                580                 585                 590

Lys Ala Pro Val Leu Leu Ser Ser Leu Asp Arg Lys Gly Ile Val Thr
            595                 600                 605

Thr Ser Arg Arg Asp Trp Lys Ser Asp Leu Ser Leu Glu Arg Val Ser
    610                 615                 620

Val Leu Glu Phe Leu Leu Gln Val His Gly Ser Glu Asp Gln Asp Phe
625                 630                 635                 640

Gly Asn Tyr Tyr Cys Ser Val Thr Pro Trp Val Lys Ser Pro Thr Gly
                645                 650                 655

Ser Trp Gln Lys Glu Ala Glu Ile His Ser Lys Pro Val Phe Ile Thr
                660                 665                 670

Val Lys Met Asp Val Leu Asn Ala Phe Lys Tyr Pro Leu Leu Ile Gly
            675                 680                 685

Val Gly Leu Ser Thr Val Ile Gly Leu Leu Ser Cys Leu Ile Gly Tyr
    690                 695                 700

Cys Ser Ser His Trp Cys Cys Lys Lys Glu Val Gln Glu Thr Arg Arg
```

-continued

```
705                710                715                720

Glu Arg Arg Arg Leu Met Ser Met Glu Met Asp
                725                730

<210> SEQ ID NO 3
<211> LENGTH: 611
<212> TYPE: PRT
<213> ORGANISM: Homo sapiens

<400> SEQUENCE: 3

Val Ala Thr Val Val Ile Gln Pro Ser Val Leu Arg Ala Ala Val Pro
1               5                   10                  15

Lys Asn Val Ser Val Ala Glu Gly Lys Glu Leu Asp Leu Thr Cys Asn
                20                  25                  30

Ile Thr Thr Asp Arg Ala Asp Asp Val Arg Pro Glu Val Thr Trp Ser
            35                  40                  45

Phe Ser Arg Met Pro Asp Ser Thr Leu Pro Gly Ser Arg Val Leu Ala
        50                  55                  60

Arg Leu Asp Arg Asp Ser Leu Val His Ser Ser Pro His Val Ala Leu
65                  70                  75                  80

Ser His Val Asp Ala Arg Ser Tyr His Leu Leu Val Arg Asp Val Ser
                85                  90                  95

Lys Glu Asn Ser Gly Tyr Tyr Tyr Cys His Val Ser Leu Trp Ala Pro
                100                 105                 110

Gly His Asn Arg Ser Trp His Lys Val Ala Glu Ala Val Ser Ser Pro
            115                 120                 125

Ala Gly Val Gly Val Thr Trp Leu Glu Pro Asp Tyr Gln Val Tyr Leu
        130                 135                 140

Asn Ala Ser Lys Val Pro Gly Phe Ala Asp Asp Pro Thr Glu Leu Ala
145                 150                 155                 160

Cys Arg Val Val Asp Thr Lys Ser Gly Glu Ala Asn Val Arg Phe Thr
                165                 170                 175

Val Ser Trp Tyr Tyr Arg Met Asn Arg Arg Ser Asp Asn Val Val Thr
                180                 185                 190

Ser Glu Leu Leu Ala Val Met Asp Gly Asp Trp Thr Leu Lys Tyr Gly
            195                 200                 205

Glu Arg Ser Lys Gln Arg Ala Gln Asp Gly Asp Phe Ile Phe Ser Lys
        210                 215                 220

Glu His Thr Asp Thr Phe Asn Phe Arg Ile Gln Arg Thr Thr Glu Glu
225                 230                 235                 240

Asp Arg Gly Asn Tyr Tyr Cys Val Val Ser Ala Trp Thr Lys Gln Arg
                245                 250                 255

Asn Asn Ser Trp Val Lys Ser Lys Asp Val Phe Ser Lys Pro Val Asn
            260                 265                 270

Ile Phe Trp Ala Leu Glu Asp Ser Val Leu Val Val Lys Ala Arg Gln
            275                 280                 285

Pro Lys Pro Phe Phe Ala Ala Gly Asn Thr Phe Glu Met Thr Cys Lys
        290                 295                 300

Val Ser Ser Lys Asn Ile Lys Ser Pro Arg Tyr Ser Val Leu Ile Met
305                 310                 315                 320

Ala Glu Lys Pro Val Gly Asp Leu Ser Ser Pro Asn Glu Thr Lys Tyr
                325                 330                 335

Ile Ile Ser Leu Asp Gln Asp Ser Val Val Lys Leu Glu Asn Trp Thr
            340                 345                 350
```

-continued

```
Asp Ala Ser Arg Val Asp Gly Val Val Leu Glu Lys Val Gln Glu Asp
        355                 360                 365

Glu Phe Arg Tyr Arg Met Tyr Gln Thr Gln Val Ser Asp Ala Gly Leu
    370                 375                 380

Tyr Arg Cys Met Val Thr Ala Trp Ser Pro Val Arg Gly Ser Leu Trp
385                 390                 395                 400

Arg Glu Ala Ala Thr Ser Leu Ser Asn Pro Ile Glu Ile Asp Phe Gln
                405                 410                 415

Thr Ser Gly Pro Ile Phe Asn Ala Ser Val His Ser Asp Thr Pro Ser
            420                 425                 430

Val Ile Arg Gly Asp Leu Ile Lys Leu Phe Cys Ile Ile Thr Val Glu
        435                 440                 445

Gly Ala Ala Leu Asp Pro Asp Asp Met Ala Phe Asp Val Ser Trp Phe
    450                 455                 460

Ala Val His Ser Phe Gly Leu Asp Lys Ala Pro Val Leu Leu Ser Ser
465                 470                 475                 480

Leu Asp Arg Lys Gly Ile Val Thr Thr Ser Arg Arg Asp Trp Lys Ser
            485                 490                 495

Asp Leu Ser Leu Glu Arg Val Ser Val Leu Glu Phe Leu Leu Gln Val
        500                 505                 510

His Gly Ser Glu Asp Gln Asp Phe Gly Asn Tyr Tyr Cys Ser Val Thr
        515                 520                 525

Pro Trp Val Lys Ser Pro Thr Gly Ser Trp Gln Lys Glu Ala Glu Ile
    530                 535                 540

His Ser Lys Pro Val Phe Ile Thr Val Lys Met Asp Val Leu Asn Ala
545                 550                 555                 560

Phe Lys Tyr Pro Leu Leu Ile Gly Val Gly Leu Ser Thr Val Ile Gly
                565                 570                 575

Leu Leu Ser Cys Leu Ile Gly Tyr Cys Ser Ser His Trp Cys Cys Lys
            580                 585                 590

Lys Glu Val Gln Glu Thr Arg Arg Glu Arg Arg Arg Leu Met Ser Met
        595                 600                 605

Glu Met Asp
    610

<210> SEQ ID NO 4
<211> LENGTH: 485
<212> TYPE: PRT
<213> ORGANISM: Homo sapiens

<400> SEQUENCE: 4

Ser Pro Ala Gly Val Gly Val Thr Trp Leu Glu Pro Asp Tyr Gln Val
1                 5                  10                  15

Tyr Leu Asn Ala Ser Lys Val Pro Gly Phe Ala Asp Asp Pro Thr Glu
            20                  25                  30

Leu Ala Cys Arg Val Val Asp Thr Lys Ser Gly Glu Ala Asn Val Arg
        35                  40                  45

Phe Thr Val Ser Trp Tyr Tyr Arg Met Asn Arg Arg Ser Asp Asn Val
    50                  55                  60

Val Thr Ser Glu Leu Leu Ala Val Met Asp Gly Asp Trp Thr Leu Lys
65                  70                  75                  80

Tyr Gly Glu Arg Ser Lys Gln Arg Ala Gln Asp Gly Asp Phe Ile Phe
                85                  90                  95

Ser Lys Glu His Thr Asp Thr Phe Asn Phe Arg Ile Gln Arg Thr Thr
            100                 105                 110
```

```
Glu Glu Asp Arg Gly Asn Tyr Tyr Cys Val Val Ser Ala Trp Thr Lys
        115                 120                 125

Gln Arg Asn Asn Ser Trp Val Lys Ser Lys Asp Val Phe Ser Lys Pro
        130                 135                 140

Val Asn Ile Phe Trp Ala Leu Glu Asp Ser Val Leu Val Val Lys Ala
145                 150                 155                 160

Arg Gln Pro Lys Pro Phe Phe Ala Ala Gly Asn Thr Phe Glu Met Thr
                165                 170                 175

Cys Lys Val Ser Ser Lys Asn Ile Lys Ser Pro Arg Tyr Ser Val Leu
                180                 185                 190

Ile Met Ala Glu Lys Pro Val Gly Asp Leu Ser Ser Pro Asn Glu Thr
                195                 200                 205

Lys Tyr Ile Ile Ser Leu Asp Gln Asp Ser Val Val Lys Leu Glu Asn
        210                 215                 220

Trp Thr Asp Ala Ser Arg Val Asp Gly Val Val Leu Glu Lys Val Gln
225                 230                 235                 240

Glu Asp Glu Phe Arg Tyr Arg Met Tyr Gln Thr Gln Val Ser Asp Ala
                245                 250                 255

Gly Leu Tyr Arg Cys Met Val Thr Ala Trp Ser Pro Val Arg Gly Ser
                260                 265                 270

Leu Trp Arg Glu Ala Ala Thr Ser Leu Ser Asn Pro Ile Glu Ile Asp
                275                 280                 285

Phe Gln Thr Ser Gly Pro Ile Phe Asn Ala Ser Val His Ser Asp Thr
        290                 295                 300

Pro Ser Val Ile Arg Gly Asp Leu Ile Lys Leu Phe Cys Ile Ile Thr
305                 310                 315                 320

Val Glu Gly Ala Ala Leu Asp Pro Asp Asp Met Ala Phe Asp Val Ser
                325                 330                 335

Trp Phe Ala Val His Ser Phe Gly Leu Asp Lys Ala Pro Val Leu Leu
                340                 345                 350

Ser Ser Leu Asp Arg Lys Gly Ile Val Thr Thr Ser Arg Arg Asp Trp
                355                 360                 365

Lys Ser Asp Leu Ser Leu Glu Arg Val Ser Val Leu Glu Phe Leu Leu
        370                 375                 380

Gln Val His Gly Ser Glu Asp Gln Asp Phe Gly Asn Tyr Tyr Cys Ser
385                 390                 395                 400

Val Thr Pro Trp Val Lys Ser Pro Thr Gly Ser Trp Gln Lys Glu Ala
                405                 410                 415

Glu Ile His Ser Lys Pro Val Phe Ile Thr Val Lys Met Asp Val Leu
                420                 425                 430

Asn Ala Phe Lys Tyr Pro Leu Leu Ile Gly Val Gly Leu Ser Thr Val
                435                 440                 445

Ile Gly Leu Leu Ser Cys Leu Ile Gly Tyr Cys Ser Ser His Trp Cys
        450                 455                 460

Cys Lys Lys Glu Val Gln Glu Thr Arg Arg Glu Arg Arg Arg Leu Met
465                 470                 475                 480

Ser Met Glu Met Asp
                485
```

<210> SEQ ID NO 5
<211> LENGTH: 343
<212> TYPE: PRT
<213> ORGANISM: Homo sapiens

```
<400> SEQUENCE: 5

Lys Pro Val Asn Ile Phe Trp Ala Leu Glu Asp Ser Val Leu Val Val
1               5                   10                  15

Lys Ala Arg Gln Pro Lys Pro Phe Phe Ala Ala Gly Asn Thr Phe Glu
            20                  25                  30

Met Thr Cys Lys Val Ser Ser Lys Asn Ile Lys Ser Pro Arg Tyr Ser
            35                  40                  45

Val Leu Ile Met Ala Glu Lys Pro Val Gly Asp Leu Ser Ser Pro Asn
        50                  55                  60

Glu Thr Lys Tyr Ile Ile Ser Leu Asp Gln Asp Ser Val Val Lys Leu
65                  70                  75                  80

Glu Asn Trp Thr Asp Ala Ser Arg Val Asp Gly Val Val Leu Glu Lys
                85                  90                  95

Val Gln Glu Asp Glu Phe Arg Tyr Arg Met Tyr Gln Thr Gln Val Ser
            100                 105                 110

Asp Ala Gly Leu Tyr Arg Cys Met Val Thr Ala Trp Ser Pro Val Arg
            115                 120                 125

Gly Ser Leu Trp Arg Glu Ala Ala Thr Ser Leu Ser Asn Pro Ile Glu
        130                 135                 140

Ile Asp Phe Gln Thr Ser Gly Pro Ile Phe Asn Ala Ser Val His Ser
145                 150                 155                 160

Asp Thr Pro Ser Val Ile Arg Gly Asp Leu Ile Lys Leu Phe Cys Ile
                165                 170                 175

Ile Thr Val Glu Gly Ala Ala Leu Asp Pro Asp Asp Met Ala Phe Asp
            180                 185                 190

Val Ser Trp Phe Ala Val His Ser Phe Gly Leu Asp Lys Ala Pro Val
            195                 200                 205

Leu Leu Ser Ser Leu Asp Arg Lys Gly Ile Val Thr Thr Ser Arg Arg
        210                 215                 220

Asp Trp Lys Ser Asp Leu Ser Leu Glu Arg Val Ser Val Leu Glu Phe
225                 230                 235                 240

Leu Leu Gln Val His Gly Ser Glu Asp Gln Asp Phe Gly Asn Tyr Tyr
                245                 250                 255

Cys Ser Val Thr Pro Trp Val Lys Ser Pro Thr Gly Ser Trp Gln Lys
            260                 265                 270

Glu Ala Glu Ile His Ser Lys Pro Val Phe Ile Thr Val Lys Met Asp
            275                 280                 285

Val Leu Asn Ala Phe Lys Tyr Pro Leu Leu Ile Gly Val Gly Leu Ser
        290                 295                 300

Thr Val Ile Gly Leu Leu Ser Cys Leu Ile Gly Tyr Cys Ser Ser His
305                 310                 315                 320

Trp Cys Cys Lys Lys Glu Val Gln Glu Thr Arg Arg Glu Arg Arg Arg
                325                 330                 335

Leu Met Ser Met Glu Met Asp
                340

<210> SEQ ID NO 6
<211> LENGTH: 217
<212> TYPE: PRT
<213> ORGANISM: Homo sapiens

<400> SEQUENCE: 6

Val Arg Gly Ser Leu Trp Arg Glu Ala Ala Thr Ser Leu Ser Asn Pro
1               5                   10                  15
```

-continued

```
Ile Glu Ile Asp Phe Gln Thr Ser Gly Pro Ile Phe Asn Ala Ser Val
        20                  25                  30

His Ser Asp Thr Pro Ser Val Ile Arg Gly Asp Leu Ile Lys Leu Phe
        35                  40                  45

Cys Ile Ile Thr Val Glu Gly Ala Ala Leu Asp Pro Asp Asp Met Ala
        50                  55                  60

Phe Asp Val Ser Trp Phe Ala Val His Ser Phe Gly Leu Asp Lys Ala
65                  70                  75                  80

Pro Val Leu Leu Ser Ser Leu Asp Arg Lys Gly Ile Val Thr Thr Ser
                85                  90                  95

Arg Arg Asp Trp Lys Ser Asp Leu Ser Leu Glu Arg Val Ser Val Leu
                100                 105                 110

Glu Phe Leu Leu Gln Val His Gly Ser Glu Asp Gln Asp Phe Gly Asn
        115                 120                 125

Tyr Tyr Cys Ser Val Thr Pro Trp Val Lys Ser Pro Thr Gly Ser Trp
        130                 135                 140

Gln Lys Glu Ala Glu Ile His Ser Lys Pro Val Phe Ile Thr Val Lys
145                 150                 155                 160

Met Asp Val Leu Asn Ala Phe Lys Tyr Pro Leu Leu Ile Gly Val Gly
                165                 170                 175

Leu Ser Thr Val Ile Gly Leu Leu Ser Cys Leu Ile Gly Tyr Cys Ser
                180                 185                 190

Ser His Trp Cys Cys Lys Lys Glu Val Gln Glu Thr Arg Arg Glu Arg
                195                 200                 205

Arg Arg Leu Met Ser Met Glu Met Asp
        210                 215
```

```
<210> SEQ ID NO 7
<211> LENGTH: 66
<212> TYPE: PRT
<213> ORGANISM: Homo sapiens

<400> SEQUENCE: 7

Ser Lys Pro Val Phe Ile Thr Val Lys Met Asp Val Leu Asn Ala Phe
1               5                   10                  15

Lys Tyr Pro Leu Leu Ile Gly Val Gly Leu Ser Thr Val Ile Gly Leu
                20                  25                  30

Leu Ser Cys Leu Ile Gly Tyr Cys Ser Ser His Trp Cys Cys Lys Lys
        35                  40                  45

Glu Val Gln Glu Thr Arg Arg Glu Arg Arg Arg Leu Met Ser Met Glu
        50                  55                  60

Met Asp
65
```

```
<210> SEQ ID NO 8
<211> LENGTH: 21
<212> TYPE: PRT
<213> ORGANISM: Homo sapiens

<400> SEQUENCE: 8

Met Gly Arg Leu Ala Ser Arg Pro Leu Leu Leu Ala Leu Leu Ser Leu
1               5                   10                  15

Ala Leu Cys Arg Gly
                20
```

```
<210> SEQ ID NO 9
<211> LENGTH: 385
```

-continued

```
<212> TYPE: PRT
<213> ORGANISM: Homo sapiens

<400> SEQUENCE: 9

Met Ala Ala Ala Leu Phe Val Leu Leu Gly Phe Ala Leu Leu Gly Thr
1               5                   10                  15

His Gly Ala Ser Gly Ala Ala Gly Phe Val Gln Ala Pro Leu Ser Gln
            20                  25                  30

Gln Arg Trp Val Gly Gly Ser Val Glu Leu His Cys Glu Ala Val Gly
        35                  40                  45

Ser Pro Val Pro Glu Ile Gln Trp Trp Phe Glu Gly Gln Gly Pro Asn
    50                  55                  60

Asp Thr Cys Ser Gln Leu Trp Asp Gly Ala Arg Leu Asp Arg Val His
65              70                  75                  80

Ile His Ala Thr Tyr His Gln His Ala Ala Ser Thr Ile Ser Ile Asp
                85                  90                  95

Thr Leu Val Glu Glu Asp Thr Gly Thr Tyr Glu Cys Arg Ala Ser Asn
            100                 105                 110

Asp Pro Asp Arg Asn His Leu Thr Arg Ala Pro Arg Val Lys Trp Val
        115                 120                 125

Arg Ala Gln Ala Val Val Leu Val Leu Glu Pro Gly Thr Val Phe Thr
    130                 135                 140

Thr Val Glu Asp Leu Gly Ser Lys Ile Leu Leu Thr Cys Ser Leu Asn
145                 150                 155                 160

Asp Ser Ala Thr Glu Val Thr Gly His Arg Trp Leu Lys Gly Gly Val
                165                 170                 175

Val Leu Lys Glu Asp Ala Leu Pro Gly Gln Lys Thr Glu Phe Lys Val
            180                 185                 190

Asp Ser Asp Asp Gln Trp Gly Glu Tyr Ser Cys Val Phe Leu Pro Glu
        195                 200                 205

Pro Met Gly Thr Ala Asn Ile Gln Leu His Gly Pro Pro Arg Val Lys
    210                 215                 220

Ala Val Lys Ser Ser Glu His Ile Asn Glu Gly Glu Thr Ala Met Leu
225                 230                 235                 240

Val Cys Lys Ser Glu Ser Val Pro Pro Val Thr Asp Trp Ala Trp Tyr
                245                 250                 255

Lys Ile Thr Asp Ser Glu Asp Lys Ala Leu Met Asn Gly Ser Glu Ser
            260                 265                 270

Arg Phe Phe Val Ser Ser Ser Gln Gly Arg Ser Glu Leu His Ile Glu
        275                 280                 285

Asn Leu Asn Met Glu Ala Asp Pro Gly Gln Tyr Arg Cys Asn Gly Thr
    290                 295                 300

Ser Ser Lys Gly Ser Asp Gln Ala Ile Ile Thr Leu Arg Val Arg Ser
305                 310                 315                 320

His Leu Ala Ala Leu Trp Pro Phe Leu Gly Ile Val Ala Glu Val Leu
                325                 330                 335

Val Leu Val Thr Ile Ile Phe Ile Tyr Glu Lys Arg Arg Lys Pro Glu
            340                 345                 350

Asp Val Leu Asp Asp Asp Asp Ala Gly Ser Ala Pro Leu Lys Ser Ser
        355                 360                 365

Gly Gln His Gln Asn Asp Lys Gly Lys Asn Val Arg Gln Arg Asn Ser
    370                 375                 380

Ser
385
```

```
<210> SEQ ID NO 10
<211> LENGTH: 247
<212> TYPE: PRT
<213> ORGANISM: Homo sapiens

<400> SEQUENCE: 10

Pro Gly Thr Val Phe Thr Thr Val Glu Asp Leu Gly Ser Lys Ile Leu
1               5                   10                  15

Leu Thr Cys Ser Leu Asn Asp Ser Ala Thr Glu Val Thr Gly His Arg
            20                  25                  30

Trp Leu Lys Gly Gly Val Val Leu Lys Glu Asp Ala Leu Pro Gly Gln
        35                  40                  45

Lys Thr Glu Phe Lys Val Asp Ser Asp Asp Gln Trp Gly Glu Tyr Ser
    50                  55                  60

Cys Val Phe Leu Pro Glu Pro Met Gly Thr Ala Asn Ile Gln Leu His
65                  70                  75                  80

Gly Pro Pro Arg Val Lys Ala Val Lys Ser Ser Glu His Ile Asn Glu
                85                  90                  95

Gly Glu Thr Ala Met Leu Val Cys Lys Ser Glu Ser Val Pro Pro Val
            100                 105                 110

Thr Asp Trp Ala Trp Tyr Lys Ile Thr Asp Ser Glu Asp Lys Ala Leu
        115                 120                 125

Met Asn Gly Ser Glu Ser Arg Phe Phe Val Ser Ser Ser Gln Gly Arg
    130                 135                 140

Ser Glu Leu His Ile Glu Asn Leu Asn Met Glu Ala Asp Pro Gly Gln
145                 150                 155                 160

Tyr Arg Cys Asn Gly Thr Ser Ser Lys Gly Ser Asp Gln Ala Ile Ile
                165                 170                 175

Thr Leu Arg Val Arg Ser His Leu Ala Ala Leu Trp Pro Phe Leu Gly
            180                 185                 190

Ile Val Ala Glu Val Leu Val Leu Val Thr Ile Ile Phe Ile Tyr Glu
        195                 200                 205

Lys Arg Arg Lys Pro Glu Asp Val Leu Asp Asp Asp Asp Ala Gly Ser
    210                 215                 220

Ala Pro Leu Lys Ser Ser Gly Gln His Gln Asn Asp Lys Gly Lys Asn
225                 230                 235                 240

Val Arg Gln Arg Asn Ser Ser
                245

<210> SEQ ID NO 11
<211> LENGTH: 168
<212> TYPE: PRT
<213> ORGANISM: Homo sapiens

<400> SEQUENCE: 11

His Gly Pro Pro Arg Val Lys Ala Val Lys Ser Ser Glu His Ile Asn
1               5                   10                  15

Glu Gly Glu Thr Ala Met Leu Val Cys Lys Ser Glu Ser Val Pro Pro
            20                  25                  30

Val Thr Asp Trp Ala Trp Tyr Lys Ile Thr Asp Ser Glu Asp Lys Ala
        35                  40                  45

Leu Met Asn Gly Ser Glu Ser Arg Phe Phe Val Ser Ser Ser Gln Gly
    50                  55                  60

Arg Ser Glu Leu His Ile Glu Asn Leu Asn Met Glu Ala Asp Pro Gly
65                  70                  75                  80
```

```
Gln Tyr Arg Cys Asn Gly Thr Ser Ser Lys Gly Ser Asp Gln Ala Ile
                85                  90                  95

Ile Thr Leu Arg Val Arg Ser His Leu Ala Ala Leu Trp Pro Phe Leu
            100                 105                 110

Gly Ile Val Ala Glu Val Leu Val Leu Val Thr Ile Ile Phe Ile Tyr
        115                 120                 125

Glu Lys Arg Arg Lys Pro Glu Asp Val Leu Asp Asp Asp Asp Ala Gly
    130                 135                 140

Ser Ala Pro Leu Lys Ser Ser Gly Gln His Gln Asn Asp Lys Gly Lys
145                 150                 155                 160

Asn Val Arg Gln Arg Asn Ser Ser
            165
```

```
<210> SEQ ID NO 12
<211> LENGTH: 66
<212> TYPE: PRT
<213> ORGANISM: Homo sapiens

<400> SEQUENCE: 12

Ser His Leu Ala Ala Leu Trp Pro Phe Leu Gly Ile Val Ala Glu Val
1               5                   10                  15

Leu Val Leu Val Thr Ile Ile Phe Ile Tyr Glu Lys Arg Arg Lys Pro
            20                  25                  30

Glu Asp Val Leu Asp Asp Asp Asp Ala Gly Ser Ala Pro Leu Lys Ser
        35                  40                  45

Ser Gly Gln His Gln Asn Asp Lys Gly Lys Asn Val Arg Gln Arg Asn
    50                  55                  60

Ser Ser
65
```

```
<210> SEQ ID NO 13
<211> LENGTH: 18
<212> TYPE: PRT
<213> ORGANISM: Homo sapiens

<400> SEQUENCE: 13

Met Ala Ala Ala Leu Phe Val Leu Leu Gly Phe Ala Leu Leu Gly Thr
1               5                   10                  15

His Gly
```

```
<210> SEQ ID NO 14
<211> LENGTH: 613
<212> TYPE: PRT
<213> ORGANISM: Homo sapiens

<400> SEQUENCE: 14

Met Gly Ala Leu Arg Pro Thr Leu Leu Pro Pro Ser Leu Pro Leu Leu
1               5                   10                  15

Leu Leu Leu Met Leu Gly Met Gly Cys Trp Ala Arg Glu Val Leu Val
            20                  25                  30

Pro Glu Gly Pro Leu Tyr Arg Val Ala Gly Thr Ala Val Ser Ile Ser
        35                  40                  45

Cys Asn Val Thr Gly Tyr Glu Gly Pro Ala Gln Gln Asn Phe Glu Trp
    50                  55                  60

Phe Leu Tyr Arg Pro Glu Ala Pro Asp Thr Ala Leu Gly Ile Val Ser
65                  70                  75                  80

Thr Lys Asp Thr Gln Phe Ser Tyr Ala Val Phe Lys Ser Arg Val Val
```

-continued

```
                  85              90              95

Ala Gly Glu Val Gln Val Gln Arg Leu Gln Gly Asp Ala Val Val Leu
            100             105             110

Lys Ile Ala Arg Leu Gln Ala Gln Asp Ala Gly Ile Tyr Glu Cys His
            115             120             125

Thr Pro Ser Thr Asp Thr Arg Tyr Leu Gly Ser Tyr Ser Gly Lys Val
            130             135             140

Glu Leu Arg Val Leu Pro Asp Val Leu Gln Val Ser Ala Ala Pro Pro
145             150             155             160

Gly Pro Arg Gly Arg Gln Ala Pro Thr Ser Pro Pro Arg Met Thr Val
            165             170             175

His Glu Gly Gln Glu Leu Ala Leu Gly Cys Leu Ala Arg Thr Ser Thr
            180             185             190

Gln Lys His Thr His Leu Ala Val Ser Phe Gly Arg Ser Val Pro Glu
            195             200             205

Ala Pro Val Gly Arg Ser Thr Leu Gln Glu Val Val Gly Ile Arg Ser
            210             215             220

Asp Leu Ala Val Glu Ala Gly Ala Pro Tyr Ala Glu Arg Leu Ala Ala
225             230             235             240

Gly Glu Leu Arg Leu Gly Lys Glu Gly Thr Asp Arg Tyr Arg Met Val
            245             250             255

Val Gly Gly Ala Gln Ala Gly Asp Ala Gly Thr Tyr His Cys Thr Ala
            260             265             270

Ala Glu Trp Ile Gln Asp Pro Asp Gly Ser Trp Ala Gln Ile Ala Glu
            275             280             285

Lys Arg Ala Val Leu Ala His Val Asp Val Gln Thr Leu Ser Ser Gln
            290             295             300

Leu Ala Val Thr Val Gly Pro Gly Glu Arg Arg Ile Gly Pro Gly Glu
305             310             315             320

Pro Leu Glu Leu Leu Cys Asn Val Ser Gly Ala Leu Pro Pro Ala Gly
            325             330             335

Arg His Ala Ala Tyr Ser Val Gly Trp Glu Met Ala Pro Ala Gly Ala
            340             345             350

Pro Gly Pro Gly Arg Leu Val Ala Gln Leu Asp Thr Glu Gly Val Gly
            355             360             365

Ser Leu Gly Pro Gly Tyr Glu Gly Arg His Ile Ala Met Glu Lys Val
            370             375             380

Ala Ser Arg Thr Tyr Arg Leu Arg Leu Glu Ala Ala Arg Pro Gly Asp
385             390             395             400

Ala Gly Thr Tyr Arg Cys Leu Ala Lys Ala Tyr Val Arg Gly Ser Gly
            405             410             415

Thr Arg Leu Arg Glu Ala Ala Ser Ala Arg Ser Arg Pro Leu Pro Val
            420             425             430

His Val Arg Glu Glu Gly Val Val Leu Glu Ala Val Ala Trp Leu Ala
            435             440             445

Gly Gly Thr Val Tyr Arg Gly Glu Thr Ala Ser Leu Leu Cys Asn Ile
            450             455             460

Ser Val Arg Gly Gly Pro Pro Gly Leu Arg Leu Ala Ala Ser Trp Trp
465             470             475             480

Val Glu Arg Pro Glu Asp Gly Glu Leu Ser Ser Val Pro Ala Gln Leu
            485             490             495

Val Gly Gly Val Gly Gln Asp Gly Val Ala Glu Leu Gly Val Arg Pro
            500             505             510
```

```
Gly Gly Gly Pro Val Ser Val Glu Leu Val Gly Pro Arg Ser His Arg
        515                 520                 525

Leu Arg Leu His Ser Leu Gly Pro Glu Asp Glu Gly Val Tyr His Cys
        530                 535                 540

Ala Pro Ser Ala Trp Val Gln His Ala Asp Tyr Ser Trp Tyr Gln Ala
545                 550                 555                 560

Gly Ser Ala Arg Ser Gly Pro Val Thr Val Tyr Pro Tyr Met His Ala
                565                 570                 575

Leu Asp Thr Leu Phe Val Pro Leu Leu Val Gly Thr Gly Val Ala Leu
                580                 585                 590

Val Thr Gly Ala Thr Val Leu Gly Thr Ile Thr Cys Cys Phe Met Lys
        595                 600                 605

Arg Leu Arg Lys Arg
        610

<210> SEQ ID NO 15
<211> LENGTH: 456
<212> TYPE: PRT
<213> ORGANISM: Homo sapiens

<400> SEQUENCE: 15

Ala Pro Pro Gly Pro Arg Gly Arg Gln Ala Pro Thr Ser Pro Pro Arg
1               5                   10                  15

Met Thr Val His Glu Gly Gln Glu Leu Ala Leu Gly Cys Leu Ala Arg
                20                  25                  30

Thr Ser Thr Gln Lys His Thr His Leu Ala Val Ser Phe Gly Arg Ser
            35                  40                  45

Val Pro Glu Ala Pro Val Gly Arg Ser Thr Leu Gln Glu Val Val Gly
        50                  55                  60

Ile Arg Ser Asp Leu Ala Val Glu Ala Gly Ala Pro Tyr Ala Glu Arg
65                  70                  75                  80

Leu Ala Ala Gly Glu Leu Arg Leu Gly Lys Glu Gly Thr Asp Arg Tyr
                85                  90                  95

Arg Met Val Val Gly Gly Ala Gln Ala Gly Asp Ala Gly Thr Tyr His
                100                 105                 110

Cys Thr Ala Ala Glu Trp Ile Gln Asp Pro Asp Gly Ser Trp Ala Gln
        115                 120                 125

Ile Ala Glu Lys Arg Ala Val Leu Ala His Val Asp Val Gln Thr Leu
        130                 135                 140

Ser Ser Gln Leu Ala Val Thr Val Gly Pro Gly Glu Arg Arg Ile Gly
145                 150                 155                 160

Pro Gly Glu Pro Leu Glu Leu Leu Cys Asn Val Ser Gly Ala Leu Pro
                165                 170                 175

Pro Ala Gly Arg His Ala Ala Tyr Ser Val Gly Trp Glu Met Ala Pro
                180                 185                 190

Ala Gly Ala Pro Gly Pro Gly Arg Leu Val Ala Gln Leu Asp Thr Glu
        195                 200                 205

Gly Val Gly Ser Leu Gly Pro Gly Tyr Glu Gly Arg His Ile Ala Met
        210                 215                 220

Glu Lys Val Ala Ser Arg Thr Tyr Arg Leu Arg Leu Glu Ala Ala Arg
225                 230                 235                 240

Pro Gly Asp Ala Gly Thr Tyr Arg Cys Leu Ala Lys Ala Tyr Val Arg
                245                 250                 255

Gly Ser Gly Thr Arg Leu Arg Glu Ala Ala Ser Ala Arg Ser Arg Pro
```

-continued

```
            260              265              270
Leu Pro Val His Val Arg Glu Glu Gly Val Val Leu Glu Ala Val Ala
        275              280              285

Trp Leu Ala Gly Gly Thr Val Tyr Arg Gly Glu Thr Ala Ser Leu Leu
    290              295              300

Cys Asn Ile Ser Val Arg Gly Gly Pro Pro Gly Leu Arg Leu Ala Ala
305              310              315              320

Ser Trp Trp Val Glu Arg Pro Glu Asp Gly Glu Leu Ser Ser Val Pro
            325              330              335

Ala Gln Leu Val Gly Gly Val Gly Gln Asp Gly Val Ala Glu Leu Gly
        340              345              350

Val Arg Pro Gly Gly Gly Pro Val Ser Val Glu Leu Val Gly Pro Arg
        355              360              365

Ser His Arg Leu Arg Leu His Ser Leu Gly Pro Glu Asp Glu Gly Val
    370              375              380

Tyr His Cys Ala Pro Ser Ala Trp Val Gln His Ala Asp Tyr Ser Trp
385              390              395              400

Tyr Gln Ala Gly Ser Ala Arg Ser Gly Pro Val Thr Val Tyr Pro Tyr
            405              410              415

Met His Ala Leu Asp Thr Leu Phe Val Pro Leu Leu Val Gly Thr Gly
            420              425              430

Val Ala Leu Val Thr Gly Ala Thr Val Leu Gly Thr Ile Thr Cys Cys
        435              440              445

Phe Met Lys Arg Leu Arg Lys Arg
    450              455

<210> SEQ ID NO 16
<211> LENGTH: 320
<212> TYPE: PRT
<213> ORGANISM: Homo sapiens

<400> SEQUENCE: 16

Ala His Val Asp Val Gln Thr Leu Ser Ser Gln Leu Ala Val Thr Val
1               5               10               15

Gly Pro Gly Glu Arg Arg Ile Gly Pro Gly Glu Pro Leu Glu Leu Leu
            20               25               30

Cys Asn Val Ser Gly Ala Leu Pro Pro Ala Gly Arg His Ala Ala Tyr
            35               40               45

Ser Val Gly Trp Glu Met Ala Pro Ala Gly Ala Pro Gly Pro Gly Arg
    50               55               60

Leu Val Ala Gln Leu Asp Thr Glu Gly Val Gly Ser Leu Gly Pro Gly
65               70               75               80

Tyr Glu Gly Arg His Ile Ala Met Glu Lys Val Ala Ser Arg Thr Tyr
            85               90               95

Arg Leu Arg Leu Glu Ala Ala Arg Pro Gly Asp Ala Gly Thr Tyr Arg
            100              105              110

Cys Leu Ala Lys Ala Tyr Val Arg Gly Ser Gly Thr Arg Leu Arg Glu
            115              120              125

Ala Ala Ser Ala Arg Ser Arg Pro Leu Pro Val His Val Arg Glu Glu
    130              135              140

Gly Val Val Leu Glu Ala Val Ala Trp Leu Ala Gly Gly Thr Val Tyr
145              150              155              160

Arg Gly Glu Thr Ala Ser Leu Leu Cys Asn Ile Ser Val Arg Gly Gly
            165              170              175
```

```
Pro Pro Gly Leu Arg Leu Ala Ala Ser Trp Trp Val Glu Arg Pro Glu
            180                 185                 190

Asp Gly Glu Leu Ser Ser Val Pro Ala Gln Leu Val Gly Gly Val Gly
            195                 200                 205

Gln Asp Gly Val Ala Glu Leu Gly Val Arg Pro Gly Gly Gly Pro Val
    210                 215                 220

Ser Val Glu Leu Val Gly Pro Arg Ser His Arg Leu Arg Leu His Ser
225                 230                 235                 240

Leu Gly Pro Glu Asp Glu Gly Val Tyr His Cys Ala Pro Ser Ala Trp
                245                 250                 255

Val Gln His Ala Asp Tyr Ser Trp Tyr Gln Ala Gly Ser Ala Arg Ser
            260                 265                 270

Gly Pro Val Thr Val Tyr Pro Tyr Met His Ala Leu Asp Thr Leu Phe
            275                 280                 285

Val Pro Leu Leu Val Gly Thr Gly Val Ala Leu Val Thr Gly Ala Thr
    290                 295                 300

Val Leu Gly Thr Ile Thr Cys Cys Phe Met Lys Arg Leu Arg Lys Arg
305                 310                 315                 320

<210> SEQ ID NO 17
<211> LENGTH: 179
<212> TYPE: PRT
<213> ORGANISM: Homo sapiens

<400> SEQUENCE: 17

Arg Glu Glu Gly Val Val Leu Glu Ala Val Ala Trp Leu Ala Gly Gly
1               5                   10                  15

Thr Val Tyr Arg Gly Glu Thr Ala Ser Leu Leu Cys Asn Ile Ser Val
            20                  25                  30

Arg Gly Gly Pro Pro Gly Leu Arg Leu Ala Ala Ser Trp Trp Val Glu
            35                  40                  45

Arg Pro Glu Asp Gly Glu Leu Ser Ser Val Pro Ala Gln Leu Val Gly
    50                  55                  60

Gly Val Gly Gln Asp Gly Val Ala Glu Leu Gly Val Arg Pro Gly Gly
65                  70                  75                  80

Gly Pro Val Ser Val Glu Leu Val Gly Pro Arg Ser His Arg Leu Arg
                85                  90                  95

Leu His Ser Leu Gly Pro Glu Asp Glu Gly Val Tyr His Cys Ala Pro
            100                 105                 110

Ser Ala Trp Val Gln His Ala Asp Tyr Ser Trp Tyr Gln Ala Gly Ser
            115                 120                 125

Ala Arg Ser Gly Pro Val Thr Val Tyr Pro Tyr Met His Ala Leu Asp
    130                 135                 140

Thr Leu Phe Val Pro Leu Leu Val Gly Thr Gly Val Ala Leu Val Thr
145                 150                 155                 160

Gly Ala Thr Val Leu Gly Thr Ile Thr Cys Cys Phe Met Lys Arg Leu
                165                 170                 175

Arg Lys Arg

<210> SEQ ID NO 18
<211> LENGTH: 24
<212> TYPE: PRT
<213> ORGANISM: Homo sapiens

<400> SEQUENCE: 18

Val Ala Leu Val Thr Gly Ala Thr Val Leu Gly Thr Ile Thr Cys Cys
```

```
1               5                   10                  15

Phe Met Lys Arg Leu Arg Lys Arg
            20

<210> SEQ ID NO 19
<211> LENGTH: 27
<212> TYPE: PRT
<213> ORGANISM: Homo sapiens

<400> SEQUENCE: 19

Met Gly Ala Leu Arg Pro Thr Leu Leu Pro Pro Ser Leu Pro Leu Leu
1               5                   10                  15

Leu Leu Leu Met Leu Gly Met Gly Cys Trp Ala
            20                  25

<210> SEQ ID NO 20
<211> LENGTH: 1195
<212> TYPE: PRT
<213> ORGANISM: Homo sapiens

<400> SEQUENCE: 20

Met Lys Cys Phe Phe Pro Val Leu Ser Cys Leu Ala Val Leu Gly Val
1               5                   10                  15

Val Ser Ala Gln Arg Gln Val Thr Val Gln Glu Gly Pro Leu Tyr Arg
            20                  25                  30

Thr Glu Gly Ser His Ile Thr Ile Trp Cys Asn Val Ser Gly Tyr Gln
            35                  40                  45

Gly Pro Ser Glu Gln Asn Phe Gln Trp Ser Ile Tyr Leu Pro Ser Ser
        50                  55                  60

Pro Glu Arg Glu Val Gln Ile Val Ser Thr Met Asp Ser Ser Phe Pro
65                  70                  75                  80

Tyr Ala Ile Tyr Thr Gln Arg Val Arg Gly Gly Lys Ile Phe Ile Glu
                85                  90                  95

Arg Val Gln Gly Asn Ser Thr Leu Leu His Ile Thr Asp Leu Gln Ala
            100                 105                 110

Arg Asp Ala Gly Glu Tyr Glu Cys His Thr Pro Ser Thr Asp Lys Gln
            115                 120                 125

Tyr Phe Gly Ser Tyr Ser Ala Lys Met Asn Leu Val Val Ile Pro Asp
        130                 135                 140

Ser Leu Gln Thr Thr Ala Met Pro Gln Thr Leu His Arg Val Glu Gln
145                 150                 155                 160

Asp Pro Leu Glu Leu Thr Cys Glu Val Ala Ser Glu Thr Ile Gln His
                165                 170                 175

Ser His Leu Ser Val Ala Trp Leu Arg Gln Lys Val Gly Glu Lys Pro
            180                 185                 190

Val Glu Val Ile Ser Leu Ser Arg Asp Phe Met Leu His Ser Ser Ser
            195                 200                 205

Glu Tyr Ala Gln Arg Gln Ser Leu Gly Glu Val Arg Leu Asp Lys Leu
        210                 215                 220

Gly Arg Thr Thr Phe Arg Leu Thr Ile Phe His Leu Gln Pro Ser Asp
225                 230                 235                 240

Gln Gly Glu Phe Tyr Cys Glu Ala Ala Glu Trp Ile Gln Asp Pro Asp
                245                 250                 255

Gly Ser Trp Tyr Ala Met Thr Arg Lys Arg Ser Glu Gly Ala Val Val
                260                 265                 270

Asn Val Gln Pro Thr Asp Lys Glu Phe Thr Val Arg Leu Glu Thr Glu
```

```
                275                 280                 285

Lys Arg Leu His Thr Val Gly Glu Pro Val Glu Phe Arg Cys Ile Leu
    290                 295                 300

Glu Ala Gln Asn Val Pro Asp Arg Tyr Phe Ala Val Ser Trp Ala Phe
305                 310                 315                 320

Asn Ser Ser Leu Ile Ala Thr Met Gly Pro Asn Ala Val Pro Val Leu
                325                 330                 335

Asn Ser Glu Phe Ala His Arg Glu Ala Arg Gly Gln Leu Lys Val Ala
                340                 345                 350

Lys Glu Ser Asp Ser Val Phe Val Leu Lys Ile Tyr His Leu Arg Gln
                355                 360                 365

Glu Asp Ser Gly Lys Tyr Asn Cys Arg Val Thr Glu Arg Glu Lys Thr
                370                 375                 380

Val Thr Gly Glu Phe Ile Asp Lys Glu Ser Lys Arg Pro Lys Asn Ile
385                 390                 395                 400

Pro Ile Ile Val Leu Pro Leu Lys Ser Ser Ile Ser Val Glu Val Ala
                405                 410                 415

Ser Asn Ala Ser Val Ile Leu Glu Gly Glu Asp Leu Arg Phe Ser Cys
                420                 425                 430

Ser Val Arg Thr Ala Gly Arg Pro Gln Gly Arg Phe Ser Val Ile Trp
                435                 440                 445

Gln Leu Val Asp Arg Gln Asn Arg Arg Ser Asn Ile Met Trp Leu Asp
                450                 455                 460

Arg Asp Gly Thr Val Gln Pro Gly Ser Ser Tyr Trp Glu Arg Ser Ser
465                 470                 475                 480

Phe Gly Gly Val Gln Met Glu Gln Val Gln Pro Asn Ser Phe Ser Leu
                485                 490                 495

Gly Ile Phe Asn Ser Arg Lys Glu Asp Glu Gly Gln Tyr Glu Cys His
                500                 505                 510

Val Thr Glu Trp Val Arg Ala Val Asp Gly Glu Trp Gln Ile Val Gly
                515                 520                 525

Glu Arg Arg Ala Ser Thr Pro Ile Ser Ile Thr Ala Leu Glu Met Gly
                530                 535                 540

Phe Ala Val Thr Ala Ile Ser Arg Thr Pro Gly Val Thr Tyr Ser Asp
545                 550                 555                 560

Ser Phe Asp Leu Gln Cys Ile Ile Lys Pro His Tyr Pro Ala Trp Val
                565                 570                 575

Pro Val Ser Val Thr Trp Arg Phe Gln Pro Val Gly Thr Val Glu Phe
                580                 585                 590

His Asp Leu Val Thr Phe Thr Arg Asp Gly Gly Val Gln Trp Gly Asp
                595                 600                 605

Arg Ser Ser Ser Phe Arg Thr Arg Thr Ala Ile Glu Lys Ala Glu Ser
                610                 615                 620

Ser Asn Asn Val Arg Leu Ser Ile Ser Arg Ala Ser Asp Thr Glu Ala
625                 630                 635                 640

Gly Lys Tyr Gln Cys Val Ala Glu Leu Trp Arg Lys Asn Tyr Asn Asn
                645                 650                 655

Thr Trp Thr Arg Leu Ala Glu Arg Thr Ser Asn Leu Leu Glu Ile Arg
                660                 665                 670

Val Leu Gln Pro Val Thr Lys Leu Gln Val Ser Lys Ser Lys Arg Thr
                675                 680                 685

Leu Thr Leu Val Glu Asn Lys Pro Ile Gln Leu Asn Cys Ser Val Lys
                690                 695                 700
```

Ser Gln Thr Ser Gln Asn Ser His Phe Ala Val Leu Trp Tyr Val His
705             710                 715                 720

Lys Pro Ser Asp Ala Asp Gly Lys Leu Ile Leu Lys Thr Thr His Asn
                725                 730                 735

Ser Ala Phe Glu Tyr Gly Thr Tyr Ala Glu Glu Glu Gly Leu Arg Ala
            740                 745                 750

Arg Leu Gln Phe Glu Arg His Val Ser Gly Gly Leu Phe Ser Leu Thr
            755                 760                 765

Val Gln Arg Ala Glu Val Ser Asp Ser Gly Ser Tyr Tyr Cys His Val
        770                 775                 780

Glu Glu Trp Leu Leu Ser Pro Asn Tyr Ala Trp Tyr Lys Leu Ala Glu
785                 790                 795                 800

Glu Val Ser Gly Arg Thr Glu Val Thr Val Lys Gln Pro Asp Ser Arg
                805                 810                 815

Leu Arg Leu Ser Gln Ala Gln Gly Asn Leu Ser Val Leu Glu Thr Arg
            820                 825                 830

Gln Val Gln Leu Glu Cys Val Val Leu Asn Arg Thr Ser Ile Thr Ser
        835                 840                 845

Gln Leu Met Val Glu Trp Phe Val Trp Lys Pro Asn His Pro Glu Arg
    850                 855                 860

Glu Thr Val Ala Arg Leu Ser Arg Asp Ala Thr Phe His Tyr Gly Glu
865                 870                 875                 880

Gln Ala Ala Lys Asn Asn Leu Lys Gly Arg Leu His Leu Glu Ser Pro
                885                 890                 895

Ser Pro Gly Val Tyr Arg Leu Phe Ile Gln Asn Val Ala Val Gln Asp
            900                 905                 910

Ser Gly Thr Tyr Ser Cys His Val Glu Glu Trp Leu Pro Ser Pro Ser
            915                 920                 925

Gly Met Trp Tyr Lys Arg Ala Glu Asp Thr Ala Gly Gln Thr Ala Leu
    930                 935                 940

Thr Val Met Arg Pro Asp Ala Ser Leu Gln Val Asp Thr Val Val Pro
945                 950                 955                 960

Asn Ala Thr Val Ser Glu Lys Ala Ala Phe Gln Leu Asp Cys Ser Ile
                965                 970                 975

Val Ser Arg Ser Ser Gln Asp Ser Arg Phe Ala Val Ala Trp Tyr Ser
            980                 985                 990

Leu Arg Thr Lys Ala Gly Gly Lys  Arg Ser Ser Pro Gly  Leu Glu Glu
        995                 1000                1005

Gln Glu  Glu Glu Arg Glu Glu  Glu Glu Glu Glu Glu  Glu Asp Asp
    1010                1015                1020

Asp Asp  Asp Asp Pro Thr Glu  Arg Thr Ala Leu Leu  Ser Val Gly
    1025                1030                1035

Pro Asp  Ala Val Phe Gly Pro  Glu Gly Ser Pro Trp  Glu Gly Arg
    1040                1045                1050

Leu Arg  Phe Gln Arg Leu Ser  Pro Val Leu Tyr Arg  Leu Thr Val
    1055                1060                1065

Leu Gln  Ala Ser Pro Gln Asp  Thr Gly Asn Tyr Ser  Cys His Val
    1070                1075                1080

Glu Glu  Trp Leu Pro Ser Pro  Gln Lys Glu Trp Tyr  Arg Leu Thr
    1085                1090                1095

Glu Glu  Glu Ser Ala Pro Ile  Gly Ile Arg Val Leu  Asp Thr Ser
    1100                1105                1110

```
Pro Thr Leu Gln Ser Ile Ile Cys Ser Asn Asp Ala Leu Phe Tyr
    1115                1120                1125

Phe Val Phe Phe Tyr Pro Phe Pro Ile Phe Gly Ile Leu Ile Ile
    1130                1135                1140

Thr Ile Leu Leu Val Arg Phe Lys Ser Arg Asn Ser Ser Lys Asn
    1145                1150                1155

Ser Asp Gly Lys Asn Gly Val Pro Leu Leu Trp Ile Lys Glu Pro
    1160                1165                1170

His Leu Asn Tyr Ser Pro Thr Cys Leu Glu Pro Pro Val Leu Ser
    1175                1180                1185

Ile His Pro Gly Ala Ile Asp
    1190                1195

<210> SEQ ID NO 21
<211> LENGTH: 798
<212> TYPE: PRT
<213> ORGANISM: Homo sapiens

<400> SEQUENCE: 21

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
        50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
            195                 200                 205

Ser Glu Gln Asn Cys Thr Ser Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
            275                 280                 285
```

-continued

```
Lys Leu Gly Gly Ile Val Leu Pro Asn Asp Gly Gln Cys His Leu Glu
    290             295             300

Asn Asn Met Tyr Thr Met Ser His Tyr Tyr Asp Tyr Pro Ser Ile Ala
305             310             315             320

His Leu Val Gln Lys Leu Ser Glu Asn Asn Ile Gln Thr Ile Phe Ala
            325             330             335

Val Thr Glu Glu Phe Gln Pro Val Tyr Lys Glu Leu Lys Asn Leu Ile
        340             345             350

Pro Lys Ser Ala Val Gly Thr Leu Ser Ala Asn Ser Ser Asn Val Ile
        355             360             365

Gln Leu Ile Ile Asp Ala Tyr Asn Ser Leu Ser Ser Glu Val Ile Leu
    370             375             380

Glu Asn Gly Lys Leu Ser Glu Gly Val Thr Ile Ser Tyr Lys Ser Tyr
385             390             395             400

Cys Lys Asn Gly Val Asn Gly Thr Gly Glu Asn Gly Arg Lys Cys Ser
            405             410             415

Asn Ile Ser Ile Gly Asp Glu Val Gln Phe Glu Ile Ser Ile Thr Ser
            420             425             430

Asn Lys Cys Pro Lys Lys Asp Ser Asp Ser Phe Lys Ile Arg Pro Leu
            435             440             445

Gly Phe Thr Glu Glu Val Glu Val Ile Leu Gln Tyr Ile Cys Glu Cys
    450             455             460

Glu Cys Gln Ser Glu Gly Ile Pro Glu Ser Pro Lys Cys His Glu Gly
465             470             475             480

Asn Gly Thr Phe Glu Cys Gly Ala Cys Arg Cys Asn Glu Gly Arg Val
            485             490             495

Gly Arg His Cys Glu Cys Ser Thr Asp Glu Val Asn Ser Glu Asp Met
            500             505             510

Asp Ala Tyr Cys Arg Lys Glu Asn Ser Ser Glu Ile Cys Ser Asn Asn
            515             520             525

Gly Glu Cys Val Cys Gly Gln Cys Val Cys Arg Lys Arg Asp Asn Thr
    530             535             540

Asn Glu Ile Tyr Ser Gly Lys Phe Cys Glu Cys Asp Asn Phe Asn Cys
545             550             555             560

Asp Arg Ser Asn Gly Leu Ile Cys Gly Gly Asn Gly Val Cys Lys Cys
            565             570             575

Arg Val Cys Glu Cys Asn Pro Asn Tyr Thr Gly Ser Ala Cys Asp Cys
            580             585             590

Ser Leu Asp Thr Ser Thr Cys Glu Ala Ser Asn Gly Gln Ile Cys Asn
            595             600             605

Gly Arg Gly Ile Cys Glu Cys Gly Val Cys Lys Cys Thr Asp Pro Lys
    610             615             620

Phe Gln Gly Gln Thr Cys Glu Met Cys Gln Thr Cys Leu Gly Val Cys
625             630             635             640

Ala Glu His Lys Glu Cys Val Gln Cys Arg Ala Phe Asn Lys Gly Glu
            645             650             655

Lys Lys Asp Thr Cys Thr Gln Glu Cys Ser Tyr Phe Asn Ile Thr Lys
            660             665             670

Val Glu Ser Arg Asp Lys Leu Pro Gln Pro Val Gln Pro Asp Pro Val
            675             680             685

Ser His Cys Lys Glu Lys Asp Val Asp Asp Cys Trp Phe Tyr Phe Thr
    690             695             700
```

-continued

```
Tyr Ser Val Asn Gly Asn Asn Glu Val Met Val His Val Val Glu Asn
705             710             715             720

Pro Glu Cys Pro Thr Gly Pro Asp Ile Ile Pro Ile Val Ala Gly Val
            725             730             735

Val Ala Gly Ile Val Leu Ile Gly Leu Ala Leu Leu Leu Ile Trp Lys
        740             745             750

Leu Leu Met Ile Ile His Asp Arg Arg Glu Phe Ala Lys Phe Glu Lys
        755             760             765

Glu Lys Met Asn Ala Lys Trp Asp Thr Gly Glu Asn Pro Ile Tyr Lys
770             775             780

Ser Ala Val Thr Thr Val Val Asn Pro Lys Tyr Glu Gly Lys
785             790             795

<210> SEQ ID NO 22
<211> LENGTH: 1032
<212> TYPE: PRT
<213> ORGANISM: Homo sapiens

<400> SEQUENCE: 22

Met Ala Trp Glu Ala Arg Arg Glu Pro Gly Pro Arg Arg Ala Ala Val
1               5               10              15

Arg Glu Thr Val Met Leu Leu Leu Cys Leu Gly Val Pro Thr Gly Arg
                20              25              30

Pro Tyr Asn Val Asp Thr Glu Ser Ala Leu Leu Tyr Gln Gly Pro His
            35              40              45

Asn Thr Leu Phe Gly Tyr Ser Val Val Leu His Ser His Gly Ala Asn
        50              55              60

Arg Trp Leu Leu Val Gly Ala Pro Thr Ala Asn Trp Leu Ala Asn Ala
65              70              75              80

Ser Val Ile Asn Pro Gly Ala Ile Tyr Arg Cys Arg Ile Gly Lys Asn
                85              90              95

Pro Gly Gln Thr Cys Glu Gln Leu Gln Leu Gly Ser Pro Asn Gly Glu
            100             105             110

Pro Cys Gly Lys Thr Cys Leu Glu Glu Arg Asp Asn Gln Trp Leu Gly
        115             120             125

Val Thr Leu Ser Arg Gln Pro Gly Glu Asn Gly Ser Ile Val Thr Cys
        130             135             140

Gly His Arg Trp Lys Asn Ile Phe Tyr Ile Lys Asn Glu Asn Lys Leu
145             150             155             160

Pro Thr Gly Gly Cys Tyr Gly Val Pro Pro Asp Leu Arg Thr Glu Leu
            165             170             175

Ser Lys Arg Ile Ala Pro Cys Tyr Gln Asp Tyr Val Lys Lys Phe Gly
            180             185             190

Glu Asn Phe Ala Ser Cys Gln Ala Gly Ile Ser Ser Phe Tyr Thr Lys
            195             200             205

Asp Leu Ile Val Met Gly Ala Pro Gly Ser Ser Tyr Trp Thr Gly Ser
        210             215             220

Leu Phe Val Tyr Asn Ile Thr Thr Asn Lys Tyr Lys Ala Phe Leu Asp
225             230             235             240

Lys Gln Asn Gln Val Lys Phe Gly Ser Tyr Leu Gly Tyr Ser Val Gly
                245             250             255

Ala Gly His Phe Arg Ser Gln His Thr Thr Glu Val Val Gly Gly Ala
            260             265             270

Pro Gln His Glu Gln Ile Gly Lys Ala Tyr Ile Phe Ser Ile Asp Glu
        275             280             285
```

```
Lys Glu Leu Asn Ile Leu His Glu Met Lys Gly Lys Lys Leu Gly Ser
    290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
                325                 330                 335

Gly Arg Val Phe Val Tyr Ile Asn Ser Gly Ser Gly Ala Val Met Asn
                340                 345                 350

Ala Met Glu Thr Asn Leu Val Gly Ser Asp Lys Tyr Ala Ala Arg Phe
                355                 360                 365

Gly Glu Ser Ile Val Asn Leu Gly Asp Ile Asp Asn Asp Gly Phe Glu
    370                 375                 380

Asp Val Ala Ile Gly Ala Pro Gln Glu Asp Asp Leu Gln Gly Ala Ile
385                 390                 395                 400

Tyr Ile Tyr Asn Gly Arg Ala Asp Gly Ile Ser Ser Thr Phe Ser Gln
                405                 410                 415

Arg Ile Glu Gly Leu Gln Ile Ser Lys Ser Leu Ser Met Phe Gly Gln
                420                 425                 430

Ser Ile Ser Gly Gln Ile Asp Ala Asp Asn Asn Gly Tyr Val Asp Val
                435                 440                 445

Ala Val Gly Ala Phe Arg Ser Asp Ser Ala Val Leu Leu Arg Thr Arg
    450                 455                 460

Pro Val Val Ile Val Asp Ala Ser Leu Ser His Pro Glu Ser Val Asn
465                 470                 475                 480

Arg Thr Lys Phe Asp Cys Val Glu Asn Gly Trp Pro Ser Val Cys Ile
                485                 490                 495

Asp Leu Thr Leu Cys Phe Ser Tyr Lys Gly Lys Glu Val Pro Gly Tyr
                500                 505                 510

Ile Val Leu Phe Tyr Asn Met Ser Leu Asp Val Asn Arg Lys Ala Glu
                515                 520                 525

Ser Pro Pro Arg Phe Tyr Phe Ser Ser Asn Gly Thr Ser Asp Val Ile
    530                 535                 540

Thr Gly Ser Ile Gln Val Ser Ser Arg Glu Ala Asn Cys Arg Thr His
545                 550                 555                 560

Gln Ala Phe Met Arg Lys Asp Val Arg Asp Ile Leu Thr Pro Ile Gln
                565                 570                 575

Ile Glu Ala Ala Tyr His Leu Gly Pro His Val Ile Ser Lys Arg Ser
                580                 585                 590

Thr Glu Glu Phe Pro Pro Leu Gln Pro Ile Leu Gln Gln Lys Lys Glu
    595                 600                 605

Lys Asp Ile Met Lys Lys Thr Ile Asn Phe Ala Arg Phe Cys Ala His
    610                 615                 620

Glu Asn Cys Ser Ala Asp Leu Gln Val Ser Ala Lys Ile Gly Phe Leu
625                 630                 635                 640

Lys Pro His Glu Asn Lys Thr Tyr Leu Ala Val Gly Ser Met Lys Thr
                645                 650                 655

Leu Met Leu Asn Val Ser Leu Phe Asn Ala Gly Asp Asp Ala Tyr Glu
                660                 665                 670

Thr Thr Leu His Val Lys Leu Pro Val Gly Leu Tyr Phe Ile Lys Ile
                675                 680                 685

Leu Glu Leu Glu Glu Lys Gln Ile Asn Cys Glu Val Thr Asp Asn Ser
    690                 695                 700
```

```
Gly Val Val Gln Leu Asp Cys Ser Ile Gly Tyr Ile Tyr Val Asp His
705                 710                 715                 720

Leu Ser Arg Ile Asp Ile Ser Phe Leu Leu Asp Val Ser Ser Leu Ser
                725                 730                 735

Arg Ala Glu Glu Asp Leu Ser Ile Thr Val His Ala Thr Cys Glu Asn
                740                 745                 750

Glu Glu Glu Met Asp Asn Leu Lys His Ser Arg Val Thr Val Ala Ile
                755                 760                 765

Pro Leu Lys Tyr Glu Val Lys Leu Thr Val His Gly Phe Val Asn Pro
770                 775                 780

Thr Ser Phe Val Tyr Gly Ser Asn Asp Glu Asn Glu Pro Glu Thr Cys
785                 790                 795                 800

Met Val Glu Lys Met Asn Leu Thr Phe His Val Ile Asn Thr Gly Asn
                805                 810                 815

Ser Met Ala Pro Asn Val Ser Val Glu Ile Met Val Pro Asn Ser Phe
                820                 825                 830

Ser Pro Gln Thr Asp Lys Leu Phe Asn Ile Leu Asp Val Gln Thr Thr
                835                 840                 845

Thr Gly Glu Cys His Phe Glu Asn Tyr Gln Arg Val Cys Ala Leu Glu
                850                 855                 860

Gln Gln Lys Ser Ala Met Gln Thr Leu Lys Gly Ile Val Arg Phe Leu
865                 870                 875                 880

Ser Lys Thr Asp Lys Arg Leu Leu Tyr Cys Ile Lys Ala Asp Pro His
                885                 890                 895

Cys Leu Asn Phe Leu Cys Asn Phe Gly Lys Met Glu Ser Gly Lys Glu
                900                 905                 910

Ala Ser Val His Ile Gln Leu Glu Gly Arg Pro Ser Ile Leu Glu Met
                915                 920                 925

Asp Glu Thr Ser Ala Leu Lys Phe Glu Ile Arg Ala Thr Gly Phe Pro
                930                 935                 940

Glu Pro Asn Pro Arg Val Ile Glu Leu Asn Lys Asp Glu Asn Val Ala
945                 950                 955                 960

His Val Leu Leu Glu Gly Leu His His Gln Arg Pro Lys Arg Tyr Phe
                965                 970                 975

Thr Ile Val Ile Ile Ser Ser Ser Leu Leu Leu Gly Leu Ile Val Leu
                980                 985                 990

Leu Leu Ile Ser Tyr Val Met Trp Lys Ala Gly Phe Phe Lys Arg Gln
                995                 1000                1005

Tyr Lys Ser Ile Leu Gln Glu Glu Asn Arg Arg Asp Ser Trp Ser
    1010                1015                1020

Tyr Ile Asn Ser Lys Ser Asn Asp Asp
    1025                1030
```

```
<210> SEQ ID NO 23
<211> LENGTH: 661
<212> TYPE: PRT
<213> ORGANISM: Homo sapiens

<400> SEQUENCE: 23
```

```
Met Glu Leu Gln Pro Pro Glu Ala Ser Ile Ala Val Val Ser Ile Pro
1                 5                 10                 15

Arg Gln Leu Pro Gly Ser His Ser Glu Ala Gly Val Gln Gly Leu Ser
                20                25                30

Ala Gly Asp Asp Ser Glu Leu Gly Ser His Cys Val Ala Gln Thr Gly
                35                40                45
```

```
Leu Glu Leu Leu Ala Ser Gly Asp Pro Leu Pro Ser Ala Ser Gln Asn
    50              55              60

Ala Glu Met Ile Glu Thr Gly Ser Asp Cys Val Thr Gln Ala Gly Leu
65              70              75              80

Gln Leu Leu Ala Ser Ser Asp Pro Pro Ala Leu Ala Ser Lys Asn Ala
            85              90              95

Glu Val Thr Glu Thr Gly Phe His His Val Ser Gln Ala Asp Ile Glu
            100             105             110

Phe Leu Thr Ser Ile Asp Pro Thr Ala Ser Ala Ser Gly Ser Ala Gly
        115             120             125

Ile Thr Gly Thr Met Ser Gln Asp Thr Glu Val Asp Met Lys Glu Val
    130             135             140

Glu Leu Asn Glu Leu Glu Pro Glu Lys Gln Pro Met Asn Ala Ala Ser
145             150             155             160

Gly Ala Ala Met Ser Leu Ala Gly Ala Glu Lys Asn Gly Leu Val Lys
            165             170             175

Ile Lys Val Ala Glu Asp Glu Ala Glu Ala Ala Ala Ala Lys Phe
        180             185             190

Thr Gly Leu Ser Lys Glu Glu Leu Leu Lys Val Ala Gly Ser Pro Gly
        195             200             205

Trp Val Arg Thr Arg Trp Ala Leu Leu Leu Leu Phe Trp Leu Gly Trp
    210             215             220

Leu Gly Met Leu Ala Gly Ala Val Val Ile Ile Val Arg Ala Pro Arg
225             230             235             240

Cys Arg Glu Leu Pro Ala Gln Lys Trp Trp His Thr Gly Ala Leu Tyr
            245             250             255

Arg Ile Gly Asp Leu Gln Ala Phe Gln Gly His Gly Ala Gly Asn Leu
            260             265             270

Ala Gly Leu Lys Gly Arg Leu Asp Tyr Leu Ser Ser Leu Lys Val Lys
        275             280             285

Gly Leu Val Leu Gly Pro Ile His Lys Asn Gln Lys Asp Asp Val Ala
    290             295             300

Gln Thr Asp Leu Leu Gln Ile Asp Pro Asn Phe Gly Ser Lys Glu Asp
305             310             315             320

Phe Asp Ser Leu Leu Gln Ser Ala Lys Lys Lys Ser Ile Arg Val Ile
            325             330             335

Leu Asp Leu Thr Pro Asn Tyr Arg Gly Glu Asn Ser Trp Phe Ser Thr
            340             345             350

Gln Val Asp Thr Val Ala Thr Lys Val Lys Asp Ala Leu Glu Phe Trp
        355             360             365

Leu Gln Ala Gly Val Asp Gly Phe Gln Val Arg Asp Ile Glu Asn Leu
    370             375             380

Lys Asp Ala Ser Ser Phe Leu Ala Glu Trp Gln Asn Ile Thr Lys Gly
385             390             395             400

Phe Ser Glu Asp Arg Leu Leu Ile Ala Gly Thr Asn Ser Ser Asp Leu
            405             410             415

Gln Gln Ile Leu Ser Leu Leu Glu Ser Asn Lys Asp Leu Leu Leu Thr
            420             425             430

Ser Ser Tyr Leu Ser Asp Ser Gly Ser Thr Gly Glu His Thr Lys Ser
        435             440             445

Leu Val Thr Gln Tyr Leu Asn Ala Thr Gly Asn Arg Trp Cys Ser Trp
    450             455             460
```

-continued

```
Ser Leu Ser Gln Ala Arg Leu Leu Thr Ser Phe Leu Pro Ala Gln Leu
465                 470                 475                 480

Leu Arg Leu Tyr Gln Leu Met Leu Phe Thr Leu Pro Gly Thr Pro Val
                485                 490                 495

Phe Ser Tyr Gly Asp Glu Ile Gly Leu Asp Ala Ala Ala Leu Pro Gly
            500                 505                 510

Gln Pro Met Glu Ala Pro Val Met Leu Trp Asp Glu Ser Ser Phe Pro
        515                 520                 525

Asp Ile Pro Gly Ala Val Ser Ala Asn Met Thr Val Lys Gly Gln Ser
        530                 535                 540

Glu Asp Pro Gly Ser Leu Leu Ser Leu Phe Arg Arg Leu Ser Asp Gln
545                 550                 555                 560

Arg Ser Lys Glu Arg Ser Leu Leu His Gly Asp Phe His Ala Phe Ser
                565                 570                 575

Ala Gly Pro Gly Leu Phe Ser Tyr Ile Arg His Trp Asp Gln Asn Glu
            580                 585                 590

Arg Phe Leu Val Val Leu Asn Phe Gly Asp Val Gly Leu Ser Ala Gly
            595                 600                 605

Leu Gln Ala Ser Asp Leu Pro Ala Ser Ala Ser Leu Pro Ala Lys Ala
        610                 615                 620

Asp Leu Leu Leu Ser Thr Gln Pro Gly Arg Glu Glu Gly Ser Pro Leu
625                 630                 635                 640

Glu Leu Glu Arg Leu Lys Leu Glu Pro His Glu Gly Leu Leu Leu Arg
                645                 650                 655

Phe Pro Tyr Ala Ala
            660

<210> SEQ ID NO 24
<211> LENGTH: 1023
<212> TYPE: PRT
<213> ORGANISM: Homo sapiens

<400> SEQUENCE: 24

Met Gly Lys Gly Val Gly Arg Asp Lys Tyr Glu Pro Ala Ala Val Ser
1               5                   10                  15

Glu Gln Gly Asp Lys Lys Gly Lys Lys Gly Lys Lys Asp Arg Asp Met
                20                  25                  30

Asp Glu Leu Lys Lys Glu Val Ser Met Asp Asp His Lys Leu Ser Leu
            35                  40                  45

Asp Glu Leu His Arg Lys Tyr Gly Thr Asp Leu Ser Arg Gly Leu Thr
        50                  55                  60

Ser Ala Arg Ala Ala Glu Ile Leu Ala Arg Asp Gly Pro Asn Ala Leu
65                  70                  75                  80

Thr Pro Pro Pro Thr Thr Pro Glu Trp Ile Lys Phe Cys Arg Gln Leu
                85                  90                  95

Phe Gly Gly Phe Ser Met Leu Leu Trp Ile Gly Ala Ile Leu Cys Phe
            100                 105                 110

Leu Ala Tyr Ser Ile Gln Ala Ala Thr Glu Glu Glu Pro Gln Asn Asp
        115                 120                 125

Asn Leu Tyr Leu Gly Val Val Leu Ser Ala Val Val Ile Ile Thr Gly
        130                 135                 140

Cys Phe Ser Tyr Tyr Gln Glu Ala Lys Ser Ser Lys Ile Met Glu Ser
145                 150                 155                 160

Phe Lys Asn Met Val Pro Gln Gln Ala Leu Val Ile Arg Asn Gly Glu
                165                 170                 175
```

-continued

```
Lys Met Ser Ile Asn Ala Glu Glu Val Val Val Gly Asp Leu Val Glu
        180                 185                 190

Val Lys Gly Gly Asp Arg Ile Pro Ala Asp Leu Arg Ile Ile Ser Ala
        195                 200                 205

Asn Gly Cys Lys Val Asp Asn Ser Ser Leu Thr Gly Glu Ser Glu Pro
        210                 215                 220

Gln Thr Arg Ser Pro Asp Phe Thr Asn Glu Asn Pro Leu Glu Thr Arg
225                 230                 235                 240

Asn Ile Ala Phe Phe Ser Thr Asn Cys Val Glu Gly Thr Ala Arg Gly
                245                 250                 255

Ile Val Val Tyr Thr Gly Asp Arg Thr Val Met Gly Arg Ile Ala Thr
                260                 265                 270

Leu Ala Ser Gly Leu Glu Gly Gly Gln Thr Pro Ile Ala Ala Glu Ile
                275                 280                 285

Glu His Phe Ile His Ile Ile Thr Gly Val Ala Val Phe Leu Gly Val
        290                 295                 300

Ser Phe Phe Ile Leu Ser Leu Ile Leu Glu Tyr Thr Trp Leu Glu Ala
305                 310                 315                 320

Val Ile Phe Leu Ile Gly Ile Ile Val Ala Asn Val Pro Glu Gly Leu
                325                 330                 335

Leu Ala Thr Val Thr Val Cys Leu Thr Leu Thr Ala Lys Arg Met Ala
                340                 345                 350

Arg Lys Asn Cys Leu Val Lys Asn Leu Glu Ala Val Glu Thr Leu Gly
        355                 360                 365

Ser Thr Ser Thr Ile Cys Ser Asp Lys Thr Gly Thr Leu Thr Gln Asn
370                 375                 380

Arg Met Thr Val Ala His Met Trp Phe Asp Asn Gln Ile His Glu Ala
385                 390                 395                 400

Asp Thr Thr Glu Asn Gln Ser Gly Val Ser Phe Asp Lys Thr Ser Ala
                405                 410                 415

Thr Trp Leu Ala Leu Ser Arg Ile Ala Gly Leu Cys Asn Arg Ala Val
                420                 425                 430

Phe Gln Ala Asn Gln Glu Asn Leu Pro Ile Leu Lys Arg Ala Val Ala
        435                 440                 445

Gly Asp Ala Ser Glu Ser Ala Leu Leu Lys Cys Ile Glu Leu Cys Cys
        450                 455                 460

Gly Ser Val Lys Glu Met Arg Glu Arg Tyr Ala Lys Ile Val Glu Ile
465                 470                 475                 480

Pro Phe Asn Ser Thr Asn Lys Tyr Gln Leu Ser Ile His Lys Asn Pro
                485                 490                 495

Asn Thr Ser Glu Pro Gln His Leu Leu Val Met Lys Gly Ala Pro Glu
        500                 505                 510

Arg Ile Leu Asp Arg Cys Ser Ser Ile Leu Leu His Gly Lys Glu Gln
        515                 520                 525

Pro Leu Asp Glu Glu Leu Lys Asp Ala Phe Gln Asn Ala Tyr Leu Glu
        530                 535                 540

Leu Gly Gly Leu Gly Glu Arg Val Leu Gly Phe Cys His Leu Phe Leu
545                 550                 555                 560

Pro Asp Glu Gln Phe Pro Glu Gly Phe Gln Phe Asp Thr Asp Asp Val
                565                 570                 575

Asn Phe Pro Ile Asp Asn Leu Cys Phe Val Gly Leu Ile Ser Met Ile
                580                 585                 590
```

-continued

```
Asp Pro Pro Arg Ala Ala Val Pro Asp Ala Val Gly Lys Cys Arg Ser
        595             600             605

Ala Gly Ile Lys Val Ile Met Val Thr Gly Asp His Pro Ile Thr Ala
    610             615             620

Lys Ala Ile Ala Lys Gly Val Gly Ile Ile Ser Glu Gly Asn Glu Thr
625             630             635             640

Val Glu Asp Ile Ala Ala Arg Leu Asn Ile Pro Val Ser Gln Val Asn
            645             650             655

Pro Arg Asp Ala Lys Ala Cys Val Val His Gly Ser Asp Leu Lys Asp
            660             665             670

Met Thr Ser Glu Gln Leu Asp Asp Ile Leu Lys Tyr His Thr Glu Ile
        675             680             685

Val Phe Ala Arg Thr Ser Pro Gln Gln Lys Leu Ile Ile Val Glu Gly
    690             695             700

Cys Gln Arg Gln Gly Ala Ile Val Ala Val Thr Gly Asp Gly Val Asn
705             710             715             720

Asp Ser Pro Ala Leu Lys Lys Ala Asp Ile Gly Val Ala Met Gly Ile
            725             730             735

Ala Gly Ser Asp Val Ser Lys Gln Ala Ala Asp Met Ile Leu Leu Asp
            740             745             750

Asp Asn Phe Ala Ser Ile Val Thr Gly Val Glu Glu Gly Arg Leu Ile
        755             760             765

Phe Asp Asn Leu Lys Lys Ser Ile Ala Tyr Thr Leu Thr Ser Asn Ile
    770             775             780

Pro Glu Ile Thr Pro Phe Leu Ile Phe Ile Ile Ala Asn Ile Pro Leu
785             790             795             800

Pro Leu Gly Thr Val Thr Ile Leu Cys Ile Asp Leu Gly Thr Asp Met
            805             810             815

Val Pro Ala Ile Ser Leu Ala Tyr Glu Gln Ala Glu Ser Asp Ile Met
            820             825             830

Lys Arg Gln Pro Arg Asn Pro Lys Thr Asp Lys Leu Val Asn Glu Arg
        835             840             845

Leu Ile Ser Met Ala Tyr Gly Gln Ile Gly Met Ile Gln Ala Leu Gly
    850             855             860

Gly Phe Phe Thr Tyr Phe Val Ile Leu Ala Glu Asn Gly Phe Leu Pro
865             870             875             880

Ile His Leu Leu Gly Leu Arg Val Asp Trp Asp Asp Arg Trp Ile Asn
            885             890             895

Asp Val Glu Asp Ser Tyr Gly Gln Gln Trp Thr Tyr Glu Gln Arg Lys
            900             905             910

Ile Val Glu Phe Thr Cys His Thr Ala Phe Phe Val Ser Ile Val Val
            915             920             925

Val Gln Trp Ala Asp Leu Val Ile Cys Lys Thr Arg Arg Asn Ser Val
    930             935             940

Phe Gln Gln Gly Met Lys Asn Lys Ile Leu Ile Phe Gly Leu Phe Glu
945             950             955             960

Glu Thr Ala Leu Ala Ala Phe Leu Ser Tyr Cys Pro Gly Met Gly Val
            965             970             975

Ala Leu Arg Met Tyr Pro Leu Lys Pro Thr Trp Trp Phe Cys Ala Phe
            980             985             990

Pro Tyr Ser Leu Leu Ile Phe Val  Tyr Asp Glu Val Arg  Lys Leu Ile
        995             1000             1005

Ile Arg  Arg Arg Pro Gly Gly  Trp Val Glu Lys Glu  Thr Tyr Tyr
```

-continued

```
            1010                1015                1020

<210> SEQ ID NO 25
<211> LENGTH: 1020
<212> TYPE: PRT
<213> ORGANISM: Homo sapiens

<400> SEQUENCE: 25

Met Gly Arg Gly Ala Gly Arg Glu Tyr Ser Pro Ala Ala Thr Thr Ala
1               5                   10                  15

Glu Asn Gly Gly Gly Lys Lys Lys Gln Lys Glu Lys Glu Leu Asp Glu
                20                  25                  30

Leu Lys Lys Glu Val Ala Met Asp Asp His Lys Leu Ser Leu Asp Glu
        35                  40                  45

Leu Gly Arg Lys Tyr Gln Val Asp Leu Ser Lys Gly Leu Thr Asn Gln
    50                  55                  60

Arg Ala Gln Asp Val Leu Ala Arg Asp Gly Pro Asn Ala Leu Thr Pro
65                  70                  75                  80

Pro Pro Thr Thr Pro Glu Trp Val Lys Phe Cys Arg Gln Leu Phe Gly
                85                  90                  95

Gly Phe Ser Ile Leu Leu Trp Ile Gly Ala Ile Leu Cys Phe Leu Ala
                100                 105                 110

Tyr Gly Ile Gln Ala Ala Met Glu Asp Glu Pro Ser Asn Asp Asn Leu
        115                 120                 125

Tyr Leu Gly Val Val Leu Ala Ala Val Val Ile Val Thr Gly Cys Phe
    130                 135                 140

Ser Tyr Tyr Gln Glu Ala Lys Ser Ser Lys Ile Met Asp Ser Phe Lys
145                 150                 155                 160

Asn Met Val Pro Gln Gln Ala Leu Val Ile Arg Glu Gly Glu Lys Met
                165                 170                 175

Gln Ile Asn Ala Glu Glu Val Val Val Gly Asp Leu Val Glu Val Lys
        180                 185                 190

Gly Gly Asp Arg Val Pro Ala Asp Leu Arg Ile Ile Ser Ser His Gly
        195                 200                 205

Cys Lys Val Asp Asn Ser Ser Leu Thr Gly Glu Ser Glu Pro Gln Thr
    210                 215                 220

Arg Ser Pro Glu Phe Thr His Glu Asn Pro Leu Glu Thr Arg Asn Ile
225                 230                 235                 240

Cys Phe Phe Ser Thr Asn Cys Val Glu Gly Thr Ala Arg Gly Ile Val
                245                 250                 255

Ile Ala Thr Gly Asp Arg Thr Val Met Gly Arg Ile Ala Thr Leu Ala
                260                 265                 270

Ser Gly Leu Glu Val Gly Arg Thr Pro Ile Ala Met Glu Ile Glu His
        275                 280                 285

Phe Ile Gln Leu Ile Thr Gly Val Ala Val Phe Leu Gly Val Ser Phe
    290                 295                 300

Phe Val Leu Ser Leu Ile Leu Gly Tyr Ser Trp Leu Glu Ala Val Ile
305                 310                 315                 320

Phe Leu Ile Gly Ile Ile Val Ala Asn Val Pro Glu Gly Leu Leu Ala
                325                 330                 335

Thr Val Thr Val Cys Leu Thr Leu Thr Ala Lys Arg Met Ala Arg Lys
                340                 345                 350

Asn Cys Leu Val Lys Asn Leu Glu Ala Val Glu Thr Leu Gly Ser Thr
        355                 360                 365
```

-continued

```
Ser Thr Ile Cys Ser Asp Lys Thr Gly Thr Leu Thr Gln Asn Arg Met
    370             375                 380

Thr Val Ala His Met Trp Phe Asp Asn Gln Ile His Glu Ala Asp Thr
385             390                 395                 400

Thr Glu Asp Gln Ser Gly Ala Thr Phe Asp Lys Arg Ser Pro Thr Trp
                405                 410                 415

Thr Ala Leu Ser Arg Ile Ala Gly Leu Cys Asn Arg Ala Val Phe Lys
                420             425                 430

Ala Gly Gln Glu Asn Ile Ser Val Ser Lys Arg Asp Thr Ala Gly Asp
            435                 440                 445

Ala Ser Glu Ser Ala Leu Leu Lys Cys Ile Glu Leu Ser Cys Gly Ser
    450             455                 460

Val Arg Lys Met Arg Asp Arg Asn Pro Lys Val Ala Glu Ile Pro Phe
465             470                 475                 480

Asn Ser Thr Asn Lys Tyr Gln Leu Ser Ile His Glu Arg Glu Asp Ser
                485                 490                 495

Pro Gln Ser His Val Leu Val Met Lys Gly Ala Pro Glu Arg Ile Leu
                500                 505                 510

Asp Arg Cys Ser Thr Ile Leu Val Gln Gly Lys Glu Ile Pro Leu Asp
            515                 520                 525

Lys Glu Met Gln Asp Ala Phe Gln Asn Ala Tyr Met Glu Leu Gly Gly
    530                 535                 540

Leu Gly Glu Arg Val Leu Gly Phe Cys Gln Leu Asn Leu Pro Ser Gly
545                 550                 555                 560

Lys Phe Pro Arg Gly Phe Lys Phe Asp Thr Asp Glu Leu Asn Phe Pro
                565                 570                 575

Thr Glu Lys Leu Cys Phe Val Gly Leu Met Ser Met Ile Asp Pro Pro
                580                 585                 590

Arg Ala Ala Val Pro Asp Ala Val Gly Lys Cys Arg Ser Ala Gly Ile
            595                 600                 605

Lys Val Ile Met Val Thr Gly Asp His Pro Ile Thr Ala Lys Ala Ile
    610                 615                 620

Ala Lys Gly Val Gly Ile Ile Ser Glu Gly Asn Glu Thr Val Glu Asp
625                 630                 635                 640

Ile Ala Ala Arg Leu Asn Ile Pro Met Ser Gln Val Asn Pro Arg Glu
                645                 650                 655

Ala Lys Ala Cys Val Val His Gly Ser Asp Leu Lys Asp Met Thr Ser
                660                 665                 670

Glu Gln Leu Asp Glu Ile Leu Lys Asn His Thr Glu Ile Val Phe Ala
            675                 680                 685

Arg Thr Ser Pro Gln Gln Lys Leu Ile Ile Val Glu Gly Cys Gln Arg
    690                 695                 700

Gln Gly Ala Ile Val Ala Val Thr Gly Asp Gly Val Asn Asp Ser Pro
705                 710                 715                 720

Ala Leu Lys Lys Ala Asp Ile Gly Ile Ala Met Gly Ile Ser Gly Ser
                725                 730                 735

Asp Val Ser Lys Gln Ala Ala Asp Met Ile Leu Leu Asp Asp Asn Phe
                740                 745                 750

Ala Ser Ile Val Thr Gly Val Glu Glu Gly Arg Leu Ile Phe Asp Asn
            755                 760                 765

Leu Lys Lys Ser Ile Ala Tyr Thr Leu Thr Ser Asn Ile Pro Glu Ile
    770                 775                 780

Thr Pro Phe Leu Leu Phe Ile Ile Ala Asn Ile Pro Leu Pro Leu Gly
```

```
785                790                795                800

Thr Val Thr Ile Leu Cys Ile Asp Leu Gly Thr Asp Met Val Pro Ala
                805                810                815

Ile Ser Leu Ala Tyr Glu Ala Ala Glu Ser Asp Ile Met Lys Arg Gln
                820                825                830

Pro Arg Asn Ser Gln Thr Asp Lys Leu Val Asn Glu Arg Leu Ile Ser
                835                840                845

Met Ala Tyr Gly Gln Ile Gly Met Ile Gln Ala Leu Gly Gly Phe Phe
    850                855                860

Thr Tyr Phe Val Ile Leu Ala Glu Asn Gly Phe Leu Pro Ser Arg Leu
865                870                875                880

Leu Gly Ile Arg Leu Asp Trp Asp Asp Arg Thr Met Asn Asp Leu Glu
                885                890                895

Asp Ser Tyr Gly Gln Glu Trp Thr Tyr Glu Gln Arg Lys Val Val Glu
                900                905                910

Phe Thr Cys His Thr Ala Phe Phe Ala Ser Ile Val Val Val Gln Trp
                915                920                925

Ala Asp Leu Ile Ile Cys Lys Thr Arg Arg Asn Ser Val Phe Gln Gln
    930                935                940

Gly Met Lys Asn Lys Ile Leu Ile Phe Gly Leu Leu Glu Glu Thr Ala
945                950                955                960

Leu Ala Ala Phe Leu Ser Tyr Cys Pro Gly Met Gly Val Ala Leu Arg
                965                970                975

Met Tyr Pro Leu Lys Val Thr Trp Trp Phe Cys Ala Phe Pro Tyr Ser
                980                985                990

Leu Leu Ile Phe Ile Tyr Asp Glu  Val Arg Lys Leu Ile  Leu Arg Arg
                995                1000                1005

Tyr Pro  Gly Gly Trp Val Glu  Lys Glu Thr Tyr Tyr
    1010                1015                1020
```

<210> SEQ ID NO 26
<211> LENGTH: 1026
<212> TYPE: PRT
<213> ORGANISM: Homo sapiens

<400> SEQUENCE: 26

```
Met Gly Ser Gly Gly Ser Asp Ser Tyr Arg Ile Ala Thr Ser Gln Asp
1                5                10                15

Lys Lys Asp Asp Lys Asp Ser Pro Lys Lys Asn Lys Gly Lys Glu Arg
                20                25                30

Arg Asp Leu Asp Asp Leu Lys Lys Glu Val Ala Met Thr Glu His Lys
                35                40                45

Met Ser Val Glu Glu Val Cys Arg Lys Tyr Asn Thr Asp Cys Val Gln
    50                55                60

Gly Leu Thr His Ser Lys Ala Gln Glu Ile Leu Ala Arg Asp Gly Pro
65                70                75                80

Asn Ala Leu Thr Pro Pro Thr Thr Pro Glu Trp Val Lys Phe Cys
                85                90                95

Arg Gln Leu Phe Gly Gly Phe Ser Ile Leu Leu Trp Ile Gly Ala Ile
                100                105                110

Leu Cys Phe Leu Ala Tyr Gly Ile Gln Ala Gly Thr Glu Asp Asp Pro
                115                120                125

Ser Gly Asp Asn Leu Tyr Leu Gly Ile Val Leu Ala Ala Val Val Ile
    130                135                140
```

-continued

```
Ile Thr Gly Cys Phe Ser Tyr Tyr Gln Glu Ala Lys Ser Ser Lys Ile
145             150             155             160

Met Glu Ser Phe Lys Asn Met Val Pro Gln Gln Ala Leu Val Ile Arg
            165             170             175

Glu Gly Glu Lys Met Gln Val Asn Ala Glu Glu Val Val Val Gly Asp
            180             185             190

Leu Val Glu Ile Lys Gly Gly Asp Arg Val Pro Ala Asp Leu Arg Ile
            195             200             205

Ile Ser Ala His Gly Cys Lys Val Asp Asn Ser Ser Leu Thr Gly Glu
            210             215             220

Ser Glu Pro Gln Thr Arg Ser Pro Asp Cys Thr His Asp Asn Pro Leu
225             230             235             240

Glu Thr Arg Asn Ile Thr Phe Phe Ser Thr Asn Cys Val Glu Gly Thr
            245             250             255

Ala Arg Gly Val Val Val Ala Thr Gly Asp Arg Thr Val Met Gly Arg
            260             265             270

Ile Ala Thr Leu Ala Ser Gly Leu Glu Val Gly Lys Thr Pro Ile Ala
            275             280             285

Ile Glu Ile Glu His Phe Ile Gln Leu Ile Thr Gly Val Ala Val Phe
            290             295             300

Leu Gly Val Ser Phe Phe Ile Leu Ser Leu Ile Leu Gly Tyr Thr Trp
305             310             315             320

Leu Glu Ala Val Ile Phe Leu Ile Gly Ile Ile Val Ala Asn Val Pro
            325             330             335

Glu Gly Leu Leu Ala Thr Val Thr Val Cys Leu Thr Leu Thr Ala Lys
            340             345             350

Arg Met Ala Arg Lys Asn Cys Leu Val Lys Asn Leu Glu Ala Val Glu
            355             360             365

Thr Leu Gly Ser Thr Ser Thr Ile Cys Ser Asp Lys Thr Gly Thr Leu
            370             375             380

Thr Gln Asn Arg Met Thr Val Ala His Met Trp Phe Asp Asn Gln Ile
385             390             395             400

His Glu Ala Asp Thr Thr Glu Asp Gln Ser Gly Thr Ser Phe Asp Lys
            405             410             415

Ser Ser His Thr Trp Val Ala Leu Ser His Ile Ala Gly Leu Cys Asn
            420             425             430

Arg Ala Val Phe Lys Gly Gly Gln Asp Asn Ile Pro Val Leu Lys Arg
            435             440             445

Asp Val Ala Gly Asp Ala Ser Glu Ser Ala Leu Leu Lys Cys Ile Glu
            450             455             460

Leu Ser Ser Gly Ser Val Lys Leu Met Arg Glu Arg Asn Lys Lys Val
465             470             475             480

Ala Glu Ile Pro Phe Asn Ser Thr Asn Lys Tyr Gln Leu Ser Ile His
            485             490             495

Glu Thr Glu Asp Pro Asn Asp Asn Arg Tyr Leu Leu Val Met Lys Gly
            500             505             510

Ala Pro Glu Arg Ile Leu Asp Arg Cys Ser Thr Ile Leu Leu Gln Gly
            515             520             525

Lys Glu Gln Pro Leu Asp Glu Glu Met Lys Glu Ala Phe Gln Asn Ala
            530             535             540

Tyr Leu Glu Leu Gly Gly Leu Gly Glu Arg Val Leu Gly Phe Cys His
545             550             555             560

Tyr Tyr Leu Pro Glu Glu Gln Phe Pro Lys Gly Phe Ala Phe Asp Cys
```

-continued

```
                     565                 570                 575

Asp Asp Val Asn Phe Thr Thr Asp Asn Leu Cys Phe Val Gly Leu Met
                 580                 585                 590

Ser Met Ile Asp Pro Pro Arg Ala Ala Val Pro Asp Ala Val Gly Lys
                 595                 600                 605

Cys Arg Ser Ala Gly Ile Lys Val Ile Met Val Thr Gly Asp His Pro
             610                 615                 620

Ile Thr Ala Lys Ala Ile Ala Lys Gly Val Gly Ile Ile Ser Glu Gly
         625                 630                 635                 640

Asn Glu Thr Val Glu Asp Ile Ala Ala Arg Leu Asn Ile Pro Val Ser
                 645                 650                 655

Gln Val Asn Pro Arg Asp Ala Lys Ala Cys Val Ile His Gly Thr Asp
                 660                 665                 670

Leu Lys Asp Phe Thr Ser Glu Gln Ile Asp Glu Ile Leu Gln Asn His
                 675                 680                 685

Thr Glu Ile Val Phe Ala Arg Thr Ser Pro Gln Gln Lys Leu Ile Ile
             690                 695                 700

Val Glu Gly Cys Gln Arg Gln Gly Ala Ile Val Ala Val Thr Gly Asp
         705                 710                 715                 720

Gly Val Asn Asp Ser Pro Ala Leu Lys Lys Ala Asp Ile Gly Val Ala
                 725                 730                 735

Met Gly Ile Ala Gly Ser Asp Val Ser Lys Gln Ala Ala Asp Met Ile
             740                 745                 750

Leu Leu Asp Asp Asn Phe Ala Ser Ile Val Thr Gly Val Glu Glu Gly
             755                 760                 765

Arg Leu Ile Phe Asp Asn Leu Lys Lys Ser Ile Ala Tyr Thr Leu Thr
         770                 775                 780

Ser Asn Ile Pro Glu Ile Thr Pro Phe Leu Leu Phe Ile Met Ala Asn
         785                 790                 795                 800

Ile Pro Leu Pro Leu Gly Thr Ile Thr Ile Leu Cys Ile Asp Leu Gly
                 805                 810                 815

Thr Asp Met Val Pro Ala Ile Ser Leu Ala Tyr Glu Ala Ala Glu Ser
             820                 825                 830

Asp Ile Met Lys Arg Gln Pro Arg Asn Pro Arg Thr Asp Lys Leu Val
             835                 840                 845

Asn Glu Arg Leu Ile Ser Met Ala Tyr Gly Gln Ile Gly Met Ile Gln
         850                 855                 860

Ala Leu Gly Gly Phe Phe Ser Tyr Phe Val Ile Leu Ala Glu Asn Gly
     865                 870                 875                 880

Phe Leu Pro Gly Asn Leu Val Gly Ile Arg Leu Asn Trp Asp Asp Arg
                 885                 890                 895

Thr Val Asn Asp Leu Glu Asp Ser Tyr Gly Gln Gln Trp Thr Tyr Glu
                 900                 905                 910

Gln Arg Lys Val Val Glu Phe Thr Cys His Thr Ala Phe Phe Val Ser
             915                 920                 925

Ile Val Val Val Gln Trp Ala Asp Leu Ile Ile Cys Lys Thr Arg Arg
         930                 935                 940

Asn Ser Val Phe Gln Gln Gly Met Lys Asn Lys Ile Leu Ile Phe Gly
     945                 950                 955                 960

Leu Phe Glu Glu Thr Ala Leu Ala Ala Phe Leu Ser Tyr Cys Pro Gly
                 965                 970                 975

Met Asp Val Ala Leu Arg Met Tyr Pro Leu Lys Pro Ser Trp Trp Phe
                 980                 985                 990
```

```
Cys Ala Phe Pro Tyr Ser Phe Leu  Ile Phe Val Tyr Asp  Glu Ile Arg
        995                1000                 1005

Lys Leu  Ile Leu Arg Arg Asn  Pro Gly Gly Trp Val  Glu Lys Glu
    1010                1015                 1020

Thr Tyr  Tyr
    1025

<210> SEQ ID NO 27
<211> LENGTH: 1029
<212> TYPE: PRT
<213> ORGANISM: Homo sapiens

<400> SEQUENCE: 27

Met Gly Leu Trp Gly Lys Lys Gly Thr Val Ala Pro His Asp Gln Ser
1               5                   10                  15

Pro Arg Arg Arg Pro Lys Lys Gly Leu Ile Lys Lys Lys Met Val Lys
                20                  25                  30

Arg Glu Lys Gln Lys Arg Asn Met Glu Glu Leu Lys Lys Glu Val Val
        35                  40                  45

Met Asp Asp His Lys Leu Thr Leu Glu Glu Leu Ser Thr Lys Tyr Ser
    50                  55                  60

Val Asp Leu Thr Lys Gly His Ser His Gln Arg Ala Lys Glu Ile Leu
65                  70                  75                  80

Thr Arg Gly Gly Pro Asn Thr Val Thr Pro Pro Thr Thr Pro Glu
                85                  90                  95

Trp Val Lys Phe Cys Lys Gln Leu Phe Gly Gly Phe Ser Leu Leu Leu
            100                 105                 110

Trp Thr Gly Ala Ile Leu Cys Phe Val Ala Tyr Ser Ile Gln Ile Tyr
        115                 120                 125

Phe Asn Glu Glu Pro Thr Lys Asp Asn Leu Tyr Leu Ser Ile Val Leu
    130                 135                 140

Ser Val Val Val Ile Val Thr Gly Cys Phe Ser Tyr Tyr Gln Glu Ala
145                 150                 155                 160

Lys Ser Ser Lys Ile Met Glu Ser Phe Lys Asn Met Val Pro Gln Gln
            165                 170                 175

Ala Leu Val Ile Arg Gly Gly Glu Lys Met Gln Ile Asn Val Gln Glu
            180                 185                 190

Val Val Leu Gly Asp Leu Val Glu Ile Lys Gly Gly Asp Arg Val Pro
        195                 200                 205

Ala Asp Leu Arg Leu Ile Ser Ala Gln Gly Cys Lys Val Asp Asn Ser
    210                 215                 220

Ser Leu Thr Gly Glu Ser Glu Pro Gln Ser Arg Ser Pro Asp Phe Thr
225                 230                 235                 240

His Glu Asn Pro Leu Glu Thr Arg Asn Ile Cys Phe Phe Ser Thr Asn
            245                 250                 255

Cys Val Glu Gly Thr Ala Arg Gly Ile Val Ile Ala Thr Gly Asp Ser
            260                 265                 270

Thr Val Met Gly Arg Ile Ala Ser Leu Thr Ser Gly Leu Ala Val Gly
        275                 280                 285

Gln Thr Pro Ile Ala Ala Glu Ile Glu His Phe Ile His Leu Ile Thr
    290                 295                 300

Val Val Ala Val Phe Leu Gly Val Thr Phe Phe Ala Leu Ser Leu Leu
305                 310                 315                 320

Leu Gly Tyr Gly Trp Leu Glu Ala Ile Ile Phe Leu Ile Gly Ile Ile
```

-continued

```
              325              330              335

Val Ala Asn Val Pro Glu Gly Leu Leu Ala Thr Val Thr Val Cys Leu
            340              345              350

Thr Leu Thr Ala Lys Arg Met Ala Arg Lys Asn Cys Leu Val Lys Asn
            355              360              365

Leu Glu Ala Val Glu Thr Leu Gly Ser Thr Ser Thr Ile Cys Ser Asp
        370              375              380

Lys Thr Gly Thr Leu Thr Gln Asn Arg Met Thr Val Ala His Met Trp
385              390              395              400

Phe Asp Met Thr Val Tyr Glu Ala Asp Thr Thr Glu Glu Gln Thr Gly
                405              410              415

Lys Thr Phe Thr Lys Ser Ser Asp Thr Trp Phe Met Leu Ala Arg Ile
            420              425              430

Ala Gly Leu Cys Asn Arg Ala Asp Phe Lys Ala Asn Gln Glu Ile Leu
        435              440              445

Pro Ile Ala Lys Arg Ala Thr Thr Gly Asp Ala Ser Glu Ser Ala Leu
    450              455              460

Leu Lys Phe Ile Glu Gln Ser Tyr Ser Ser Val Ala Glu Met Arg Glu
465              470              475              480

Lys Asn Pro Lys Val Ala Glu Ile Pro Phe Asn Ser Thr Asn Lys Tyr
                485              490              495

Gln Met Ser Ile His Leu Arg Glu Asp Ser Ser Gln Thr His Val Leu
            500              505              510

Met Met Lys Gly Ala Pro Glu Arg Ile Leu Glu Phe Cys Ser Thr Phe
            515              520              525

Leu Leu Asn Gly Gln Glu Tyr Ser Met Asn Asp Glu Met Lys Glu Ala
        530              535              540

Phe Gln Asn Ala Tyr Leu Glu Leu Gly Gly Leu Gly Glu Arg Val Leu
545              550              555              560

Gly Phe Cys Phe Leu Asn Leu Pro Ser Ser Phe Ser Lys Gly Phe Pro
                565              570              575

Phe Asn Thr Asp Glu Ile Asn Phe Pro Met Asp Asn Leu Cys Phe Val
            580              585              590

Gly Leu Ile Ser Met Ile Asp Pro Pro Arg Ala Ala Val Pro Asp Ala
        595              600              605

Val Ser Lys Cys Arg Ser Ala Gly Ile Lys Val Ile Met Val Thr Gly
    610              615              620

Asp His Pro Ile Thr Ala Lys Ala Ile Ala Lys Gly Val Gly Ile Ile
625              630              635              640

Ser Glu Gly Thr Glu Thr Ala Glu Glu Val Ala Ala Arg Leu Lys Ile
                645              650              655

Pro Ile Ser Lys Val Asp Ala Ser Ala Ala Lys Ala Ile Val Val His
            660              665              670

Gly Ala Glu Leu Lys Asp Ile Gln Ser Lys Gln Leu Asp Gln Ile Leu
        675              680              685

Gln Asn His Pro Glu Ile Val Phe Ala Arg Thr Ser Pro Gln Gln Lys
        690              695              700

Leu Ile Ile Val Glu Gly Cys Gln Arg Leu Gly Ala Val Val Ala Val
705              710              715              720

Thr Gly Asp Gly Val Asn Asp Ser Pro Ala Leu Lys Lys Ala Asp Ile
                725              730              735

Gly Ile Ala Met Gly Ile Ser Gly Ser Asp Val Ser Lys Gln Ala Ala
            740              745              750
```

-continued

```
Asp Met Ile Leu Leu Asp Asp Asn Phe Ala Ser Ile Val Thr Gly Val
        755                 760                 765

Glu Glu Gly Arg Leu Ile Phe Asp Asn Leu Lys Lys Ser Ile Met Tyr
    770                 775                 780

Thr Leu Thr Ser Asn Ile Pro Glu Ile Thr Pro Phe Leu Met Phe Ile
785                 790                 795                 800

Ile Leu Gly Ile Pro Leu Pro Leu Gly Thr Ile Thr Ile Leu Cys Ile
            805                 810                 815

Asp Leu Gly Thr Asp Met Val Pro Ala Ile Ser Leu Ala Tyr Glu Ser
        820                 825                 830

Ala Glu Ser Asp Ile Met Lys Arg Leu Pro Arg Asn Pro Lys Thr Asp
        835                 840                 845

Asn Leu Val Asn His Arg Leu Ile Gly Met Ala Tyr Gly Gln Ile Gly
        850                 855                 860

Met Ile Gln Ala Leu Ala Gly Phe Phe Thr Tyr Phe Val Ile Leu Ala
865                 870                 875                 880

Glu Asn Gly Phe Arg Pro Val Asp Leu Leu Gly Ile Arg Leu His Trp
            885                 890                 895

Glu Asp Lys Tyr Leu Asn Asp Leu Glu Asp Ser Tyr Gly Gln Gln Trp
        900                 905                 910

Thr Tyr Glu Gln Arg Lys Val Val Glu Phe Thr Cys Gln Thr Ala Phe
        915                 920                 925

Phe Val Thr Ile Val Val Val Gln Trp Ala Asp Leu Ile Ile Ser Lys
    930                 935                 940

Thr Arg Arg Asn Ser Leu Phe Gln Gln Gly Met Arg Asn Lys Val Leu
945                 950                 955                 960

Ile Phe Gly Ile Leu Glu Glu Thr Leu Leu Ala Ala Phe Leu Ser Tyr
            965                 970                 975

Thr Pro Gly Met Asp Val Ala Leu Arg Met Tyr Pro Leu Lys Ile Thr
        980                 985                 990

Trp Trp Leu Cys Ala Ile Pro Tyr  Ser Ile Leu Ile Phe  Val Tyr Asp
        995                 1000                 1005

Glu Ile  Arg Lys Leu Leu Ile  Arg Gln His Pro Asp  Gly Trp Val
    1010                 1015                 1020

Glu Arg  Glu Thr Tyr Tyr
    1025
```

<210> SEQ ID NO 28
<211> LENGTH: 279
<212> TYPE: PRT
<213> ORGANISM: Homo sapiens

<400> SEQUENCE: 28

```
Met Thr Lys Asn Glu Lys Lys Ser Leu Asn Gln Ser Leu Ala Glu Trp
1               5                   10                  15

Lys Leu Phe Ile Tyr Asn Pro Thr Thr Gly Glu Phe Leu Gly Arg Thr
            20                  25                  30

Ala Lys Ser Trp Gly Leu Ile Leu Leu Phe Tyr Leu Val Phe Tyr Gly
        35                  40                  45

Phe Leu Ala Ala Leu Phe Ser Phe Thr Met Trp Val Met Leu Gln Thr
    50                  55                  60

Leu Asn Asp Glu Val Pro Lys Tyr Arg Asp Gln Ile Pro Ser Pro Gly
65                  70                  75                  80

Leu Met Val Phe Pro Lys Pro Val Thr Ala Leu Glu Tyr Thr Phe Ser
```

```
                  85                    90                    95

Arg Ser Asp Pro Thr Ser Tyr Ala Gly Tyr Ile Glu Asp Leu Lys Lys
                 100                   105                   110

Phe Leu Lys Pro Tyr Thr Leu Glu Glu Gln Lys Asn Leu Thr Val Cys
                 115                   120                   125

Pro Asp Gly Ala Leu Phe Glu Gln Lys Gly Pro Val Tyr Val Ala Cys
                 130                   135                   140

Gln Phe Pro Ile Ser Leu Leu Gln Ala Cys Ser Gly Met Asn Asp Pro
145                   150                   155                   160

Asp Phe Gly Tyr Ser Gln Gly Asn Pro Cys Ile Leu Val Lys Met Asn
                 165                   170                   175

Arg Ile Ile Gly Leu Lys Pro Glu Gly Val Pro Arg Ile Asp Cys Val
                 180                   185                   190

Ser Lys Asn Glu Asp Ile Pro Asn Val Ala Val Tyr Pro His Asn Gly
                 195                   200                   205

Met Ile Asp Leu Lys Tyr Phe Pro Tyr Tyr Gly Lys Lys Leu His Val
                 210                   215                   220

Gly Tyr Leu Gln Pro Leu Val Ala Val Gln Val Ser Phe Ala Pro Asn
225                   230                   235                   240

Asn Thr Gly Lys Glu Val Thr Val Glu Cys Lys Ile Asp Gly Ser Ala
                 245                   250                   255

Asn Leu Lys Ser Gln Asp Asp Arg Asp Lys Phe Leu Gly Arg Val Met
                 260                   265                   270

Phe Lys Ile Thr Ala Arg Ala
                 275

<210> SEQ ID NO 29
<211> LENGTH: 1258
<212> TYPE: PRT
<213> ORGANISM: Homo sapiens

<400> SEQUENCE: 29

Met Gly Asp Met Ala Asn Asn Ser Val Ala Tyr Ser Gly Val Lys Asn
1               5                     10                    15

Ser Leu Lys Glu Ala Asn His Asp Gly Asp Phe Gly Ile Thr Leu Ala
                 20                    25                    30

Glu Leu Arg Ala Leu Met Glu Leu Arg Ser Thr Asp Ala Leu Arg Lys
                 35                    40                    45

Ile Gln Glu Ser Tyr Gly Asp Val Tyr Gly Ile Cys Thr Lys Leu Lys
                 50                    55                    60

Thr Ser Pro Asn Glu Gly Leu Ser Gly Asn Pro Ala Asp Leu Glu Arg
65                    70                    75                    80

Arg Glu Ala Val Phe Gly Lys Asn Phe Ile Pro Pro Lys Lys Pro Lys
                 85                    90                    95

Thr Phe Leu Gln Leu Val Trp Glu Ala Leu Gln Asp Val Thr Leu Ile
                 100                   105                   110

Ile Leu Glu Ile Ala Ala Ile Val Ser Leu Gly Leu Ser Phe Tyr Gln
                 115                   120                   125

Pro Pro Glu Gly Asp Asn Ala Leu Cys Gly Glu Val Ser Val Gly Glu
                 130                   135                   140

Glu Glu Gly Glu Gly Glu Thr Gly Trp Ile Glu Gly Ala Ala Ile Leu
145                   150                   155                   160

Leu Ser Val Val Cys Val Val Leu Val Thr Ala Phe Asn Asp Trp Ser
                 165                   170                   175
```

-continued

```
Lys Glu Lys Gln Phe Arg Gly Leu Gln Ser Arg Ile Glu Gln Glu Gln
            180                 185                 190

Lys Phe Thr Val Ile Arg Gly Gly Gln Val Ile Gln Ile Pro Val Ala
            195                 200                 205

Asp Ile Thr Val Gly Asp Ile Ala Gln Val Lys Tyr Gly Asp Leu Leu
            210                 215                 220

Pro Ala Asp Gly Ile Leu Ile Gln Gly Asn Asp Leu Lys Ile Asp Glu
225                 230                 235                 240

Ser Ser Leu Thr Gly Glu Ser Asp His Val Lys Lys Ser Leu Asp Lys
                245                 250                 255

Asp Pro Leu Leu Leu Ser Gly Thr His Val Met Glu Gly Ser Gly Arg
                260                 265                 270

Met Val Val Thr Ala Val Gly Val Asn Ser Gln Thr Gly Ile Ile Phe
            275                 280                 285

Thr Leu Leu Gly Ala Gly Gly Glu Glu Glu Lys Lys Asp Glu Lys
            290                 295                 300

Lys Lys Glu Lys Lys Asn Lys Lys Gln Asp Gly Ala Ile Glu Asn Arg
305                 310                 315                 320

Asn Lys Ala Lys Ala Gln Asp Gly Ala Ala Met Glu Met Gln Pro Leu
                325                 330                 335

Lys Ser Glu Glu Gly Gly Asp Gly Asp Glu Lys Asp Lys Lys Lys Ala
            340                 345                 350

Asn Leu Pro Lys Lys Glu Lys Ser Val Leu Gln Gly Lys Leu Thr Lys
            355                 360                 365

Leu Ala Val Gln Ile Gly Lys Ala Gly Leu Leu Met Ser Ala Ile Thr
            370                 375                 380

Val Ile Ile Leu Val Leu Tyr Phe Val Ile Asp Thr Phe Trp Val Gln
385                 390                 395                 400

Lys Arg Pro Trp Leu Ala Glu Cys Thr Pro Ile Tyr Ile Gln Tyr Phe
                405                 410                 415

Val Lys Phe Phe Ile Ile Gly Val Thr Val Leu Val Val Ala Val Pro
            420                 425                 430

Glu Gly Leu Pro Leu Ala Val Thr Ile Ser Leu Ala Tyr Ser Val Lys
            435                 440                 445

Lys Met Met Lys Asp Asn Asn Leu Val Arg His Leu Asp Ala Cys Glu
            450                 455                 460

Thr Met Gly Asn Ala Thr Ala Ile Cys Ser Asp Lys Thr Gly Thr Leu
465                 470                 475                 480

Thr Met Asn Arg Met Thr Val Val Gln Ala Tyr Ile Asn Glu Lys His
                485                 490                 495

Tyr Lys Lys Val Pro Glu Pro Glu Ala Ile Pro Pro Asn Ile Leu Ser
            500                 505                 510

Tyr Leu Val Thr Gly Ile Ser Val Asn Cys Ala Tyr Thr Ser Lys Ile
            515                 520                 525

Leu Pro Pro Glu Lys Glu Gly Gly Leu Pro Arg His Val Gly Asn Lys
            530                 535                 540

Thr Glu Cys Ala Leu Leu Gly Leu Leu Leu Asp Leu Lys Arg Asp Tyr
545                 550                 555                 560

Gln Asp Val Arg Asn Glu Ile Pro Glu Glu Ala Leu Tyr Lys Val Tyr
                565                 570                 575

Thr Phe Asn Ser Val Arg Lys Ser Met Ser Thr Val Leu Lys Asn Ser
            580                 585                 590

Asp Gly Ser Tyr Arg Ile Phe Ser Lys Gly Ala Ser Glu Ile Ile Leu
```

```
              595                   600                   605

Lys Lys Cys Phe Lys Ile Leu Ser Ala Asn Gly Glu Ala Lys Val Phe
    610                   615                   620

Arg Pro Arg Asp Arg Asp Asp Ile Val Lys Thr Val Ile Glu Pro Met
625                   630                   635                   640

Ala Ser Glu Gly Leu Arg Thr Ile Cys Leu Ala Phe Arg Asp Phe Pro
                  645                   650                   655

Ala Gly Glu Pro Glu Pro Glu Trp Asp Asn Glu Asn Asp Ile Val Thr
                  660                   665                   670

Gly Leu Thr Cys Ile Ala Val Val Gly Ile Glu Asp Pro Val Arg Pro
                  675                   680                   685

Glu Val Pro Asp Ala Ile Lys Lys Cys Gln Arg Ala Gly Ile Thr Val
                  690                   695                   700

Arg Met Val Thr Gly Asp Asn Ile Asn Thr Ala Arg Ala Ile Ala Thr
705                   710                   715                   720

Lys Cys Gly Ile Leu His Pro Gly Glu Asp Phe Leu Cys Leu Glu Gly
                  725                   730                   735

Lys Asp Phe Asn Arg Arg Ile Arg Asn Glu Lys Gly Glu Ile Glu Gln
                  740                   745                   750

Glu Arg Ile Asp Lys Ile Trp Pro Lys Leu Arg Val Leu Ala Arg Ser
                  755                   760                   765

Ser Pro Thr Asp Lys His Thr Leu Val Lys Gly Ile Ile Asp Ser Thr
                  770                   775                   780

Val Ser Asp Gln Arg Gln Val Val Ala Val Thr Gly Asp Gly Thr Asn
785                   790                   795                   800

Asp Gly Pro Ala Leu Lys Lys Ala Asp Val Gly Phe Ala Met Gly Ile
                  805                   810                   815

Ala Gly Thr Asp Val Ala Lys Glu Ala Ser Asp Ile Ile Leu Thr Asp
                  820                   825                   830

Asp Asn Phe Thr Ser Ile Val Lys Ala Val Met Trp Gly Arg Asn Val
                  835                   840                   845

Tyr Asp Ser Ile Ser Lys Phe Leu Gln Phe Gln Leu Thr Val Asn Val
    850                   855                   860

Val Ala Val Ile Val Ala Phe Thr Gly Ala Cys Ile Thr Gln Asp Ser
865                   870                   875                   880

Pro Leu Lys Ala Val Gln Met Leu Trp Val Asn Leu Ile Met Asp Thr
                  885                   890                   895

Leu Ala Ser Leu Ala Leu Ala Thr Glu Pro Pro Thr Glu Ser Leu Leu
                  900                   905                   910

Leu Arg Lys Pro Tyr Gly Arg Asn Lys Pro Leu Ile Ser Arg Thr Met
                  915                   920                   925

Met Lys Asn Ile Leu Gly His Ala Phe Tyr Gln Leu Val Val Val Phe
    930                   935                   940

Thr Leu Leu Phe Ala Gly Glu Lys Phe Phe Asp Ile Asp Ser Gly Arg
945                   950                   955                   960

Asn Ala Pro Leu His Ala Pro Pro Ser Glu His Tyr Thr Ile Val Phe
                  965                   970                   975

Asn Thr Phe Val Leu Met Gln Leu Phe Asn Glu Ile Asn Ala Arg Lys
                  980                   985                   990

Ile His Gly Glu Arg Asn Val Phe  Glu Gly Ile Phe Asn  Asn Ala Ile
    995                   1000                  1005

Phe Cys  Thr Ile Val Leu Gly  Thr Phe Val Val Gln  Ile Ile Ile
    1010                  1015                  1020
```

-continued

```
Val Gln Phe Gly Gly Lys Pro Phe Ser Cys Ser Glu Leu Ser Ile
    1025            1030            1035

Glu Gln Trp Leu Trp Ser Ile Phe Leu Gly Met Gly Thr Leu Leu
    1040            1045            1050

Trp Gly Gln Leu Ile Ser Thr Ile Pro Thr Ser Arg Leu Lys Phe
    1055            1060            1065

Leu Lys Glu Ala Gly His Gly Thr Gln Lys Glu Glu Ile Pro Glu
    1070            1075            1080

Glu Glu Leu Ala Glu Asp Val Glu Glu Ile Asp His Ala Glu Arg
    1085            1090            1095

Glu Leu Arg Arg Gly Gln Ile Leu Trp Phe Arg Gly Leu Asn Arg
    1100            1105            1110

Ile Gln Thr Gln Met Asp Val Val Asn Ala Phe Gln Ser Gly Ser
    1115            1120            1125

Ser Ile Gln Gly Ala Leu Arg Arg Gln Pro Ser Ile Ala Ser Gln
    1130            1135            1140

His His Asp Val Thr Asn Ile Ser Thr Pro Thr His Ile Arg Val
    1145            1150            1155

Val Asn Ala Phe Arg Ser Ser Leu Tyr Glu Gly Leu Glu Lys Pro
    1160            1165            1170

Glu Ser Arg Ser Ser Ile His Asn Phe Met Thr His Pro Glu Phe
    1175            1180            1185

Arg Ile Glu Asp Ser Glu Pro His Ile Pro Leu Ile Asp Asp Thr
    1190            1195            1200

Asp Ala Glu Asp Asp Ala Pro Thr Lys Arg Asn Ser Ser Pro Pro
    1205            1210            1215

Pro Ser Pro Asn Lys Asn Asn Asn Ala Val Asp Ser Gly Ile His
    1220            1225            1230

Leu Thr Ile Glu Met Asn Lys Ser Ala Thr Ser Ser Ser Pro Gly
    1235            1240            1245

Ser Pro Leu His Ser Leu Glu Thr Ser Leu
    1250            1255
```

```
<210> SEQ ID NO 30
<211> LENGTH: 1272
<212> TYPE: PRT
<213> ORGANISM: Homo sapiens

<400> SEQUENCE: 30
```

```
Met Gly Asp Met Thr Asn Ser Asp Phe Tyr Ser Lys Asn Gln Arg Asn
1               5               10              15

Glu Ser Ser His Gly Gly Glu Phe Gly Cys Thr Met Glu Glu Leu Arg
            20              25              30

Ser Leu Met Glu Leu Arg Gly Thr Glu Ala Val Val Lys Ile Lys Glu
        35              40              45

Thr Tyr Gly Asp Thr Glu Ala Ile Cys Arg Arg Leu Lys Thr Ser Pro
    50              55              60

Val Glu Gly Leu Pro Gly Thr Ala Pro Asp Leu Glu Lys Arg Lys Gln
65              70              75              80

Ile Phe Gly Gln Asn Phe Ile Pro Pro Lys Lys Pro Lys Thr Phe Leu
                85              90              95

Gln Leu Val Trp Glu Ala Leu Gln Asp Val Thr Leu Ile Ile Leu Glu
            100             105             110

Ile Ala Ala Ile Ile Ser Leu Gly Leu Ser Phe Tyr His Pro Pro Gly
```

```
              115              120              125
Glu Gly Asn Glu Gly Cys Ala Thr Ala Gln Gly Gly Ala Glu Asp Glu
    130              135              140

Gly Glu Ala Glu Ala Gly Trp Ile Glu Gly Ala Ala Ile Leu Leu Ser
145              150              155              160

Val Ile Cys Val Val Leu Val Thr Ala Phe Asn Asp Trp Ser Lys Glu
                165              170              175

Lys Gln Phe Arg Gly Leu Gln Ser Arg Ile Glu Gln Glu Gln Lys Phe
            180              185              190

Thr Val Val Arg Ala Gly Gln Val Val Gln Ile Pro Val Ala Glu Ile
            195              200              205

Val Val Gly Asp Ile Ala Gln Val Lys Tyr Gly Asp Leu Leu Pro Ala
    210              215              220

Asp Gly Leu Phe Ile Gln Gly Asn Asp Leu Lys Ile Asp Glu Ser Ser
225              230              235              240

Leu Thr Gly Glu Ser Asp Gln Val Arg Lys Ser Val Asp Lys Asp Pro
            245              250              255

Met Leu Leu Ser Gly Thr His Val Met Glu Gly Ser Gly Arg Met Leu
            260              265              270

Val Thr Ala Val Gly Val Asn Ser Gln Thr Gly Ile Ile Phe Thr Leu
            275              280              285

Leu Gly Ala Gly Gly Glu Glu Glu Lys Lys Asp Lys Lys Gly Val
    290              295              300

Lys Lys Gly Asp Gly Leu Gln Leu Pro Ala Ala Asp Gly Ala Ala Ala
305              310              315              320

Ser Asn Ala Ala Asp Ser Ala Asn Ala Ser Leu Val Asn Gly Lys Met
            325              330              335

Gln Asp Gly Asn Val Asp Ala Ser Gln Ser Lys Ala Lys Gln Gln Asp
            340              345              350

Gly Ala Ala Ala Met Glu Met Gln Pro Leu Lys Ser Ala Glu Gly Gly
            355              360              365

Asp Ala Asp Asp Arg Lys Lys Ala Ser Met His Lys Lys Glu Lys Ser
    370              375              380

Val Leu Gln Gly Lys Leu Thr Lys Leu Ala Val Gln Ile Gly Lys Ala
385              390              395              400

Gly Leu Val Met Ser Ala Ile Thr Val Ile Ile Leu Val Leu Tyr Phe
            405              410              415

Thr Val Asp Thr Phe Val Val Asn Lys Lys Pro Trp Leu Pro Glu Cys
            420              425              430

Thr Pro Val Tyr Val Gln Tyr Phe Val Lys Phe Phe Ile Ile Gly Val
            435              440              445

Thr Val Leu Val Val Ala Val Pro Glu Gly Leu Pro Leu Ala Val Thr
    450              455              460

Ile Ser Leu Ala Tyr Ser Val Lys Lys Met Met Lys Asp Asn Asn Leu
465              470              475              480

Val Arg His Leu Asp Ala Cys Glu Thr Met Gly Asn Ala Thr Ala Ile
            485              490              495

Cys Ser Asp Lys Thr Gly Thr Leu Thr Thr Asn Arg Met Thr Val Val
            500              505              510

Gln Ala Tyr Val Gly Asp Val His Tyr Lys Glu Ile Pro Asp Pro Ser
            515              520              525

Ser Ile Asn Thr Lys Thr Met Glu Leu Leu Ile Asn Ala Ile Ala Ile
    530              535              540
```

```
Asn Ser Ala Tyr Thr Thr Lys Ile Leu Pro Pro Glu Lys Glu Gly Ala
545                 550                 555                 560

Leu Pro Arg Gln Val Gly Asn Lys Thr Glu Cys Gly Leu Leu Gly Phe
                565                 570                 575

Val Leu Asp Leu Lys Gln Asp Tyr Glu Pro Val Arg Ser Gln Met Pro
                580                 585                 590

Glu Glu Lys Leu Tyr Lys Val Tyr Thr Phe Asn Ser Val Arg Lys Ser
            595                 600                 605

Met Ser Thr Val Ile Lys Leu Pro Asp Glu Ser Phe Arg Met Tyr Ser
        610                 615                 620

Lys Gly Ala Ser Glu Ile Val Leu Lys Lys Cys Cys Lys Ile Leu Asn
625                 630                 635                 640

Gly Ala Gly Glu Pro Arg Val Phe Arg Pro Arg Asp Arg Asp Glu Met
                645                 650                 655

Val Lys Lys Val Ile Glu Pro Met Ala Cys Asp Gly Leu Arg Thr Ile
                660                 665                 670

Cys Val Ala Tyr Arg Asp Phe Pro Ser Ser Pro Glu Pro Asp Trp Asp
                675                 680                 685

Asn Glu Asn Asp Ile Leu Asn Glu Leu Thr Cys Ile Cys Val Val Gly
        690                 695                 700

Ile Glu Asp Pro Val Arg Pro Glu Val Pro Glu Ala Ile Arg Lys Cys
705                 710                 715                 720

Gln Arg Ala Gly Ile Thr Val Arg Met Val Thr Gly Asp Asn Ile Asn
                725                 730                 735

Thr Ala Arg Ala Ile Ala Ile Lys Cys Gly Ile Ile His Pro Gly Glu
                740                 745                 750

Asp Phe Leu Cys Leu Glu Gly Lys Glu Phe Asn Arg Arg Ile Arg Asn
                755                 760                 765

Glu Lys Gly Glu Ile Glu Gln Glu Arg Ile Asp Lys Ile Trp Pro Lys
        770                 775                 780

Leu Arg Val Leu Ala Arg Ser Ser Pro Thr Asp Lys His Thr Leu Val
785                 790                 795                 800

Lys Gly Ile Ile Asp Ser Thr His Thr Glu Gln Arg Gln Val Val Ala
                805                 810                 815

Val Thr Gly Asp Gly Thr Asn Asp Gly Pro Ala Leu Lys Lys Ala Asp
                820                 825                 830

Val Gly Phe Ala Met Gly Ile Ala Gly Thr Asp Val Ala Lys Glu Ala
            835                 840                 845

Ser Asp Ile Ile Leu Thr Asp Asp Asn Phe Ser Ser Ile Val Lys Ala
        850                 855                 860

Val Met Trp Gly Arg Asn Val Tyr Asp Ser Ile Ser Lys Phe Leu Gln
865                 870                 875                 880

Phe Gln Leu Thr Val Asn Val Val Ala Val Ile Val Ala Phe Thr Gly
                885                 890                 895

Ala Cys Ile Thr Gln Asp Ser Pro Leu Lys Ala Val Gln Met Leu Trp
                900                 905                 910

Val Asn Leu Ile Met Asp Thr Phe Ala Ser Leu Ala Leu Ala Thr Glu
            915                 920                 925

Pro Pro Thr Glu Thr Leu Leu Leu Arg Lys Pro Tyr Gly Arg Asn Lys
        930                 935                 940

Pro Leu Ile Ser Arg Thr Met Met Lys Asn Ile Leu Gly His Ala Val
945                 950                 955                 960
```

```
Tyr Gln Leu Ala Leu Ile Phe Thr Leu Leu Phe Val Gly Glu Lys Met
                965                 970                 975

Phe Gln Ile Asp Ser Gly Arg Asn Ala Pro Leu His Ser Pro Pro Ser
                980                 985                 990

Glu His Tyr Thr Ile Ile Phe Asn  Thr Phe Val Met Met  Gln Leu Phe
            995                 1000                1005

Asn Glu  Ile Asn Ala Arg Lys  Ile His Gly Glu Arg  Asn Val Phe
    1010                1015                1020

Asp Gly  Ile Phe Arg Asn Pro  Ile Phe Cys Thr Ile  Val Leu Gly
    1025                1030                1035

Thr Phe  Ala Ile Gln Ile Val  Ile Val Gln Phe Gly  Gly Lys Pro
    1040                1045                1050

Phe Ser  Cys Ser Pro Leu Gln  Leu Asp Gln Trp Met  Trp Cys Ile
    1055                1060                1065

Phe Ile  Gly Leu Gly Glu Leu  Val Trp Gly Gln Val  Ile Ala Thr
    1070                1075                1080

Ile Pro  Thr Ser Arg Leu Lys  Phe Leu Lys Glu Ala  Gly Arg Leu
    1085                1090                1095

Thr Gln  Lys Glu Glu Ile Pro  Glu Glu Glu Leu Asn  Glu Asp Val
    1100                1105                1110

Glu Glu  Ile Asp His Ala Glu  Arg Glu Leu Arg Arg  Gly Gln Ile
    1115                1120                1125

Leu Trp  Phe Arg Gly Leu Asn  Arg Ile Gln Thr Gln  Ile Glu Val
    1130                1135                1140

Val Asn  Thr Phe Lys Ser Gly  Ala Ser Phe Gln Gly  Ala Leu Arg
    1145                1150                1155

Arg Gln  Ser Ser Val Thr Ser  Gln Ser Gln Asp Ile  Arg Val Val
    1160                1165                1170

Lys Ala  Phe Arg Ser Ser Leu  Tyr Glu Gly Leu Glu  Lys Pro Glu
    1175                1180                1185

Ser Arg  Thr Ser Ile His Asn  Phe Met Ala His Pro  Glu Phe Arg
    1190                1195                1200

Ile Glu  Asp Ser Gln Pro His  Ile Pro Leu Ile Asp  Asp Thr Asp
    1205                1210                1215

Leu Glu  Glu Asp Ala Ala Leu  Lys Gln Asn Ser Ser  Pro Pro Ser
    1220                1225                1230

Ser Leu  Asn Lys Asn Asn Ser  Ala Ile Asp Ser Gly  Ile Asn Leu
    1235                1240                1245

Thr Thr  Asp Thr Ser Lys Ser  Ala Thr Ser Ser Ser  Pro Gly Ser
    1250                1255                1260

Pro Ile  His Ser Leu Glu Thr  Ser Leu
    1265                1270
```

<210> SEQ ID NO 31
<211> LENGTH: 874
<212> TYPE: PRT
<213> ORGANISM: Homo sapiens

<400> SEQUENCE: 31

```
Met Gly Asp Met Ala Asn Ser Ser Ile Glu Phe His Pro Lys Pro Gln
1               5                   10                  15

Gln Gln Arg Asp Val Pro Gln Ala Gly Gly Phe Gly Cys Thr Leu Ala
            20                  25                  30

Glu Leu Arg Thr Leu Met Glu Leu Arg Gly Ala Glu Ala Leu Gln Lys
        35                  40                  45
```

```
Ile Glu Glu Ala Tyr Gly Asp Val Ser Gly Leu Cys Arg Arg Leu Lys
    50                  55                  60

Thr Ser Pro Thr Glu Gly Leu Ala Asp Asn Thr Asn Asp Leu Glu Lys
65                  70                  75                  80

Arg Arg Gln Ile Tyr Gly Gln Asn Phe Ile Pro Pro Lys Gln Pro Lys
                85                  90                  95

Thr Phe Leu Gln Leu Val Trp Glu Ala Leu Gln Asp Val Thr Leu Ile
                100                 105                 110

Ile Leu Glu Val Ala Ala Ile Val Ser Leu Gly Leu Ser Phe Tyr Ala
                115                 120                 125

Pro Pro Gly Glu Glu Ser Glu Ala Cys Gly Asn Val Ser Gly Gly Ala
        130                 135                 140

Glu Asp Glu Gly Glu Ala Glu Ala Gly Trp Ile Glu Gly Ala Ala Ile
145                 150                 155                 160

Leu Leu Ser Val Ile Cys Val Val Leu Val Thr Ala Phe Asn Asp Trp
                165                 170                 175

Ser Lys Glu Lys Gln Phe Arg Gly Leu Gln Ser Arg Ile Glu Gln Glu
                180                 185                 190

Gln Lys Phe Thr Val Ile Arg Asn Gly Gln Leu Leu Gln Val Pro Val
                195                 200                 205

Ala Ala Leu Val Val Gly Asp Ile Ala Gln Val Lys Tyr Gly Asp Leu
        210                 215                 220

Leu Pro Ala Asp Gly Val Leu Ile Gln Ala Asn Asp Leu Lys Ile Asp
225                 230                 235                 240

Glu Ser Ser Leu Thr Gly Glu Ser Asp His Val Arg Lys Ser Ala Asp
                245                 250                 255

Lys Asp Pro Met Leu Leu Ser Gly Thr His Val Met Glu Gly Ser Gly
                260                 265                 270

Arg Met Val Val Thr Ala Val Gly Val Asn Ser Gln Thr Gly Ile Ile
                275                 280                 285

Phe Thr Leu Leu Gly Ala Gly Gly Glu Glu Glu Lys Lys Asp Lys
        290                 295                 300

Lys Gly Lys Gln Gln Asp Gly Ala Met Glu Ser Ser Gln Thr Lys Ala
305                 310                 315                 320

Lys Lys Gln Asp Gly Ala Val Ala Met Glu Met Gln Pro Leu Lys Ser
                325                 330                 335

Ala Glu Gly Gly Glu Met Glu Glu Arg Glu Lys Lys Lys Ala Asn Ala
                340                 345                 350

Pro Lys Lys Glu Lys Ser Val Leu Gln Gly Lys Leu Thr Lys Leu Ala
        355                 360                 365

Val Gln Ile Gly Lys Ala Gly Leu Val Met Ser Ala Ile Thr Val Ile
        370                 375                 380

Ile Leu Val Leu Tyr Phe Val Ile Glu Thr Phe Val Val Glu Gly Arg
385                 390                 395                 400

Thr Trp Leu Ala Glu Cys Thr Pro Val Tyr Val Gln Tyr Phe Val Lys
                405                 410                 415

Phe Phe Ile Ile Gly Val Thr Val Leu Val Val Ala Val Pro Glu Gly
                420                 425                 430

Leu Pro Leu Ala Val Thr Ile Ser Leu Ala Tyr Ser Val Lys Lys Met
        435                 440                 445

Met Lys Asp Asn Asn Leu Val Arg His Leu Asp Ala Cys Glu Thr Met
    450                 455                 460
```

```
Gly Asn Ala Thr Ala Ile Cys Ser Asp Lys Thr Gly Thr Leu Thr Thr
465                 470                 475                 480

Asn Arg Met Thr Val Val Gln Ser Tyr Leu Gly Asp Thr His Tyr Lys
                485                 490                 495

Glu Ile Pro Ala Pro Ser Ala Leu Thr Pro Lys Ile Leu Asp Leu Leu
            500                 505                 510

Val His Ala Ile Ser Ile Asn Ser Ala Tyr Thr Thr Lys Ile Leu Pro
            515                 520                 525

Pro Glu Lys Glu Gly Ala Leu Pro Arg Gln Val Gly Asn Lys Thr Glu
        530                 535                 540

Cys Ala Leu Leu Gly Phe Val Leu Asp Leu Lys Arg Asp Phe Gln Pro
545                 550                 555                 560

Val Arg Glu Gln Ile Pro Glu Asp Lys Leu Tyr Lys Val Tyr Thr Phe
                565                 570                 575

Asn Ser Val Arg Lys Ser Met Ser Thr Val Ile Arg Met Pro Asp Gly
                580                 585                 590

Gly Phe Arg Leu Phe Ser Lys Gly Ala Ser Glu Ile Leu Leu Lys Lys
            595                 600                 605

Cys Thr Asn Ile Leu Asn Ser Asn Gly Glu Leu Arg Gly Phe Arg Pro
        610                 615                 620

Arg Asp Arg Asp Asp Met Val Arg Lys Ile Ile Glu Pro Met Ala Cys
625                 630                 635                 640

Asp Gly Leu Arg Thr Ile Cys Ile Ala Tyr Arg Asp Phe Ser Ala Gly
                645                 650                 655

Gln Glu Pro Asp Trp Asp Asn Glu Asn Glu Val Val Gly Asp Leu Thr
            660                 665                 670

Cys Ile Ala Val Val Gly Ile Glu Asp Pro Val Arg Pro Glu Val Pro
            675                 680                 685

Glu Ala Ile Arg Lys Cys Gln Arg Ala Gly Ile Thr Val Arg Met Val
        690                 695                 700

Thr Gly Asp Asn Ile Asn Thr Ala Arg Ala Ile Ala Ala Lys Cys Gly
705                 710                 715                 720

Ile Ile Gln Pro Gly Glu Asp Phe Leu Cys Leu Glu Gly Lys Glu Phe
                725                 730                 735

Asn Arg Arg Ile Arg Asn Glu Lys Gly Glu Ile Glu Gln Glu Arg Leu
            740                 745                 750

Asp Lys Val Trp Pro Lys Leu Arg Val Leu Ala Arg Ser Ser Pro Thr
            755                 760                 765

Asp Lys His Thr Leu Val Lys Gly Ile Ile Asp Ser Thr Thr Gly Glu
        770                 775                 780

Gln Arg Gln Val Val Ala Val Thr Gly Asp Gly Thr Asn Asp Gly Pro
785                 790                 795                 800

Ala Leu Lys Lys Ala Asp Val Gly Phe Ala Met Gly Ile Ala Gly Thr
                805                 810                 815

Asp Val Ala Lys Glu Ala Ser Asp Ile Ile Leu Thr Asp Asp Asn Phe
            820                 825                 830

Thr Ser Ile Val Lys Ala Val Met Trp Gly Arg Asn Val Tyr Asp Ser
            835                 840                 845

Ile Ser Lys Phe Leu Gln Phe Gln Leu Thr Val Asn Val Val Ala Val
        850                 855                 860

Ile Val Ala Phe Thr Gly Ala Cys Ile Thr
865                 870
```

-continued

```
<210> SEQ ID NO 32
<211> LENGTH: 1241
<212> TYPE: PRT
<213> ORGANISM: Homo sapiens

<400> SEQUENCE: 32

Met Thr Asn Pro Ser Asp Arg Val Leu Pro Ala Asn Ser Met Ala Glu
1               5                   10                  15

Ser Arg Glu Gly Asp Phe Gly Cys Thr Val Met Glu Leu Arg Lys Leu
            20                  25                  30

Met Glu Leu Arg Ser Arg Asp Ala Leu Thr Gln Ile Asn Val His Tyr
        35                  40                  45

Gly Gly Val Gln Asn Leu Cys Ser Arg Leu Lys Thr Ser Pro Val Glu
    50                  55                  60

Gly Leu Ser Gly Asn Pro Ala Asp Leu Glu Lys Arg Arg Gln Val Phe
65                  70                  75                  80

Gly His Asn Val Ile Pro Pro Lys Lys Pro Lys Thr Phe Leu Glu Leu
                85                  90                  95

Val Trp Glu Ala Leu Gln Asp Val Thr Leu Ile Ile Leu Glu Ile Ala
            100                 105                 110

Ala Ile Ile Ser Leu Val Leu Ser Phe Tyr Arg Pro Ala Gly Glu Glu
        115                 120                 125

Asn Glu Leu Cys Gly Gln Val Ala Thr Thr Pro Glu Asp Glu Asn Glu
    130                 135                 140

Ala Gln Ala Gly Trp Ile Glu Gly Ala Ala Ile Leu Phe Ser Val Ile
145                 150                 155                 160

Ile Val Val Leu Val Thr Ala Phe Asn Asp Trp Ser Lys Glu Lys Gln
                165                 170                 175

Phe Arg Gly Leu Gln Cys Arg Ile Glu Gln Glu Gln Lys Phe Ser Ile
            180                 185                 190

Ile Arg Asn Gly Gln Leu Ile Gln Leu Pro Val Ala Glu Ile Val Val
        195                 200                 205

Gly Asp Ile Ala Gln Val Lys Tyr Gly Asp Leu Leu Pro Ala Asp Gly
    210                 215                 220

Ile Leu Ile Gln Gly Asn Asp Leu Lys Ile Asp Glu Ser Ser Leu Thr
225                 230                 235                 240

Gly Glu Ser Asp His Val Lys Lys Ser Leu Asp Lys Asp Pro Met Leu
            245                 250                 255

Leu Ser Gly Thr His Val Met Glu Gly Ser Gly Arg Met Val Val Thr
            260                 265                 270

Ala Val Gly Val Asn Ser Gln Thr Gly Ile Ile Leu Thr Leu Leu Gly
        275                 280                 285

Val Asn Glu Asp Asp Glu Gly Glu Lys Lys Lys Gly Lys Lys Gln
    290                 295                 300

Gly Val Pro Glu Asn Arg Asn Lys Ala Lys Thr Gln Asp Gly Val Ala
305                 310                 315                 320

Leu Glu Ile Gln Pro Leu Asn Ser Gln Glu Gly Ile Asp Asn Glu Glu
            325                 330                 335

Lys Asp Lys Lys Ala Val Lys Val Pro Lys Lys Glu Lys Ser Val Leu
            340                 345                 350

Gln Gly Lys Leu Thr Arg Leu Ala Val Gln Ile Gly Lys Ala Gly Leu
        355                 360                 365

Leu Met Ser Ala Leu Thr Val Phe Ile Leu Ile Leu Tyr Phe Val Ile
    370                 375                 380
```

-continued

```
Asp Asn Phe Val Ile Asn Arg Arg Pro Trp Leu Pro Glu Cys Thr Pro
385             390             395             400

Ile Tyr Ile Gln Tyr Phe Val Lys Phe Phe Ile Ile Gly Ile Thr Val
            405             410             415

Leu Val Val Ala Val Pro Glu Gly Leu Pro Leu Ala Val Thr Ile Ser
        420             425             430

Leu Ala Tyr Ser Val Lys Lys Met Met Lys Asp Asn Asn Leu Val Arg
        435             440             445

His Leu Asp Ala Cys Glu Thr Met Gly Asn Ala Thr Ala Ile Cys Ser
    450             455             460

Asp Lys Thr Gly Thr Leu Thr Met Asn Arg Met Thr Val Val Gln Ala
465             470             475             480

Tyr Ile Gly Gly Ile His Tyr Arg Gln Ile Pro Ser Pro Asp Val Phe
            485             490             495

Leu Pro Lys Val Leu Asp Leu Ile Val Asn Gly Ile Ser Ile Asn Ser
        500             505             510

Ala Tyr Thr Ser Lys Ile Leu Pro Pro Glu Lys Glu Gly Gly Leu Pro
        515             520             525

Arg Gln Val Gly Asn Lys Thr Glu Cys Ala Leu Leu Gly Phe Val Thr
    530             535             540

Asp Leu Lys Gln Asp Tyr Gln Ala Val Arg Asn Glu Val Pro Glu Glu
545             550             555             560

Lys Leu Tyr Lys Val Tyr Thr Phe Asn Ser Val Arg Lys Ser Met Ser
            565             570             575

Thr Val Ile Arg Asn Pro Asn Gly Gly Phe Arg Met Tyr Ser Lys Gly
            580             585             590

Ala Ser Glu Ile Ile Leu Arg Lys Cys Asn Arg Ile Leu Asp Arg Lys
        595             600             605

Gly Glu Ala Val Pro Phe Lys Asn Lys Asp Arg Asp Asp Met Val Arg
    610             615             620

Thr Val Ile Glu Pro Met Ala Cys Asp Gly Leu Arg Thr Ile Cys Ile
625             630             635             640

Ala Tyr Arg Asp Phe Asp Asp Thr Glu Pro Ser Trp Asp Asn Glu Asn
            645             650             655

Glu Ile Leu Thr Glu Leu Thr Cys Ile Ala Val Val Gly Ile Glu Asp
            660             665             670

Pro Val Arg Pro Glu Val Pro Asp Ala Ile Ala Lys Cys Lys Gln Ala
        675             680             685

Gly Ile Thr Val Arg Met Val Thr Gly Asp Asn Ile Asn Thr Ala Arg
    690             695             700

Ala Ile Ala Thr Lys Cys Gly Ile Leu Thr Pro Gly Asp Asp Phe Leu
705             710             715             720

Cys Leu Glu Gly Lys Glu Phe Asn Arg Leu Ile Arg Asn Glu Lys Gly
            725             730             735

Glu Val Glu Gln Glu Lys Leu Asp Lys Ile Trp Pro Lys Leu Arg Val
        740             745             750

Leu Ala Arg Ser Ser Pro Thr Asp Lys His Thr Leu Val Lys Gly Ile
        755             760             765

Ile Asp Ser Thr Val Gly Glu His Arg Gln Val Val Ala Val Thr Gly
    770             775             780

Asp Gly Thr Asn Asp Gly Pro Ala Leu Lys Lys Ala Asp Val Gly Phe
785             790             795             800

Ala Met Gly Ile Ala Gly Thr Asp Val Ala Lys Glu Ala Ser Asp Ile
```

-continued

```
              805              810              815

Ile Leu Thr Asp Asp Asn Phe Thr Ser Ile Val Lys Ala Val Met Trp
              820              825              830

Gly Arg Asn Val Tyr Asp Ser Ile Ser Lys Phe Leu Gln Phe Gln Leu
         835              840              845

Thr Val Asn Val Val Ala Val Ile Val Ala Phe Thr Gly Ala Cys Ile
    850              855              860

Thr Gln Asp Ser Pro Leu Lys Ala Val Gln Met Leu Trp Val Asn Leu
865              870              875              880

Ile Met Asp Thr Phe Ala Ser Leu Ala Leu Ala Thr Glu Pro Pro Thr
              885              890              895

Glu Ser Leu Leu Lys Arg Arg Pro Tyr Gly Arg Asn Lys Pro Leu Ile
         900              905              910

Ser Arg Thr Met Met Lys Asn Ile Leu Gly His Ala Phe Tyr Gln Leu
         915              920              925

Ile Val Ile Phe Ile Leu Val Phe Ala Gly Glu Lys Phe Phe Asp Ile
    930              935              940

Asp Ser Gly Arg Lys Ala Pro Leu His Ser Pro Pro Ser Gln His Tyr
945              950              955              960

Thr Ile Val Phe Asn Thr Phe Val Leu Met Gln Leu Phe Asn Glu Ile
              965              970              975

Asn Ser Arg Lys Ile His Gly Glu Lys Asn Val Phe Ser Gly Ile Tyr
         980              985              990

Arg Asn Ile Ile Phe Cys Ser Val  Val Leu Gly Thr Phe  Ile Cys Gln
         995             1000              1005

Ile Phe  Ile Val Glu Phe Gly  Gly Lys Pro Phe Ser  Cys Thr Ser
    1010             1015              1020

Leu Ser  Leu Ser Gln Trp Leu  Trp Cys Leu Phe Ile  Gly Ile Gly
    1025             1030              1035

Glu Leu  Leu Trp Gly Gln Phe  Ile Ser Ala Ile Pro  Thr Arg Ser
    1040             1045              1050

Leu Lys  Phe Leu Lys Glu Ala  Gly His Gly Thr Thr  Lys Glu Glu
    1055             1060              1065

Ile Thr  Lys Asp Ala Glu Gly  Leu Asp Glu Ile Asp  His Ala Glu
    1070             1075              1080

Met Glu  Leu Arg Arg Gly Gln  Ile Leu Trp Phe Arg  Gly Leu Asn
    1085             1090              1095

Arg Ile  Gln Thr Gln Ile Asp  Val Ile Asn Thr Phe  Gln Thr Gly
    1100             1105              1110

Ala Ser  Phe Lys Gly Val Leu  Arg Arg Gln Asn Met  Gly Gln His
    1115             1120              1125

Leu Asp  Val Lys Leu Val Pro  Ser Ser Ser Tyr Ile  Lys Val Val
    1130             1135              1140

Lys Ala  Phe His Ser Ser Leu  His Glu Ser Ile Gln  Lys Pro Tyr
    1145             1150              1155

Asn Gln  Lys Ser Ile His Ser  Phe Met Thr His Pro  Glu Phe Ala
    1160             1165              1170

Ile Glu  Glu Glu Leu Pro Arg  Thr Pro Leu Leu Asp  Glu Glu Glu
    1175             1180              1185

Glu Glu  Asn Pro Asp Lys Ala  Ser Lys Phe Gly Thr  Arg Val Leu
    1190             1195              1200

Leu Leu  Asp Gly Glu Val Thr  Pro Tyr Ala Asn Thr  Asn Asn Asn
    1205             1210              1215
```

-continued

```
Ala Val  Asp Cys Asn Gln Val  Gln Leu Pro Gln Ser  Asp Ser Ser
    1220             1225             1230

Leu Gln  Ser Leu Glu Thr Ser  Val
    1235             1240

<210> SEQ ID NO 33
<211> LENGTH: 193
<212> TYPE: PRT
<213> ORGANISM: Homo sapiens

<400> SEQUENCE: 33

Gly Pro Ile Phe Asn Ala Ser Val His Ser Asp Thr Pro Ser Val Ile
1               5                   10                  15

Arg Gly Asp Leu Ile Lys Leu Phe Cys Ile Ile Thr Val Glu Gly Ala
            20                  25                  30

Ala Leu Asp Pro Asp Asp Met Ala Phe Asp Val Ser Trp Phe Ala Val
        35                  40                  45

His Ser Phe Gly Leu Asp Lys Ala Pro Val Leu Leu Ser Ser Leu Asp
    50                  55                  60

Arg Lys Gly Ile Val Thr Thr Ser Arg Arg Asp Trp Lys Ser Asp Leu
65                  70                  75                  80

Ser Leu Glu Arg Val Ser Val Leu Glu Phe Leu Leu Gln Val His Gly
            85                  90                  95

Ser Glu Asp Gln Asp Phe Gly Asn Tyr Tyr Cys Ser Val Thr Pro Trp
            100                 105                 110

Val Lys Ser Pro Thr Gly Ser Trp Gln Lys Glu Ala Glu Ile His Ser
        115                 120                 125

Lys Pro Val Phe Ile Thr Val Lys Met Asp Val Leu Asn Ala Phe Lys
    130                 135                 140

Tyr Pro Leu Leu Ile Gly Val Gly Leu Ser Thr Val Ile Gly Leu Leu
145                 150                 155                 160

Ser Cys Leu Ile Gly Tyr Cys Ser Ser His Trp Cys Cys Lys Lys Glu
            165                 170                 175

Val Gln Glu Thr Arg Arg Glu Arg Arg Arg Leu Met Ser Met Glu Met
            180                 185                 190

Asp

<210> SEQ ID NO 34
<211> LENGTH: 1021
<212> TYPE: PRT
<213> ORGANISM: Homo sapiens

<400> SEQUENCE: 34

Met Ala Gly Ile Ser Tyr Val Ala Ser Phe Phe Leu Leu Leu Thr Lys
1               5                   10                  15

Leu Ser Ile Gly Gln Arg Glu Val Thr Val Gln Lys Gly Pro Leu Phe
            20                  25                  30

Arg Ala Glu Gly Tyr Pro Val Ser Ile Gly Cys Asn Val Thr Gly His
            35                  40                  45

Gln Gly Pro Ser Glu Gln His Phe Gln Trp Ser Val Tyr Leu Pro Thr
    50                  55                  60

Asn Pro Thr Gln Glu Val Gln Ile Ile Ser Thr Lys Asp Ala Ala Phe
65                  70                  75                  80

Ser Tyr Ala Val Tyr Thr Gln Arg Val Arg Ser Gly Asp Val Tyr Val
            85                  90                  95
```

```
Glu Arg Val Gln Gly Asn Ser Val Leu Leu His Ile Ser Lys Leu Gln
              100                 105                 110

Met Lys Asp Ala Gly Glu Tyr Glu Cys His Thr Pro Asn Thr Asp Glu
              115                 120                 125

Lys Tyr Tyr Gly Ser Tyr Ser Ala Lys Thr Asn Leu Ile Val Ile Pro
          130                 135                 140

Asp Thr Leu Ser Ala Thr Met Ser Ser Gln Thr Leu Gly Lys Glu Glu
145                 150                 155                 160

Gly Glu Pro Leu Ala Leu Thr Cys Glu Ala Ser Lys Ala Thr Ala Gln
                  165                 170                 175

His Thr His Leu Ser Val Thr Trp Tyr Leu Thr Gln Asp Gly Gly Gly
              180                 185                 190

Ser Gln Ala Thr Glu Ile Ile Ser Leu Ser Lys Asp Phe Ile Leu Val
              195                 200                 205

Pro Gly Pro Leu Tyr Thr Glu Arg Phe Ala Ala Ser Asp Val Gln Leu
          210                 215                 220

Asn Lys Leu Gly Pro Thr Thr Phe Arg Leu Ser Ile Glu Arg Leu Gln
225                 230                 235                 240

Ser Ser Asp Gln Gly Gln Leu Phe Cys Glu Ala Thr Glu Trp Ile Gln
                  245                 250                 255

Asp Pro Asp Glu Thr Trp Met Phe Ile Thr Lys Lys Gln Thr Asp Gln
              260                 265                 270

Thr Thr Leu Arg Ile Gln Pro Ala Val Lys Asp Phe Gln Val Asn Ile
              275                 280                 285

Thr Ala Asp Ser Leu Phe Ala Glu Gly Lys Pro Leu Glu Leu Val Cys
          290                 295                 300

Leu Val Val Ser Ser Gly Arg Asp Pro Gln Leu Gln Gly Ile Trp Phe
305                 310                 315                 320

Phe Asn Gly Thr Glu Ile Ala His Ile Asp Ala Gly Gly Val Leu Gly
                  325                 330                 335

Leu Lys Asn Asp Tyr Lys Glu Arg Ala Ser Gln Gly Glu Leu Gln Val
              340                 345                 350

Ser Lys Leu Gly Pro Lys Ala Phe Ser Leu Lys Ile Phe Ser Leu Gly
              355                 360                 365

Pro Glu Asp Glu Gly Ala Tyr Arg Cys Val Val Ala Glu Val Met Lys
          370                 375                 380

Thr Arg Thr Gly Ser Trp Gln Val Leu Gln Arg Lys Gln Ser Pro Asp
385                 390                 395                 400

Ser His Val His Leu Arg Lys Pro Ala Ala Arg Ser Val Val Met Ser
                  405                 410                 415

Thr Lys Asn Lys Gln Gln Val Val Trp Glu Gly Glu Thr Leu Ala Phe
              420                 425                 430

Leu Cys Lys Ala Gly Gly Ala Glu Ser Pro Leu Ser Val Ser Trp Trp
          435                 440                 445

His Ile Pro Arg Asp Gln Thr Gln Pro Glu Phe Val Ala Gly Met Gly
          450                 455                 460

Gln Asp Gly Ile Val Gln Leu Gly Ala Ser Tyr Gly Val Pro Ser Tyr
465                 470                 475                 480

His Gly Asn Thr Arg Leu Glu Lys Met Asp Trp Ala Thr Phe Gln Leu
                  485                 490                 495

Glu Ile Thr Phe Thr Ala Ile Thr Asp Ser Gly Thr Tyr Glu Cys Arg
              500                 505                 510

Val Ser Glu Lys Ser Arg Asn Gln Ala Arg Asp Leu Ser Trp Thr Gln
```

-continued

```
              515                 520                 525
Lys Ile Ser Val Thr Val Lys Ser Leu Glu Ser Ser Leu Gln Val Ser
    530                 535                 540
Leu Met Ser Arg Gln Pro Gln Val Met Leu Thr Asn Thr Phe Asp Leu
545                 550                 555                 560
Ser Cys Val Val Arg Ala Gly Tyr Ser Asp Leu Lys Val Pro Leu Thr
                565                 570                 575
Val Thr Trp Gln Phe Gln Pro Ala Ser Ser His Ile Phe His Gln Leu
                580                 585                 590
Ile Arg Ile Thr His Asn Gly Thr Ile Glu Trp Gly Asn Phe Leu Ser
                595                 600                 605
Arg Phe Gln Lys Lys Thr Lys Val Ser Gln Ser Leu Phe Arg Ser Gln
    610                 615                 620
Leu Leu Val His Asp Ala Thr Glu Glu Glu Thr Gly Val Tyr Gln Cys
625                 630                 635                 640
Glu Val Glu Val Tyr Asp Arg Asn Ser Leu Tyr Asn Asn Arg Pro Pro
                645                 650                 655
Arg Ala Ser Ala Ile Ser His Pro Leu Arg Ile Ala Val Thr Leu Pro
                660                 665                 670
Glu Ser Lys Leu Lys Val Asn Ser Arg Ser Gln Val Gln Glu Leu Ser
                675                 680                 685
Ile Asn Ser Asn Thr Asp Ile Glu Cys Ser Ile Leu Ser Arg Ser Asn
    690                 695                 700
Gly Asn Leu Gln Leu Ala Ile Ile Trp Tyr Phe Ser Pro Val Ser Thr
705                 710                 715                 720
Asn Ala Ser Trp Leu Lys Ile Leu Glu Met Asp Gln Thr Asn Val Ile
                725                 730                 735
Lys Thr Gly Asp Glu Phe His Thr Pro Gln Arg Lys Gln Lys Phe His
                740                 745                 750
Thr Glu Lys Val Ser Gln Asp Leu Phe Gln Leu His Ile Leu Asn Val
                755                 760                 765
Glu Asp Ser Asp Arg Gly Lys Tyr His Cys Ala Val Glu Glu Trp Leu
    770                 775                 780
Leu Ser Thr Asn Gly Thr Trp His Lys Leu Gly Glu Lys Lys Ser Gly
785                 790                 795                 800
Leu Thr Glu Leu Lys Leu Lys Pro Thr Gly Ser Lys Val Arg Val Ser
                805                 810                 815
Lys Val Tyr Trp Thr Glu Asn Val Thr Glu His Arg Glu Val Ala Ile
                820                 825                 830
Arg Cys Ser Leu Glu Ser Val Gly Ser Ser Ala Thr Leu Tyr Ser Val
    835                 840                 845
Met Trp Tyr Trp Asn Arg Glu Asn Ser Gly Ser Lys Leu Leu Val His
    850                 855                 860
Leu Gln His Asp Gly Leu Leu Glu Tyr Gly Glu Glu Gly Leu Arg Arg
865                 870                 875                 880
His Leu His Cys Tyr Arg Ser Ser Thr Asp Phe Val Leu Lys Leu
                885                 890                 895
His Gln Val Glu Met Glu Asp Ala Gly Met Tyr Trp Cys Arg Val Ala
                900                 905                 910
Glu Trp Gln Leu His Gly His Pro Ser Lys Trp Ile Asn Gln Ala Ser
                915                 920                 925
Asp Glu Ser Gln Arg Met Val Leu Thr Val Leu Pro Ser Glu Pro Thr
    930                 935                 940
```

-continued

```
Leu Pro Ser Arg Ile Cys Ser Ser Ala Pro Leu Leu Tyr Phe Leu Phe
945                 950                 955                 960

Ile Cys Pro Phe Val Leu Leu Leu Leu Leu Leu Ile Ser Leu Leu Cys
                965                 970                 975

Leu Tyr Trp Lys Ala Arg Lys Leu Ser Thr Leu Arg Ser Asn Thr Arg
            980                 985                 990

Lys Glu Lys Ala Leu Trp Val Asp  Leu Lys Glu Ala Gly  Gly Val Thr
        995                 1000                 1005

Thr Asn  Arg Arg Glu Asp Glu  Glu Glu Asp Glu Gly  Asn
    1010                 1015                 1020

<210> SEQ ID NO 35
<211> LENGTH: 20
<212> TYPE: PRT
<213> ORGANISM: Homo sapiens

<400> SEQUENCE: 35

Met Ala Gly Ile Ser Tyr Val Ala Ser Phe Phe Leu Leu Leu Thr Lys
1                 5                 10                 15

Leu Ser Ile Gly
            20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cgttggcagt ccgccttaac                                                  20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
catagtcact gacgttgcag                                                  20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttgtggagct tgcaagcacc                                                  20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
```

-continued

```
gttctttatg tggagctcca                                                          20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tatcccttgc tgatcggcgt                                                          20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gctgcagtac ccgatgagac                                                          20

<210> SEQ ID NO 42
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu His Ser Ala Gly Gly Gly Gly Ser Asp Tyr Lys Asp Asp Asp
1               5                   10                  15

Lys Gly Gly Gly Gly Ser Leu Ser Asn Pro Ile Glu Ile Asp Phe Gln
            20                  25                  30

Thr Ser Gly Pro Ile Phe
        35

<210> SEQ ID NO 43
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu His Ser Ala Gly Gly Gly Gly Ser Asp Tyr Lys Asp Asp Asp
1               5                   10                  15

Lys Gly Gly Gly Gly Ser Ile Glu Ile Asp Phe Gln Thr Ser Gly Pro
            20                  25                  30

Ile Phe

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44
```

```
Glu His Ser Ala Gly Gly Gly Gly Ser Asp Tyr Lys Asp Asp Asp Asp
1               5                   10                  15

Lys Gly Gly Gly Gly Ser Phe Gln Thr Ser Gly Pro Ile Phe
            20                  25                  30

<210> SEQ ID NO 45
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu His Ser Ala Gly Gly Gly Gly Ser Asp Tyr Lys Asp Asp Asp Asp
1               5                   10                  15

Lys Gly Gly Gly Gly Ser Gly Pro Ile Phe
            20                  25

<210> SEQ ID NO 46
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Phe Ile Thr Val Lys Met Asp Thr Leu Asp Pro Arg Ser Phe Leu Leu
1               5                   10                  15

Arg Asn Pro Asn Asp Lys Tyr Glu Pro Phe Trp Glu Asp Glu Glu Lys
            20                  25                  30

Asn Glu Ser Gly Ser Asp Lys Thr His Thr
        35                  40

<210> SEQ ID NO 47
<211> LENGTH: 967
<212> TYPE: PRT
<213> ORGANISM: Homo sapiens

<400> SEQUENCE: 47

Met Ala Lys Gly Phe Tyr Ile Ser Lys Ser Leu Gly Ile Leu Gly Ile
1               5                   10                  15

Leu Leu Gly Val Ala Ala Val Cys Thr Ile Ile Ala Leu Ser Val Val
            20                  25                  30

Tyr Ser Gln Glu Lys Asn Lys Asn Ala Asn Ser Ser Pro Val Ala Ser
        35                  40                  45

Thr Thr Pro Ser Ala Ser Ala Thr Thr Asn Pro Ala Ser Ala Thr Thr
    50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140

Ser Gln Pro Pro Asp Ile Asp Lys Thr Glu Leu Val Glu Pro Thr Glu
```

-continued

```
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
                180                 185                 190

Phe Tyr Arg Ser Glu Tyr Met Glu Gly Asn Val Arg Lys Val Val Ala
            195                 200                 205

Thr Thr Gln Met Gln Ala Ala Asp Ala Arg Lys Ser Phe Pro Cys Phe
    210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
                260                 265                 270

Pro Lys Met Ser Thr Tyr Leu Leu Ala Phe Ile Val Ser Glu Phe Asp
            275                 280                 285

Tyr Val Glu Lys Gln Ala Ser Asn Gly Val Leu Ile Arg Ile Trp Ala
    290                 295                 300

Arg Pro Ser Ala Ile Ala Ala Gly His Gly Asp Tyr Ala Leu Asn Val
305                 310                 315                 320

Thr Gly Pro Ile Leu Asn Phe Phe Ala Gly His Tyr Asp Thr Pro Tyr
                325                 330                 335

Pro Leu Pro Lys Ser Asp Gln Ile Gly Leu Pro Asp Phe Asn Ala Gly
                340                 345                 350

Ala Met Glu Asn Trp Gly Leu Val Thr Tyr Arg Glu Asn Ser Leu Leu
            355                 360                 365

Phe Asp Pro Leu Ser Ser Ser Ser Asn Lys Glu Arg Val Val Thr
    370                 375                 380

Val Ile Ala His Glu Leu Ala His Gln Trp Phe Gly Asn Leu Val Thr
385                 390                 395                 400

Ile Glu Trp Trp Asn Asp Leu Trp Leu Asn Glu Gly Phe Ala Ser Tyr
                405                 410                 415

Val Glu Tyr Leu Gly Ala Asp Tyr Ala Glu Pro Thr Trp Asn Leu Lys
            420                 425                 430

Asp Leu Met Val Leu Asn Asp Val Tyr Arg Val Met Ala Val Asp Ala
            435                 440                 445

Leu Ala Ser Ser His Pro Leu Ser Thr Pro Ala Ser Glu Ile Asn Thr
    450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
            485                 490                 495

Lys Gln Gly Leu Ala Ser Tyr Leu His Thr Phe Ala Tyr Gln Asn Thr
            500                 505                 510

Ile Tyr Leu Asn Leu Trp Asp His Leu Gln Glu Ala Val Asn Asn Arg
            515                 520                 525

Ser Ile Gln Leu Pro Thr Thr Val Arg Asp Ile Met Asn Arg Trp Thr
    530                 535                 540

Leu Gln Met Gly Phe Pro Val Ile Thr Val Asp Thr Ser Thr Gly Thr
545                 550                 555                 560

Leu Ser Gln Glu His Phe Leu Leu Asp Pro Asp Ser Asn Val Thr Arg
                565                 570                 575
```

```
Pro Ser Glu Phe Asn Tyr Val Trp Ile Val Pro Ile Thr Ser Ile Arg
            580                 585                 590

Asp Gly Arg Gln Gln Gln Asp Tyr Trp Leu Ile Asp Val Arg Ala Gln
            595                 600                 605

Asn Asp Leu Phe Ser Thr Ser Gly Asn Glu Trp Val Leu Leu Asn Leu
            610                 615                 620

Asn Val Thr Gly Tyr Tyr Arg Val Asn Tyr Asp Glu Glu Asn Trp Arg
625                 630                 635                 640

Lys Ile Gln Thr Gln Leu Gln Arg Asp His Ser Ala Ile Pro Val Ile
                645                 650                 655

Asn Arg Ala Gln Ile Ile Asn Asp Ala Phe Asn Leu Ala Ser Ala His
            660                 665                 670

Lys Val Pro Val Thr Leu Ala Leu Asn Asn Thr Leu Phe Leu Ile Glu
            675                 680                 685

Glu Arg Gln Tyr Met Pro Trp Glu Ala Ala Leu Ser Ser Leu Ser Tyr
            690                 695                 700

Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
                725                 730                 735

Thr Asn Asn Trp Arg Glu Ile Pro Glu Asn Leu Met Asp Gln Tyr Ser
                740                 745                 750

Glu Val Asn Ala Ile Ser Thr Ala Cys Ser Asn Gly Val Pro Glu Cys
            755                 760                 765

Glu Glu Met Val Ser Gly Leu Phe Lys Gln Trp Met Glu Asn Pro Asn
            770                 775                 780

Asn Asn Pro Ile His Pro Asn Leu Arg Ser Thr Val Tyr Cys Asn Ala
785                 790                 795                 800

Ile Ala Gln Gly Gly Glu Glu Glu Trp Asp Phe Ala Trp Glu Gln Phe
                805                 810                 815

Arg Asn Ala Thr Leu Val Asn Glu Ala Asp Lys Leu Arg Ala Ala Leu
            820                 825                 830

Ala Cys Ser Lys Glu Leu Trp Ile Leu Asn Arg Tyr Leu Ser Tyr Thr
            835                 840                 845

Leu Asn Pro Asp Leu Ile Arg Lys Gln Asp Ala Thr Ser Thr Ile Ile
850                 855                 860

Ser Ile Thr Asn Asn Val Ile Gly Gln Gly Leu Val Trp Asp Phe Val
865                 870                 875                 880

Gln Ser Asn Trp Lys Lys Leu Phe Asn Asp Tyr Gly Gly Gly Ser Phe
                885                 890                 895

Ser Phe Ser Asn Leu Ile Gln Ala Val Thr Arg Arg Phe Ser Thr Glu
            900                 905                 910

Tyr Glu Leu Gln Gln Leu Glu Gln Phe Lys Lys Asp Asn Glu Glu Thr
            915                 920                 925

Gly Phe Gly Ser Gly Thr Arg Ala Leu Glu Gln Ala Leu Glu Lys Thr
            930                 935                 940

Lys Ala Asn Ile Lys Trp Val Lys Glu Asn Lys Glu Val Val Leu Gln
945                 950                 955                 960

Trp Phe Thr Glu Asn Ser Lys
                965
```

<210> SEQ ID NO 48
<211> LENGTH: 750

<212> TYPE: PRT
<213> ORGANISM: Homo sapiens

<400> SEQUENCE: 48

```
Met Gly Lys Ser Glu Ser Gln Met Asp Ile Thr Asp Ile Asn Thr Pro
1               5                   10                  15

Lys Pro Lys Lys Lys Gln Arg Trp Thr Pro Leu Glu Ile Ser Leu Ser
            20                  25                  30

Val Leu Val Leu Leu Leu Thr Ile Ile Ala Val Thr Met Ile Ala Leu
        35                  40                  45

Tyr Ala Thr Tyr Asp Asp Gly Ile Cys Lys Ser Ser Asp Cys Ile Lys
        50                  55                  60

Ser Ala Ala Arg Leu Ile Gln Asn Met Asp Ala Thr Thr Glu Pro Cys
65                  70                  75                  80

Thr Asp Phe Phe Lys Tyr Ala Cys Gly Gly Trp Leu Lys Arg Asn Val
                85                  90                  95

Ile Pro Glu Thr Ser Ser Arg Tyr Gly Asn Phe Asp Ile Leu Arg Asp
            100                 105                 110

Glu Leu Glu Val Val Leu Lys Asp Val Leu Gln Glu Pro Lys Thr Glu
        115                 120                 125

Asp Ile Val Ala Val Gln Lys Ala Lys Ala Leu Tyr Arg Ser Cys Ile
        130                 135                 140

Asn Glu Ser Ala Ile Asp Ser Arg Gly Gly Glu Pro Leu Leu Lys Leu
145                 150                 155                 160

Leu Pro Asp Ile Tyr Gly Trp Pro Val Ala Thr Glu Asn Trp Glu Gln
                165                 170                 175

Lys Tyr Gly Ala Ser Trp Thr Ala Glu Lys Ala Ile Ala Gln Leu Asn
            180                 185                 190

Ser Lys Tyr Gly Lys Lys Val Leu Ile Asn Leu Phe Val Gly Thr Asp
            195                 200                 205

Asp Lys Asn Ser Val Asn His Val Ile His Ile Asp Gln Pro Arg Leu
        210                 215                 220

Gly Leu Pro Ser Arg Asp Tyr Tyr Glu Cys Thr Gly Ile Tyr Lys Glu
225                 230                 235                 240

Ala Cys Thr Ala Tyr Val Asp Phe Met Ile Ser Val Ala Arg Leu Ile
                245                 250                 255

Arg Gln Glu Glu Arg Leu Pro Ile Asp Glu Asn Gln Leu Ala Leu Glu
            260                 265                 270

Met Asn Lys Val Met Glu Leu Glu Lys Glu Ile Ala Asn Ala Thr Ala
            275                 280                 285

Lys Pro Glu Asp Arg Asn Asp Pro Met Leu Leu Tyr Asn Lys Met Thr
        290                 295                 300

Leu Ala Gln Ile Gln Asn Asn Phe Ser Leu Glu Ile Asn Gly Lys Pro
305                 310                 315                 320

Phe Ser Trp Leu Asn Phe Thr Asn Glu Ile Met Ser Thr Val Asn Ile
                325                 330                 335

Ser Ile Thr Asn Glu Glu Asp Val Val Val Tyr Ala Pro Glu Tyr Leu
            340                 345                 350

Thr Lys Leu Lys Pro Ile Leu Thr Lys Tyr Ser Ala Arg Asp Leu Gln
        355                 360                 365

Asn Leu Met Ser Trp Arg Phe Ile Met Asp Leu Val Ser Ser Leu Ser
        370                 375                 380

Arg Thr Tyr Lys Glu Ser Arg Asn Ala Phe Arg Lys Ala Leu Tyr Gly
385                 390                 395                 400
```

-continued

```
Thr Thr Ser Glu Thr Ala Thr Trp Arg Arg Cys Ala Asn Tyr Val Asn
            405                 410                 415

Gly Asn Met Glu Asn Ala Val Gly Arg Leu Tyr Val Glu Ala Ala Phe
            420                 425                 430

Ala Gly Glu Ser Lys His Val Val Glu Asp Leu Ile Ala Gln Ile Arg
            435                 440                 445

Glu Val Phe Ile Gln Thr Leu Asp Asp Leu Thr Trp Met Asp Ala Glu
    450                 455                 460

Thr Lys Lys Arg Ala Glu Glu Lys Ala Leu Ala Ile Lys Glu Arg Ile
465                 470                 475                 480

Gly Tyr Pro Asp Asp Ile Val Ser Asn Asp Asn Lys Leu Asn Asn Glu
                485                 490                 495

Tyr Leu Glu Leu Asn Tyr Lys Glu Asp Glu Tyr Phe Glu Asn Ile Ile
            500                 505                 510

Gln Asn Leu Lys Phe Ser Gln Ser Lys Gln Leu Lys Lys Leu Arg Glu
            515                 520                 525

Lys Val Asp Lys Asp Glu Trp Ile Ser Gly Ala Ala Val Val Asn Ala
    530                 535                 540

Phe Tyr Ser Ser Gly Arg Asn Gln Ile Val Phe Pro Ala Gly Ile Leu
545                 550                 555                 560

Gln Pro Pro Phe Phe Ser Ala Gln Gln Ser Asn Ser Leu Asn Tyr Gly
                565                 570                 575

Gly Ile Gly Met Val Ile Gly His Glu Ile Thr His Gly Phe Asp Asp
            580                 585                 590

Asn Gly Arg Asn Phe Asn Lys Asp Gly Asp Leu Val Asp Trp Trp Thr
            595                 600                 605

Gln Gln Ser Ala Ser Asn Phe Lys Glu Gln Ser Gln Cys Met Val Tyr
    610                 615                 620

Gln Tyr Gly Asn Phe Ser Trp Asp Leu Ala Gly Gly Gln His Leu Asn
625                 630                 635                 640

Gly Ile Asn Thr Leu Gly Glu Asn Ile Ala Asp Asn Gly Gly Leu Gly
                645                 650                 655

Gln Ala Tyr Arg Ala Tyr Gln Asn Tyr Ile Lys Lys Asn Gly Glu Glu
            660                 665                 670

Lys Leu Leu Pro Gly Leu Asp Leu Asn His Lys Gln Leu Phe Phe Leu
            675                 680                 685

Asn Phe Ala Gln Val Trp Cys Gly Thr Tyr Arg Pro Glu Tyr Ala Val
    690                 695                 700

Asn Ser Ile Lys Thr Asp Val His Ser Pro Gly Asn Phe Arg Ile Ile
705                 710                 715                 720

Gly Thr Leu Gln Asn Ser Ala Glu Phe Ser Glu Ala Phe His Cys Arg
                725                 730                 735

Lys Asn Ser Tyr Met Asn Pro Glu Lys Lys Cys Arg Val Trp
            740                 745                 750
```

```
<210> SEQ ID NO 49
<211> LENGTH: 925
<212> TYPE: PRT
<213> ORGANISM: Homo sapiens

<400> SEQUENCE: 49
```

```
Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
```

-continued

```
                20              25              30

Arg Ser His Ala Ala Glu Ala Pro Gly Asp Pro Gln Ala Ala Ala Ser
            35              40              45

Leu Leu Ala Pro Met Asp Val Gly Glu Glu Pro Leu Glu Lys Ala Ala
        50              55              60

Arg Ala Arg Thr Ala Lys Asp Pro Asn Thr Tyr Lys Val Leu Ser Leu
65              70              75              80

Val Leu Ser Val Cys Val Leu Thr Thr Ile Leu Gly Cys Ile Phe Gly
                85              90              95

Leu Lys Pro Ser Cys Ala Lys Glu Val Lys Ser Cys Lys Gly Arg Cys
            100             105             110

Phe Glu Arg Thr Phe Gly Asn Cys Arg Cys Asp Ala Ala Cys Val Glu
            115             120             125

Leu Gly Asn Cys Cys Leu Asp Tyr Gln Glu Thr Cys Ile Glu Pro Glu
        130             135             140

His Ile Trp Thr Cys Asn Lys Phe Arg Cys Gly Glu Lys Arg Leu Thr
145             150             155             160

Arg Ser Leu Cys Ala Cys Ser Asp Asp Cys Lys Asp Lys Gly Asp Cys
                165             170             175

Cys Ile Asn Tyr Ser Ser Val Cys Gln Gly Glu Lys Ser Trp Val Glu
            180             185             190

Glu Pro Cys Glu Ser Ile Asn Glu Pro Gln Cys Pro Ala Gly Phe Glu
            195             200             205

Thr Pro Pro Thr Leu Leu Phe Ser Leu Asp Gly Phe Arg Ala Glu Tyr
        210             215             220

Leu His Thr Trp Gly Gly Leu Leu Pro Val Ile Ser Lys Leu Lys Lys
225             230             235             240

Cys Gly Thr Tyr Thr Lys Asn Met Arg Pro Val Tyr Pro Thr Lys Thr
            245             250             255

Phe Pro Asn His Tyr Ser Ile Val Thr Gly Leu Tyr Pro Glu Ser His
            260             265             270

Gly Ile Ile Asp Asn Lys Met Tyr Asp Pro Lys Met Asn Ala Ser Phe
            275             280             285

Ser Leu Lys Ser Lys Glu Lys Phe Asn Pro Glu Trp Tyr Lys Gly Glu
        290             295             300

Pro Ile Trp Val Thr Ala Lys Tyr Gln Gly Leu Lys Ser Gly Thr Phe
305             310             315             320

Phe Trp Pro Gly Ser Asp Val Glu Ile Asn Gly Ile Phe Pro Asp Ile
            325             330             335

Tyr Lys Met Tyr Asn Gly Ser Val Pro Phe Glu Glu Arg Ile Leu Ala
            340             345             350

Val Leu Gln Trp Leu Gln Leu Pro Lys Asp Glu Arg Pro His Phe Tyr
            355             360             365

Thr Leu Tyr Leu Glu Glu Pro Asp Ser Ser Gly His Ser Tyr Gly Pro
        370             375             380

Val Ser Ser Glu Val Ile Lys Ala Leu Gln Arg Val Asp Gly Met Val
385             390             395             400

Gly Met Leu Met Asp Gly Leu Lys Glu Leu Asn Leu His Arg Cys Leu
            405             410             415

Asn Leu Ile Leu Ile Ser Asp His Gly Met Glu Gln Gly Ser Cys Lys
            420             425             430

Lys Tyr Ile Tyr Leu Asn Lys Tyr Leu Gly Asp Val Lys Asn Ile Lys
            435             440             445
```

```
Val Ile Tyr Gly Pro Ala Ala Arg Leu Arg Pro Ser Asp Val Pro Asp
    450             455             460

Lys Tyr Tyr Ser Phe Asn Tyr Glu Gly Ile Ala Arg Asn Leu Ser Cys
465             470             475             480

Arg Glu Pro Asn Gln His Phe Lys Pro Tyr Leu Lys His Phe Leu Pro
                485             490             495

Lys Arg Leu His Phe Ala Lys Ser Asp Arg Ile Glu Pro Leu Thr Phe
            500             505             510

Tyr Leu Asp Pro Gln Trp Gln Leu Ala Leu Asn Pro Ser Glu Arg Lys
        515             520             525

Tyr Cys Gly Ser Gly Phe His Gly Ser Asp Asn Val Phe Ser Asn Met
    530             535             540

Gln Ala Leu Phe Val Gly Tyr Gly Pro Gly Phe Lys His Gly Ile Glu
545             550             555             560

Ala Asp Thr Phe Glu Asn Ile Glu Val Tyr Asn Leu Met Cys Asp Leu
                565             570             575

Leu Asn Leu Thr Pro Ala Pro Asn Asn Gly Thr His Gly Ser Leu Asn
            580             585             590

His Leu Leu Lys Asn Pro Val Tyr Thr Pro Lys His Pro Lys Glu Val
        595             600             605

His Pro Leu Val Gln Cys Pro Phe Thr Arg Asn Pro Arg Asp Asn Leu
    610             615             620

Gly Cys Ser Cys Asn Pro Ser Ile Leu Pro Ile Glu Asp Phe Gln Thr
625             630             635             640

Gln Phe Asn Leu Thr Val Ala Glu Glu Lys Ile Ile Lys His Glu Thr
                645             650             655

Leu Pro Tyr Gly Arg Pro Arg Val Leu Gln Lys Glu Asn Thr Ile Cys
            660             665             670

Leu Leu Ser Gln His Gln Phe Met Ser Gly Tyr Ser Gln Asp Ile Leu
        675             680             685

Met Pro Leu Trp Thr Ser Tyr Thr Val Asp Arg Asn Asp Ser Phe Ser
    690             695             700

Thr Glu Asp Phe Ser Asn Cys Leu Tyr Gln Asp Phe Arg Ile Pro Leu
705             710             715             720

Ser Pro Val His Lys Cys Ser Phe Tyr Lys Asn Asn Thr Lys Val Ser
                725             730             735

Tyr Gly Phe Leu Ser Pro Pro Gln Leu Asn Lys Asn Ser Ser Gly Ile
            740             745             750

Tyr Ser Glu Ala Leu Leu Thr Thr Asn Ile Val Pro Met Tyr Gln Ser
        755             760             765

Phe Gln Val Ile Trp Arg Tyr Phe His Asp Thr Leu Leu Arg Lys Tyr
    770             775             780

Ala Glu Glu Arg Asn Gly Val Asn Val Val Ser Gly Pro Val Phe Asp
785             790             795             800

Phe Asp Tyr Asp Gly Arg Cys Asp Ser Leu Glu Asn Leu Arg Gln Lys
                805             810             815

Arg Arg Val Ile Arg Asn Gln Glu Ile Leu Ile Pro Thr His Phe Phe
            820             825             830

Ile Val Leu Thr Ser Cys Lys Asp Thr Ser Gln Thr Pro Leu His Cys
        835             840             845

Glu Asn Leu Asp Thr Leu Ala Phe Ile Leu Pro His Arg Thr Asp Asn
    850             855             860
```

```
Ser Glu Ser Cys Val His Gly Lys His Asp Ser Ser Trp Val Glu Glu
865             870             875             880

Leu Leu Met Leu His Arg Ala Arg Ile Thr Asp Val Glu His Ile Thr
                885             890             895

Gly Leu Ser Phe Tyr Gln Gln Arg Lys Glu Pro Val Ser Asp Ile Leu
            900             905             910

Lys Leu Lys Thr His Leu Pro Thr Phe Ser Gln Glu Asp
        915             920             925

<210> SEQ ID NO 50
<211> LENGTH: 923
<212> TYPE: PRT
<213> ORGANISM: Homo sapiens

<400> SEQUENCE: 50

Met Glu Arg Gly Leu Pro Leu Leu Cys Ala Val Leu Ala Leu Val Leu
1               5               10              15

Ala Pro Ala Gly Ala Phe Arg Asn Asp Lys Cys Gly Asp Thr Ile Lys
            20              25              30

Ile Glu Ser Pro Gly Tyr Leu Thr Ser Pro Gly Tyr Pro His Ser Tyr
        35              40              45

His Pro Ser Glu Lys Cys Glu Trp Leu Ile Gln Ala Pro Asp Pro Tyr
    50              55              60

Gln Arg Ile Met Ile Asn Phe Asn Pro His Phe Asp Leu Glu Asp Arg
65              70              75              80

Asp Cys Lys Tyr Asp Tyr Val Glu Val Phe Asp Gly Glu Asn Glu Asn
            85              90              95

Gly His Phe Arg Gly Lys Phe Cys Gly Lys Ile Ala Pro Pro Pro Val
            100             105             110

Val Ser Ser Gly Pro Phe Leu Phe Ile Lys Phe Val Ser Asp Tyr Glu
            115             120             125

Thr His Gly Ala Gly Phe Ser Ile Arg Tyr Glu Ile Phe Lys Arg Gly
        130             135             140

Pro Glu Cys Ser Gln Asn Tyr Thr Thr Pro Ser Gly Val Ile Lys Ser
145             150             155             160

Pro Gly Phe Pro Glu Lys Tyr Pro Asn Ser Leu Glu Cys Thr Tyr Ile
            165             170             175

Val Phe Val Pro Lys Met Ser Glu Ile Ile Leu Glu Phe Glu Ser Phe
            180             185             190

Asp Leu Glu Pro Asp Ser Asn Pro Pro Gly Gly Met Phe Cys Arg Tyr
            195             200             205

Asp Arg Leu Glu Ile Trp Asp Gly Phe Pro Asp Val Gly Pro His Ile
        210             215             220

Gly Arg Tyr Cys Gly Gln Lys Thr Pro Gly Arg Ile Arg Ser Ser Ser
225             230             235             240

Gly Ile Leu Ser Met Val Phe Tyr Thr Asp Ser Ala Ile Ala Lys Glu
            245             250             255

Gly Phe Ser Ala Asn Tyr Ser Val Leu Gln Ser Ser Val Ser Glu Asp
            260             265             270

Phe Lys Cys Met Glu Ala Leu Gly Met Glu Ser Gly Glu Ile His Ser
            275             280             285

Asp Gln Ile Thr Ala Ser Ser Gln Tyr Ser Thr Asn Trp Ser Ala Glu
        290             295             300

Arg Ser Arg Leu Asn Tyr Pro Glu Asn Gly Trp Thr Pro Gly Glu Asp
305             310             315             320
```

```
Ser Tyr Arg Glu Trp Ile Gln Val Asp Leu Gly Leu Leu Arg Phe Val
            325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
            355                 360                 365

Trp Ile Thr Ile Lys Glu Gly Asn Lys Pro Val Leu Phe Gln Gly Asn
    370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
            405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
    450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
            485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
    530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
            565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Asp Gln Ala
            595                 600                 605

Asn Cys His Ser Gly Thr Gly Asp Asp Phe Gln Leu Thr Gly Gly Thr
    610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
            645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
            725                 730                 735
```

-continued

```
Arg Val Lys Leu Arg Tyr Gln Lys Pro Glu Glu Tyr Asp Gln Leu Val
            740             745                 750

Trp Met Ala Ile Gly His Gln Gly Asp His Trp Lys Glu Gly Arg Val
            755             760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
                820                 825                 830

Tyr Glu Gly Glu Gly Glu Gly Asp Lys Asn Ile Ser Arg Lys Pro Gly
            835                 840                 845

Asn Val Leu Lys Thr Leu Asp Pro Ile Leu Ile Thr Ile Ile Ala Met
    850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910

Lys Leu Asn Thr Gln Ser Thr Tyr Ser Glu Ala
            915                 920
```

MEMBRANE PROTEIN SCAFFOLDS FOR EXOSOME ENGINEERING

1. CROSS-REFERENCE TO RELATED APPLICATIONS

This PCT application claims the priority benefit of U.S. Provisional Application Nos. 62/801,065, filed Feb. 4, 2019; 62/801,636, filed Feb. 5, 2019; and 62/851,581, filed May 22, 2019, each of which is herein incorporated by reference in its entirety.

2. REFERENCE TO SEQUENCE LISTING SUBMITTED ELECTRONICALLY VIA EFS-WEB

The content of the electronically submitted sequence listing in ASCII text file (Name: 4000_031PC03_SeqListing_ST25.txt; Size: 205,964; and Date of Creation: Feb. 4, 2020) filed with the application is herein incorporated by reference in its entirety.

3. FIELD OF THE DISCLOSURE

The present disclosure relates to engineered extracellular vesicles (EVs) (e.g., exosomes) that comprise one or more exogenous proteins that are not naturally expressed in cells from which the EVs are produced (i.e., heterologous exosomal vesicle proteins), and methods of producing and using such EVs.

4. BACKGROUND OF THE DISCLOSURE

Extracellular vesicles (EVs) (e.g., exosomes) are important mediators of intercellular communication. They are also important biomarkers in the diagnosis and prognosis of many diseases, such as cancer. As drug delivery vehicles, EVs (e.g., exosomes) offer many advantages over traditional drug delivery methods as a new treatment modality in many therapeutic areas.

The use of EVs (e.g., exosomes) for therapeutic purposes requires that EVs (e.g., exosomes) be free or mostly free of impurities including but not limited to contaminant proteins, DNA, carbohydrates, and lipids. Current purification methods do not offer sufficient selectivity to remove significant amounts of these impurities so additional processes are desired to improve purity.

Furthermore, as EVs (e.g., exosomes) become more frequently used in the treatment of human disease, they may struggle to meet clinical expectations because of heterogeneity in their physicochemical parameters that confer molecular targeting, immune evasion, and controlled drug release. This is mainly due to the heterogeneity and complexity of EV (e.g., exosome) properties (e.g., composition, size, shape, rigidity, surface charge, hydrophilicity, stability, and ligand type and density), payload properties (e.g., drug type, solubility, loading, potency, dosing, immune response, and release kinetics), and in vivo physiological barriers to EV (e.g., exosome) trafficking (e.g., immune surveillance, particle extravasation, tissue targeting, tissue penetration, and cellular uptake). Although a considerable amount of effort has been made, effective methods for obtaining discrete sub-populations of therapeutic EVs (e.g., exosomes) with desired properties, e.g., EVs (e.g., exosomes) containing therapeutic payloads and having appropriate targeting moieties, are not yet readily available.

Suitable methods for generating, isolating and purifying discrete sub-populations of EVs (e.g., exosomes) are needed to better enable therapeutic use and other applications of EV (e.g., exosome)-based technologies.

5. BRIEF SUMMARY OF THE DISCLOSURE

An aspect of the present disclosure relates to novel EV (e.g., exosome) compositions, methods for preparing these compositions, and therapeutic methods of using the compositions. Specifically, the compositions and methods relate to extracellular vesicles comprising a heterologous extracellular vesicle protein (HEVP) or a fragment thereof, wherein the extracellular vesicle is produced from a producer cell which does not naturally express the HEVP, and wherein the HEVP is produced naturally by a donor cell. In addition, the present disclosure relates to the use of HEVPs that are enriched on the surface of the donor EVs (e.g., exosomes). Examples of HEVPs described herein include CD13, MME, ENPP1, and NRP1, particularly as recombinantly expressed on the surface of EVs (e.g., exosomes) produced by non-mesenchymal cells (e.g., by CHO cells in the case of CD13, MME, ENPP1 and/or NRP1; and/or by HEK cells in the case of CD13, MME, and NRP1). These HEVP proteins can be used to engineer EVs (e.g., exosomes) as described in U.S. Pat. No. 10,195,290 (incorporated by reference herein in its entirety).

In one embodiment, then, the disclosure provides an extracellular vesicle comprising at least one heterologous extracellular vesicle protein (HEVP) or a fragment thereof, wherein the extracellular vesicle is produced from a producer cell which does not naturally express the HEVP, and wherein the HEVP is produced naturally by a donor cell. In a certain embodiment, the extracellular vesicle comprises 2, 3, 4, 5, 6, 7, 8, 9 or 10 heterologous extracellular vesicle proteins (HEVPs) or fragments thereof, wherein the extracellular vesicle is produced from a producer cell which does not naturally express the HEVPs, and wherein the HEVPs are produced naturally by a donor cell. In general, unless otherwise specified, the references to "at least one HEVP" and "2, 3, 4, 5 . . . HEVPs" indicate the presence (if greater than one) of distinct types or varieties of HEVPs (e.g., HEVPs with different amino acid sequences), and not to the amount of HEVP molecules (of any type) on the EV (e.g., exosome), which will be much larger.

In certain embodiments, the level of the at least one HEVP in the EVs (e.g., exosomes) produced by the donor cell is equal to or greater than about 20, about 80, about 125, or about 200 peptide spectral matches (PSM) measured using liquid chromatography with tandem mass spectrometry (LC-MS/MS). In some aspects, the at least one HEVP is produced naturally by a donor cell which produces exosomes, and wherein the level of HEVP in the exosomes produced by the donor cell is equal to or greater than about 20 peptide spectral matches (PSM) measured using liquid chromatography with tandem mass spectrometry (LC-MS/MS). In some aspects, the at least one HEVP is produced naturally by a donor cell which produces exosomes, and wherein the level of HEVP in the exosomes produced by the donor cell is equal to or greater than about 80 peptide spectral matches (PSM) measured using LC-MS/MS. In some aspects, the at least one HEVP is produced naturally by a donor cell which produces exosomes, and wherein the level of HEVP in the exosomes produced by the donor cell is equal to or greater than about 125 peptide spectral matches (PSM) measuring using LC-MS/MS. In some aspects, the at least one HEVP is produced naturally by a donor cell which produces exosomes, and wherein the level of HEVP in the exosomes produced by the donor cell is equal to or greater than about 170 peptide spectral matches (PSM) measuring using LC-MS/MS. In some aspects, the at least one HEVP is produced naturally by a donor cell which produces exosomes, and wherein the level of HEVP in the exosomes produced by the donor cell is equal to or greater than about 200 peptide spectral matches (PSM) measuring using LC-MS/MS. In some aspects, the at least one HEVP is produced naturally by a donor cell which produces exosomes, and wherein the level of HEVP in the exosomes produced by the donor cell is equal to or greater than about 700 peptide spectral matches (PSM) measuring using LC-MS/MS. In some aspects, the at least one HEVP is produced naturally by a donor cell which produces exosomes, and wherein the level of HEVP in the exosomes produced by the donor cell is about 177 peptide spectral matches (PSM) measuring using LC-MS/MS. In some aspects, the at least one HEVP is produced naturally by a donor cell which produces exosomes, and wherein the level of HEVP in the exosomes produced by the donor cell is about 742 peptide spectral matches (PSM) measuring using LC-MS/MS.

In certain embodiments, the level of the at least one HEVP in the EVs (e.g., exosomes) produced by the donor cell is between about 20 and about 80 PSM, or between about 80 and about 200 PSM measured using LC-MS/MS. In some aspects, the level of the at least one HEVP in the exosomes produced by the donor cell is between 20 and 80 peptide spectral matches (PSM) measured using LC-MS/MS. In some aspects, the level of the at least one HEVP in the exosomes produced by the donor cell is between 80 and 200 peptide spectral matches (PSM) measured using LC-MS/MS. In some aspects, the level of the at least one HEVP in the exosomes produced by the donor cell is between about 150 and about 750 peptide spectral matches (PSM) measured using LC-MS/MS. In certain embodiments, the at least one HEVP is produced naturally by a donor cell which produces exosomes, and wherein the level of the at least one HEVP in the exosomes produced by the donor cell is equal to or greater than about 5% of the total protein content of the exosomes produced by the donor cell.

Additional embodiments include extracellular vesicles such as those described in the Summary above, wherein the at least one HEVP or fragment thereof is a fusion protein. As used herein, the term "fusion protein" refers to two or more proteins that are attached to each other. As described herein, in some aspects, a fusion protein comprises a HEVP and an exogenous biologically active molecule (e.g., antigen, targeting moiety, adjuvant, and/or immune modulator). In some aspects, the two or more proteins (e.g., HEVP and an exogenous biologically active molecule) can be fused to one another. In some aspects, the two or more proteins (e.g., HEVP and an exogenous biologically active molecule) can be attached to each other via a linker. In related embodiments, the at least one HEVP or fragment thereof is modified by the addition of a functional moiety. In related embodiments, the functional moiety has affinity to a binding agent. In related embodiments, the functional moiety is an affinity tag. In certain embodiments, the affinity tag is a peptide. In other related embodiments, the functional moiety is a therapeutic compound. In still other related embodiments, the therapeutic compound is selected from the group consisting of a natural peptide, a recombinant peptide, a synthetic peptide, and any combination thereof. In still other related embodiments, the therapeutic compound is selected from the group consisting of nucleotides, amino acids, lipids, carbohydrates, small molecules, and any combination thereof. In still other related embodiments, the therapeutic compound is an antibody or a fragment thereof. In additional related embodiments, the therapeutic compound is an enzyme, a ligand, a receptor, or a fragment thereof. In other related embodiments, the functional moiety is a targeting moiety which, in some embodiments, can be specific to (e.g.,) an organ, a tissue, or a cell. In related embodiments, wherein the at least one HEVP is a fusion protein, the fusion protein comprises a linker. In related embodiments, the EVs (e.g., exosomes) described above further comprise a linker between the at least one HEVP or fragment thereof and a functional moiety attached thereto. In related embodiments, the linker is a flexible linker or a rigid linker. In other related embodiments, the linker is a straight-chain carbon linker, a branched-chain carbon linker, a heterocyclic carbon linker, or a peptide linker. In other related embodiments, the linker is a cleavable linker.

The present disclosure also includes the extracellular vesicles described in the Summary above, wherein the producer cell is selected from the group consisting of human embryonic kidney (HEK) cell, Chinese hamster ovary (CHO) cell, metastatic breast-231 (MB-231) cell, Raji cell, primary human embryonic retinal sixth generation (PER.C6) cell, CEVEC's amniocyte production (CAP) cell, mesenchymal stem cell (MSC), and any combination thereof. In related embodiments, the at least one HEVP is selected from the group consisting of a lung fibroblast EVP, an aortic endothelium cell EVP, an acute myeloid leukemia cell EVP, a monocyte EVP, a B-cell lymphoma EVP, a macrophage EVP, a brain endothelium cell EVP, a mesenchymal cell EVP, and any combination thereof. In related embodiments, the at least one HEVP is a human EVP, mouse EVP, rat VEP, dog EVP, or monkey EVP. In still other related embodiments, the at least one HEVP is selected from the group consisting of CD13, MME, ENPP1, and NRP1, or a fragment thereof. In still other related embodiments, the at least one HEVP is selected from the group consisting of CD13, MME, ENPP1, and NRP1, or a fragment thereof, and the producer cell is a CHO cell. In another related embodiment, the at least one HEVP is selected from the group consisting of CD13, MME, and NRP1, or a fragment thereof and the producer cell is a CHO cell or an HEK cell.

In another related embodiment, the at least one HEVP in an extracellular vesicle described above is selected from the group consisting of PTGFRN, BSG, IGSF3, ITGB1, ITGA4, SLC3A2, ATP transporter, or a fragment thereof, and any combination thereof. In some aspects, the producer cell is a cell which does not naturally produce these proteins. In a related embodiment, an extracellular vesicle as described in the Summary above further comprises an EVP selected from the group consisting of PTGFRN, BSG, IGSF3, ITGB1, ITGA4, SLC3A2, ATP transporter, or a fragment thereof, and any combination thereof.

In related embodiments, the disclosure provides an extracellular vesicle (e.g., exosome) disclosed herein, wherein the producer cell is a non-human cell and wherein the at least one HEVP is a human HEVP. Alternatively, the producer cell can be a human cell and the at least one HEVP is a non-human HEVP.

Additional related embodiments include pharmaceutical formulations comprising any of the extracellular vesicle described above. Another aspect of the present disclosure includes a kit comprising an extracellular vesicle or pharmaceutical formulation described in the Summary above, wherein the extracellular vesicle or pharmaceutical formulation is contained in a container or package, and wherein the kit further comprises instructions describing a recommended use of the extracellular vesicle or pharmaceutical formulation.

The present disclosure also includes methods for treating a patient in need thereof, comprising administering to the patient an effective amount of the any of the extracellular vesicle or pharmaceutical formation described above.

The present disclosure further provides a method of expressing a non-naturally occurring protein in an EV derived from a cell, comprising transfecting a nucleic acid encoding at least one heterologous extracellular vesicle protein (HEVP) or a fragment thereof in the cell and isolating an EV comprising the HEVP or a fragment thereof from the cell, wherein the HEVP is not naturally occurring in the EV derived from the cell. In certain aspects, the EV comprises any of the EVs disclosed in the present disclosure. In some aspects, method of expressing a non-naturally occurring protein in an EV can further comprise characterizing the HEVP of the EV.

The HEVPs described herein can be used in various embodiments of the present disclosure. One aspect of the present disclosure relates to generating a fusion protein by conjugating the HEVP with a functional compound (e.g., exogenous biologically active molecules disclosed herein), and producing an engineered EV (e.g., exosome) containing the modified protein on the surface. For example, a native full-length or a biologically active fragment of the therapeutic protein can be transported to the surface of EVs (e.g., exosomes) by being conjugated to the HEVP-enriched proteins or fragments thereof. The methods using the HEVPs described herein are believed to be, in some cases, improved in certain aspects relative to other related systems (e.g., Lamp2B, PDGFR, lactadherin CD9, CD63 and/or CD81, or fragments thereof).

Another aspect of the present disclosure relates to purification of an EV (e.g., exosome) by affinity purification from a heterogeneous solution such as cell culture media or plasma using the HEVPs. Some embodiments relate to isolation of a sub-population of EVs (e.g., exosomes) from the total EVs (e.g., exosomes) by using surface markers specific to a sub-population of EVs (e.g., exosomes).

Another aspect of the present disclosure relates to methods of removing EVs (e.g., exosomes) from a sample when EVs (e.g., exosomes) are a contaminating product. For example, natural or engineered viruses can be purified from contaminating EVs (e.g., exosomes). The HEVPs described herein thus can be used to selectively remove EVs (e.g., exosomes) from biological processes where other particles of similar size, shape, and/or charge are the desirable product.

Another aspect of the present disclosure relates to generation or use of a surface-engineered EV (e.g., exosome) designed for more efficient affinity purification, or for presentation of a targeting moiety or a therapeutically relevant protein (e.g., exogenous biologically active molecules disclosed herein) on the surface. For example, the EV (e.g., exosome) surfaces can be modified to contain the full-length HEVPs and/or a fragment or a modified protein of the HEVPs on the surface at a higher density.

The present disclosure further relates to a producer cell or a method of generating the producer cell for producing such a surface-engineered EV (e.g., exosome). An exogenous polynucleotide (e.g., encoding a HEVP) can be introduced transiently or stably into a producer cell to make the producer cell to generate a surface-engineered EV (e.g., exosome).

Specifically, an aspect of the present disclosure relates to a method of isolating an EV (e.g., exosome), comprising the steps of: (1) providing a sample comprising the EV (e.g., exosome); (2) contacting the sample with a binding agent having affinity to a target protein, wherein the target protein comprises a HEVP (e.g., CD13, MME, ENPP1, or NRP1, or a fragment or a variant thereof); and (3) isolating the EV (e.g., exosome) based on a binding between the target protein and the binding agent.

In some embodiments, the sample is obtained from a cell grown in vitro, optionally wherein the cell is an HEK293 cell, a Chinese hamster ovary (CHO) cell, or a mesenchymal stem cell (MSC). In some embodiments, the sample is obtained from a body fluid of a subject.

In some embodiments, the cell is genetically modified to express the target protein. In some embodiments, the cell comprises an expression plasmid encoding the target protein. In some embodiments, the cell is genetically modified to comprise an exogenous sequence expressing a tag having affinity to the binding agent, wherein the exogenous sequence is inserted into a genome of the cell. In some embodiments, the exogenous sequence is inserted in a genomic site located at 3' or 5' end of an endogenous sequence encoding a HEVP (e.g., CD13, MME, ENPP1, or NRP1). In some embodiments, the endogenous sequence does not encode IGSF8. In some embodiments, the exogenous sequence is inserted in a genomic site located within an endogenous sequence encoding a HEVP (e.g., CD13, MME, ENPP1, or NRP1).

In some embodiments, the target protein is a fusion protein comprising the tag, and CD13, MME, ENPP1, or NRP1, or a fragment or a variant thereof. In some embodiments, the EV (e.g., exosome) comprises the target protein. In some embodiments, the target protein is not IGSF8 or a fragment or modification thereof. In some embodiments, the cell is genetically modified to have a reduced expression of ADAM10.

In some embodiments, the EV (e.g., exosome) comprises the target protein. In some embodiments, the target protein is selected from CD13, MME, ENPP1, and NRP1. In some embodiments, the target protein comprises a fragment or a variant of CD13, MME, ENPP1, or NRP1. In some embodiments, the target protein comprises a polypeptide of SEQ ID NO: 33. In some embodiments, the target protein is a fusion protein comprising CD13, MME, ENPP1, or NRP1 or a fragment or a variant thereof, and an affinity tag, wherein the affinity tag has affinity to the binding agent. In some embodiments, the target protein does not comprise IGSF8 or a fragment or modification thereof.

In some embodiments, the binding agent comprises an immunoglobulin, a protein, a peptide, or a small molecule. In some embodiments, the binding agent is attached to a solid support, optionally wherein the solid support comprises a porous agarose bead, a microtiter plate, a magnetic bead, or a membrane.

In some embodiments, the solid support forms a chromatography column. In some embodiments, the step of contacting the sample with the binding agent is performed by applying the sample to the chromatography column.

In some embodiments, the method further comprises the steps of: (1) contacting a subset of the sample with a different binding agent having affinity to a different target protein; and (2) isolating the EV (e.g., exosome) based on a binding between the different target protein and the different binding agent. In some embodiments, the different target protein comprises CD13, MME, ENPP1, or NRP1 or a fragment or a variant thereof. In some aspects, the target protein comprises CD13 (or a fragment or variant thereof). In some aspects, the target protein comprises MME (or a fragment or variant thereof). In some aspects, the target protein comprises ENPP1 (or a fragment or variant thereof). In some aspects, the target protein comprises NRP1 (or a fragment or variant thereof). In some embodiments, the different target protein comprises a polypeptide of SEQ ID NO: 33.

Another aspect of the present disclosure relates to an EV (e.g., exosome) produced by the methods provided herein.

In yet another aspect, the present disclosure relates to a pharmaceutical composition comprising the EV (e.g., exosome) of the present disclosure and an excipient. In some embodiments, the pharmaceutical composition comprises a lower concentration of macromolecules than the sample comprising the EV (e.g., exosome) source, wherein the macromolecules are nucleic acids, contaminant proteins, lipids, carbohydrates, metabolites, or a combination thereof. In some embodiments, the pharmaceutical composition is substantially free of the macromolecules.

Another aspect of the present disclosure relates to an EV (e.g., exosome) comprising a target protein wherein at least a part of the target protein is expressed from an exogenous sequence, and the target protein comprises a HEVP (e.g., CD13, MME, ENPP1, or NRP1 or a fragment or a variant thereof). In some aspects, the target protein comprises CD13 (or a fragment or variant thereof). In some aspects, the target protein comprises MME (or a fragment or variant thereof). In some aspects, the target protein comprises ENPP1 (or a fragment or variant thereof). In some aspects, the target protein comprises NRP1 (or a fragment or variant thereof). In some embodiments, the target protein does not comprise IGSF8 or a fragment or a variant thereof. In some embodiments, the target protein comprises a polypeptide of SEQ ID NO: 33.

In some embodiments, the EV (e.g., exosome) is isolated based on a binding between the target protein and a binding agent.

In some embodiments, the EV (e.g., exosome) is produced from a cell genetically modified to comprise the exogenous sequence, optionally wherein the cell is an HEK293 cell, a Chinese hamster ovary (CHO) cell, or a mesenchymal stem cell (MSC). In some embodiments, the cell is genetically modified to have a reduced expression of ADAM10.

In some embodiments, the cell comprises a plasmid comprising the exogenous sequence.

In some embodiments, the cell comprises the exogenous sequence inserted into a genome of the cell. In some embodiments, the exogenous sequence is inserted into a genomic site located 3' or 5' end of a genomic sequence encoding CD13, MME, ENPP1, or NRP1. In some embodiments, the exogenous sequence is inserted into a genomic sequence encoding CD13, MME, ENPP1, or NRP1. In some embodiments, the exogenous sequence does not encode IGSF8.

In some embodiments, the target protein is a fusion protein comprising CD13, MME, ENPP1, or NRP1, or a fragment or a variant thereof, and an affinity tag, wherein the affinity tag has affinity to the binding agent. In some embodiments, the target protein does not comprise IGSF8 or a fragment thereof.

In some embodiments, the target protein is a fusion protein comprising CD13, MME, ENPP1, or NRP1, or a fragment or a variant thereof, and a therapeutic compound. In some embodiments, the target protein does not comprise IGSF8 or a fragment thereof.

The therapeutic compound can be selected from a group consisting of a natural peptide, a recombinant peptide, a synthetic peptide. In some embodiments, the therapeutic compound comprises a linker. The therapeutic compound can be selected from the group consisting of nucleotides, amino acids, lipids, carbohydrates, and small molecules.

Functional moieties and related compounds, e.g., therapeutic compounds, that can be attached to HEVPs or fragments thereof include antibodies or fragments or variants thereof. A functional compound that is a peptide can be an enzyme, a ligand, a receptor, or a fragment or a variant thereof. A therapeutic peptide can be an antimicrobial peptide or a fragment or a variant thereof.

In some embodiments, the target protein is a fusion protein comprising CD13, MME, ENPP1, or NRP1, or a fragment or a variant thereof, and a targeting moiety. The targeting moiety can be specific to an organ, a tissue, or a cell. In some embodiments, the target protein does not comprise IGSF8 or a fragment thereof.

In some embodiments, the EV (e.g., exosome) further comprises a second, different target protein, wherein the different target protein comprises CD13, MME, ENPP1, or NRP1, or a fragment or a variant thereof. In some embodiments, the EV (e.g., exosome) is isolated based on a binding between the different target protein and a different binding agent. In some embodiments, the target protein does not comprise IGSF8 or a fragment thereof.

In one aspect, the present disclosure relates to a pharmaceutical composition comprising the EV (e.g., exosome) of the present disclosure and an excipient.

In some embodiments, the pharmaceutical compositions are substantially free of macromolecules, wherein the macromolecules are selected from nucleic acids, contaminant proteins, lipids, carbohydrates, metabolites, and a combination thereof.

In one aspect, the present disclosure is directed to a cell for producing the EV (e.g., exosome) presented herein.

Specifically, some embodiments relate to a cell for producing EVs (e.g., exosomes), comprising an exogenous sequence inserted into a genomic sequence encoding CD13, MME, ENPP1, or NRP1, wherein the exogenous sequence and the genomic sequence encodes a fusion protein. In some embodiments, the genomic sequence does not encode IGSF8.

The exogenous sequence can encode an affinity tag.

The exogenous sequence can encode a therapeutic peptide. The therapeutic peptide can be selected from a group consisting of a natural peptide, a recombinant peptide, a synthetic peptide, or a linker to a therapeutic compound. The therapeutic compound can be selected from the group consisting of nucleotides, amino acids, lipids, carbohydrates, and small molecules. The therapeutic peptide can be an antibody or a fragment or a variant thereof. The therapeutic peptide can be an enzyme, a ligand, a receptor, or a fragment or a variant thereof. The therapeutic peptide can be an antimicrobial peptide or a fragment or a variant thereof.

The exogenous sequence can encode a targeting moiety. The targeting moiety can be specific to an organ, a tissue, or a cell.

In some embodiments, the cell line is genetically modified to have a reduced expression of ADAM10.

In one aspect, the present disclosure provides an EV (e.g., exosome) produced from the cell line of the present disclosure. In some embodiments, the EV (e.g., exosome) includes the fusion protein on the surface at a higher density than a different fusion protein on the surface of a different EV (e.g., exosome), wherein the different EV (e.g., exosome) is produced from a different cell line comprising the exogenous sequence inserted into a different genomic sequence encoding a conventional EV (e.g., exosome) protein, wherein the exogenous sequence and the different genomic sequence encodes the different fusion protein. In some embodiments, the conventional EV (e.g., exosome) protein is selected from the group consisting of CD9, CD63, CD81, PDGFR, GPI anchor proteins, LAMP2, LAMP2B, and a fragment thereof.

In another aspect, the present disclosure relates to a method of isolating a non-exosomal material, comprising the steps of: providing a sample comprising an EV (e.g., exosome) and the non-EV (e.g., exosome) material; contacting the sample with a binding agent having affinity to a target protein, wherein the target protein comprises CD13, MME, ENPP1, or NRP1 or a fragment or a variant thereof, thereby inducing the EV (e.g., exosome) to bind to the binding agent; and isolating the non-EV (e.g., exosome) material. In some aspects, the target protein comprises CD13 (or a fragment or variant thereof). In some aspects, the target protein comprises MME (or a fragment or variant thereof). In some aspects, the target protein comprises ENPP1 (or a fragment or variant thereof). In some aspects, the target protein comprises NRP1 (or a fragment or variant thereof).

In some embodiments, the non-exosomal material is virus or a protein. In some embodiments, the non-exosomal material is lentivirus, retrovirus, adeno-associated virus, or other enveloped or non-enveloped virus. In some embodiments, the non-exosomal material is a recombinant protein. In some embodiments, the isolated non-exosomal material is substantially free of EVs (e.g., exosomes).

In some embodiments, the target protein further comprises an affinity tag, wherein the affinity tag has affinity to the binding agent. In some embodiments, the target protein comprises a polypeptide of SEQ ID NO: 33. In some embodiments, the binding agent comprises an immunoglobulin, a protein, a peptide, or a small molecule. In some embodiments, the binding agent is attached to a solid support, optionally wherein the solid support comprises a porous agarose bead, a microtiter plate, a magnetic bead, or a membrane. In some embodiments, the solid support forms a chromatography column. In some embodiments, the step of contacting the sample with the binding agent is performed by applying the sample to the chromatography column.

In some embodiments, the methods of purification described herein are used for purification of nanovesicles. In some embodiments, the compositions and methods described herein are directed to nanovesicles. Additional embodiments of the present disclosure are described in more detail below.

6. BRIEF DESCRIPTION OF THE FIGURES

FIG. 1 provides a dot graph showing peptide spectrum matches of individual proteins identified in either mesenchymal stem cell (MSC)-derived (y-axis) or HEK293-derived (x-axis) EVs (e.g., exosomes). The individual dots correspond to a different protein. CD13 and MME (shown using arrows) are both enriched in MSC-derived EVs but are not detected in HEK293-derived EVs. The table below the dot graph shows the molecule weight (MW) of CD13 and MME proteins and their relative expression in HEK293 (HEK) and MSC cells.

Figure 2B:
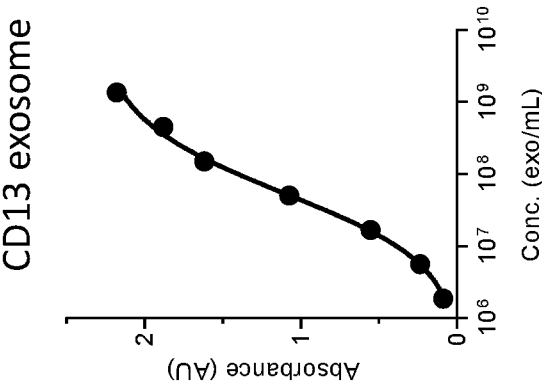
Figure 2B:
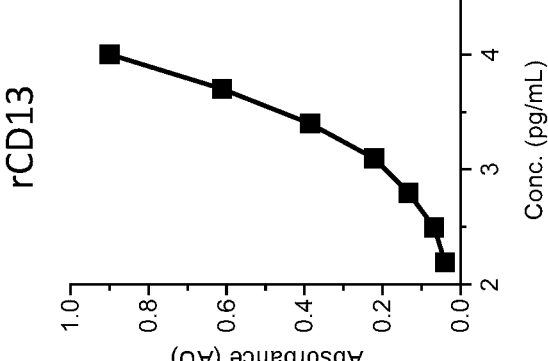
Figure 2A:
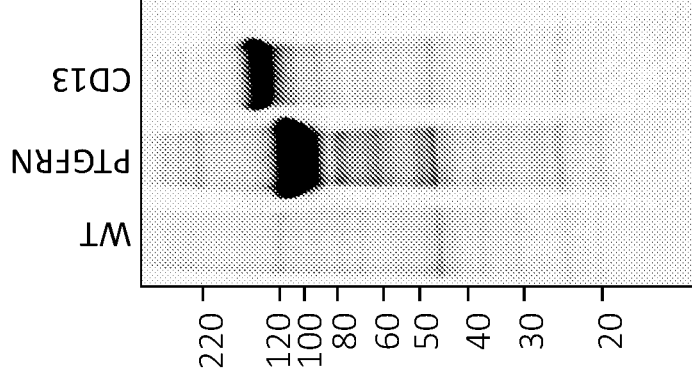

FIGS. 2A and 2B show expression of CD13 and PTGFRN proteins in EVs (e.g., exosomes) derived from HEK293 producer cells that have been modified to overexpress either PTGFRN or CD13. FIG. 2A provides SDS-PAGE analysis of wild-type (WT) (i.e., non-modified), PTGFRN overexpressing, and CD13 overexpressing HEK293-derived EVs. FIG. 2B provides a quantitation of CD13 protein expression on engineered HEK293-derived EVs by ELISA using a recombination CD13 (rCD13) standard. The graph shown on the left is the standard. The graph shown on the right is for the EVs (e.g., exosomes).

Figures 3A, 3B:
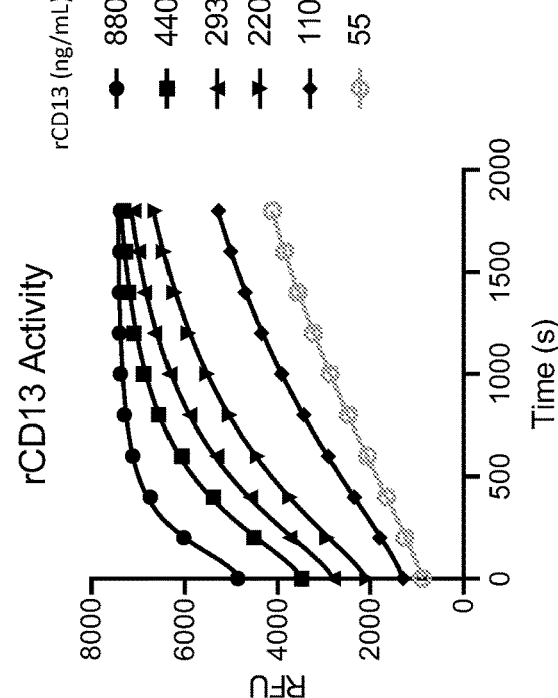

FIGS. 3A and 3B provide the bioactivity analysis of CD13 protein expressed on the engineered HEK293-derived EVs (e.g., exosomes). FIG. 3A shows the enzymatic activity of recombinant CD13 protein (rCD13) using a commercially available CD13 activity assay kit (BioVision K523). FIG. 3B shows the bioactivity of CD13 protein expressed on the engineered HEK293-derived EVs (e.g., exosomes) using the same CD13 activity assay kit. The recombinant CD13 proteins were tested at 6 different concentrations: (i) 880 ng/mL, (ii) 440 ng/mL, (iii) 293 ng/mL, (iv) 220 ng/mL, (v) 110 ng/mL, and (vi) 55 ng/mL. In FIG. 3B, the EVs were tested at three different concentrations: (i) $1.6 \times 10^{10}$ p/mL, (ii) $7.9 \times 10^9$ p/mL, and (iii) $4.0 \times 10^9$ p/mL. Non-engineered EVs (i.e., wild-type) were used as control.

Figures 4A, 4B:
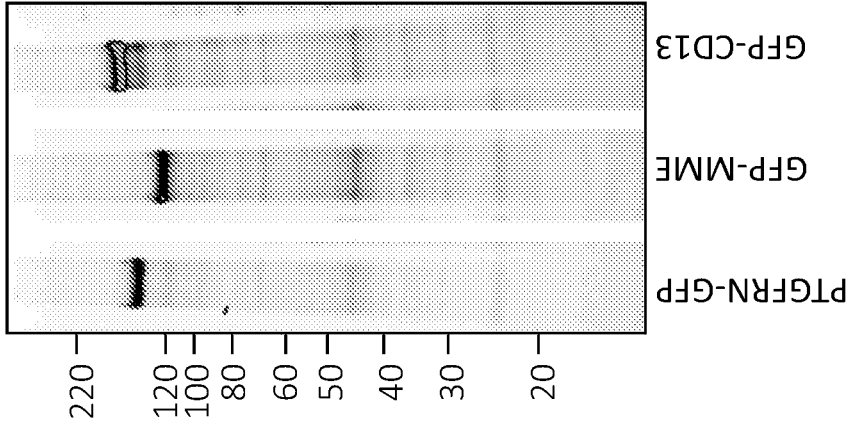

FIGS. 4A and 4B provide expression analysis of GFP conjugated to CD13 and MME proteins expressed on engineered HEK293-derived EVs (e.g., exosomes). FIG. 4A shows GFP expression as measured using SDS-PAGE analysis. EVs expressing GFP conjugated to PTGFRN (PTGFRN-GFP) were used as control. FIG. 4B shows a comparison of the expression of GFP conjugated to one of the following scaffold proteins: (i) LAMP2B, (ii) pDisplay, (iii) PTGFRN, (iv) MME, and (v) CD13. GFP was measured spectrophotometrically. The raw fluorescence measurements are shown for each of the different scaffold proteins.

7. DETAILED DESCRIPTION

7.1. Definitions

Unless defined otherwise, all technical and scientific terms used herein have the meaning commonly understood by a person skilled in the art to which this disclosure belongs. As used herein, the following terms have the meanings ascribed to them below.

As used herein, the term "extracellular vesicle" or "EV" refers to a cell-derived vesicle comprising a membrane that encloses an internal space. Extracellular vesicles comprise all membrane-bound vesicles (e.g., exosomes, nanovesicles) that have a smaller diameter than the cell from which they are derived. Generally extracellular vesicles range in diameter from 20 nm to 1000 nm, and can comprise various macromolecular cargo either within the internal space (i.e., lumen), displayed on the external surface of the extracellular vesicle, and/or spanning the membrane. The cargo can comprise nucleic acids, proteins, carbohydrates, lipids, small molecules, and/or combinations thereof. In some aspects, an EV (e.g., exosomes) comprises one or more cargos or other exogenous biologically active molecules. In some aspects, an EV (e.g., exosomes) can comprise one or more scaffold moieties. In certain aspects, the one or more scaffold moieties are not naturally expressed in cells from which the EVs (e.g., exosomes) are produced. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, prokaryotic or eukaryotic cells, and/or cultured cells. As described herein, in some aspects, the EVs (e.g., exosomes) disclosed herein are produced by cells that have been modified to express one or more transgene products. Accordingly, the EVs of the present disclosure do not comprise naturally occurring EVs (e.g., exosomes).

As used herein the term "exosome" refers to a cell-derived small (between 20-300 nm in diameter, more preferably 40-200 nm in diameter) vesicle comprising a membrane that encloses an internal space, and which is generated from a cell (e.g., producer cell) by direct plasma membrane budding or by fusion of the late endosome with the plasma membrane. In certain aspects, exosomes of the present disclosure has a diameter between about 20-290 nm, 20-280 nm, 20-270 nm, 20-260 nm, 20-250 nm, 20-240 nm, 20-230 nm, 20-220 nm, 20-210 nm, 20-200 nm, 20-190 nm, 20-180 nm, 20-170 nm, 20-160 nm, 20-150 nm, 20-140 nm, 20-130 nm, 20-120 nm, 20-110 nm, 20-100 nm, 20-90 nm, 20-80 nm, 20-70 nm, 20-60 nm, 20-50 nm, 20-40 nm, 20-30 nm, 30-300 nm, 30-290 nm, 30-280 nm, 30-270 nm, 30-260 nm, 30-250 nm, 30-240 nm, 30-230 nm, 30-220 nm, 30-210 nm, 30-200 nm, 30-190 nm, 30-180 nm, 30-170 nm, 30-160 nm, 30-150 nm, 30-140 nm, 30-130 nm, 30-120 nm, 30-110 nm, 30-100 nm, 30-90 nm, 30-80 nm, 30-70 nm, 30-60 nm, 30-50 nm, 30-40 nm, 40-300 nm, 40-290 nm, 40-280 nm, 40-270 nm, 40-260 nm, 40-250 nm, 40-240 nm, 40-230 nm, 40-220 nm, 40-210 nm, 40-200 nm, 40-190 nm, 40-180 nm, 40-170 nm, 40-160 nm, 40-150 nm, 40-140 nm, 40-130 nm, 40-120 nm, 40-110 nm, 40-100 nm, 40-90 nm, 40-80 nm, 40-70 nm, 40-60 nm, 40-50 nm, 50-300 nm, 50-290 nm, 50-280 nm, 50-270 nm, 50-260 nm, 50-250 nm, 50-240 nm, 50-230 nm, 50-220 nm, 50-210 nm, 50-200 nm, 50-190 nm, 50-180 nm, 50-170 nm, 50-160 nm, 50-150 nm, 50-140 nm, 50-130 nm, 50-120 nm, 50-110 nm, 50-100 nm, 50-90 nm, 50-80 nm, 50-70 nm, 50-60 nm, 60-300 nm, 60-290 nm, 60-280 nm, 60-270 nm, 60-260 nm, 60-250 nm, 60-240 nm, 60-230 nm, 60-220 nm, 60-210 nm, 60-200 nm, 60-190 nm, 60-180 nm, 60-170 nm, 60-160 nm, 60-150 nm, 60-140 nm, 60-130 nm, 60-120 nm, 60-110 nm, 60-100 nm, 60-90 nm, 60-80 nm, 60-70 nm, 70-300 nm, 70-290 nm, 70-280 nm, 70-270 nm, 70-260 nm, 70-250 nm, 70-240 nm, 70-230 nm, 70-220 nm, 70-210 nm, 70-200 nm, 70-190 nm, 70-180 nm, 70-170 nm, 70-160 nm, 70-150 nm, 70-140 nm, 70-130 nm, 70-120 nm, 70-110 nm, 70-100 nm, 70-90 nm, 70-80 nm, 80-300 nm, 80-290 nm, 80-280 nm, 80-270 nm, 80-260 nm, 80-250 nm, 80-240 nm, 80-230 nm, 80-220 nm, 80-210 nm, 80-200 nm, 80-190 nm, 80-180 nm, 80-170 nm, 80-160 nm, 80-150 nm, 80-140 nm, 80-130 nm, 80-120 nm, 80-110 nm, 80-100 nm, 80-90 nm, 90-300 nm, 90-290 nm, 90-280 nm, 90-270 nm, 90-260 nm, 90-250 nm, 90-240 nm, 90-230 nm, 90-220 nm, 90-210 nm, 90-200 nm, 90-190 nm, 90-180 nm, 90-170 nm, 90-160 nm, 90-150 nm, 90-140 nm, 90-130 nm, 90-120 nm, 90-110 nm, 90-100 nm, 100-300 nm, 110-290 nm, 120-280 nm, 130-270 nm, 140-260 nm, 150-250 nm, 160-240 nm, 170-230 nm, 180-220 nm, or 190-210 nm. The size of the EV (e.g., exosome) described herein can be measured according to methods described, infra.

In some aspects, an EV (e.g., exosome) of the present disclosure comprises a bi-lipid membrane, comprising an interior surface and an exterior surface. In certain aspects, the interior surface faces the inner core (i.e., lumen) of the EV (e.g., exosome). In certain aspects, the exterior surface can be in contact with the endosome, the multivesicular bodies, or the membrane/cytoplasm of a producer cell or a target cell.

In some aspects, the EV (e.g., exosome) membrane comprises lipids and fatty acids. In some aspects, the EV (e.g., exosome) membrane comprises phospholipids, glycolipids, fatty acids, sphingolipids, phosphoglycerides, sterols, cholesterols, and phosphatidylserines.

In some aspects, the EV (e.g., exosome) membrane comprises an inner leaflet and an outer leaflet. The composition of the inner and outer leaflet can be determined by transbilayer distribution assays known in the art, see, e.g., Kuypers et al., *Biohim Biophys Acta* 1985 819:170. In some aspects, the composition of the outer leaflet is between approximately 70-90% choline phospholipids, between approximately 0-15% acidic phospholipids, and between approximately 5-30% phosphatidylethanolamine. In some aspects, the composition of the inner leaflet is between approximately 15-40% choline phospholipids, between approximately 10-50% acidic phospholipids, and between approximately 30-60% phosphatidylethanolamine.

In some aspects, the exosome comprises lipid or fatty acid and polypeptide and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. As described herein, in some aspects, exosomes of the present disclosure comprise one or more scaffold moieties. In certain aspects, the one or more scaffold moieties are not naturally expressed in cells from which the exosomes are produced. The exosome can be derived from a producer cell, and isolated from the producer cell based on its size, density, biochemical parameters, or a combination thereof. An exosome is a species of extracellular vesicle. Generally, exosome production/biogenesis does not result in the destruction of the producer cell. In some aspects, exosomes of the present disclosure are produced by cells that express one or more transgene products. The exosomes of the present disclosure are modified (e.g., engineered to overexpress a protein that is not naturally expressed in the producer cell) and therefore, do not comprise naturally occurring exosomes.

As used herein, the term "heterologous exosomal vesicle protein" or "HEVP" refers to a protein that is heterologously expressed in EVs (e.g., exosomes) produced by a particular cell type where that cell type does not naturally express the protein, but wherein the protein is expressed naturally in the EVs (e.g., exosomes) of a different cell type. The latter cell type is referred to herein as a "donor cell" and the former cell type is referred to herein as a "producer cell."

As used herein, the term "nanovesicle" refers to a cell-derived small (between 20-250 nm in diameter, more preferably 30-150 nm in diameter) vesicle comprising a membrane that encloses an internal space, and which is generated from a cell (e.g., producer cell) by direct or indirect manipulation such that the nanovesicle would not be produced by the producer cell without the manipulation. Appropriate manipulations of the producer cell include but are not limited to serial extrusion, treatment with alkaline solutions, sonication, or combinations thereof. The production of nanovesicles can, in some instances, result in the destruction of the producer cell. In some aspects, populations of nanovesicles described herein are substantially free of vesicles that are derived from producer cells by way of direct budding from the plasma membrane or fusion of the late endosome with the plasma membrane. In some aspects, the nanovesicle comprises lipid or fatty acid and polypeptide, and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. In some aspects, nanovesicles described herein disclosure comprise one or more scaffold moieties. In certain aspects, the one or more scaffold moieties are not naturally expressed in cells from which the nanovesicles are produced. The nanovesicle, once it is derived from a producer cell according to the above-described manipulation, can be isolated from the producer cell based on its size, density, biochemical parameters, or a combination thereof. A nanovesicle is a species of extracellular vesicle. As used herein, nanovesicles have been modified (e.g., engineered to overexpress a protein that is not naturally expressed in the producer cell) and therefore, do not comprise naturally occurring nanovesicles.

As used herein the term "surface-engineered exosome" refers to an exosome with a membrane or the surface modified in its composition, so that the membrane or the surface of the engineered exosomes is different from either that of the exosome prior to the modification or that of a naturally occurring exosome. The engineering can be on the surface of the exosome or in the membrane of the exosome so that the surface of the exosome is changed. For example, the membrane is modified in its composition of a protein, a lipid, a small molecule, a carbohydrate, etc. The composition can be changed by a chemical, a physical, or a biological method or by being produced from a cell previously or concurrently modified by a chemical, a physical, or a biological method. Specifically, the composition can be changed by a genetic engineering or by being produced from a cell previously modified by genetic engineering. As disclosed herein, in some aspects, a surface-engineered exosome disclosed herein comprises one or more exogenous proteins (e.g., scaffold moieties, e.g., heterologous exosomal vesicle proteins disclosed herein), or a fragment or variant thereof, that can be exposed to the surface of the exosome or can be an anchoring point (attachment) for a moiety exposed on the surface of the exosome. In certain aspects, the one or more scaffold moieties are not naturally expressed in cells from which the exosomes are produced. In some aspects, a surface-engineered exosome comprises a higher expression (e.g., higher number) of a natural exosome protein (e.g., PTGFRN) or a fragment or variant thereof that can be exposed to the surface of the exosome or can be an anchoring point (attachment) for a moiety exposed on the surface of the exosome. While the above definition is provided in the context of exosomes, other types of extracellular vesicles can also be surface-engineered in a similar manner. Therefore, unless indicated otherwise, disclosures relating to surface-engineered exosomes can equally apply to other extracellular vesicles.

As used herein, the term "lumen-engineered exosome" refers to an exosome with the membrane or the lumen of the exosome modified in its composition, so that the lumen of the engineered exosome is different from that of the exosome prior to the modification or of the naturally occurring exosome. The engineering can be directly in the lumen or in the membrane of the exosome so that the lumen of the exosome is changed. For example, the membrane is modified in its composition of a protein, a lipid, a small molecule, a carbohydrate, etc. so that the lumen of the exosome is modified. The composition can be changed by a chemical, a physical, or a biological method or by being produced from a cell previously modified by a chemical, a physical, or a biological method. Specifically, the composition can be changed by a genetic engineering or by being produced from a cell previously modified by genetic engineering. In some aspects, a lumen-engineered exosome comprises one or more exogenous biologically active molecules (e.g., scaffold moieties, e.g., heterologous exosomal vesicle proteins disclosed herein). In certain aspects, the exogenous biologically active molecules can comprise an exogenous protein (i.e., a protein that the EV, e.g., exosome does not naturally express) or a fragment or variant thereof that can be exposed in the lumen of the exosome or can be an anchoring point (attachment) for a moiety exposed on the inner layer of the exosome. In certain aspects, the one or more scaffold moieties are not naturally expressed in cells from which the exosomes are produced. In some aspects, a lumen-engineered exosome comprises a higher expression of a natural exosome protein or a fragment or variant thereof that can be exposed to the lumen of the exosome or can be an anchoring point (attachment) for a moiety exposed in the lumen of the exosome. While the above definition is provided in the context of exosomes, other types of extracellular vesicles can also be lumen-engineered in a similar manner. Therefore, unless indicated otherwise, disclosures relating to lumen-engineered exosomes can equally apply to other extracellular vesicles.

As used herein, the term "a modification," when used in the context of a protein, refers to a protein having at least about 15% sequence identity to the non-mutant amino acid sequence of the protein. A modification of a protein includes a fragment or a variant of the protein. A modification of a protein can further include chemical, or physical modification to a fragment or a variant of the protein.

The term "modified," when used in the context of EVs, e.g., exosomes described herein, refers to an alteration or engineering of an EV, e.g., exosome and/or its producer cell, such that the modified EV, e.g., exosome is different from a naturally-occurring EV, e.g., exosome. In some aspects, a modified EV, e.g., exosome described herein comprises a membrane that differs in composition of a protein, a lipid, a small molecular, a carbohydrate, etc. compared to the membrane of a naturally-occurring EV, e.g., exosome (e.g., membrane comprises higher density or number of natural exosome proteins and/or membrane comprises multiple (e.g., at least two) biologically active molecules that are not naturally found in exosomes (e.g., therapeutic molecules (e.g., antigen), targeting moiety, adjuvant, and/or immune modulator). As used herein, biologically active molecules that are not naturally found in exosomes are also described as "exogenous biologically active molecules." Non-limiting examples of such exogenous biologically active molecules include the heterologous exosomal vesicle proteins disclosed herein (e.g., CD13, MME, ENPP1, or NRP1), therapeutic molecules (e.g., antigens), targeting moieties, adjuvants, immune modulators, or combinations thereof. In certain aspects, such modifications to the membrane changes the exterior surface of the EV, e.g., exosome (e.g., surface-engineered EVs, e.g., exosomes described herein).

As used herein, the terms "scaffold moiety" and "scaffold" can be used interchangeably and refer to a molecule that can be used to anchor a cargo or any other exogenous biologically active molecule of interest (e.g., targeting moiety, adjuvant, and/or immune modulator) to the EV, e.g., on the exterior surface of the EV, e.g., exosome. In certain aspects, a scaffold moiety comprises a synthetic molecule. In some aspects, a scaffold moiety comprises a non-polypeptide moiety. In some aspects, a scaffold moiety comprises a lipid, carbohydrate, or protein that naturally exists in the EV, e.g., exosome. In some aspects, a scaffold moiety comprises a lipid, carbohydrate, or protein that does not naturally exist in the EV, e.g., exosome. In some aspects, a scaffold moiety comprises a heterologous exosomal vesicle protein disclosed herein. In some aspects, a scaffold moiety can be a whole protein or a fragment thereof (e.g., functional fragment, e.g., the smallest fragment that is capable of anchoring another moiety on the exterior surface or on the luminal surface of the EV, e.g., exosome). Non-limiting examples of other scaffold moieties that can be used with the present disclosure include: Scaffold X, Scaffold Y, CD9, CD63, CD81, PDGFR, GPI anchor proteins, lactadherin, LAMP2, and LAMP2B.

As used herein, the term "Scaffold X" refers to exosome proteins that have recently been identified on the surface of exosomes. See, e.g., U.S. Pat. No. 10,195,290, which is incorporated herein by reference in its entirety. Non-limiting examples of Scaffold X proteins include: prostaglandin F2 receptor negative regulator ("the PTGFRN protein"); basigin ("the BSG protein"); immunoglobulin superfamily member 2 ("the IGSF2 protein"); immunoglobulin superfamily member 3 ("the IGSF3 protein"); immunoglobulin superfamily member 8 ("the IGSF8 protein"); integrin beta-1 ("the ITGB1 protein); integrin alpha-4 ("the ITGA4 protein"); 4F2 cell-surface antigen heavy chain ("the SLC3A2 protein"); and a class of ATP transporter proteins ("the ATP1A1 protein," "the ATP1A2 protein," "the ATP1A3 protein," "the ATP1A4 protein," "the ATP1B3 protein," "the ATP2B1 protein," "the ATP2B2 protein," "the ATP2B3 protein," "the ATP2B protein").

As used herein, the term "Scaffold Y" refers to exosome proteins that were newly identified within the lumen of exosomes. See, e.g., International Appl. No. PCT/US2018/061679, which is incorporated herein by reference in its entirety. Non-limiting examples of Scaffold Y proteins include: myristoylated alanine rich Protein Kinase C substrate ("the MARCKS protein"); myristoylated alanine rich Protein Kinase C substrate like 1 ("the MARCKSL1 protein"); and brain acid soluble protein 1 ("the BASP1 protein").

As used herein the term "a fragment" of a protein refers to an amino acid sequence of a protein that is shorter than the naturally-occurring sequence, e.g., N- and/or C-terminally deleted and/or any other part of the protein deleted in comparison to the naturally occurring protein. Preferably, a fragment of a heterologous exosomal vesicle protein disclosed herein (e.g., CD13, MME, ENPP1, or NRP1) retains the ability to be specifically targeted to EVs (e.g., exosomes). In some aspects, a fragment of a heterologous exosomal vesicle protein disclosed herein retains the ability to anchor another moiety on the exterior surface or on the luminal surface of the EV (e.g., exosome). Such a fragment is also referred to as "functional fragment". As used herein, the term "functional fragment" can refer to a protein fragment that retains protein function. In some aspects, the term "functional fragment" refers to a protein fragment that is capable of being expressed in a cell line that does not naturally express the full length protein. Whether a fragment is a functional fragment in that sense can be assessed by any art known methods to determine the protein content of EVs (e.g., exosomes) including Western Blots, FACS analysis and fusions of the fragments with autofluorescent proteins like, e.g. GFP. In some aspects, a heterologous exosomal vesicle protein disclosed herein retains at least about 50%, at least about 60%, at least about 70%, at least about 80%, at least about 90%, or about 100% of the ability, e.g., an ability to anchor a moiety, of the naturally occurring heterologous exosomal vesicle protein. In a particular embodiment, the fragment of CD13, MME, ENPP1, or NRP1 retains at least about 50%, at least about 60%, at least about 70%, at least about 80%, at least about 90%, or about 100% of the ability of the naturally occurring CD13, MME, ENPP1, or NRP1 to be specifically targeted to EVs (e.g., exosomes) and/or anchor another moiety on the EVs (e.g., on the exterior surface).

As used herein the term "variant" of a protein refers to a protein that shares a certain amino acid sequence identity with another protein upon alignment by a method known in the art. A variant of a protein can include a substitution, insertion, deletion, frameshift or rearrangement in another protein. In a particular embodiment, the variant is a variant having at least about 70% identity to CD13 (also known in the art as, e.g., membrane alanyl aminopeptidase, alanyl aminopeptidase (AAP), aminopeptidase N (AP-N), aminopeptidase M, GP150, LAP1, P150, PEPN, ANPEP, or microsomal aminopeptidase), MME (also known in the art as, e.g., membrane metallo-endopeptidase, neprilysin, neural endopeptidase (NEP), cluster of differentiation 10 (CD10), common acute lymphoblastic leukemia antigen (CALLA), skin fibroblast elastase, atriopeptidase, or enkephalinase), ENPP1 (also known in the art as, e.g., ectonucleotide pyrophasphatase/phosphodiesterase family member 1, phosphodiesterase/nucleotide pyrophosphatase 1, plasma-cell membrane glycoprotein PC-1, membrane component chromosome 6 surface marker 1, alkaline phosphodiesterase 1, Ly-41 antigen, ARHR2, or COLED), or NRP1 (also known in the art as, e.g., neuropilin 1, vascular endothelial cell growth factor 165 receptor (VEGF165R), CD304, BDCA4, NP1, or NRP). In some embodiments, variants or variants of fragments of CD13 share at least about 70%, at least about 80%, at least about 85%, at least about 90%, at least about 95%, or at least about 99% sequence identity with CD13 according to SEQ ID NO: 47 or with a functional fragment thereof. In some embodiments, variants or variants of fragments of MME share at least about 70%, at least about 80%, at least about 85%, at least about 90%, at least about 95%, or at least about 99% sequence identity with MME according to SEQ ID NO: 48 or with a functional fragment thereof. In some embodiments, variants or variants of fragments of ENPP1 share at least about 70%, at least about 80%, at least about 85%, at least about 90%, at least about 95%, or at least about 99% sequence identity with ENPP1 according to SEQ ID NO: 49 or with a functional fragment thereof. In some embodiments, variants or variants of fragments of NRP1 share at least about 70%, at least about 80%, at least about 85%, at least about 90%, at least about 95%, or at least about 99% sequence identity with NRP1 according to SEQ ID NO: 50 or with a functional fragment thereof. In each of above cases, it is preferred that the variant or variant of a fragment retain a function of the protein (e.g., the ability to be specifically targeted to EVs (e.g., exosomes)).

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

Methods of alignment of sequences for comparison are well-known in the art. Various programs and alignment algorithms are described in: Smith and Waterman, Adv. Appl. Math. 2: 482 (1981); Needleman and Wunsch, J. Mol. Bio. 48: 443 (1970); Pearson and Lipman, Methods in Mol. Biol. 24: 307-31 (1988); Higgins and Sharp, Gene 73: 15 237-44 (1988); Higgins and Sharp, CABIOS 5: 151-3 (1989) Corpet et al., Nuc. Acids Res. 16: 10881-90 (1988); Huang et al., Comp. Appl. BioSci. 8: 155-65 (1992); and Pearson et al., Meth. Mol. Biol. 24: 307-31 (1994). The NCBI Basic Local Alignment Search Tool (BLAST) [Altschul 20 et al., J. Mol. Biol. 215: 403-10 (1990) J is available from several sources, including the National Center for Biological Information (NCBI, Bethesda, Md.) and on the Internet, for use in connection with the sequence analysis programs blastp, blasm, blastx, tblastn and tblastx. BLAST and a description of how to determine sequence identify using the program can be accessed at the official website of NCBI (National Center for Biotechnology Information) under NIH (National Institute of Health).

Recitation of any protein provided herein encompasses a functional variant of the protein. The term "functional variant" of a protein refers to a variant of the protein that retains the ability to be specifically targeted to EVs (e.g., exosomes).

The polynucleotide variants can contain alterations in the coding regions, non-coding regions, or both. In one aspect, the polynucleotide variants contain alterations which produce silent substitutions, additions, or deletions, but do not alter the properties or activities of the encoded polypeptide. In another aspect, nucleotide variants are produced by silent substitutions due to the degeneracy of the genetic code. In other aspects, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present disclosure. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some aspects, Scaffold X and/or Scaffold Y is modified at any convenient location.

As used herein the terms "linked to," "conjugated to," and "anchored to" are used interchangeably and refer to a covalent or non-covalent bond formed between a first moiety (e.g., scaffold moiety, e.g., heterologous exosomal vesicle protein) and a second moiety (e.g., payload).

As used herein the term "producer cell" refers to a cell used for generating an EV (e.g., exosome). A producer cell can be a cell cultured in vitro, or a cell in vivo. A producer cell includes, but is not limited to, a cell known to be effective in generating EVs, e.g., EVs (e.g., exosomes), e.g., HEK293 cells, Chinese hamster ovary (CHO) cells, mesenchymal stem cells (MSCs), BJ human foreskin fibroblast cells, fHDF fibroblast cells, AGE.HN® neuronal precursor cells, CAP® amniocyte cells, adipose mesenchymal stem cells, RPTEC/TERT1 cells. In certain aspects, a producer cell is not an antigen-presenting cell. In some aspects, a producer cell is not a dendritic cell, a B cell, a mast cell, a macrophage, a neutrophil, a Kupffer-Browicz cell, a cell derived from any of these cells, or any combination thereof. As disclosed herein, in some aspects, a producer cell of the present disclosure has been modified to express one or more transgene products. In some aspects, a producer cell has been modified to express a protein (e.g., heterologous exosomal vesicle protein) that the producer cell does not naturally express. In some aspects, the EVs, e.g., exosomes, useful in the present disclosure do not carry an antigen on MHC class I or class II molecule exposed on the surface of the EV, e.g., exosome, but instead can carry an antigen in the lumen of the EV, e.g., exosome or on the surface of the EV, e.g., exosome, by attachment to a scaffold moiety.

As used herein, an "MHC class I molecule" refers to a protein product of a wild-type or variant HLA class I gene encoding an MHC class I molecule. Accordingly, "HLA class I molecule" and "MHC class I molecule" are used interchangeably herein.

MHC class I molecules are one of two primary classes of major histocompatibility complex (MHC) molecules (the other being MHC class II) and are found on the cell surface of all nucleated cells in the bodies of jawed vertebrates. They also occur on platelets, but not on red blood cells. Their function is to display peptide fragments of proteins from within the cell to cytotoxic T cells; this will trigger an immediate response from the immune system against a particular non-self antigen displayed with the help of an MHC class I protein. Because MHC class I molecules present peptides derived from cytosolic proteins, the pathway of MHC class I presentation is often called cytosolic or endogenous pathway.

In humans, the HLAs corresponding to MHC class I are HLA-A, HLA-B, and HLA-C. The MHC Class I molecule comprises two protein chains: the alpha chain and the β2-microglobulin (β2m) chain. Human β2m is encoded by the B2M gene. Class I MHC molecules bind peptides generated mainly from degradation of cytosolic proteins by the proteasome. The MHC I:peptide complex is then inserted via endoplasmic reticulum into the external plasma membrane of the cell. The epitope peptide is bound on extracellular parts of the class I MHC molecule. Thus, the function of the class I MHC is to display intracellular proteins to cytotoxic T cells (CTLs). However, class I MHC can also present peptides generated from exogenous proteins, in a process known as cross-presentation.

A normal cell will display peptides from normal cellular protein turnover on its class I MHC, and CTLs will not be activated in response to them due to central and peripheral tolerance mechanisms. When a cell expresses foreign proteins, such as after viral infection, a fraction of the class I MHC will display these peptides on the cell surface. Consequently, CTLs specific for the MHC:peptide complex will recognize and kill presenting cells. Alternatively, class I MHC itself can serve as an inhibitory ligand for natural killer cells (NKs). Reduction in the normal levels of surface class I MHC, a mechanism employed by some viruses and certain tumors to evade CTL responses, activates NK cell killing.

As used herein, an "MHC class II molecule" refers to a protein product of a wild-type or variant HLA class II gene encoding an MHC class II molecule. Accordingly, "HLA class II molecule" and "MHC class II molecule" are used interchangeably herein.

MHC class II molecules are a class of major histocompatibility complex (MHC) molecules normally found only on professional antigen-presenting cells such as dendritic cells, mononuclear phagocytes, some endothelial cells, thymic epithelial cells, and B cells. These cells are important in initiating immune responses. The antigens presented by class II peptides are derived from extracellular proteins (not cytosolic as in MHC class I).

Like MHC class I molecules, class II molecules are also heterodimers, but in this case consist of two homogenous peptides, an α and β chain, both of which are encoded in the MHC. The subdesignation α1, α2, etc. refers to separate domains within the HLA gene; each domain is usually encoded by a different exon within the gene, and some genes have further domains that encode leader sequences, transmembrane sequences, etc. These molecules have both extracellular regions as well as a transmembrane sequence and a cytoplasmic tail. The α1 and β1 regions of the chains come together to make a membrane-distal peptide-binding domain, while the α2 and β2 regions, the remaining extracellular parts of the chains, form a membrane-proximal immunoglobulin-like domain. The antigen binding groove, where the antigen or peptide binds, is made up of two α-helixes walls and β-sheet. Because the antigen-binding groove of MHC class II molecules is open at both ends while the corresponding groove on class I molecules is closed at each end, the antigens presented by MHC class II molecules are longer, generally between 15 and 24 amino acid residues long. Loading of a MHC class II molecule occurs by phagocytosis; extracellular proteins are endocytosed, digested in lysosomes, and the resulting epitopic peptide fragments are loaded onto MHC class II molecules prior to their migration to the cell surface. In humans, the MHC class II protein complex is encoded by the human leukocyte antigen gene complex (HLA). HLAs corresponding to MHC class II are HLA-DP, HLA-DM, HLA-DOA, HLA-DOB, HLA-DQ, and HLA-DR. Mutations in the HLA gene complex can lead to bare lymphocyte syndrome (BLS), which is a type of MHC class II deficiency.

As used herein, the term "target protein" refers to a protein that can be targeted to the surface of an EV (e.g., exosome). The target protein can be a non-mutant protein that is naturally targeted to an EV (e.g., exosome) membrane, or a fragment or a variant of the non-mutant protein. The target protein can be a fusion protein containing a flag tag, a therapeutic peptide, a targeting moiety, or other peptide attached to the non-mutant protein or a variant or a fragment of the non-mutant protein. The target protein can comprise a transmembrane protein, an integral protein, a peripheral protein, or a soluble protein attached to the membrane by a linker.

As used herein, the term "contaminant protein" refers to a protein that is not associated with an EV (e.g., exosome). For example, a contaminant protein includes a protein, not enclosed in the EV (e.g., exosome) and not attached to or incorporated into the membrane of the EV (e.g., exosome).

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired EVs (e.g., exosomes), that have undergone one or more processes of purification, e.g., a selection or an enrichment of the desired EV (e.g., exosome) preparation. In some embodiments, isolating or purifying as used herein is the process of removing, partially removing (e.g., a fraction) of the EVs (e.g., exosomes) from a sample containing producer cells. In some embodiments, an isolated EV (e.g., exosome) composition has no detectable undesired activity or, alternatively, the level or amount of the undesired activity is at or below an acceptable level or amount. In other embodiments, an isolated EV (e.g., exosome) composition has an amount and/or concentration of desired EVs (e.g., exosomes) at or above an acceptable amount and/or concentration. In other embodiments, the isolated EV (e.g., exosome) composition is enriched as compared to the starting material (e.g., producer cell preparations) from which the composition is obtained. This enrichment can be by at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, at least about 99.9%, at least about 99.99%, at least about 99.999%, at least about 99.9999%, or greater than about 99.9999% as compared to the starting material. In some embodiments, isolated EV (e.g., exosome) preparations are substantially free of residual biological products. In some embodiments, the isolated EV (e.g., exosome) preparations are about 100% free, about 99% free, about 98% free, about 97% free, about 96% free, about 95% free, about 94% free, about 93% free, about 92% free, about 91% free, or about 90% free of any contaminating biological matter. Residual biological products can include abiotic materials (including chemicals) or unwanted nucleic acids, proteins, lipids, or metabolites. Substantially free of residual biological products can also mean that the EV (e.g., exosome) composition contains no detectable producer cells and that only EVs (e.g., exosomes) are detectable.

The term "excipient" or "carrier" refers to an inert substance added to a pharmaceutical composition to further facilitate administration of a compound. The term "pharmaceutically-acceptable carrier" or "pharmaceutically-acceptable excipient" encompasses any of the agents approved by a regulatory agency of the US Federal government or listed in the US Pharmacopeia for use in animals, including humans, as well as any carrier or diluent that does not cause significant irritation to a subject and does not abrogate the biological activity and properties of the administered compound. Included are excipients and carriers that are useful in preparing a pharmaceutical composition and are generally safe, non-toxic, and desirable.

As used herein, the term "payload" refers to a therapeutic agent that acts on a target (e.g., a target cell) that is contacted with the EV (e.g., exosome). Non-limiting examples of payload that can be included on the EV, e.g., exosome, are a therapeutic molecule (e.g., antigen or immunosuppressive agent), an adjuvant, and/or an immune modulator. Payloads that can be introduced into an EV (e.g., exosome) and/or a producer cell include therapeutic agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, siRNA, antisense oligonucleotide, a phosphorodiamidate morpholino oligomer (PMO), or a peptide-conjugated phosphorodiamidate morpholino oligomer (PPMO)), amino acids (e.g., amino acids comprising a detectable moiety or a toxin or that disrupt translation), polypeptides (e.g., enzymes), lipids, carbohydrates, and small molecules (e.g., small molecule drugs and toxins).

As used herein, the term "biologically active molecule" refers to an agent that has activity in a biological system (e.g., a cell or a human subject), including, but not limited to a protein, polypeptide or peptide including, but not limited to, a structural protein, an enzyme, a cytokine (such as an interferon and/or an interleukin) an antibiotic, a polyclonal or monoclonal antibody, or an effective part thereof, such as an Fv fragment, which antibody or part thereof can be natural, synthetic or humanized, a peptide hormone, a receptor, a signaling molecule or other protein; a nucleic acid, as defined below, including, but not limited to, an oligonucleotide or modified oligonucleotide, an antisense oligonucleotide or modified antisense oligonucleotide, cDNA, genomic DNA, an artificial or natural chromosome (e.g. a yeast artificial chromosome) or a part thereof, RNA, including mRNA, tRNA, rRNA or a ribozyme, or a peptide nucleic acid (PNA); a virus or virus-like particles; a nucleotide or ribonucleotide or synthetic analogue thereof, which can be modified or unmodified; an amino acid or analogue thereof, which can be modified or unmodified; a non-peptide (e.g., steroid) hormone; a proteoglycan; a lipid; or a carbohydrate. In certain aspects, a biologically active molecule comprises a therapeutic molecule (e.g., an antigen), a targeting moiety (e.g., an antibody or an antigen-binding fragment thereof), an adjuvant, an immune modulator, or any combination thereof. In some aspects, the biologically active molecule comprises a macromolecule (e.g., a protein, an antibody, an enzyme, a peptide, DNA, RNA, or any combination thereof). In some aspects, the biologically active molecule comprises a small molecule (e.g., an antisense oligomer (ASO), a phosphorodiamidate morpholino oligomer (PMO), a peptide-conjugated phosphorodiamidate morpholino oligomer (PPMO), an siRNA, STING, a pharmaceutical drug, or any combination thereof). In some aspects, the biologically active molecules are exogenous to the EVs, i.e., not naturally found in the EVs.

As used herein, the term "therapeutic compound" refers to any molecule that can treat and/or prevent a disease or disorder in a subject (e.g., human subject).

In some aspects, a therapeutic molecule comprises an antigen. As used herein, the term "antigen" refers to any agent that when introduced into a subject elicits an immune response (cellular or humoral) to itself. In some aspects, an antigen is not expressed on major histocompatibility complex I and/or II molecules. In other aspects, while an antigen in the EV, e.g., exosome, is not expressed as MHC class I or II complex, the EV, e.g., exosome, can still contain MHC class I/II molecules on the surface of the EV, e.g., exosome. Accordingly, in certain aspects, EVs, e.g., exosomes, disclosed herein do not directly interact with T-cell receptors (TCRs) of T cells to induce an immune response against the antigen. Similarly, in certain aspects, EVs, e.g., exosomes, of the present disclosure do not transfer the antigen directly to the surface of the target cell (e.g., dendritic cell) through cross-dressing. Cross-dressing is a mechanism commonly used by EVs, e.g., exosomes, derived from dendritic cells (DEX) to induce T cell activation. See Pitt, J. M., et al., *J Clin Invest* 126(4): 1224-32 (2016). In other aspects, the EVs, e.g., exosomes, of the present disclosure are engulfed by antigen presenting cells and can be expressed on the surface of the antigen presenting cells as WIC class I and/or WIC class II complex.

In some aspects, a therapeutic molecule comprises an immunosuppressive agent. As used herein, the term "immunosuppressive agent" refers to any agent (e.g., therapeutic molecule) that slows or halts an immune response in a subject. Immunosuppressive agents can be given to a subject to prevent the subject's immune system from mounting an immune response after an organ transplant or for treating a disease that is caused by an overactive immune system. Examples of immunosuppressive agents include, but are not limited to, a calcineurin inhibitor, such as, but not limited to, cyclosporine, ISA(TX) 247, tacrolimus or calcineurin, a target of rapamycin, such as, but not limited to, sirolimus, everolimus, FK778 or TAFA-93, an interleukin-2 α-chain blocker, such as, but not limited to, basiliximab and daclizumab, an inhibitor of inosine monophosphate dehydrogenase, such as mycophenolate mofetil, an inhibitor of dihydrofolic acid reductase, such as, but not limited to, methotrexate, a corticosteroid, such as, but not limited to, prednisolone and methylprednisolone, or an immunosuppressive antimetabolite, such as, but not limited to, azathioprine. In certain aspects, an immunosuppressive agent comprises an antisense oligonucleotide. In some aspects, an EV disclosed herein (e.g., exosome) can comprise both an antigen and an immunosuppressive agent. Not to be bound by any one theory, an EV (e.g., exosome) comprising both an antigen and an immunosuppressive agent can be used to induce tolerance to the antigen.

As used herein, the term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)$_2$, Fab, Fab', and F(ab')$_2$, F(ab1)$_2$, Fv, dAb, and Fd fragments, diabodies, and antibody-related polypeptides. Antibody includes bispecific antibodies and multispecific antibodies so long as they exhibit the desired biological activity or function. In some aspects, the antibody or antigen-binding fragment thereof comprises a scFv, scFab, scFab-Fc, nanobody, or any combination thereof. In some aspects, the antibody or antigen-binding fragment thereof comprises an agonist antibody, a blocking antibody, a targeting antibody, a fragment thereof, or a combination thereof. In some aspects, the agonist antibody is a CD40L agonist. In some aspects, the blocking antibody binds a target protein selected from programmed death 1 (PD-1), programmed death ligand 1 (PD-L1), cytotoxic T-lymphocyte-associated protein 4, and any combination thereof.

As used herein, the term "immune modulator" refers to an agent that acts on a target (e.g., a target cell) that is contacted with the extracellular vesicle, and regulates the immune system. Non-limiting examples of immune modulator that can be introduced into an EV (e.g., exosome) and/or a producer cell include agents such as, modulators of checkpoint inhibitors, ligands of checkpoint inhibitors, cytokines, derivatives thereof, or any combination thereof. The immune modulator can also include an agonist, an antagonist, an antibody, an antigen-binding fragment, a polynucleotide, such as siRNA, antisense oligonucleotide, phosphorodiamidate morpholino oligomer (PMO), peptide-conjugated phosphorodiamidate morpholino oligomer (PPMO), miRNA, lncRNA, mRNA, DNA, or a small molecule.

As used herein, "a mammalian subject" includes all mammals, including without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like).

The terms "individual," "subject," "host," and "patient," are used interchangeably herein and refer to any mammalian subject for whom diagnosis, treatment, or therapy is desired, particularly humans. The methods described herein are applicable to both human therapy and veterinary applications. In some embodiments, the subject is a mammal, and in other embodiments the subject is a human.

As used herein, the term "substantially free" means that the sample comprising EVs (e.g., exosomes) comprise less than about 10% of macromolecules by mass/volume (m/v) percentage concentration. Some fractions can contain less than about 0.001%, less than about 0.01%, less than about 0.05%, less than about 0.1%, less than about 0.2%, less than about 0.3%, less than about 0.4%, less than about 0.5%, less than about 0.6%, less than about 0.7%, less than about 0.8%, less than about 0.9%, less than about 1%, less than about 2%, less than about 3%, less than about 4%, less than about 5%, less than about 6%, less than about 7%, less than about 8%, less than about 9%, or less than about 10% (m/v) of macromolecules.

As used herein, the term "macromolecule" means nucleic acids, contaminant proteins, lipids, carbohydrates, metabolites, or a combination thereof.

As used herein, the term "conventional exosome protein" means a protein previously known to be enriched in EVs (e.g., exosomes), including but is not limited to CD9, CD63, CD81, PDGFR, GPI anchor proteins, lactadherin LAMP2, and LAMP2B, a fragment thereof, or a peptide that binds thereto.

As used herein, the term "linker" refers to any molecular structure that can conjugate a peptide or a protein to another molecule (e.g., a different peptide or protein, a small molecule, etc.). Suitable linkers are well known to those of skill in the art and include, but are not limited to, straight or branched-chain carbon linkers, heterocyclic carbon linkers, or peptide linkers (see, e.g., Chen et al., *Advanced Drug Delivery Reviews,* 2013, Vol. 65:10, pp. 1357-1369). The linkers can be joined to the carboxyl and amino terminal amino acids through their terminal carboxyl or amino groups or through their reactive side-chain groups. In addition, in some aspects, linkers can be classified as flexible or rigid, and they can be cleavable (e.g., comprise one or more protease-cleavable sites, which can be located within the sequence of the linker or flanking the linker at either end of the linker sequence).

"Administering," as used herein, means to give a composition comprising an EV, e.g., exosome, disclosed herein to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. EVs, e.g., exosomes can be administered as part of a pharmaceutical composition comprising at least one excipient.

An "immune response," as used herein, refers to a biological response within a vertebrate against foreign agents or abnormal, e.g., cancerous cells, which response protects the organism against these agents and diseases caused by them. An immune response is mediated by the action of one or more cells of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a CD4+ cell, a CD8+ T cell, or a Treg cell, or activation or inhibition of any other cell of the immune system, e.g., NK cell. Accordingly an immune response can comprise a humoral immune response (e.g., mediated by B-cells), cellular immune response (e.g., mediated by T cells), or both humoral and cellular immune responses. In some aspects, an immune response is an "inhibitory" immune response. An inhibitory immune response is an immune response that blocks or diminishes the effects of a stimulus (e.g., antigen). In certain aspects, the inhibitory immune response comprises the production of inhibitory antibodies against the stimulus. In some aspects, an immune response is a "stimulatory" immune response. A stimulatory immune response is an immune response that results in the generation of effectors cells (e.g., cytotoxic T lymphocytes) that can destroy and clear a target antigen (e.g., tumor antigen or viruses).

"Treat," "treatment," or "treating," as used herein, refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition. The term also include prophylaxis or prevention of a disease or condition or its symptoms thereof. In one aspect, the term "treating" or "treatment" means inducing an immune response in a subject against an antigen.

"Prevent" or "preventing," as used herein, refers to decreasing or reducing the occurrence or severity of a particular outcome. In some aspects, preventing an outcome is achieved through prophylactic treatment.

7.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

The term "about" indicates and encompasses an indicated value and a range above and below that value. In certain embodiments, the term "about" indicates the designated value ±10%, ±5%, or ±1%. In certain embodiments, where applicable, the term "about" indicates the designated value (s) ±one standard deviation of that value(s).

Throughout this disclosure, the term "a" or "an" entity refers to one or more of that entity; for example, "an antibody" is understood to represent one or more antibodies. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

7.3. EV (e.g., Exosome) Proteins

An aspect of the present disclosure relates to identification, use and modification of heterologous exosomal vesicle proteins (HEVPs), which are highly enriched on EV (e.g., exosome) membranes produced from certain producer cells. As described herein, different cells (e.g., mesenchymal stem cells vs. HEK293) naturally express different proteins. EVs (e.g., exosomes) produced from a cell express one or more proteins that are naturally expressed in the producer cell. Accordingly, EVs (e.g., exosomes) produced from different producer cells can have different protein composition. HEVPs can be identified by analyzing highly purified EVs (e.g., exosomes) with mass spectrometry or other methods known in the art.

The HEVPs of the present disclosure include various membrane proteins, such as transmembrane proteins, integral proteins and peripheral proteins, enriched on the EV (e.g., exosome) membranes. They include various CD proteins, transporters, integrins, lectins and cadherins. Specifically, the proteins include, but are not limited to, CD13, MME, ENPP1, and NRP1. In some aspects, the HEVP is CD13 (or a fragment or variant thereof). In some aspects, the HEVP is MME (or a fragment or variant thereof). In some aspects, the HEVP is ENPP1 (or a fragment or variant thereof). In some aspects, the HEVP is NRP1 (or a fragment or variant thereof). In some aspects, the HEVP is a type II transmembrane protein. Non-limiting examples of type II transmembrane proteins that can be used with the present disclosure include CD252, CD154, CD178, CD70, CD153, CD137, CD253, CD254, CD256, CD257, CD258, TL1, GITRL, and combinations thereof.

The present disclosure shows that an exosomal vesicle protein (e.g., HEVP) that is expressed only in the EVs derived from certain cell types (e.g., EVs from MSCs) can be engineered to be expressed on an EV derived from other cell types that do not naturally express the exosomal vesicle protein (e.g., EVs from HEK293). One or more HEVPs identified herein can be selectively used depending on a producer cell, production condition, purification methods, or intended application of the EVs (e.g., exosomes). For example, HEVPs enriched on a specific population of EVs (e.g., exosomes) can be used to purify the specific population of EVs (e.g., exosomes). HEVPs enriched on the surface of certain EVs (e.g., exosomes) with a specific size range, a targeting moiety, a charge density, a payload, etc. can be identified and used in some embodiments of the present disclosure. In some embodiments, more than one HEVP can be used, concurrently or subsequently, for the generation, purification, and isolation of therapeutic EVs (e.g., exosomes).

7.4. Surface-Engineered and/or Lumen-Engineered EVs (e.g., Exosomes)

Another aspect of the present disclosure relates to generation and use of surface-engineered EVs (e.g., exosomes). In some aspects, present disclosure relates to generation and use of lumen-engineered EVs (e.g., exosomes). Surface-engineered and/or lumen-engineered EVs (e.g., exosomes) have a membrane modified in its compositions. For example, their membrane compositions can be modified by changing the protein, lipid or glycan content of the membrane.

In some embodiments, the surface-engineered and/or lumen engineered EVs (e.g., exosomes) are generated by chemical and/or physical methods, such as PEG-induced fusion and/or ultrasonic fusion.

In other embodiments, the surface-engineered and/or lumen-engineered EVs (e.g., exosomes) are generated by genetic engineering. EVs (e.g., exosomes) produced from a genetically-modified producer cell or a progeny of the genetically-modified cell can contain modified membrane compositions. In some aspects, the genetically-modified producer cell or progeny of the genetically-modified cell comprises one or more exogenous proteins that are not naturally found in the cell. In certain aspects, the one or more exogenous proteins are scaffold moieties, such as the heterologous exosomal vesicle proteins (HEVP) disclosed herein. In some embodiments, surface-engineered and/or lumen-engineered EVs (e.g., exosomes) have the HEVP at a higher or lower density (compared to the density of HEVP expression in a cell that naturally expresses the HEVP) or include a variant or a fragment of the HEVP.

For example, surface-engineered and/or lumen-engineered EVs (e.g., exosomes) can be produced from a cell transformed with an exogenous sequence encoding the HEVP or a variant or a fragment of the HEVP. EVs (e.g., exosomes) including proteins expressed from the exogenous sequence can include modified membrane protein compositions.

Various modifications or fragments of the HEVP can be used for the embodiments of the present disclosure. For example, proteins modified to have enhanced affinity to a binding agent can be used for generating surface-engineered and/or lumen-engineered EVs (e.g., exosomes) that can be purified using the binding agent. Proteins modified to be more effectively targeted to EVs (e.g., exosomes) and/or membranes can be used. Proteins modified to comprise a minimal fragment required for specific and effective targeting to EV (e.g., exosome) membranes can be also used. In some aspects, HEVPs (including fragments and variants thereof) that are capable of anchoring a cargo or any other exogenously biologically active molecules (e.g., those disclosed herein) can be used in constructing a surface-engineered and/or lumen-engineered EV (e.g., exosome). In certain aspects, HEVPs (including fragments and variants thereof) that are capable of anchoring certain classes of proteins can be used.

For example, in some aspects, HEVPs are type I transmembrane proteins, and such HEVPs can be used to anchor the extracellular domain of a type I protein to the EVs (e.g., exosomes). In certain aspects, the expression of the extracellular domain of a type I protein on the EV (e.g., exosome) is increased when anchored to a type I transmembrane HEVP, compared to the corresponding expression when the protein is anchored to a different type of scaffold moiety (e.g., a non-type I transmembrane HEVP) or to the corresponding expression when the protein is overexpressed in an EV (e.g., exosome) producer cell that naturally expresses the protein.

In some aspects, HEVPs are type II transmembrane proteins, and such HEVPs can be used to anchor the extracellular domain of a type II protein to the EVs (e.g., exosomes). In certain aspects, the expression of the extracellular domain of a type II protein on the EV (e.g., exosome) is increased when anchored to a type II transmembrane HEVP, compared to the corresponding expression when the protein is anchored to a different type of scaffold moiety (e.g., a non-type II transmembrane HEVP) or to the corresponding expression when the protein is overexpressed in an EV (e.g., exosome) producer cell that naturally expresses the protein.

In some aspects, HEVPs are type III transmembrane proteins, and such HEVPs can be used to anchor the extracellular domains of a type III protein to the EVs (e.g., exosomes). In certain aspects, the expression of the extracellular domains of a type III protein on the EV (e.g., exosome) is increased when anchored to a type III transmembrane HEVP, compared to the corresponding expression when the protein is anchored to a different type of scaffold moiety (e.g., a non-type III transmembrane HEVP) or to the corresponding expression when the protein is overexpressed in an EV (e.g., exosome) producer cell that naturally expresses the protein.

In some aspects, HEVPs are type IV transmembrane proteins, and such HEVPs can be used to anchor the extracellular domain of a type IV protein to the EVs (e.g., exosome). In certain aspects, the expression of the extracellular domain of a type IV protein on the EV (e.g., exosome) is increased when anchored to a type IV transmembrane HEVP, compared to the corresponding expression when the protein is anchored to a different type of scaffold moiety (e.g., a non-type IV transmembrane HEVP) or to the corresponding expression when the protein is overexpressed in an EV (e.g., exosome) producer cell that naturally expresses the protein.

Fusion proteins can be also used; for example, HEVPs or their fragments fused to an affinity tag (e.g., His tag, GST tag, glutathione-S-transferase, S-peptide, HA, Myc, FLAG™ (Sigma-Aldrich Co.), MBP, SUMO, and Protein A) can be used for purification or removal of the surface-engineered EVs (e.g., exosomes) with a binding agent specific to the affinity tag.

Fusion proteins having a therapeutic activity can be also used for generating surface-engineered EVs (e.g., exosomes). Accordingly, in some aspects, an EV (e.g., exosome) disclosed herein has been engineered or modified to express the fusion protein and can be used to deliver one or more (e.g., two, three, four, five or more) therapeutic molecules to a target. For example, the fusion protein can comprise a HEVP (e.g., CD13, MME, ENPP1, or NRP1, or a fragment or a variant thereof), and a therapeutic compound (e.g., peptide). In some aspects, the fusion protein comprises CD13 (or a fragment or variant thereof) and a therapeutic compound. In some aspects, the fusion protein comprises MME (or a fragment or variant thereof) and a therapeutic compound. In some aspects, the fusion protein comprises ENPP1 (or a fragment or variant thereof) and a therapeutic compound. In some aspects, the fusion protein comprises NRP1 (or a fragment or variant thereof) and a therapeutic compound. In some aspects, the therapeutic compound is fused directly to the HEVP. In some aspects, the therapeutic compound is anchored to the HEVP via a linker (e.g., those disclosed herein).

In some aspects, the linker is a peptide linker. In some aspects, the peptide linker can comprise at least about two, at least about three, at least about four, at least about five, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 amino acids.

In some aspects, the peptide linker is synthetic, i.e., non-naturally occurring. In some aspects, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in some aspects the peptide linker can comprise non-naturally occurring polypeptides which are modified forms of naturally occurring polypeptides (e.g., comprising a mutation such as an addition, substitution or deletion).

Linkers can be susceptible to cleavage ("cleavable linker") thereby facilitating release of the exogenous biologically active molecule (e.g., targeting moiety, therapeutic molecule, adjuvant, or immune modulator).

In some aspects, the linker is a "reduction-sensitive linker." In some aspects, the reduction-sensitive linker contains a disulfide bond. In some aspects, the linker is an "acid labile linker." In some aspects, the acid labile linker contains hydrazone. Suitable acid labile linkers also include, for example, a cis-aconitic linker, a hydrazide linker, a thiocarbamoyl linker, or any combination thereof.

In some aspects, the linker comprises a non-cleavable linker.

In some aspects, the therapeutic peptide is selected from the group consisting of a natural peptide, a recombinant peptide, a synthetic peptide, or a linker to a therapeutic compound. The therapeutic compound can be nucleotides, amino acids, lipids, carbohydrates, or small molecules. The therapeutic peptide can be an antibody, an enzyme, a ligand, a receptor, an antimicrobial peptide or a fragment or a variant thereof. In some embodiments, the therapeutic peptide is a nucleic acid binding protein. The nucleic acid binding protein can be Dicer, an Argonaute protein, TRBP, or MS2 bacteriophage coat protein. In some embodiments, the nucleic acid binding protein additionally comprises one or more RNA or DNA molecules. The one or more RNA can be a miRNA, siRNA, antisense oligonucleotide, phosphorodiamidate morpholino oligomer (PMO), peptide-conjugated phosphorodiamidate morpholino oligomer (PPMO), guide RNA, lincRNA, mRNA, antisense RNA, dsRNA, or combinations thereof.

In some embodiments, the therapeutic peptide is a part of a protein-protein interaction system. In some embodiments, the protein-protein interaction system comprises an FRB-FKBP interaction system, e.g., the FRB-FKBP interaction system as described in Banaszynski et al., J Am Chem Soc. 2005 Apr. 6; 127(13):4715-21.

In some aspects, a therapeutic molecule which can be anchored to a HEVP and expressed on an EV (e.g., exosome) comprises an antigen. In certain aspects, the antigen comprises a tumor antigen. Non-limiting examples of tumor antigens include: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen (CTA), MART-1 gp100, TNF-related apoptosis-inducing ligand, Brachyury (preferentially expressed antigen in melanoma (PRAME)), or combinations thereof. In further aspects, an antigen can comprise a neoantigen. As used herein, the term "neoantigen," refers to antigens encoded by tumor-specific mutated genes. In some aspects, the antigen is derived from a bacterium, a virus, fungus, protozoa, or any combination thereof. In some aspects, the antigen is derived from an oncogenic virus. In further aspects, the antigen is derived from a group comprising: a Human Gamma herpes virus 4 (Epstein Barr virus), influenza A virus, influenza B virus, cytomegalovirus, *Staphylococcus aureus, Mycobacterium tuberculosis, Chlamydia trachomatis*, HIV-1, HIV-2, corona viruses (e.g., MERS-CoV and SARS CoV), filoviruses (e.g., Marburg and Ebola), *Streptococcus pyogenes, Streptococcus pneumoniae*, Plasmodia species (e.g., *vivax* and *falciparum*), Chikungunya virus, Human Papilloma virus (HPV), Hepatitis B, Hepatitis C, human herpes virus 8, herpes simplex virus 2 (HSV2), *Klebsiella* sp., *Pseudomonas aeruginosa, Enterococcus* sp., *Proteus* sp., *Enterobacter* sp., *Actinobacter* sp., coagulase-negative staphylococci (CoNS), *Mycoplasma* sp., or combinations thereof.

In some aspects, a therapeutic molecule comprises an immunosuppressive agent. Accordingly, in certain aspects, an EV disclosed herein comprises a HEVP and an immunosuppressive agent.

Non-limiting examples of other suitable therapeutic molecules include pharmacologically active drugs and genetically active molecules, including antineoplastic agents, anti-inflammatory agents, hormones or hormone antagonists, ion channel modifiers, and neuroactive agents. Examples of suitable payloads of therapeutic agents include those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Suitable payloads further include toxins, and biological and chemical warfare agents, for example see Somani, S. M. (ed.), Chemical Warfare Agents, Academic Press, New York (1992)).

In some aspects, a therapeutic molecule comprises a self-antigen. As used herein, the term "self-antigen" refers to an antigen that is expressed by a host cell or tissue. Under normal healthy state, such antigens are recognized by the body as self and do not elicit an immune response. However, under certain diseased conditions, a body's own immune system can recognize self-antigens as foreign and mount an immune response against them, resulting in autoimmunity. In certain aspects, EVs, e.g., exosomes, of the present disclosure can comprise a self-antigen (i.e., the self (germline) protein to which T cell responses have been induced and resulted in autoimmunity). Such EVs, e.g., exosomes, can be used to target the autoreactive T cells and suppress their activity. Non-limiting examples of self-antigens (including the associated disease or disorder) include: beta-cell proteins (type I diabetes), myelin oligodendrocyte glycoprotein (MOG, multiple sclerosis), synovial proteins (rheumatoid arthritis), or combinations thereof.

In some aspects, the therapeutic molecule comprises an antibody or antigen-binding fragment thereof. In some aspects, the therapeutic molecule comprises at least 2, at least 3, at least 4, or at least 5 antibodies or antigen-binding fragments thereof. In some aspects, the antibody or antigen-binding fragment thereof comprises a scFv, scFab, scFab-Fc, nanobody, or any combination thereof. In some aspects, the antibody or antigen-binding fragment thereof comprises an agonist antibody, blocking antibody, a targeting antibody, a fragment thereof, or a combination thereof. In some aspects, the agonist antibody is a CD40L agonist. In some aspects, the blocking antibody binds a target protein selected from programmed death 1 (PD-1), programmed death ligand 1

(PD-L1), cytotoxic T-lymphocyte-associated protein 4, and any combination thereof. In some aspects, the EV, e.g., exosome, comprises an anti-IL12 antibody or an antigen-binding fragment thereof and an anti-CD40L antibody or antigen-binding fragment thereof.

The fusion proteins can be targeted to the surface of EVs (e.g., exosomes) and provide a therapeutic activity to the EV (e.g., exosome). In some embodiments, the fusion protein does not comprise IGSF8 or a fragment or modification thereof.

In some embodiments, fusion proteins having a targeting moiety are used. For example, fusion proteins can comprise a HEVP (e.g., CD13, MME, ENPP1, or NRP1, or a fragment or a variant thereof), and a targeting moiety. In some aspects, the fusion protein comprises CD13 and a targeting moiety. In some aspects, the fusion protein comprises MME and a targeting moiety. In some aspects, the fusion protein comprises ENPP1 and a targeting moiety. In some aspects, the fusion protein comprises NRP1 and a targeting moiety. The targeting moiety can be used for targeting the EV (e.g., exosome) to a specific organ, tissue, or cell for a treatment using the EV (e.g., exosome). In certain aspects, the targeting moiety binds to a marker (or target molecules) expressed on a cell or a population of cells. In certain aspects, the marker is expressed on multiple cell types, e.g., all antigen-present cells (e.g., dendritic cells, macrophages, and B lymphocytes). In some aspects, the marker is expressed only on a specific population of cells (e.g., dendritic cells). Non-limiting examples of markers that are expressed on specific population of cells (e.g., dendritic cells) include a C-type lectin domain family 9 member A (CLEC9A) protein, a dendritic cell-specific intercellular adhesion molecule-3-grabbing non-integrin (DC-SIGN), CD207, CD40, Clec6, dendritic cell immunoreceptor (DCIR), DEC-205, lectin-like oxidized low-density lipoprotein receptor-1 (LOX-1), MARCO, Clec12a, DC-asialoglycoprotein receptor (DC-ASGPR), DC immunoreceptor 2 (DCIR2), Dectin-1, macrophage mannose receptor (MMR), BDCA-1 (CD303, Clec4c), Dectin-2, Bst-2 (CD317), or any combination thereof.

In some embodiments, the targeting moiety is an antibody or antigen-binding fragment thereof. Antibodies and antigen-binding fragments thereof include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)$_2$, Fab, Fab', and F(ab')$_2$, F(ab1)$_2$, Fv, dAb, and Fd fragments, diabodies, and antibody-related polypeptides. Antibodies and antigen-binding fragments thereof also includes bispecific antibodies and multispecific antibodies so long as they exhibit the desired biological activity or function.

In some aspects, an EV (e.g., exosome) described herein can comprise a HEVP (e.g., CD13, MME, ENPP1, or NRP1, or a fragment or a variant thereof) and one or more exogenous biologically active molecules. In certain aspects, an exogenous biologically active molecule that can be expressed in an EV (e.g., exosome) is an adjuvant. Accordingly, in some aspects, an EV (e.g., exosome) comprises CD13 (or a fragment or variant thereof) and an adjuvant. In some aspects, an EV (e.g., exosome) comprises MME (or a fragment or variant thereof) and an adjuvant. In some aspects, an EV (e.g., exosome) comprises ENPP1 (or a fragment or variant thereof) and an adjuvant. In some aspects, an EV (e.g., exosome) comprises NRP1 (or a fragment or variant thereof) and an adjuvant. In some aspects, EVs (e.g., exosome) disclosed herein comprises two, three, four, five or more different adjuvants. As used herein, the term "adjuvant" refers to any substance that enhances the therapeutic effect of a cargo (e.g., increasing an immune response to an antigen).

In some aspects, an adjuvant useful for the present disclosure induces the activation of a cytosolic pattern recognition receptor. Non-limiting examples of cytosolic pattern recognition receptor includes: stimulator of interferon genes (STING), retinoic acid-inducible gene I (RIG-1), Melanoma Differentiation-Associated protein 5 (MDA5), Nucleotide-binding oligomerization domain, Leucine rich Repeat and Pyrin domain containing (NLRP), inflammasomes, or combinations thereof. In certain aspects, an adjuvant is a STING agonist. Stimulator of Interferon Genes (STING) is a cytosolic sensor of cyclic dinucleotides that is typically produced by bacteria. Upon activation, it leads to the production of type I interferons and initiates an immune response. In certain aspects, the STING agonist comprises a cyclic dinucleotide STING agonist or a non-cyclic dinucleotide STING agonist.

In some aspects, an adjuvant comprises a toll-like receptor (TLR) agonist. Non-limiting examples of TLR agonists include: TLR2 agonist (e.g., lipoteichoic acid, atypical LPS, MALP-2 and MALP-404, OspA, porin, LcrV, lipomannan, GPI anchor, lysophosphatidylserine, lipophosphoglycan (LPG), glycophosphatidylinositol (GPI), zymosan, hsp60, gH/gL glycoprotein, hemagglutinin), a TLR3 agonist (e.g., double-stranded RNA, e.g., poly(I:C)), a TLR4 agonist (e.g., lipopolysaccharides (LPS), lipoteichoic acid, β-defensin 2, fibronectin EDA, HMGB1, snapin, tenascin C), a TLR5 agonist (e.g., flagellin), a TLR6 agonist, a TLR7/8 agonist (e.g., single-stranded RNA, CpG-A, Poly G10, Poly G3, Resiquimod), a TLR9 agonist (e.g., unmethylated CpG DNA), and combinations thereof. Non-limiting examples of TLR agonists can be found at WO2008115319A2, US20130202707A1, US20120219615A1, US20100029585A1, WO2009030996A1, WO2009088401A2, and WO2011044246A1, each of which is incorporated by reference in its entirety.

In some embodiments, the fusion protein does not comprise IGSF8 or a fragment or modification thereof.

In some aspects, an EV (e.g., exosome) described herein can comprise a HEVP (e.g., CD13, MME, ENPP1, or NRP1, or a fragment or a variant thereof) and one or more exogenous biologically active molecules, wherein the one or more exogenous biologically molecules comprise one or more (e.g., two, three, four, five or more) immune modulators. In some aspects, an EV (e.g., exosome) comprises CD13 (or a fragment or variant thereof) and an immune modulator. In some aspects, an EV (e.g., exosome) comprises MME (or a fragment or variant thereof) and an immune modulator. In some aspects, an EV (e.g., exosome) comprises ENPP1 (or a fragment or variant thereof) and an immune modulator. In some aspects, an EV (e.g., exosome) comprises NRP1 (or a fragment or variant thereof) and an immune modulator. In certain aspects, the one or more immune modulators are expressed in combination with other exogenous biologically active molecules disclosed herein (e.g., targeting moiety, therapeutic molecule, and/or adjuvant).

In some aspects, an immune modulator comprises an inhibitor for a negative checkpoint regulator or an inhibitor for a binding partner of a negative checkpoint regulator. In certain aspects, the negative checkpoint regulator comprises cytotoxic T-lymphocyte-associated protein 4 (CTLA-4), programmed cell death protein 1 (PD-1), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, or any combination thereof.

In some aspects, the immune modulator is an inhibitor of cytotoxic T-lymphocyte-associate protein 4 (CTLA-4). In certain aspects, the CTLA-4 inhibitor is a monoclonal antibody of CTLA-4 ("anti-CTLA-4 antibody"). In certain aspects, the inhibitor is a fragment of a monoclonal antibody of CTLA-4. In certain aspects, the antibody fragment is a scFv, (scFv)$_2$, Fab, Fab', and F(ab')$_2$, F(ab1)$_2$, Fv, dAb, or Fd of a monoclonal antibody of CTLA-4. In certain aspects, the inhibitor is a nanobody, a bispecific antibody, or a multispecific antibody against CTLA-4. In some aspects, the anti-CTLA-4 antibody is ipilimumab. In other aspects, the anti-CTLA-4 antibody is tremelimumab.

In some aspects, the immune modulator is an inhibitor of programmed cell death protein 1 (PD-1). In some aspects, the immune modulator is an inhibitor of programmed death-ligand 1 (PD-L1). In some aspects, the immune modulator is an inhibitor of programmed death-ligand 2 (PD-L2). In certain aspects, the inhibitor of PD-1, PD-L1, or PD-L2 is a monoclonal antibody of PD-1 ("anti-PD-1 antibody"), PD-L1 ("anti-PD-L1 antibody"), or PD-L2 ("anti-PD-L2 antibody"). In some aspects, the inhibitor is a fragment of an anti-PD-1 antibody, anti-PD-L1 antibody, or anti-PD-L2 antibody. In certain aspects, the antibody fragment is a scFv, (scFv)$_2$, Fab, Fab', and F(ab')$_2$, F(ab1)$_2$, Fv, dAb, or Fd of a monoclonal antibody of PD-1, PD-L1, or PD-L2. In certain aspects, the inhibitor is a nanobody, a bispecific antibody, or a multispecific antibody against PD-1, PD-L1, or PD-L2. In some aspects, the anti-PD-1 antibody is nivolumab. In some aspects, the anti-PD-1 antibody is pembrolizumab. In some aspects, the anti-PD-1 antibody is pidilizumab. In some aspects, the anti-PD-L1 antibody is atezolizumab. In other aspects, the anti-PD-L1 antibody is avelumab.

In some aspects, the immune modulator is an inhibitor of lymphocyte-activated gene 3 (LAG3). In certain aspects, the inhibitor of LAG3 is a monoclonal antibody of LAG3 ("anti-LAG3 antibody"). In some aspects, the inhibitor is a fragment of an anti-LAG3 antibody, e.g., scFv, (scFv)$_2$, Fab, Fab', and F(ab')$_2$, F(ab1)$_2$, Fv, dAb, or Fd. In certain aspects, the inhibitor is a nanobody, a bispecific antibody, or a multispecific antibody against LAG3.

In some aspects, the immune modulator is an inhibitor of T-cell immunoglobulin mucin-containing protein 3 (TIM-3). In some aspects, the immune modulator is an inhibitor of B and T lymphocyte attenuator (BTLA). In some aspects, the immune modulator is an inhibitor of T cell immunoreceptor with Ig and ITIM domains (TIGIT). In some aspects, the immune modulator is an inhibitor of V-domain Ig suppressor of T cell activation (VISTA). In some aspects, the immune modulator is an inhibitor of adenosine A2a receptor (A2aR). In some aspects, the immune modulator is an inhibitor of killer cell immunoglobulin like receptor (KIR). In some aspects, the immune modulator is an inhibitor of indoleamine 2,3-dioxygenase (IDO). In some aspects, the immune modulator is an inhibitor of CD20, CD39, or CD73.

In some aspects, the immune modulator comprises an activator for a positive co-stimulatory molecule or an activator for a binding partner of a positive co-stimulatory molecule. In certain aspects, the positive co-stimulatory molecule comprises a TNF receptor superfamily member (e.g., CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, AITR, TROY, CD358, TRAMP, and XEDAR). In some aspects, the activator for a positive co-stimulatory molecule is a TNF superfamily member (e.g., TNFα, TNF-C, OX40L, CD40L, FasL, LIGHT, TL1A, CD27L, Siva, CD153, 4-1BB ligand, TRAIL, RANKL, TWEAK, APRIL, BAFF, CAMLG, NGF, BDNF, NT-3, NT-4, GITR ligand, and EDA-2).

In some aspects, the immune modulator is an activator of TNF Receptor Superfamily Member 4 (OX40). In certain aspects, the activator of OX40 is an agonistic anti-OX40 antibody. In further aspects, the activator of OX40 is a OX40 ligand (OX40L).

In some aspects, the immune modulator is an activator of CD27. In certain aspects, the activator of CD27 is an agonistic anti-CD27 antibody. In other aspects, the activator of CD27 is a CD27 ligand (CD27L).

In some aspects, the immune modulator is an activator of CD40. In certain aspects, the activator of CD40 is an agonistic anti-CD40 antibody. In some aspects, the activator of CD40 is a CD40 ligand (CD40L). In certain aspects, the CD40L is a monomeric CD40L. In other aspects, the CD40L is a trimeric CD40L.

In some aspects, the immune modulator is an activator of glucocorticoid-induced TNFR-related protein (GITR). In certain aspects, the activator of GITR is an agonistic anti-GITR antibody. In other aspects, the activator of GITR is a natural ligand of GITR.

In some aspects, the immune modulator is an activator of 4-1BB. In specific aspects, the activator of 4-1BB is an agonistic anti-4-1BB antibody. In certain aspects, the activator of 4-1BB is a natural ligand of 4-1BB.

In some aspects, the immune modulator is a Fas receptor (Fas). In such aspects, the Fas receptor is displayed on the surface of the EV, e.g., exosome. In some aspects, the immune modulator is Fas ligand (FasL). In certain aspects, the Fas ligand is displayed on the surface of the EV, e.g., exosome. In some aspects, the immune modulator is an anti-Fas antibody or an anti-FasL antibody.

In some aspects, the immune modulator is an activator of a CD28-superfamily co-stimulatory molecule. In certain aspects, the CD28-superfamily co-stimulatory molecule is ICOS or CD28. In certain aspects, the immune modulator is ICOSL, CD80, or CD86.

In some aspects, the immune modulator is an activator of inducible T cell co-stimulator (ICOS). In certain aspects, the activator of ICOS is an agonistic anti-ICOS antibody. In other aspects, the activator of ICOS is a ICOS ligand (ICOSL).

In some aspects, the immune modulator is an activator of CD28. In some aspects, the activator of CD28 is an agonistic anti-CD28 antibody. In other aspects, the activator of CD28 is a natural ligand of CD28. In certain aspects, the ligand of CD28 is CD80.

In some aspects, the immune modulator comprises a cytokine or a binding partner of a cytokine. In certain aspects, the cytokine comprises IL-2, IL-4, IL-7, IL-10, IL-12, IL-15, IL-21, or IFN-γ. In some aspects, the immune modulator comprises FLT-3 (CD135).

In some aspects, the immune modulator comprises a protein that supports intracellular interactions required for germinal center responses. In certain aspects, such a protein comprises a signaling lymphocyte activation molecule (SLAM) family member or a SLAM-associated protein (SAP). In some aspects, a SLAM family members comprises SLAM, CD48, CD229 (Ly9), Ly108, 2B4, CD84, NTB-A, CRACC, BLAME, CD2F-10, or combinations thereof.

In some aspects, the immune modulator comprises a T-cell receptor (TCR) or a derivative thereof. In certain aspects, the immune modulator is a TCR α-chain or a derivative thereof. In other aspects, the immune modulator is a TCR β-chain or a derivative thereof. In further aspects, the immune modulator is a co-receptor of the T-cell or a derivative thereof.

In some aspects, the immune modulator comprises a chimeric antigen receptor (CAR) or a derivative thereof. In certain aspects, the CAR binds to one or more of the therapeutic molecules disclosed herein (e.g., tumor antigen, e.g., alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand).

In certain aspects, the immune modulator is an activator of CD28. In certain aspects, the activator is a fragment of a monoclonal antibody of CD28. In certain aspects, the antibody fragment is a scFv, $(scFv)_2$, Fab, Fab', and $F(ab')_2$, $F(ab1)_2$, Fv, dAb, or Fd of a monoclonal antibody of CD28. In certain aspects, the activator is a nanobody, a bispecific antibody, or a multispecific antibody against CD28.

In some aspects, the immune modulator comprises a NF-κB inhibitor. Non-limiting examples of NF-κB inhibitors that can be used with the present disclosure includes: IKK complex inhibitors (e.g., TPCA-1, NF-κB Activation Inhibitor VI (BOT-64), BMS 345541, Amlexanox, SC-514 (GK 01140), IMD 0354, IKK-16), IκB degradation inhibitor (e.g., BAY 11-7082, MG-115, MG-132, Lactacystin, Epoxomicin, Parthenolide, Carfilzomib, MLN-4924 (Pevonedistat)), NF-κB nuclear translocation inhibitor (e.g., JSH-23, Rolipram), p65 acetylation inhibitor (e.g., Gallic acid, Anacardic acid), NF-κB-DNA binding inhibitor (e.g., GYY 4137, p-XSC, CV 3988, Prostaglandin E2 (PGE2)), transactivation inhibitor (e.g., LY 294002, Wortmannin, Mesalamine), or combinations thereof. See also Gupta, S. C., et al., *Biochim Biophys Acta* 1799:775-787 (2010), which is herein incorporated by reference in its entirety. In further aspects, an immune modulator comprises a COX-2 inhibitor, mTOR inhibitor (e.g., rapamycin and derivatives), prostaglandins, nonsteroidal anti-inflammatory agents (NSAIDS), antileukotriene, or combinations thereof.

In some aspects, the immune modulator is an agonist. In certain aspects, the agonist is an endogenous agonist, such as a hormone, or a neurotransmitter. In other aspects, the agonist is an exogenous agonist, such as a drug. In some aspects, the agonist is a physical agonist, which can create an agonist response without binding to the receptor. In some aspects, the agonist is a superagonist, which can produce a greater maximal response than the endogenous agonist. In certain aspects, the agonist is a full agonist with full efficacy at the receptor. In other aspects, the agonist is a partial agonist having only partial efficacy at the receptor relative to a full agonist. In some aspects, the agonist is an inverse agonist that can inhibit the constitutive activity of the receptor. In some aspects, the agonist is a co-agonist that works with other co-agonists to produce an effect on the receptor. In certain aspects, the agonist is an irreversible agonist that binds permanently to a receptor through formation of covalent bond. In certain aspects, the agonist is selective agonist for a specific type of receptor In some aspects, the immune modulator is an antagonist. In specific aspects, the antagonist is a competitive antagonist, which reversibly binds to the receptor at the same binding site as the endogenous ligand or agonist without activating the receptor. Competitive antagonist can affect the amount of agonist necessary to achieve a maximal response. In other aspects, the antagonist is a non-competitive antagonist, which binds to an active site of the receptor or an allosteric site of the receptor. Non-competitive antagonist can reduce the magnitude of the maximum response that can be attained by any amount of agonist. In further aspects, the antagonist is an uncompetitive antagonist, which requires receptor activation by an agonist before its binding to a separate allosteric binding site.

In some aspects, the immune modulator comprises an antibody or an antigen-binding fragment. The immune modulator can be a full length protein or a fragment thereof. The antibody or antigen-binding fragment can be derived from natural sources, or partly or wholly synthetically produced. In some aspects, the antibody is a monoclonal antibody. In some of these aspects, the monoclonal antibody is an IgG antibody. In certain aspects, the monoclonal antibody is an IgG1, IgG2, IgG3, or IgG4. In some other aspects, the antibody is a polyclonal antibody. In certain aspects, the antigen-binding fragment is selected from Fab, Fab', and $F(ab)_2$, $F(ab1)_2$, Fv, dAb, and Fd fragments. In certain aspects, the antigen-binding fragment is an scFv or $(scFv)_2$ fragment. In certain other aspects, the antibody or antigen-binding fragment is a NANOBODY® (single-domain antibody). In some aspects, the antibody or antigen-binding fragment is a bispecific or multispecific antibody.

In various aspects, the antibody or antigen-binding fragment is fully human. In some aspects, the antibody or antigen-binding fragment is humanized. In some aspects, the antibody or antigen-binding fragment is chimeric. In some of these aspects, the chimeric antibody has non-human V region domains and human C region domains. In some aspects, the antibody or antigen-binding fragment is non-human, such as murine or veterinary.

In certain aspects, the immune modulator is a polynucleotide. In some of these aspects, the polynucleotide includes, but is not limited to, an mRNA, a miRNA, an siRNA, antisense oligonucleotide, a phosphorodiamidate morpholino oligomer (PMO), a peptide-conjugated phosphorodiamidate morpholino oligomer (PPMO), an antisense RNA, an shRNA, a lncRNA, and a dsDNA. In some aspects, the polynucleotide is an RNA (e.g., an mRNA, a miRNA, an siRNA, an antisense RNA, an shRNA, or an lncRNA). In some of these aspects, when the polynucleotide is an mRNA, it can be translated into a desired polypeptide. In some aspects, the polynucleotide is a microRNA (miRNA) or pre-miRNA molecule. In some of these aspects, the miRNA is delivered to the cytoplasm of the target cell, such that the miRNA molecule can silence a native mRNA in the target cell. In some aspects, the polynucleotide is a small interfering RNA (siRNA) or a short hairpin RNA (shRNA) capable of interfering with the expression of an oncogene or other dysregulating polypeptides. In some of these aspects, the siRNA is delivered to the cytoplasm of the target cell, such that the siRNA molecule can silence a native mRNA in the target cell. In some aspects, the polynucleotide is an antisense RNA that is complementary to an mRNA. In some aspects, the polynucleotide is a long non-coding RNA (lncRNA) capable of regulating gene expression and modulating diseases. In some aspects, the polynucleotide is a DNA that can be transcribed into an RNA. In some of these aspects, the transcribed RNA can be translated into a desired polypeptide.

In some aspects, the immune modulator is a protein, a peptide, a glycolipid, or a glycoprotein.

In some embodiments, the EVs (e.g., surface-engineered exosomes) described herein demonstrate superior character-istics compared to EVs (e.g., surface-engineered exosomes) known in the art. For example, EVs (e.g., surface-engineered exosomes) produced by using the HEVPs provided herein contain modified proteins that are more highly enriched on their surface than EVs (e.g., exosomes) in the prior art, e.g., those produced using conventional exosome proteins. In some aspects, the expression level of the modified proteins is increased (i.e., enriched) by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, or at least about 300% or more, compared to the expression of the corresponding protein using conventional exosome proteins.

Moreover, in some aspects, the EVs (e.g., surface-engi-neered exosomes) of the present disclosure can have greater, more specific, or more controlled biological activity com-pared to EVs (e.g., surface-engineered exosomes) known in the art. For example, a surface engineered EV (e.g., exo-some) comprising a therapeutic or biologically relevant exogenous sequence fused to an HEVP protein or a fragment thereof described herein (e.g., CD13, MME, ENPP1, or NRP1 or a fragment thereof) can have more of the desired engineered characteristics than fusion to scaffolds known in the art. Scaffold proteins known in the art include tetraspanin molecules (e.g., CD63, CD81, CD9 and others), lysosome-associated membrane protein 2 (LAMP2 and LAMP2B), platelet-derived growth factor receptor (PDGFR), GPI anchor proteins, lactadherin and fragments thereof, and peptides that have affinity to any of these proteins or fragments thereof. Previously, overexpression of exogenous proteins relied on stochastic or random disposition of the exogenous proteins onto the EV (e.g., exosome) for produc-ing surface-engineered EVs (e.g., exosomes). This resulted in low-level, unpredictable density of the exogenous pro-teins on the EVs (e.g., exosomes). Thus, the HEVP proteins and fragments thereof described herein provide important advancements in novel EV (e.g., exosome) compositions and methods of making the same.

In some embodiments, the surface-engineered EV (e.g., exosome) comprising a fusion protein containing an exog-enous sequence (e.g., encoding an exogenous biologically active molecule, e.g., antigen, adjuvant, targeting moiety, and/or immune modulator) and an HEVP identified herein has a higher density of the fusion protein than similarly engineered EVs (e.g., exosomes) comprising an exogenous sequence conjugated to a conventional EV (e.g., exosome) protein known in the art (e.g., CD9, CD63, CD81, PDGFR, GPI anchor proteins, lactadherin LAMP2, and LAMP2B, a fragment thereof, or a peptide that binds thereto). In some embodiments, the fusion protein containing an HEVP as described herein is present at about 2-, about 4-, about 8-, about 16-, about 32-, about 64-, about 100-, about 200-, about 400-, about 800-, about 1,000-fold or a higher density on the EV (e.g., exosome) surface than fusion proteins on other EV (e.g., exosome) surfaces similarly modified using a conventional EV (e.g., exosome) protein. In some embodi-ments, the fusion protein containing an HEVP as described herein is present at about 2 to about 4-fold, about 4 to about 8-fold, about 8 to about 16-fold, about 16 to about 32-fold, about 32 to about 64-fold, about 64 to about 100-fold, about 100 to about 200-fold, about 200 to about 400-fold, about 400 to about 800-fold, about 800 to about 1,000-fold or to a higher density on the EV (e.g., exosome) surface than fusion proteins on other EV (e.g., exosome) surfaces simi-larly modified using a conventional EV (e.g., exosome) protein.

In some embodiments, a fusion protein of CD13, MME, ENPP1, or NRP1, a variant, a fragment, a variant of a fragment or a modification thereof is present at about 2-, about 4-, about 8-, about 16-, about 32-, about 64-, about 100-, about 200-, about 400-, about 800-, about 1,000-fold or a higher density on the EV (e.g., exosome) surface than fusion proteins on other EV (e.g., exosome) surfaces simi-larly modified using CD9. In some embodiments, a fusion protein of CD13, MME, ENPP1, or NRP1, a variant, a fragment, a variant of a fragment or a modification thereof is present at about 2-, about 4-, about 8-, about 16-, about 32-, about 64-, about 100-, about 200-, about 400-, about 800-, about 1,000-fold or a higher density on the EV (e.g., exosome) surface than fusion proteins on other EVs (e.g., exosome) surfaces similarly modified using CD63. In some embodiments, a fusion protein of CD13, MME, ENPP1, or NRP1, a variant, a fragment, a variant of a fragment or a modification thereof is present at about 2-, about 4-, about 8-, about 16-, about 32-, about 64-, about 100-, about 200-, about 400-, about 800-, about 1,000-fold or a higher density on the EV (e.g., exosome) surface than fusion proteins on other EV (e.g., exosome) surfaces similarly modified using CD81. In some embodiments, a fusion protein of CD13, MME, ENPP1, or NRP1, a variant, a fragment, a variant of a fragment or a modification thereof is present at about 2-, about 4-, about 8-, about 16-, about 32-, about 64-, about 100-, about 200-, about 400-, about 800-, about 1,000-fold or a higher density on the EV (e.g., exosome) surface than fusion proteins on other EV (e.g., exosome) surfaces simi-larly modified using PDGFR. In some embodiments, a fusion protein of CD13, MME, ENPP1, or NRP1, a variant, a fragment, a variant of a fragment or a modification thereof is present at about 2-, about 4-, about 8-, about 16-, about 32-, about 64-, about 100-, about 200-, about 400-, about 800-, about 1,000-fold or a higher density on the EV (e.g., exosome) surface than fusion proteins on other EV (e.g., exosome) surfaces similarly modified using GPI anchor proteins. In some embodiments, a fusion protein of CD13, MME, ENPP1, or NRP1, a variant, a fragment, a variant of a fragment or a modification thereof is present at about 2-, about 4-, about 8-, about 16-, about 32-, about 64-, about 100-, about 200-, about 400-, about 800-, about 1,000-fold or a higher density on the EV (e.g., exosome) surface than fusion proteins on other EV (e.g., exosome) surfaces simi-larly modified using lactadherin. In some embodiments, a fusion protein of CD13, MME, ENPP1, or NRP1, a variant, a fragment, a variant of a fragment or a modification thereof is present at about 2-, about 4-, about 8-, about 16-, about 32-, about 64-, about 100-, about 200-, about 400-, about 800-, about 1,000-fold or a higher density on the EV (e.g., exosome) surface than fusion proteins on other EV (e.g., exosome) surfaces similarly modified using LAMP2. In some embodiments, a fusion protein of CD13, MME, ENPP1, or NRP1, a variant, a fragment, a variant of a fragment or a modification thereof is present at about 2-, about 4-, about 8-, about 16-, about 32-, about 64-, about 100-, about 200-, about 400-, about 800-, about 1,000-fold or a higher density on the EV (e.g., exosome) surface than fusion proteins on other EV (e.g., exosome) surfaces similarly modified using LAMP2B. In some embodiments, a fusion protein of CD13, MME, ENPP1, or NRP1, a variant, a fragment, a variant of a fragment or a modification thereof is present at about 2-, about 4-, about 8-, about 16-, about 32-, about 64-, about 100-, about 200-, about 400-, about 800-, about 1,000-fold or a higher density on the EV (e.g., exosome) surface than fusion proteins on other EV (e.g., exosome) surfaces similarly modified using a fragment of a conventional EV (e.g., exosome) protein. In some embodiments, a fusion protein of CD13, MME, ENPP1, or NRP1, a variant, a fragment, a variant of a fragment or a modification thereof is present at about 2-, about 4-, about 8-, about 16-, about 32-, about 64-, about 100-, about 200-, about 400-, about 800-, about 1,000-fold or a higher density on the EV (e.g., exosome) surface than fusion proteins on other EV (e.g., exosome) surfaces similarly modified using a variant of a conventional EV (e.g., exosome) protein.

In particular embodiments, a fusion protein of CD13, MME, ENPP1, or NRP1, a variant, a fragment, a variant of a fragment or a modification thereof is present at about 2-, about 4-, about 8-, about 16-, about 32-, about 64-, about 100-, about 200-, about 400-, about 800-, about 1,000-fold or a higher density on the EV (e.g., exosome) surface than fusion proteins on other EV (e.g., exosome) surfaces similarly modified using a conventional EV (e.g., exosome) protein (e.g., a tetraspanin molecule, like CD63).

Fusion proteins provided herein can comprise a HEVP (e.g., CD13, MME, ENPP1, or NRP1, or a fragment or a variant thereof), and an additional peptide (e.g., exogenous biologically active molecules disclosed herein, such as antigen, targeting moiety, adjuvant, and/or immune modulator). The additional peptide can be attached to either the N terminus or the C terminus of the HEVP or a fragment or a variant thereof. The additional peptide can be located inside (in the luminal side) or outside of the EV (e.g., exosome) attached to the HEVP.

In some embodiments, fusion proteins provided herein comprise a HEVP (e.g., CD13, MME, ENPP1, or NRP1, or a fragment or a variant thereof), and two additional peptides (e.g., exogenous biologically active molecules disclosed herein, such as antigen, targeting moiety, adjuvant, and/or immune modulator). For instance, in some aspects, a fusion protein comprises CD13 (or a fragment or variant thereof) and two additional peptides. In some aspects, a fusion protein comprises MME (or a fragment or variant thereof) and two additional peptides. In some aspects, a fusion protein comprises ENPP1 (or a fragment or variant thereof) and two additional peptides. In some aspects, a fusion protein comprises NRP1 (or a fragment or variant thereof) and two additional peptides. Both of the two additional peptides can be attached to either the N terminus or the C terminus of the HEVP or a fragment or a variant thereof. In some embodiments, one of the two additional peptides is attached to the N terminus and the other of the two additional peptides is attached to the C terminus of the HEVP or a fragment or a variant thereof. The additional peptides can be located inside (in the luminal side) or outside of the EV (e.g., exosome) attached to the HEVP, or both.

7.5. Producer Cell for Production of Surface-Engineered EVs (e.g., Exosomes)

EVs (e.g., exosomes) of the present disclosure can be produced from a cell grown in vitro or a body fluid of a subject. When EVs (e.g., exosomes) are produced from in vitro cell culture, various producer cells, e.g., HEK293 cells, Chinese hamster ovary (CHO) cells, mesenchymal stem cells (MSCs), HT-1080 cells, MB-231 cells, Raji cells, PER.C6 cells, and CAP cells can be used for the present disclosure. In some aspects, the producer cell is HEK293 cells. In some aspects, the producer is MSCs.

The producer cell can be genetically modified to comprise one or more exogenous sequences to produce surface-engineered EVs (e.g., exosomes). In some aspects, the one or more exogenous sequences encode a HEVP disclosed herein. In some aspects, the one or more exogenous sequences encode an exogenous biologically active molecule disclosed herein (e.g., antigen, targeting moiety, adjuvant, and/or immune modulator). In some aspects, the one or more exogenous sequences encode both a HEVP and an exogenous biologically active molecule disclosed herein. The genetically-modified producer cell can contain the exogenous sequence introduced by transient or stable transformation. The exogenous sequence can be introduced to the producer cell as a plasmid. The exogenous sequences can be stably integrated into a genomic sequence of the producer cell, at a targeted site or in a random site. In some embodiments, a stable cell line is generated for production of surface-engineered EVs (e.g., exosomes).

In some aspects, a genetically modified producer cell disclosed herein expresses an endogenous level of HEVP. In such aspects, the exogenous sequences can be inserted into a genomic sequence of the producer cell, located within, upstream (5'-end) or downstream (3'-end) of an endogenous sequence encoding the HEVP. Various methods known in the art can be used for the introduction of the exogenous sequences into the producer cell. For example, cells modified using various gene editing methods (e.g., methods using a homologous recombination, transposon-mediated system, loxP-Cre system, CRISPR/Cas9 or TALEN) are within the scope of the present disclosure.

The exogenous sequences can comprise a sequence encoding the HEVP or a variant or a fragment of the EV (e.g., exosome) protein. An extra copy of the sequence encoding the HEVP can be introduced to produce a surface-engineered EV (e.g., exosome) having the HEVP at a higher density. An exogenous sequence encoding a variant or a fragment of the HEVP can be introduced to produce a surface-engineered EV (e.g., exosome) containing the modification or the fragment of the HEVP. An exogenous sequence encoding an affinity tag can be introduced to produce a surface-engineered EV (e.g., exosome) containing a fusion protein comprising the affinity tag attached to the HEVP. As described herein, in some aspects, an exogenous sequence encoding an exogenous biologically active molecule (e.g., antigen, targeting moiety, adjuvant, and/or immune modulator) can be introduced to produce a surface-engineered EV (e.g., exosome) containing a fusion protein comprising the exogenous biologically active molecule attached (e.g., directly or via a linker) to the HEVP.

In some embodiments, a surface-engineered EV (e.g., exosome) has a higher density of the HEVP than native EVs (e.g., exosomes) isolated from the same or similar producer cell types. In some embodiments, the HEVP is present at about 2-, about 4-, about 8-, about 16-, about 32-, about 64-, about 100-, about 200-, about 400-, about 800-, about 1,000-fold or to a higher density on the surface-engineered EV (e.g., exosome) than the native EV (e.g., exosome). In some embodiments, the HEVP is present at about 2 to about 4-fold, about 4 to about 8-fold, about 8 to about 16-fold, about 16 to about 32-fold, about 32 to about 64-fold, about 64 to about 100-fold, about 100 to about 200-fold, about 200 to about 400-fold, about 400 to about 800-fold, about 800 to about 1,000-fold or to a higher density on the surface-engineered EV (e.g., exosome) than the native EV (e.g., exosome). In some embodiments, a fusion protein comprising the HEVP is present at about 2 to about 4-fold, about 4 to about 8-fold, about 8 to about 16-fold, about 16 to about 32-fold, about 32 to about 64-fold, about 64 to about 100-fold, about 100 to about 200-fold, about 200 to about 400-fold, about 400 to about 800-fold, about 800 to about 1,000-fold or to a higher density on the surface-engineered EV (e.g., exosome) than the unmodified HEVP on the native EV (e.g., exosome). In some embodiments, a fragment or a variant of the HEVP is present at about 2 to about 4-fold, about 4 to about 8-fold, about 8 to about 16-fold, about 16 to about 32-fold, about 32 to about 64-fold, about 64 to about 100-fold, about 100 to about 200-fold, about 200 to about 400-fold, about 400 to about 800-fold, about 800 to about 1,000-fold or to a higher density on the surface-engineered EV (e.g., exosome) than the unmodified HEVP on the native EV (e.g., exosome).

In particular embodiments, CD13, a fragment or variant of CD13, or a modification thereof is present at about 2 to about 4-fold, about 4 to about 8-fold, about 8 to about 16-fold, about 16 to about 32-fold, about 32 to about 64-fold, about 64 to about 100-fold, about 100 to about 200-fold, about 200 to about 400-fold, about 400 to about 800-fold, about 800 to about 1,000-fold or to a higher density on the surface-engineered EV (e.g., exosome) than the unmodified CD13 on the native EV (e.g., exosome). In particular embodiments, MME, a fragment or a variant of MME, or a modification thereof is present at about 2 to about 4-fold, about 4 to about 8-fold, about 8 to about 16-fold, about 16 to about 32-fold, about 32 to about 64-fold, about 64 to about 100-fold, about 100 to about 200-fold, about 200 to about 400-fold, about 400 to about 800-fold, about 800 to about 1,000-fold or to a higher density on the surface-engineered EV (e.g., exosome) than the unmodified MME on the native EV (e.g., exosome). In particular embodiments, ENPP1, a fragment or a variant of ENPP1, or a modification thereof is present at about 2 to about 4-fold, about 4 to about 8-fold, about 8 to about 16-fold, about 16 to about 32-fold, about 32 to about 64-fold, about 64 to about 100-fold, about 100 to about 200-fold, about 200 to about 400-fold, about 400 to about 800-fold, about 800 to about 1,000-fold or to a higher density on the surface-engineered EV (e.g., exosome) than the unmodified ENPP1 on the native EV (e.g., exosome). In particular embodiments, NRP1, a fragment or a variant of NRP1, or a modification thereof is present at about 2 to about 4-fold, about 4 to about 8-fold, about 8 to about 16-fold, about 16 to about 32-fold, about 32 to about 64-fold, about 64 to about 100-fold, about 100 to about 200-fold, about 200 to about 400-fold, about 400 to about 800-fold, about 800 to about 1,000-fold or to a higher density on the surface-engineered EV (e.g., exosome) than the unmodified NRP1 on the native EV (e.g., exosome).

In some embodiments, the producer cell is further modified to comprise an additional exogenous sequence. For example, an additional exogenous sequence can be introduced to modulate endogenous gene expression, or produce an EV (e.g., exosome) including a certain polypeptide as a payload. In some embodiments, the producer cell is modified to comprise two exogenous sequences, one encoding the HEVP or a variant or a fragment of the HEVP, and the other encoding a payload. In some embodiments, the producer cell can be further modified to comprise an additional exogenous sequence conferring additional functionalities to EVs (e.g., exosomes), for example, specific targeting capabilities, delivery functions, enzymatic functions, increased or decreased half-life in vivo, etc. In some embodiments, the producer cell is modified to comprise two exogenous sequences, one encoding the HEVP or a variant or a fragment of the EV (e.g., exosome) protein, and the other encoding a protein conferring the additional functionalities to EVs (e.g., exosomes).

In some embodiments, the producer cell is modified to comprise two exogenous sequences, each of the two exogenous sequences encoding a fusion protein on the EV (e.g., exosome) surface. In some embodiments, a surface-engineered EV (e.g., exosome) from the producer cell has a higher density of an HEVP compared to native EVs (e.g., exosomes) isolated from an unmodified cell of the same or similar cell type. In some embodiments, surface-engineered EV (e.g., exosome) contain an HEVP at a density about 2-, about 4-, about 8-, about 16-, about 32-, about 64-, about 100-, about 200-, about 400-, about 800-, about 1,000-fold or higher than a native EV (e.g., exosome) isolated from an unmodified cell of the same or similar cell type. In some embodiments, the producer cell is further modified to comprise one, two, three, four, five, six, seven, eight, nine, or ten or more additional exogenous sequences. As described herein, in some aspects, the exogenous sequences encode one or more HEVPs disclosed herein. In some aspects, the exogenous sequences encode one or more exogenous biologically active molecules disclosed herein (e.g., antigen, targeting moiety, adjuvant, and/or immune modulator). In some aspects, the exogenous sequences encode both a HEVP and an exogenous biologically active molecule disclosed herein.

More specifically, surface-engineered EVs (e.g., exosomes) can be produced from a cell transformed with a sequence encoding one or more HEVPs or a variant thereof including, but not limited to CD13, MME, ENPP1, and NRP1. Any of the one or more HEVPs described herein can be expressed in the producer cell from a plasmid, an exogenous sequence inserted into the genome or other exogenous nucleic acid such as a synthetic messenger RNA (mRNA).

In some embodiments, the one or more HEVPs is expressed in a cell transformed with an exogenous sequence encoding its full length, endogenous form. In some embodiments, such an exogenous sequence encodes CD13 protein of SEQ ID NO: 47. In some embodiments, such an exogenous sequence encodes MME protein of SEQ ID NO: 48. In some embodiments, such an exogenous sequence encodes ENPP1 protein of SEQ ID NO: 49. In some embodiments, such an exogenous sequence encodes NRP1 protein of SEQ ID NO: 50.

Surface-engineered EVs (e.g., exosomes) can be produced from a cell transformed with a sequence encoding a fragment of one or more HEVPs including, but not limited to, CD13, MME, ENPP1, and NRP1. In some aspects, the EVs (e.g., exosomes) are produced from a cell transformed with a sequence encoding a fragment of CD13. In some aspects, the EVs (e.g., exosomes) are produced from a cell transformed with a sequence encoding a fragment of MME. In some aspects, the EVs (e.g., exosomes) are produced from a cell transformed with a sequence encoding a fragment of ENPP1. In some aspects, the EVs (e.g., exosomes) are produced from a cell transformed with a sequence encoding a fragment of NRP1. In some embodiments, the sequence encodes a fragment of the HEVP lacking at least about 5, about 10, about 50, about 100, about 200, about 300, about 400, about 500, about 600, about 700, or about 800 amino acids from the N-terminus of the native protein. In some embodiments, the sequence encodes a fragment of the HEVP lacking at least about 5, about 10, about 50, about 100, about 200, about 300, about 400, about 500, about 600, about 700, or about 800 amino acids from the C-terminus of the native protein. In some embodiments, the sequence encodes a fragment of the HEVP lacking at least about 5, about 10, about 50, about 100, about 200, about 300, about 400, about 500, about 600, about 700, or about 800 amino acids from both the N-terminus and C-terminus of the native protein. In some embodiments, the sequence encodes a fragment of the HEVP lacking one or more functional or structural domains of the native protein.

In some embodiments, the fragment of the HEVP is fused to one or more heterologous proteins (e.g., exogenous biologically active molecules, e.g., antigen, targeting moiety, adjuvant, and/or immune modulator). In some embodiments, the one or more heterologous proteins are fused to the N-terminus of the fragment. In some embodiments, the one or more heterologous proteins are fused to the C-terminus of the fragment. In some embodiments, the one or more heterologous proteins are fused to the N-terminus and the C-terminus of the fragment. In some embodiments, the one or more heterologous proteins are mammalian proteins. In some embodiments, the one or more heterologous proteins are human proteins.

Surface engineered EVs (e.g., exosomes) can be produced from a cell transformed with a sequence encoding fragments of CD13. In some embodiments, the fragments of CD13 lack one or more functional or structural domains. In some embodiments, the fragments of CD13 are fused to one or more heterologous proteins (e.g., exogenous biologically active molecules, e.g., antigen, targeting moiety, adjuvant, and/or immune modulator). The one or more heterologous proteins can be fused to the N-terminus of the CD13 fragments. The one or more heterologous proteins can be fused to the C-terminus of the CD13 fragments. In some embodiments, the one or more heterologous proteins are fused to both the N-terminus and the C-terminus of the CD13 fragments. In some embodiments, the heterologous protein is a mammalian protein. In some embodiments, the heterologous protein is a human protein. In some embodiments, the heterologous protein fused to the CD13 fragment additionally contains a signal sequence peptide.

Surface engineered EVs (e.g., exosomes) can be produced from a cell transformed with a sequence encoding fragments of MME. In some embodiments, the fragments of MME lack one or more functional or structural domains. In some embodiments, the fragments of MME are fused to one or more heterologous proteins (e.g., exogenous biologically active molecules, e.g., antigen, targeting moiety, adjuvant, and/or immune modulator). In some embodiments, the one or more heterologous proteins are fused to the N-terminus of the MME fragments. In some embodiments, the one or more heterologous proteins are fused to the C-terminus of the MME fragments. In some embodiments, the one or more heterologous proteins are fused to both the N-terminus and the C-terminus of the MME fragments. In some embodiments, the heterologous protein is a mammalian protein. In some embodiments, the heterologous protein is a human protein. In some embodiments, the heterologous protein fused to the MME fragment additionally contains a signal sequence peptide.

Surface engineered EVs (e.g., exosomes) can be produced from a cell transformed with a sequence encoding fragments of ENPP1. In some embodiments, the fragments of ENPP1 lack one or more functional or structural domains. In some embodiments, the fragments of ENPP1 are fused to one or more heterologous proteins (e.g., exogenous biologically active molecules, e.g., antigen, targeting moiety, adjuvant, and/or immune modulator). In some embodiments, the one or more heterologous proteins are fused to the N-terminus of the ENPP1 fragments. In some embodiments, the one or more heterologous proteins are fused to the C-terminus of the ENPP1 fragments. In some embodiments, the one or more heterologous proteins are fused to both the N-terminus and the C-terminus of the ENPP1 fragments. In some embodiments, the heterologous protein is a mammalian protein. In some embodiments, the heterologous protein is a human protein. In some embodiments, the heterologous protein fused to the ENPP1 fragment additionally contains a signal sequence peptide.

Surface engineered EVs (e.g., exosomes) can be produced from a cell transformed with a sequence encoding fragments of NRP1. In some embodiments, the fragments of NRP1 are fused to one or more heterologous proteins (e.g., exogenous biologically active molecules, e.g., antigen, targeting moiety, adjuvant, and/or immune modulator). In some embodiments, the one or more heterologous proteins are fused to the N-terminus of the NRP1 fragments. In some embodiments, the one or more heterologous proteins are fused to the C-terminus of the NRP1 fragments. In some embodiments, the one or more heterologous proteins are fused to both the N-terminus and the C-terminus of the NRP1 fragments. In some embodiments, the heterologous protein is a mammalian protein. In some embodiments, the heterologous protein is a human protein. In some embodiments, the heterologous protein fused to the NRP1 fragment additionally contains a signal sequence peptide.

In some embodiments, surface-engineered EVs (e.g., exosomes) comprise a polypeptide of a sequence identical or similar to a full-length or a fragment of a HEVP protein including, but not limited to, CD13, MME, ENPP1, and NRP1. In some embodiments, the peptide is at least about 50% identical to a full-length or a fragment of HEVP, e.g., at least about 50% identical to SEQ ID NOs: 47-50 (i.e., SEQ ID NOs: 47, 48, 49, or 50). In some embodiments, the polypeptide is at least about 60% identical to a full-length or a fragment of a HEVP, e.g., at least about 60% identical to SEQ ID NOs: 47-50. In some embodiments, the polypeptide is at least about 70% identical to a full-length or a fragment of a HEVP, e.g., at least about 70% identical to SEQ ID NOs: 47-50. In some embodiments, the polypeptide is at least about 80% identical to a full-length or a fragment of a HEVP, e.g., at least about 80% identical to SEQ ID NOs: 47-50. In some embodiments, the polypeptide is at least about 90% identical to a full-length or a fragment of a HEVP, e.g., at least about 90% identical to SEQ ID NOs: 47-50. In some embodiments, the polypeptide is at least about 95% identical to a full-length or a fragment of a HEVP, e.g., at least about 95% identical to SEQ ID NOs: 47-50. In some aspects, the polypeptide is at least about 96% identical to a full-length or a fragment of a HEVP, e.g., at least about 96% identical to SEQ ID NOs: 47-50. In some aspects, the polypeptide is at least about 97% identical to a full-length or a fragment of a HEVP, e.g., at least about 97% identical to SEQ ID NOs: 47-50. In some aspects, the polypeptide is at least about 98% identical to a full-length or a fragment of a HEVP, e.g., at least about 98% identical to SEQ ID NOs: 47-50. In some embodiments, the polypeptide is at least about 99% identical to a full-length or a fragment of a HEVP, e.g., at least about 99% identical to SEQ ID NOs: 47-50. In some embodiments, the polypeptide is at least about 99.9% identical to a full-length or a fragment of a HEVP, e.g., at least about 99.9% identical to SEQ ID NOs: 47-50.

7.6. Affinity Purification

Some embodiments of the present disclosure relate to isolation, purification and sub-fractionation of EVs (e.g., exosomes) using a specific binding interaction between a protein enriched on the EV (e.g., exosome) membrane and an immobilized binding agent. These methods generally comprise the steps of (1) applying or loading a sample comprising EVs (e.g., exosomes), (2) optionally washing away unbound sample components using appropriate buffers that maintain the binding interaction between the target proteins of EVs (e.g., exosomes) and binding agents, and (3) eluting (dissociating and recovering) the EVs (e.g., exosomes) from the immobilized binding agents by altering the buffer conditions so that the binding interaction no longer occurs.

Some embodiments relate to a method of removing EVs (e.g., exosomes) from a sample using a specific binding interaction between a protein enriched on the EV (e.g., exosome) membrane and an immobilized binding agent. In the cases, EVs (e.g., exosomes) bound to the binding agent are not eluted from the binding agent and a fraction which does not bind to the binding agent can be collected. The method can be used to purify a sample comprising EVs (e.g., exosomes) and a non-EV (e.g., exosomal) material such as viruses (e.g., lentivirus, retrovirus, adeno-associated virus, or any other enveloped or non-enveloped virus) or a recombinant protein (e.g., antibodies, enzymes or other polypeptides), wherein the EVs (e.g., exosomes) are contaminating particles. The bound EVs (e.g., exosomes) can be retained bound to the binding agent and the non-EV (e.g., exosomal) material is collected, substantially free of EVs (e.g., exosomes).

The target protein, used for this isolation, purification, sub-fractionation or removal process, can be an endogenous protein produced from the genome of a producer cell, a protein introduced to the producer cell by a genetic modification, or a protein modified by chemical, physical or other biological methods. In some cases, the protein is a non-mutant protein or a mutant protein, e.g., a variant or a fragment of an endogenous protein. In some cases, the protein is a fusion protein (e.g., such as those described herein).

Various binding agents having affinity to the target protein can be used for the embodiments of the present disclosure. For example, proteins, peptides, and small molecules with specific affinities to the target protein can be used as a binding agent. In some embodiments, binding agents are obtained from organic or inorganic sources. Examples of binding agents from organic sources include serum proteins, lectins or antibodies. Examples of binding agents from inorganic sources include boronic acids, metal chelates, and triazine dyes.

The binding agents can be chemically immobilized or coupled to a solid support so that EVs (e.g., exosomes) having specific affinity to the binding agent become bound. Various forms of solid support can be used, e.g., a porous agarose bead, a microtiter plate, a magnetic bead, or a membrane. In some embodiments, the solid support forms a chromatography column and can be used for affinity chromatography of EVs (e.g., exosomes).

In some cases, isolation, purification, sub-fractionation and removal of EVs (e.g., exosomes) are done by column chromatography using a column where the binding agents and the solid support are packed. In some embodiments, a sample containing EVs (e.g., exosomes) run through the column to allow setting, a wash buffer run through the column, and the elution buffer subsequently applied to the column and collected. These steps can be done at ambient pressure or with application of additional pressure.

In some cases, isolation, purification, sub-fractionation and removal of EVs (e.g., exosomes) are done using a batch treatment. For example, a sample is added to the binding agent attached to a solid support in a vessel, mixing, separating the solid support, removing the liquid phase, washing, centrifuging, adding the elution buffer, re-centrifuging and removing the elute.

In some cases, a hybrid method can be employed. For example, a sample is added to the binding agent attached to a solid support in a vessel, the solid support bound to the EVs (e.g., exosomes) is subsequently packed onto a column, and washing and elution are done on the column.

In some cases, isolation, purification, sub-fractionation and removal of EVs (e.g., exosomes) are done using a binding agent attached to microtiter plates, magnetic beads, or membranes. In the cases, a sample is added to the binding agent attached to a solid support, followed by the steps of mixing, separating the solid support, removing the liquid phase, washing, removing the washing buffer, adding the elution buffer, and removing the elute.

The binding between the binding agent and a target protein on the EV (e.g., exosome) is done in various physiological conditions optimal for specific interactions between the binding agent and the target protein on the EV (e.g., exosome). Elution of the bound (e.g., exosomes) can be achieved by changing salt concentrations, pH, pI, charge and ionic strength directly or through a gradient.

In some embodiments, a sample isolated, purified or sub-fractionated with one binding agent is subsequently processed with a different binding agent.

In some embodiments, more than one columns are used in series, where each of the multiple columns contains a different binding agent specific to a different target protein.

In some embodiments, a single column contains multiple binding agents, each specific to a different target protein.

In some cases, the binding agent and solid support are reused by introduction of a periodic sanitization step. For example, they can be sanitized with a combination of propylene glycol, isopropanol, high ionic strength, and/or sodium hydroxide.

7.6.1. Sample Preparation

The methods described herein can be used to purify, isolate, sub-fractionate or remove EVs (e.g., exosomes) from various samples comprising EVs (e.g., exosomes). In some embodiments, the sample is a clarified harvest material containing EVs (e.g., exosomes). In some cases, the sample comprises EVs (e.g., exosomes) partially purified by a purification method well known in the art. For example, ultrafiltration/diafiltration, hydroxyl apatite chromatography, hydrophobic interaction chromatography, deep filtration, or ion exchange bind/elute chromatography can be used to partially purify EVs (e.g., exosomes) before applying to a binding agent for affinity purification.

In some cases, the partially purified material is further processed to have certain physiological conditions (e.g., pH, temperature, salt concentration, salt type, polarity) for desired interaction with the binding agent. A sample can be prepared by dilution or concentration to obtain certain EV (e.g., exosome) concentrations, or by adding excipients to change structure of EVs (e.g., exosomes). In some cases, the partially purified material is applied to the binding agent without any manipulation.

7.6.2. Binding

The methods described herein requires specific interaction between a target protein of an EV (e.g., exosome) and a binding agent. High-throughput screening can be performed to identify buffer conditions ideal for the specific binding—through altering salt concentration, pH, and/or reducing polarity with an organic modifier, ethylene glycol, propylene glycol, or urea. The interaction between a target protein and a binding agent can also change depending on sample conditions (e.g., sample amount loaded per volume of chromatographic resin, concentration of EVs (e.g., exosomes), concentration of impurities), loading buffers (e.g., pH, salt concentrations, salt types, polarity), and other physical conditions (e.g., temperature). Furthermore, adding excipients that alter the structure of the EVs (e.g., exosomes) can also change their interactions. In addition, residence time can be adjusted based on differential adsorption rates between impurities and EVs (e.g., exosomes). Thus, various purification conditions described herein can be tested to identify ideal conditions for the step.

Similar approaches can be used to improve purity and yield, and aid in enriching, depleting, or isolating sub-populations of EVs (e.g., exosomes). These properties, along with maximizing load challenge and applying more stringent elution conditions, could be employed to further enhance the concentration of EVs (e.g., exosomes).

7.6.2.1. Elution

Elution of EVs (e.g., exosomes) can be achieved through altering salt concentration, pH, and/or polarity with an organic modifier, ethylene glycol, propylene glycol, or urea.

Selective elution of EVs (e.g., exosomes) can be achieved by increasing the concentration of a monovalent cationic halide salt (e.g., sodium chloride, potassium chloride, sodium bromide, lithium chloride, sodium iodide, potassium bromide, lithium bromide, sodium fluoride, potassium fluoride, lithium fluoride, lithium iodide, sodium acetate, potassium acetate, lithium acetate, and potassium iodide), a divalent or trivalent salt (e.g., calcium chloride, magnesium chloride, calcium sulfate, sodium sulfate, magnesium sulfate, chromium trichloride, chromium sulfate, sodium citrate, iron (III) chloride, yttrium (III) chloride, potassium phosphate, potassium sulfate, sodium phosphate, ferrous chloride, calcium citrate, magnesium phosphate, and ferric chloride), or a combination thereof, in the elution buffer, through the use of an increasing gradient (step or linear) of a monovalent cationic halide salt (e.g., sodium chloride, potassium chloride, sodium bromide, lithium chloride, sodium iodide, potassium bromide, lithium bromide, sodium fluoride, potassium fluoride, lithium fluoride, lithium iodide, sodium acetate, potassium acetate, lithium acetate, and potassium iodide), a divalent or trivalent salt (e.g., calcium chloride, magnesium chloride, calcium sulfate, sodium sulfate, magnesium sulfate, chromium trichloride, chromium sulfate, sodium citrate, iron (III) chloride, yttrium (III) chloride, potassium phosphate, potassium sulfate, sodium phosphate, ferrous chloride, calcium citrate, magnesium phosphate, and ferric chloride), or a combination thereof, at a fixed pH.

Substantial EV (e.g., exosome) purity can be achieved by flowing through impurities during the column loading phase, eluting impurities during selective excipient washes and selectively eluting product during elution while leaving additional impurities bound to the column. Absorbance measured from column eluates can indicate the purity of EVs (e.g., exosomes) obtained by the methods.

Elution can be also achieved by modulating the pH range, salts, organic solvents, small molecules, detergents, zwitterions, amino acids, polymers, temperature, and any combination of the above. Similar elution agents can be used to improve purity, improve yield, and/or isolate sub-populations of EVs (e.g., exosomes).

Elution can be also done with multiple elution buffers having different properties, such as pH, salts, organic solvents, small molecules, detergents, zwitterions, amino acids, polymers, temperature, and any combination of the above. A plurality of eluted fractions can be collected, wherein EVs (e.g., exosomes) collected in each fraction has different properties. For example, EVs (e.g., exosomes) collected in one fraction has a higher purity, a smaller or larger average size, a preferred composition, etc. than EVs (e.g., exosomes) in other fractions.

Elution buffers with different properties can be applied as a continuous flow, while a plurality of eluted fractions are collected. Eluted fractions can be collected during isocratic elution or gradient elution. Once at least one eluted fraction is collected, a composition of the eluted fraction can be analyzed. For example, the concentration of EVs (e.g., exosomes), a host cell protein, a contaminant protein, DNA, carbohydrates, or lipids can be measured in each eluted fraction. Other properties of EVs (e.g., exosomes) in each eluted fraction can be also measured. The properties include an average size, an average charge density, and other physiological properties related to bio-distribution, cellular uptake, half-life, pharmacodynamics, potency, dosing, immune response, loading efficiency, stability, or reactivity to other compounds.

7.6.2.2. Washing

Optionally, purity of EVs (e.g., exosomes) can be further improved by washing samples prior to elution. In some embodiments, excipient can be a washing buffer. The excipient can be a solution having specific pH ranges, salts, organic solvents, small molecules, detergents, zwitterions, amino acids, polymers, and any combination of the above.

More specifically, the excipient can comprise arginine, lysine, glycine, histidine, calcium, sodium, lithium, potassium, iodide, magnesium, iron, zinc, manganese, urea, propylene glycol, aluminum, ammonium, guanidinium polyethylene glycol, EDTA, EGTA, a detergent, chloride, sulfate, carboxylic acids, sialic acids, phosphate, acetate, glycine, borate, formate, perchlorate, bromine, nitrate, dithiothreitol, beta mercaptoethanol, or tri-n-butyl phosphate.

The excipient can also comprise a detergent, selected from the group consisting of cetyl trimethylammonium chloride, octoxynol-9, TRITON™ X-100 (i.e., polyethylene glycol p-(1,1,3,3-tetramethylbutyl)-phenyl ether) and TRITON™ CG-110 available from Sigma-Aldrich; sodium dodecyl sulfate; sodium lauryl sulfate; deoxycholic acid; Polysorbate 80 (i.e., Polyoxyethylene (20) sorbitan monooleate); Polysorbate 20 (i.e., Polyoxyethylene (20) sorbitan monolaurate); alcohol ethoxylate; alkyl polyethylene glycol ether; decyl glucoside; octoglucosides; SafeCare; ECOSURF™ EH9, ECOSURF™ EH6, ECOSURF™ EH3, ECOSURF™ SA7, and ECOSURF™ SA9 available from DOW Chemical; LUTENSOL™ M5, LUTENSOL™ XL, LUTENSOL™ XP and APG™ 325 N available from BASF; TOMADOL™ 900 available from AIR PRODUCTS; NATSURF™ 265 available from CRODA; SAFECARE™1000 available from Bestchem, TERGITOL™ L64 available from DOW; caprylic acid; CHEMBETAINE™ LEC available from Lubrizol; and Mackol DG.

7.6.3. Other Methods for Improving Outcome

The amount of EVs (e.g., exosomes) that can be loaded per volume of chromatographic resin can be improved by modulating the feed material, for example, by increasing the concentration of EVs (e.g., exosomes), decreasing the concentration of impurities, altering the pH, decreasing the salt concentrations, decreasing the ionic strength, or altering the specific sub-populations of EVs (e.g., exosomes). Owing to mass transfer constraints and slow adsorption and desorption of EVs (e.g., exosomes) on the resin, the amount of EVs (e.g., exosomes) that can be loaded per volume of chromatographic resin can be increased by slowing the flow rate during column loading, employing longer columns to increase the residence time.

7.7. Applications

7.7.1. Purification of EVs (e.g., Exosomes)

The use of EVs (e.g., exosomes) for medical purposes requires that the EVs (e.g., exosomes) be free or mostly free of impurities including but not limited to macromolecules, such as nucleic acids, contaminant proteins, lipids, carbohydrates, metabolites, small molecules, metals, or a combination thereof. The present disclosure provides a method of purifying EVs (e.g., exosomes) from contaminating macromolecules. In some embodiments, purified EVs (e.g., exosomes) are substantially free of contaminating macromolecules.

7.7.2. Sub-Fractionation of EVs (e.g., Exosomes)

Embodiments of the present disclosure further provide methods for sub-fractionating populations of EVs (e.g., exosomes) based on their membrane protein, size, charge density, ligand type (e.g., tetraspanins) and heparin or other sulfated carbohydrate binding sites. The choice of affinity tag, loading and elution buffer compositions and protocols can result in elution of different sub-populations of EVs (e.g., exosomes).

For example, embodiments of the present disclosure provide methods of purifying a population of EVs (e.g., exosomes) with a smaller or larger size. The size of EVs (e.g., exosomes) can be determined by methods available in the field. For example, the size can be measured by nanoparticle tracking analysis, multi-angle light scattering, single angle light scattering, size exclusion chromatography, analytical ultracentrifugation, field flow fractionation, laser diffraction, tunable resistive pulse sensing, or dynamic light scattering.

Embodiments of the present disclosure further relate to methods of sub-fractionating EVs (e.g., exosomes) based on their charge density. The charge density of EVs (e.g., exosomes) can be determined by potentiometric titration, anion exchange, cation exchange, isoelectric focusing, zeta potential, capillary electrophoresis, capillary zone electrophoresis, gel electrophoresis, or any combination thereof.

Embodiments of the present disclosure also relate to sub-fractionating EVs (e.g., exosomes) based on other physiological properties, such as bio-distribution, cellular uptake, half-life, pharmacodynamics, potency, dosing, immune response, loading efficiency, stability, or reactivity to other compounds. The method enables isolation of a population of EVs (e.g., exosomes) that are appropriate for a specific application.

7.7.3. Uses

In some aspects, the present disclosure provides methods of preventing and/or treating a disease or disorder in a subject in need thereof, comprising administering an EV (e.g., exosome) disclosed herein.

In some aspects, a disease or disorder that can be treated with the present methods comprises a cancer, hemophilia, diabetes, growth factor deficiency, eye diseases, graft-versus-host disease (GvHD), autoimmune diseases, gastrointestinal diseases, cardiovascular diseases, respiratory diseases, allergic diseases, degenerative diseases, infectious diseases, fibrotic diseases, or any combination thereof. In certain aspects, a disease or disorder that can be treated is associated with chronic inflammation. In some aspects, the treatment is prophylactic. In some aspects, the EVs (e.g., exosomes) of the present disclosure are used to induce an immune response. In some aspects, the EVs of the present disclosure are used to vaccinate a subject.

In some aspects, the disease or disorder is a cancer. In some aspects, the disease or disorder is a graft-versus-host disease (GvHD). In some aspects, the disease or disorder is an infectious disease.

As described herein, cells (e.g., producer cells) can be modified to express a protein (e.g. HEVP) that is not naturally expressed in the cells (i.e., heterologous protein). In some aspects, such modification results in EVs (e.g., exosomes) produced from the modified cell to express the heterologous protein. Accordingly, in some aspects, the present disclosure provides a method of expressing a non-naturally occurring protein (i.e., heterologous protein) in an EV (e.g., exosome) derived from a cell. In some aspects, the method comprises transfecting a cell with a nucleic acid encoding at least one heterologous protein (e.g., HEVPs disclosed herein) (or a fragment or variant thereof) and isolating an EV (e.g., exosome) produced from the cell, wherein the EV (e.g., exosome) comprises the at least one heterologous protein and wherein the heterologous protein is not naturally expressed in an EV derived from the cell.

In some aspects, an EV (e.g., exosome) produced from the above-described cell (i.e., transfected with a nucleic acid encoding at least one heterologous protein) comprises at least 2, at least 3, at least 4, at least 5, at least 6, at least 7, at least 8, at least 9, or at least 10 heterologous proteins. In certain aspects, the heterologous proteins are different (e.g., an exosome is engineered to express both CD13 and MME proteins, wherein the exosomes are produced from a cell that does not naturally express CD13 and MME proteins). In some aspects, the heterologous proteins are the same, such that the total amount of heterologous proteins expressed in an EV (e.g., exosome) is greater than an EV produced from a cell that naturally expresses the heterologous proteins.

To quantify the amount or level of heterologous proteins (e.g., HEVPs) expressed on an EV (e.g., exosome), any appropriate method known in the art can be used. In some aspects, the amount of proteins (e.g., HEVPs) expressed on an EV (e.g., exosome) can be assessed by measuring the number of peptide spectral matches in a given sample comprising an EV (e.g., exosome) using liquid chromatography with tandem mass spectrometry (LC-MS/MS). See Examples 1 and 3. As used herein, "peptide spectral match" (PSM) refers to a system which assigns a numerical value to a peptide-spectrum pair (P,S) expressing the likelihood that the fragmentation of a peptide with sequence P is recorded in the experimental mass spectrum S. Frank, A. M., *J Proteome Res*, 8(5): 2241-2252 (May 2009). PSMs correlate with protein abundance in a given sample.

In some aspects, the level (or amount) of heterologous proteins (e.g., HEVPs) expressed in an EV (e.g., exosome) produced from a cell disclosed herein (e.g., transfected with a nucleic acid encoding at least one heterologous proteins) is at least about 10 peptide spectral matches (PSMs), at least about 20 PSMs, at least about 30 PSMs, at least about 40 PSMs, at least about 50 PSMs, at least about 60 PSMs, at least about 70 PSMs, at least about 80 PSMs, at least about 90 PSMs, at least about 100 PSMs, at least about 110 PSMs, at least about 120 PSMs, at least about 130 PSMs, at least about 140 PSMs, at least about 150 PSMs, at least about 160 PSMs, at least about 170 PSMs, at least about 180 PSMs, at least about 190 PSMs, at least about 200 PSMs, at least about 210 PSMs, at least about 220 PSMs, at least about 230 PSMs, at least about 240 PSMs, at least about 250 PSMs, at least about 260 PSMs, at least about 270 PSMs, at least about 280 PSMs, at least about 290 PSMs, at least about 300 PSMs, at least about 350 PSMs, at least about 400 PSMs, at least about 450 PSMs, at least about 500 PMSs, at least about 550 PSMs, at least about 600 PSMs, at least about 650 PSMs, at least about 700 PSMs, at least about 750 PSMs, at least about 800 PSMs, at least about 850 PSMs, at least about 900 PSMs, at least about 950 PSMs, or at least about 1,000 or more PSMs, as measured using LC-MS/MS.

In certain aspects, the level of heterologous proteins (e.g., HEVPs) expressed in an EV (e.g., exosome) is equal to or greater than about 125 PSMs, as measured using LC-MS/ MS. In certain aspects, the level of heterologous proteins (e.g., HEVPs) expressed in an EV (e.g., exosome) is equal to or greater than about 150 PSMs, as measured using LC-MS/MS. In some aspects, the level of heterologous proteins (e.g., HEVPs) expressed in an EV (e.g., exosome) is equal to or greater than about 200 PSMs. In certain aspects, the level of heterologous proteins (e.g., HEVPs) expressed in an EV (e.g., exosome) is equal to or greater than about 700 PSMs, as measured using LC-MS/MS. In some aspects, the level of heterologous proteins (e.g., HEVPs, e.g., MME) expressed in an EV (e.g., exosome) is about 177 PSMs, as measured using LC-MS/MS. In some aspects, the level of heterologous proteins (e.g., HEVPs, e.g., CD13) expressed in an EV (e.g., exosome) is about 742 PSMs, as measured using LC-MS/MS.

In some aspects, level of heterologous proteins (e.g., HEVPs) expressed in an EV (e.g. exosome) is between about 20 and about 80 PSMs, as measured using LC-MS/MS. In some aspects, the level of heterologous proteins (e.g., HEVPs) expressed in an EV (e.g. exosome) is between about 80 and about 200 PSMs, as measured using LC-MS/MS. In some aspects, the level of heterologous proteins (e.g., HEVPs) expressed in an EV (e.g. exosome) is between about 150 PSMs and about 750 PSMs, as measured using LC-MS/ MS.

7.8. Characterization of EVs (e.g., Exosomes)

In some embodiments, the methods described herein further comprise the step of characterizing EVs (e.g., exosomes) contained in each collected fraction. In some embodiments, contents of the EVs (e.g., exosomes) can be extracted for study and characterization. In some embodiments, EVs (e.g., exosomes) are isolated and characterized by metrics including, but not limited to, size, shape, morphology, or molecular compositions such as nucleic acids, proteins, metabolites, and lipids.

7.8.1. Measurement of the Contents of EVs (e.g., Exosomes)

EVs (e.g., exosomes) can include proteins, peptides, RNA, DNA, and lipids. Total RNA can be extracted using acid-phenol:chloroform extraction. RNA can then be purified using a glass-fiber filter under conditions that recover small-RNA containing total RNA, or that separate small RNA species less than 200 nucleotides in length from longer RNA species such as mRNA. Because the RNA is eluted in a small volume, in some aspects, no alcohol precipitation step can be required for isolation of the RNA.

EV (e.g., exome) compositions can be assessed by methods known in the art including, but not limited to, transcriptomics, sequencing, proteomics, mass spectrometry, or HPLC.

The composition of nucleotides associated with isolated EVs (e.g., exosomes) (including RNAs and DNAs) can be measured using a variety of techniques that are well known to those of skill in the art (e.g., quantitative or semi-quantitative RT-PCR, Northern blot analysis, solution hybridization detection). In a particular embodiment, the level of at least one RNA is measured by reverse transcribing RNA from the EV (e.g., exosome) composition to provide a set of target oligodeoxynucleotides, hybridizing the target oligodeoxynucleotides to one or more RNA-specific probe oligonucleotides (e.g., a microarray that comprises RNA-specific probe oligonucleotides) to provide a hybridization profile for the EV (e.g., exosome) composition, and comparing the EV (e.g., exosome) composition hybridization profile to a hybridization profile generated from a control sample. An alteration in the signal of at least one RNA in the test sample relative to the control sample is indicative of the RNA composition.

Also, a microarray can be prepared from gene-specific oligonucleotide probes generated from known RNA sequences. The array can contain two different oligonucleotide probes for each RNA, one containing the active, mature sequence and the other being specific for the precursor of the RNA (for example miRNA and pre-miRNAs). The array can also contain controls, such as one or more mouse sequences differing from human orthologs by only a few bases, which can serve as controls for hybridization stringency conditions. tRNAs and other RNAs (e.g., rRNAs, mRNAs) from both species can also be printed on the microchip, providing an internal, relatively stable, positive control for specific hybridization. One or more appropriate controls for non-specific hybridization can also be included on the microchip. For this purpose, sequences are selected based upon the absence of any homology with any known RNAs.

The microarray can be fabricated using techniques known in the art. For example, probe oligonucleotides of an appropriate length, e.g., 40 nucleotides, are 5'-amine modified at position C6 and printed on activated slides using commercially available microarray systems, e.g., the GeneMachine OmniGrid.™ 100 Microarrayer and Amersham Code-Link.™ Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6.times. SSPE/30% formamide at 25° C. for 18 hours, followed by washing in 0.75.times. TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary RNAs, in the EV (e.g., exosome) preparation. According to one embodiment, the labeled cDNA oligomer is a biotin-labeled cDNA, prepared from a biotin-labeled primer. The microarray is then processed by direct detection of the biotin containing transcripts using, e.g., Streptavidin-Alexa647 conjugate, and scanned utilizing conventional scanning methods. Image intensities of each spot on the array are proportional to the abundance of the corresponding RNA in the EV (e.g., exosome).

Data mining work is completed by bioinformatics, including scanning chips, signal acquisition, image processing, normalization, statistic treatment and data comparison as well as pathway analysis. As such, microarray can profile hundreds and thousands of polynucleotides simultaneously with high throughput performance. Microarray profiling analysis of mRNA expression has successfully provided valuable data for gene expression studies in basic research. And the technique has been further put into practice in the pharmaceutical industry and in clinical diagnosis. With increasing amounts of miRNA data becoming available, and with accumulating evidence of the importance of miRNA in gene regulation, microarray becomes a useful technique for high through-put miRNA studies. The analysis of miRNA levels utilizing polynucleotide probes can be carried out in a variety of physical formats as well. For example, the use of microtiter plates or automation can be used to facilitate the processing of large numbers of test samples.

7.8.2. Measurement of the Size of EVs (e.g., Exosomes)

In some embodiments, the methods described herein comprise measuring the size of EVs (e.g., exosomes) and/or populations of EVs (e.g., exosomes) included in the purified fractions. In some embodiments, EV (e.g., exosome) size is measured as the longest measurable dimension. Generally, the longest general dimension of an EV (e.g., exosome) is also referred to as its diameter.

EV (e.g., exosome) size can be measured using various methods known in the art, for example, nanoparticle tracking analysis, multi-angle light scattering, single angle light scattering, size exclusion chromatography, analytical ultra-centrifugation, field flow fractionation, laser diffraction, tunable resistive pulse sensing, or dynamic light scattering.

EV (e.g., exosome) size can be measured using dynamic light scattering (DLS) and/or multiangle light scattering (MALS). Methods of using DLS and/or MALS to measure the size of EVs (e.g., exosomes) are known to those of skill in the art, and include the nanoparticle tracking assay (NTA, e.g., using a Malvern Nanosight NS300 nanoparticle tracking device). In a specific embodiment, the EV (e.g., exosome) size is determined using a Malvern NanoSight NS300. In some embodiments, the EVs (e.g., exosomes) described herein have a longest dimension of about 20-1000 nm as measured by NTA (e.g., using a Malvern NanosightNS300). In other embodiments, the EVs (e.g., exosomes) described herein have a longest dimension of about 40-1000 nm as measured by NTA (e.g., using a Malvern NanosightNS300). In other embodiments, the EV (e.g., exosome) populations described herein comprise a population, wherein 90% of the EVs (e.g., exosomes) have a longest dimension of about 20-1000 nm as measured by NTA (e.g., using a Malvern Nanosight NS300). In other embodiments, the EV (e.g., exosome) populations described herein comprise a population, wherein 95% of the EVs (e.g., exosomes) have a longest dimension of about 20-1000 nm as measured by NTA (e.g., using a Malvern Nanosight NS300). In other embodiments, the EV (e.g., exosome) populations described herein comprise a population, wherein 99% of the EVs (e.g., exosomes) have a longest dimension of about 20-1000 nm as measured by NTA (e.g., using a Malvern Nanosight NS300). In other embodiments, the EV (e.g., exosome) populations described herein comprise a population, wherein 90% of the EVs (e.g., exosomes) have a longest dimension of about 40-1000 nm as measured by NTA (e.g., using a Malvern Nanosight NS300). In other embodiments, the EV (e.g., exosome) populations described herein comprise a population, wherein 95% of the EVs (e.g., exosomes) have a longest dimension of about 40-1000 nm as measured by NTA (e.g., using a Malvern Nanosight NS300). In other embodiments, the EV (e.g., exosome) populations described herein comprise a population, wherein 99% of the EVs (e.g., exosomes) have a longest dimension of about 40-1000 nm as measured by NTA (e.g., using a Malvern Nanosight NS300).

EV (e.g., exosome) size can be measured using tunable resistive pulse sensing (TRPS). In a specific embodiment, EV (e.g., exosome) size as measured by TRPS is determined using an iZON qNANO Gold. In some embodiments, the EVs (e.g., exosomes) described herein have a longest dimension of about 20-1000 nm as measured by TRPS (e.g., using an iZON qNano Gold). In other embodiments, the EVs (e.g., exosomes) described herein have a longest dimension of about 40-1000 nm as measured by TRPS (e.g., an iZON qNano Gold). In other embodiments, the EV (e.g., exosome) populations described herein comprise a population, wherein 90% of the EVs (e.g., exosomes) have a longest dimension of about 20-1000 nm as measured by TRPS (e.g., using an iZON qNano Gold). In other embodiments, the EV (e.g., exosome) populations described herein comprise a population, wherein 95% of the EVs (e.g., exosomes) have a longest dimension of about 20-1000 nm as measured by TRPS (e.g., using an iZON qNano Gold). In other embodiments, the EV (e.g., exosome) populations described herein comprise a population, wherein 99% of the EVs (e.g., exosomes) have a longest dimension of about 20-1000 nm as measured by TRPS (e.g., using an iZON qNano Gold). In other embodiments, the EV (e.g., exosome) populations described herein comprise a population, wherein 90% of the EVs (e.g., exosomes) have a longest dimension of about 40-1000 nm as measured by TRPS (e.g., using an iZON qNano Gold). In other embodiments, the EV (e.g., exosome) populations described herein comprise a population, wherein 95% of the EVs (e.g., exosomes) have a longest dimension of about 40-1000 nm as measured by TRPS (e.g., using an iZON qNano Gold). In other embodiments, the EV (e.g., exosome) populations described herein comprise a population, wherein 99% of the EVs (e.g., exosomes) have a longest dimension of about 40-1000 nm as measured by TRPS (e.g., using an iZON qNano Gold).

EV (e.g., exosome) size can be measured using electron microscopy. In some embodiments, the method of electron microscopy used to measure EV (e.g., exosome) size is transmission electron microscopy. In a specific embodiment, the transmission electron microscope used to measure EV (e.g., exosome) size is a Tecnai™ G2 Spirit BioTWIN. Methods of measuring EV (e.g., exosome) size using an electron microscope are well-known to those of skill in the art, and any such method can be appropriate for measuring EV (e.g., exosome) size. In some embodiments, the EVs (e.g., exosomes) described herein have a longest dimension of about 20-1000 nm as measured by a scanning electron microscope (e.g., a Tecnai™ G2 Spirit BioTWIN scanning electron microscope). In other embodiments, the EVs (e.g., exosomes) described herein have a longest dimension of about 40-1000 nm as measured by a scanning electron microscope (e.g., a Tecnai™ G2 Spirit BioTWIN scanning electron microscope). In other embodiments, the EV (e.g., exosome) populations described herein comprise a population, wherein 90% of the EVs (e.g., exosomes) have a longest dimension of about 20-1000 nm as measured by a scanning electron microscope (e.g., a Tecnai™ G2 Spirit BioTWIN scanning electron microscope). In other embodiments, the EV (e.g., exosome) populations described herein comprise a population, wherein 95% of the EVs (e.g., exosomes) have a longest dimension of about 20-1000 nm as measured by a scanning electron microscope (e.g., a Tecnai™ G2 Spirit BioTWIN scanning electron microscope). In other embodiments, the EV (e.g., exosome) populations described herein comprise a population, wherein 99% of the EVs (e.g., exosomes) have a longest dimension of about 20-1000 nm as measured by a scanning electron microscope (e.g., a Tecnai™ G2 Spirit BioTWIN scanning electron microscope). In other embodiments, the EV (e.g., exosome) populations described herein comprise a population wherein 90% of the EVs (e.g., exosomes) have a longest dimension of about 40-1000 nm as measured by a scanning electron microscope (e.g., a Tecnai™ G2 Spirit BioTWIN scanning electron microscope). In other embodiments, the EV (e.g., exosome) populations described herein comprise a population wherein 95% of the EVs (e.g., exosomes) have a longest dimension of about 40-1000 nm as measured by a scanning electron microscope (e.g., a Tecnai™ G2 Spirit BioTWIN scanning electron microscope). In other embodiments, the EV (e.g., exosome) populations described herein comprise a population wherein 99% of the EVs (e.g., exosomes) have a longest dimension of about 40-1000 nm as measured by a scanning electron microscope (e.g., a Tecnai™ G2 Spirit BioTWIN scanning electron microscope).

7.8.3. Measurement of the Charge Density of EVs (e.g., Exosomes)

In some embodiments, the methods described herein comprise measuring the charge density of EVs (e.g., exosomes) and/or populations of EVs (e.g., exosomes) included in the purified fractions. In some embodiments, the charge density is measured by potentiometric titration, anion exchange, cation exchange, isoelectric focusing, zeta potential, capillary electrophoresis, capillary zone electrophoresis, or gel electrophoresis.

7.8.4. Measurement of Density of EV (e.g., Exosome) Proteins or HEVPs

In some embodiments, the methods described herein comprise measuring the density of EV (e.g., exosome) proteins or HEVPs on the EV (e.g., exosome) surface. The surface density can be calculated or presented as the mass per unit area, the number of proteins per area, number of molecules or intensity of molecule signal per EV (e.g., exosome), molar amount of the protein, etc. The surface density can be experimentally measured by methods known in the art, for example, by using bio-layer interferometry (BLI), FACS, Western blotting, fluorescence (e.g., GFP-fusion protein) detection, nano-flow cytometry, ELISA, alphaLISA, and/or densitometry by measuring bands on a protein gel.

7.9. Pharmaceutical Compositions

Provided herein are pharmaceutical compositions comprising an EV, e.g., exosome, of the present disclosure having the desired degree of purity, and a pharmaceutically acceptable carrier or excipient, in a form suitable for administration to a subject. Pharmaceutically acceptable excipients or carriers can be determined in part by the particular composition being administered, as well as by the particular method used to administer the composition. Accordingly, there is a wide variety of suitable formulations of pharmaceutical compositions comprising a plurality of extracellular vesicles. (See, e.g., Remington's Pharmaceutical Sciences, Mack Publishing Co., Easton, Pa. 21st ed. (2005)). The pharmaceutical compositions are generally formulated sterile and in full compliance with all Good Manufacturing Practice (GMP) regulations of the U.S. Food and Drug Administration.

In some aspects, a pharmaceutical composition comprises one or more therapeutic agents and an EV, e.g., exosome, described herein. In certain aspects, the EVs, e.g., exosomes, are co-administered with of one or more additional therapeutic agents, in a pharmaceutically acceptable carrier. In some aspects, the pharmaceutical composition comprising the EV, e.g., exosome is administered prior to administration of the additional therapeutic agents. In other aspects, the pharmaceutical composition comprising the EV, e.g., exosome is administered after the administration of the additional therapeutic agents. In further aspects, the pharmaceutical composition comprising the EV, e.g., exosome is administered concurrently with the additional therapeutic agents.

7.10. Kits

Also provided herein are kits comprising one or more exosomes described herein. In some aspects, provided herein is a pharmaceutical pack or kit comprising one or more containers filled with one or more of the ingredients of the pharmaceutical compositions described herein, such as one or more exosomes provided herein, optional an instruction for use. In some aspects, the kits contain a pharmaceutical composition described herein and any prophylactic or therapeutic agent, such as those described herein.

7.11. Examples

The following examples are put forth so as to provide those of ordinary skill in the art with a complete disclosure and description of how to make and use the present disclosure, and are not intended to limit the scope of what the inventors regard as their present disclosure nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations can be used, e.g., bp, base pair(s); kb, kilobase(s); pl, picoliter(s); s or sec, second(s); min, minute(s); h or hr, hour(s); aa, amino acid(s); nt, nucleotide(s); and the like.

The practice of the present disclosure will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W. H. Freeman and Company, 1993); A L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 21th Edition (Easton, Pa.: Mack Publishing Company, 2005); Carey and Sundberg Advanced Organic Chemistry 3rd Ed. (Plenum Press) Vols A and B (1992).

7.11.1. Example 1: Identification of EV (e.g., Exosome) Proteins

7.11.1.1. Collection of EVs (e.g., Exosomes)

EVs (e.g., exosomes) were collected from the supernatant of high-density suspension cultures of bone marrow-derived MSC cells after 4 days. The supernatant was filtered and concentrated by tangential flow filtration using 1,000 kDa MWCO membranes (PXC01MC50). The concentrated cell culture supernatant was pelleted by ultracentrifugation using 100 mL Quick-Seal Ultra-Clear tubes (345778). The crude EV (e.g., exosome) pellets were further fractionated on an OPTIPREP™ (60% iodixanol w/v) density gradient by ultracentrifugation.

The pelleted material was resuspended in 1 mL PBS and 3 mL of OPTIPREP™, bringing the final iodixanol concentration to 45%. For the OPTIPREP™ gradient, a 4-tier sterile gradient was prepared with 4 mL of 45% iodixanol containing the resuspended material, 3 mL 30% iodixanol, 2 mL 22.5% iodixanol, 2 mL 17.5% iodixanol, and 1 mL PBS in a 12 mL Ultra-Clear (344059) tube for a SW 41 Ti rotor. The OPTIPREP™ gradient was ultracentrifuged at 150,000×g for 16 hours at 4° C. to separate the EV (e.g., exosome) fraction. The EV (e.g., exosome) layer was then gently collected from the top ~3 mL of the tube.

The EV (e.g., exosome) fraction was diluted in ~32 mL PBS in a 38.5 mL Ultra-Clear (344058) tube and ultracentrifuged at 133,900×g for 3 hours at 4° C. to pellet the purified EVs (e.g., exosomes). The pelleted EVs (e.g., exosomes) were then resuspended in a minimal volume of PBS (~200 μL) and stored at 4° C.

7.11.1.2. Sample Preparation for LC-MS/MS Analysis

To determine proteins specific to EVs (e.g., exosomes), the Top Fraction and Bottom Fraction of the Optiprep™ gradient were analyzed by liquid chromatography-tandem mass spectrometry. All samples were received in either phosphate-buffered saline (PBS) buffer or PBS and 5% sucrose. Prior to analysis, the total protein concentration of each sample was determined by bicinchoninic acid (BCA) assay, after which each sample was appropriately diluted to 125 μg/mL in PBS buffer. Next, 50.0 μL of each sample was added to a separate 1.5 mL microcentrifuge tube containing an equal volume of EV (e.g., exosome) lysis buffer (60 mM Tris, 400 mM GdmCl, 100 mM EDTA, 20 mM TCEP, 1.0% Triton X-100) followed by the transfer of 2.0 μL 1.0% Triton X-100 solution. All samples were then incubated at 55° C. for 60 minutes.

Protein precipitation was performed by adding 1250 μL of ethanol at −20° C. To improve efficiency, samples were vigorously vortexed for approximately 10 minutes and then incubated at −20° C. for 60 minutes. After incubation, samples were sonicated in a water bath for 5 minutes. Precipitated material was pelleted by centrifuging for 5 minutes at 15,000 g at 4° C. The supernatant was decanted, and the pelleted material was thoroughly dried using nitrogen gas. Pellets were resuspended in 30.0 μL digestion buffer (30 mM Tris, 1.0 M GdmCl, 100 mM EDTA, 50 mM TCEP, pH 8.5) which also reduced disulfide bonds. Free cysteine residues were alkylated by adding 5.0 μL alkylation solution (375 mM iodoacetamide, 50 mM Tris, pH 8.5) and incubating the resulting solution at room temperature in the dark for at least 30 minutes.

After incubation, each sample was diluted using 30.0 μL 50 mM Tris pH 8.5, and proteolytic digestion was initiated by adding 2.0 μg trypsin. All samples were mixed and then incubated overnight at 37° C. After the incubation, trypsin activity was ceased by adding 5.0 μL 10% formic acid. Prior to analysis by LC-MS/MS, each sample was desalted using Pierce C18 spin columns. At the end of this process, each sample was dried down and reconstituted in 50.0 μL of water with 0.1% formic acid and transferred to an HPLC vial for analysis.

7.11.1.3. LC-MS/MS Analysis

Samples were injected into an UltiMate 3000 RSCLnano (Thermo Fisher Scientific) low flow chromatography system, and tryptic peptides were loaded onto an Acclaim PepMap 100 C18 trapping column (75 μm×2 cm, 3 μm particle size, 100 Å pore size, Thermo Fisher Scientific) using loading mobile phase (MPL: water, 0.1% formic acid) at a flowrate of 1.000 μL/min. Peptides were eluted and separated with a gradient of mobile phase A (MPA: water, 0.1% formic acid) and mobile phase B (MPB: acetonitrile, 0.1% formic acid) at a flowrate of 300 nL/min across an EASY-Spray C18 analytical column (75 μm×25 cm, 2 μm particle size, 100 Å pore size, Thermo Fisher Scientific). The stepwise gradient used for elution began at 2% MPB, where it was held for 8 minutes during loading. The percentage MPB then increased from 2-17% over 35 minutes, again from 17-25% over 45 minutes, and finally from 25-40% over 10 minutes. The most hydrophobic species were removed by increasing to 98% MPB over 5 minutes, then holding there for 10 minutes. The total runtime for the method was 135 minutes and allowed sufficient time for column re-equilibration. Wash cycles were performed in between non-identical analytical injections to minimize carry-over.

Mass analyses were performed with a Q Exactive Basic (Thermo Fisher Scientific) mass spectrometer. Precursor ion mass spectra were measured across an m/z range of 400-1600 Da at a resolution of 70,000. The 10 most intense precursor ions were selected and fragmented in the HCD cell using a collision energy of 27, and MS/MS spectra were measured across an m/z range of 200-2000 Da at a resolution of 35,000. Ions with charge states from 2-4 were selected for fragmentation and the dynamic exclusion time was set to 30 seconds. An exclusion list containing 14 common polysiloxanes was utilized to minimize misidentification of known contaminants.

7.11.1.4. Data Processing

Proteins were first identified and quantified (label-free) using Proteome Discoverer software (version 2.1.1.21, Thermo Fisher Scientific) and the Sequest HT algorithm combined with the Target Decoy PSM Validator. Searches were performed against the full Swiss-Prot *Homo sapiens* (taxonomy 9606 version 2017-05-10: 42,153 entries) reference database, as well as a custom Uniprot database containing E1a proteins (7 entries). The following search parameters were used: enzyme, trypsin; maximum of 2 missed cleavages; minimum peptide length of 6 residues; 10 ppm precursor mass tolerance; and 0.02 Da fragment mass tolerance. The search also included specific dynamic modifications (oxidation of M; deamidation of N or Q; phosphorylation of S, T, or Y; pyro-glutamation of peptide-terminal E; and acetylation of protein N terminus) and static modifications (carbamidomethylation of C).

In the Target Decoy PSM Validator, the maximum delta Cn and both strict and relaxed target false discovery rates (FDRs) were set to 1 because the data were searched again using Scaffold software (version 4.8.2, Proteome Software Inc.). In Scaffold, the data were also searched using the X! Tandem open source algorithm to identify proteins using a protein threshold of 99.0%, a minimum of 2 peptides, and a peptide threshold of 95%.

To determine the identity of EV (e.g., exosome)-specific proteins, total peptide spectral matches (PSMs) were compared for proteins found in the top EV (e.g., exosome) fraction of the Optiprep™ gradient versus those in the lower fraction. The results showed that there are a number of membrane-associated proteins highly enriched in the EVs (e.g., exosomes) fraction. The EV (e.g., exosome) proteins included CD13, MME, ENPP1, and NRP1.

7.11.2. Example 2: Verification of Surface Protein Expression

To confirm that the EV (e.g., exosome)-specific proteins identified in the mass spectrometry studies are highly enriched on the surface of EVs (e.g., exosomes), protein blotting is carried out on total cell lysate and purified EV (e.g., exosome) populations from bone marrow-derived MSC. The total protein pattern differs substantially between total cell lysate and EV (e.g., exosome) lysate. Specifically, there is a strong band in the EV (e.g., exosome) lysate that is absent in the total cell lysate. Western blotting for CD13 reveals that the strong band corresponds to CD13, indicating that CD13 is highly enriched in EVs (e.g., exosomes) produced from bone marrow-derived MSC, and can be visually detectable in total EV (e.g., exosome) lysate.

7.11.3. Example 3: Specific Expression of Exosome Proteins

To determine the specificity of exosome proteins, mass spectrometry studies and Western blot analysis were performed (as described in Example 1) to identify potential scaffold proteins expressed on exosomes purified (see, e.g., FIG. 1) and to analyze expression of several novel exosome-associated membrane proteins on exosomes produced from various cell types. Specifically, exosomes derived from mesenchymal stem cells (MSCs) and HEK293 cells were analyzed. EV (e.g., exosome) fractions from these cell types were purified on Optiprep™ gradients and analyzed by Western blotting.

To determine the identity of different exosome proteins, total peptide spectral matches (PSMs) were compared for proteins found in exosomes derived from MSC to those found in exosomes from HEK293 cells. As shown in FIG. 1, when exosome samples from marrow-derived MSC were analyzed, CD13 was observed to be highly enriched in the exosome fraction. However, when samples from HEK293 cells were analyzed, CD13 was not detected in the exosome fraction or in any other fractions. Similar results were observed for MME (see FIG. 1).

Each of the novel surface marker proteins was similarly analyzed. The data show that certain exosome proteins (e.g., CD13 and MME) are enriched on exosomes from certain cell types (e.g., MSCs) but absent on exosomes produced from different cell types (e.g., HEK293).

7.11.4. Example 4: Overexpression of CD13 from Producer Cells

The results in Example 3 demonstrated that CD13 and other exosome proteins (e.g., MME) are not universally present on EVs (e.g., exosomes) produced from various cell types. For example, CD13 was highly enriched on exosomes produced from bone marrow-derived MSC, but absent on exosomes produced from HEK293 cells.

To determine whether CD13 can be used as an exosome scaffold protein on a producer cell, which naturally does not produce exosomes with CD13, HEK293 cells were stably transfected with a plasmid expressing full-length CD13 fused to a FLAG tag ("the CD13-FLAG plasmid"). Exosomes were purified from wild-type HEK293SF cells and HEK293SF cells transfected with the CD13-FLAG plasmid. As a control, exosomes were also purified from HEK293SF cells engineered to overexpress the PTGFRN scaffold protein.

The SDS-Page analysis results provided in FIG. 2A show that CD13-FLAG was successfully overexpressed in HEK293SF cells transfected with the CD13-FLAG plasmid. Overexpression of CD13 resulted in similar enrichment on HEK293-derived exosomes compared to PTGFRN. And, as shown in FIG. 2B (right graph), exosomes produced from the CD13-FLAG plasmid transfected HEK293SF cells also expressed high levels of CD13 on their surface. The CD13 expressed on the EVs were biologically active with activity levels comparable to that of recombinant CD13 protein (see FIGS. 3A and 3B). These results demonstrate that a producer cell (e.g., HEK293SF), which does not naturally express an exosomal protein (e.g., CD13), can be modified to produce exosomes that overexpress the exosomal protein (e.g., CD13). These results indicate that exosomal proteins such as CD13 can be used for generating engineered EVs (e.g., exosomes) comprising an heterologous exosome protein, i.e., CD13. Furthermore, EVs (e.g., exosomes) purified from modified cells disclosed herein (e.g., HEK293SF cells transfected with the CD13-FLAG plasmid) show native catalytic activity of the heterologous exosome protein (e.g., CD13).

Similar procedures can be carried out on CD13 and other HEVPs described herein using various cell types, e.g., CD13 can be introduced into CHO cells (where it is not natively expressed); MME can be introduced into CHO cells and HEK cells (where it is not natively expressed); ENPP1 can be introduced into CHO cells (where it is not natively expressed); and NRP1 can be introduced into CHO cells and HEK cells (where it is not natively expressed).

7.11.5. Example 5: Generation of Modified Exosome Proteins

As described herein, the exosomal proteins disclosed herein can be modified (e.g., truncated or attached to another moiety) to provide an EV (e.g., exosome) expressing the modified exosomal proteins to exhibit certain properties (e.g., increased targeting to certain cell types). A polynucleotide encoding a modified exosome protein is generated using a polynucleotide encoding a whole exosome protein or a truncated exosome protein. A specific truncated exosome protein is selected by screening various truncated exosome proteins and selecting a truncated protein having optimal capabilities to incorporate into exosome membranes and interact with a binding agent. Targeting of the truncated proteins to exosome membranes is tested by nano-flow cytometry.

A polynucleotide encoding a modified exosome protein is generated by adding a polynucleotide encoding an affinity tag (glutathione-S-transferase, S-peptide, FLAG tag, GFP, etc.) to the polynucleotide encoding a whole or truncated exosome protein (e.g., CD13, MME, ENPP1, and NRP1). The modified polynucleotide expresses a fusion protein. The polynucleotide is further modified to improve their targeting into exosome membranes and/or their affinity to a binding agent.

A different type of polynucleotide encoding a modified exosome protein is generated by adding a polynucleotide encoding a therapeutic peptide (e.g., an antibody, an enzyme, a ligand, a receptor, an antimicrobial peptide, a variant or a fragment thereof) to the polynucleotide encoding a whole or truncated exosome protein (e.g., CD13, MME, ENPP1, and NRP1). The modified polynucleotide expresses a fusion protein presented on the surface of an exosome. The fusion protein maintains therapeutic activity of the therapeutic peptide.

A different type of polynucleotide encoding a modified exosome protein is generated by adding a polynucleotide encoding a targeting moiety (e.g., a targeting moiety specific to a specific organ, tissue or cell) to the polynucleotide encoding a whole or truncated exosome protein (e.g., CD13, MME, ENPP1, and NRP1). The modified polynucleotide expresses a fusion protein presented on the surface of an exosome. The fusion protein allows the exosome to be targeted to a specific organ, tissue or cell.

Localization of modified exosome proteins on the exosome surface is also tested by nano flow cytometry.

7.11.6. Example 6: Generation of Surface-Engineered Exosomes

A producer cell generating surface-engineered exosomes is made by introducing an exogenous sequence encoding an exosome protein or a variant or a fragment of the exosome protein. A plasmid encoding an exosome protein is transiently transfected to induce high-level expression of the exosome protein on the exosome surface. A plasmid encoding a modified exosome protein is transiently transfected to produce exosomes having the modified exosome protein on the surface.

A polynucleotide encoding an exosome protein, a variant or a fragment of an exosome protein, or an exogenous sequence encoding an affinity tag, a therapeutic peptide or a targeting moiety is stably transformed into a producer cell to produce surface-engineered exosomes. The exogenous sequence encoding an affinity tag, a therapeutic peptide or a targeting moiety is inserted into a genomic site encoding an exosome protein to generate a fusion protein comprising the affinity tag attached to the exosome protein. A polynucleotide encoding a modified exosome protein is knocked in to a genomic site encoding an exosome protein.

A producer cell line is generated by stably transfecting at least two polynucleotides, each encoding an exosome protein, a variant or a fragment of an exosome protein, or an exogenous peptide (e.g., affinity tag, targeting moiety, therapeutic peptide). A different producer cell line is also generated by inserting two or more exogenous sequences (e.g., exogenous sequences encoding an affinity tag, a marker, a targeting peptide, a therapeutic peptide, etc.) into multiple genomic sites, within or in a close proximity to the genomic sequence encoding an exosome protein, to generate a surface-engineered exosome comprising multiple modified exosome proteins. Each of the plurality of modified exosome proteins is targeted to the surface of exosomes. The exosomes have affinities to two different binding agents and are purified by either or both of the binding agents.

7.11.7. Example 7: Isolation, Purification and Sub-Fractionation of Exosomes by Affinity Purification Binding agents for affinity purification of exosomes are developed by biopanning/directed evolution that elute under mild conditions.

The binding agent is attached to a solid support (e.g., a porous agarose bead) and formed into a conventional chromatography system (e.g., GE AKTA). A sample containing exosomes is applied to the column for affinity purification.

7.11.8. Example 8: Analysis of Different Scaffold Moieties to Target Exosomes Further to Example 6 described above, the ability of CD13 and MME proteins were tested for their ability to target proteins to the surface of exosomes derived from HEK293 cells. Briefly, plasmids expressing full-length CD13 fused to green fluorescent protein (GFP) or full-length MME fused to GFP were stably transfected into HEK293 cells. For comparison purposes, HEK293 cells engineered to overexpress PTGFRN fused to GFP were also generated.

As shown in FIG. 4A, HEK293 cells transfected with the CD13-GFP or MME-GFP plasmids expressed the particular exosomal protein of interest. The overall expression was similar to that of PTGFRN-GFP observed in the HEK293 cells engineered to overexpress PTGFRN. And, as shown in FIG. 4B, both the CD13-GFP and MME-GFP fusion proteins were properly folded and expressed in the EVs produced from the respective HEK293 producer cells.

Collectively, the above results demonstrate that certain exosomal proteins (e.g., heterologous exosomal vesicle proteins disclosed herein, e.g., CD13 and MME) can be exogenously introduced to a producer cell that does not naturally express the heterologous protein. The results further demonstrate that EVs (e.g., exosomes) produced from such modified producer cells can express the heterologous exosomal proteins, which can be used to anchor various molecules (e.g., antigen, targeting moiety, adjuvants, and/or immune modulators) to the EVs (e.g., exosomes).

8. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

9. EQUIVALENTS

The present disclosure provides, inter alia, compositions of cannabinoid and entourage compositions. The present disclosure also provides method of treating neurodegenerative diseases by administering the cannabinoid and entourage compositions. While various specific embodiments have been illustrated and described, the above specification is not restrictive. It will be appreciated that various changes can be made without departing from the spirit and scope of the disclosure(s). Many variations will become apparent to those skilled in the art upon review of this specification.

```
Informal Sequence Listing
CD13
>sp|P15144|AMPN_HUMAN Aminopeptidase N OS = Homo
sapiens OX = 9606 GN = ANPEP PE = 1 SV = 4
                                          SEQ ID 47
MAKGFYISKSLGILGILLGVAAVCTIIALSVVYSQEKNKNANSSPVASTI

PSASATTNPASATTLDQSKAWNRYRLPNILKPDSYRVTLRPYLTPNDRGL

YVFKGSSTVRFTCKEATDVIIIHSKKLNYTLSQGHRVVLRGVGGSQPPDI

DKTELVEPTEYLVVHLKGSLVKDSQYEMDSEFEGELADDLAGFYRSEYME
```

-continued

GNVRKVVATTQMQAADARKSFPCFDEPAMKAEFNITLIHPKDLTALSNML

PKGPSTPLPEDPNWNVIEFHTTPKMSTYLLAFIVSEFDYVEKQASNGVLI

RIWARPSAIAAGHGDYALNVTGPILNFFAGHYDTPYPLPKSDQIGLPDFN

AGAMENWGLVTYRENSLLFDPLSSSSSNKERVVTVIAHELAHQWFGNLVT

IEWWNDLWLNEGFASYVEYLGADYAEPTWNLKDLMVLNDVYRVMAVDALA

SSHPLSTPASEINTPAQISELFDAISYSKGASVLRMLSSFLSEDVFKQGL

ASYLHTFAYQNTIYLNLWDHLQEAVNNRSIQLPTTVRDIMNRWTLQMGFP

VITVDTSTGTLSQEHFLLDPDSNVTRPSEFNYVWIVPITSIRDGRQQQDY

WLIDVRAQNDLFSTSGNEWVLLNLNVTGYYRVNYDEENWRKIQTQLQRDH

SAIPVINRAQIINDAFNLASAHKVPVTLALNNTLFLIEERQYMPWEAALS

SLSYFKLMFDRSEVYGPMKNYLKKQVTPLFIHFRNNTNNWREIPENLMDQ

YSEVNAISTACSNGVPECEEMVSGLEKQWMENPNNNPIHPNLRSTVYCNA

IAQGGEEEWDFAWEQFRNATLVNEADKLRAALACSKELWILNRYLSYTLN

PDLIRKQDATSTIISITNNVIGQGLVWDFVQSNWKKLENDYGGGSFSFSN

LIQAVTRRFSTEYELQQLEQFKKDNEETGFGSGTRALEQALEKTKANIKW

VKENKEVVLQWFTENSK

NME
>sp|P08473|NEP_HUMAN Neprilysin OS = *Homo sapiens*
OX = 9606 GN = MME PE = 1 SV = 2
SEQ ID 48
MGKSESQMDITDINTPKPKKKQRWTPLEISLSVLVLLLTIIAVTMIALYA

TYDDGICKSSDCIKSAARLIQNMDATTEPCTDFFKYACGGWLKRNVIPET

SSRYGNFDILRDELEVVLKDVLQEPKTEDIVAVQKAKALYRSCINESAID

SRGGEPLLKLLPDIYGWPVATENWEQKYGASWTAEKAIAQLNSKYGKKVL

INLFVGTDDKNSVNHVIHIDQPRLGLPSRDYYECTGIYKEACTAYVDFMI

SVARLIRQEERLPIDENQLALEMNKVMELEKEIANATAKPEDRNDPMLLY

NKMTLAQIQNNFSLEINGKPFSWLNFTNEIMSTVNISITNEEDVVVYAPE

YLTKLKPILTKYSARDLQNLMSWRFIMDLVSSLSRTYKESRNAFRKALYG

TTSETATWRRCANYVNGNMENAVGRLYVEAAFAGESKHVVEDLIAQIREV

FIQTLDDLTWMDAETKKRAEEKALAIKERIGYPDDIVSNDNKLNNEYLEL

NYKEDEYFENIIQNLKFSQSKQLKKLREKVDKDEWISGAAVVNAFYSSGR

NQIVFPAGILQPPFFSAQQSNSLNYGGIGMVIGHEITHGFDDNGRNFNKD

GDLVDWWTQQSASNFKEQSQCMVYQYGNFSWDLAGGQHLNGINTLGENIA

DNGGLGQAYRAYQNYIKKNGEEKLLPGLDLNHKQLFFLNFAQVWCGTYRP

EYAVNSIKTDVHSPGNFRIIGTLQNSAEFSEAFHCRKNSYMNPEKKCRVW

ENPP1
>sp|P22413|ENPP1_HUMAN Ectonucleotide
pyrophosphatase/phosphodiesterase family member 1
OS = *Homo sapiens* OX = 9606 GN = ENPP1 PE = 1
SV = 2
SEQ IDD 49
MERDGCAGGGSRGGEGGGRAPREGPAGNGRDRGRSHAAEAPGDPQAAASLL

APMDVGEEPLEKAARARTAKDPNTYKVLSLVLSVCVLTTILGCIFGLKPS

CAKEVKSCKGRCFERTFGNCRCDAACVELGNCCLDYQETCIEPEHIWTCN

KFRCGEKRLTRSLCACSDDCKDKGDCCINYSSVCQGEKSWVEEPCESINE

PQCPAGFETPPTLLFSLDGFRAEYLHTWGGLLPVISKLKKCGTYTKNMRP

VYPTKTFPNHYSIVTGLYPESHGIIDNKMYDPKMNASFSLKSKEKFNPEW

YKGEPIWVTAKYQGLKSGTFFWPGSDVEINGIFPDIYKMYNGSVPFEERI

LAVLQWLQLPKDERPHFYTLYLEEPDSSGHSYGPVSSEVIKALQRVDGMV

GMLMDGLKELNLHRCLNLILISDHGMEQGSCKKYIYLNKYLGDVKNIKVI

YGPAARLRPSDVPDKYYSFNYEGIARNLSCREPNQHFKPYLKHFLPKRLH

FAKSDRIEPLTFYLDPQWQLALNPSERKYCGSGFHGSDNVFSNMQALFVG

YGPGFKHGIEADTFENIEVYNLMCDLLNLTPAPNNGTHGSLNHLLKNPVY

TPKHPKEVHPLVQCPFTRNPRDNLGCSCNPSILPIEDFQTQFNLTVAEEK

IIKHETLPYGRPRVLQKENTICLLSQHQFMSGYSQDILMPLWTSYTVDRN

DSFSTEDFSNCLYQDFRIPLSPVHKCSFYKNNTKVSYGFLSPPQLNKNSS

GIYSEALLTTNIVPMYQSFQVIWRYFHDTLLRKYAEERNGVNVVSGPVFD

FDYDGRCDSLENLRQKRRVIRNQEILIPTHFFIVLTSCKDTSQTPLHCEN

LDTLAFILPHRTDNSESCVHGKHDSSWVEELLMLHRARITDVEHITGLSF

YQQRKEPVSDILKLKTHLPTFSQED

NRP1
>sp|O14786|NRP1_HUMAN Neuropilin-1 OS = *Homo
sapiens* OX = 9606 GN = NRP1 PE = 1 SV = 3
SEQ ID 50
MERGLPLLCAVLALVLAPAGAFRNDKCGDTIKIESPGYLTSPGYPHSYHP

SEKCEWLIQAPDPYQRIMINFNPHFDLEDRDCKYDYVEVFDGENENGHFR

GKFCGKIAPPPVVSSGPFLFIKFVSDYETHGAGFSIRYEIFKRGPECSQN

YTTPSGVIKSPGFPEKYPNSLECTYIVFVPKMSEIILEFESFDLEPDSNP

PGGMFCRYDRLEIWDGFPDVGPHIGRYCGQKTPGRIRSSSGILSMVFYTD

SAIAKEGFSANYSVLQSSVSEDFKCMEALGMESGEIHSDQITASSQYSTN

WSAERSRLNYPENGWTPGEDSYREWIQVDLGLLRFVTAVGTQGAISKETK

KKYYVKTYKIDVSSNGEDWITIKEGNKPVLFQGNTNPTDVVVAVFPKPLI

TRFVRIKPATWETGISMRFEVYGCKITDYPCSGMLGMVSGLISDSQITSS

NQGDRNWMPENIRLVTSRSGWALPPAPHSYINEWLQIDLGEEKIVRGIII

QGGKHRENKVFMRKFKIGYSNNGSDWKMIMDDSKRKAKSFEGNNNYDTPE

LRTFPALSTRFIRIYPERATHGGLGLRMELLGCEVEAPTAGPTTPNGNLV

DECDDDQANCHSGTGDDFQLTGGTTVLATEKPTVIDSTIQSEFPTYGFNC

EFGWGSHKTFCHWEHDNHVQLKWSVLTSKTGPIQDHTGDGNFIYSQADEN

QKGKVARLVSPVVYSQNSAHCMTFWYHMSGSHVGTLRVKLRYQKPEEYDQ

LVWMAIGHQGDHWKEGRVLLHKSLKLYQVIFEGEIGKGNLGGIAVDDISI

NNHISQEDCAKPADLDKKNPEIKIDETGSTPGYEGEGEGDKNISRKPGNV

LKTLDPILITIIAMSALGVLLGAVCGVVLYCACWHNGMSERNLSALENYN

FELVDGVKLKKDKLNTQSTYSEA

What is claimed is:

1. An extracellular vesicle (EV) comprising a heterologous CD13 protein, wherein the EV is produced from a producer cell which does not naturally express the CD13 protein, and wherein the EV further comprises a prostaglandin F2 receptor negative regulator (PTGFRN) protein.

2. The EV of claim 1, wherein the CD13 protein in the EV has a level of about 10 peptide spectral matches (PSMs) to about 1,000 PSMs, as measured using liquid chromatography with tandem mass spectrometry (LC-MS/MS).

3. The EV of claim 1, wherein the CD13 protein is a fusion protein.

4. The EV of claim 3, wherein the fusion protein comprises a functional moiety.

5. The EV of claim 4, wherein the functional moiety comprises an affinity tag, a therapeutic compound, a targeting moiety, or a combination thereof.

6. The EV of claim 5, wherein the therapeutic compound comprises a natural peptide, a recombinant peptide, a synthetic peptide, a nucleotide, an amino acid, a lipid, a carbohydrate, a small molecule drug, an antibody or a fragment thereof, an enzyme, a ligand, a receptor, or a combination thereof.

7. The EV of claim 4, wherein the fusion protein further comprises a linker.

8. The EV of claim 7, wherein the fusion protein is conjugated to the functional moiety by the linker.

9. The EV of claim 7, wherein the linker comprises a flexible linker, a rigid linker, a cleavable linker, or a combination thereof.

10. The EV of claim 1, wherein the producer cell comprises a human embryonic kidney (HEK) cell, or a Chinese hamster ovary (CHO) cell.

11. The EV of claim 1, wherein: (i) the producer cell is a non-human cell and the CD13 protein is a human CD13 protein; or (ii) the producer is a human cell and the CD13 protein is a non-human CD13 protein.

12. The EV of claim 1, wherein the CD13 protein comprises the amino acid sequence set forth in SEQ ID NO: 47.

13. The EV of claim 1, wherein the producer cell is a CHO cell.

14. The EV of claim 1, wherein the producer cell is a HEK cell.

* * * * *